United States Patent
Kanna et al.

(10) Patent No.: US 8,637,215 B2
(45) Date of Patent: Jan. 28, 2014

(54) COLORED CURABLE COMPOSITION, COLOR FILTER AND METHOD OF PRODUCING COLOR FILTER, SOLID-STATE IMAGE SENSOR AND LIQUID CRYSTAL DISPLAY DEVICE

(75) Inventors: Shinichi Kanna, Shizuoka-ken (JP); Kazuya Oota, Shizuoka-ken (JP); Masaru Yoshikawa, Shizuoka-ken (JP); Junichi Ito, Shizuoka-ken (JP); Yoshihiko Fujie, Shizuoka-ken (JP); Shigekazu Suzuki, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 208 days.

(21) Appl. No.: 13/033,153

(22) Filed: Feb. 23, 2011

(65) Prior Publication Data
US 2011/0217636 A1    Sep. 8, 2011

(30) Foreign Application Priority Data

Feb. 26, 2010   (JP) .................................. 2010-043529
Feb. 26, 2010   (JP) .................................. 2010-043530

(51) Int. Cl.
*G02B 5/20*          (2006.01)
(52) U.S. Cl.
USPC ............................ 430/7; 430/286.1; 257/440
(58) Field of Classification Search
None
See application file for complete search history.

(56) References Cited

U.S. PATENT DOCUMENTS

| | | |
|---|---|---|
| 2005/0131114 A1 | 6/2005 | Sunahara et al. |
| 2008/0076044 A1 | 3/2008 | Mizukawa et al. |
| 2008/0171271 A1 | 7/2008 | Kim et al. |
| 2010/0036134 A1 | 2/2010 | Mori et al. |
| 2010/0271578 A1 | 10/2010 | Ohkuma et al. |
| 2012/0187351 A1* | 7/2012 | Ito et al. ........................ 252/586 |

FOREIGN PATENT DOCUMENTS

| | | |
|---|---|---|
| EP | 2141206 A1 | 1/2010 |
| JP | 2001-033616 A | 2/2001 |
| JP | 2005181383 A | 7/2005 |
| JP | 2007139959 A | 6/2007 |
| JP | 2008-292970 A | 12/2008 |
| JP | 2009-031713 A | 2/2009 |
| JP | 2010032985 A | 2/2010 |
| JP | 2010043135 A | 2/2010 |
| JP | 2010249869 A | 11/2010 |
| JP | 2010256598 A | 11/2010 |
| WO | WO 2011/040628 A1 | 4/2011 |

OTHER PUBLICATIONS

Communication, dated Feb. 7, 2013, issued in related or corresponding EP Application No. 12191064.0, 10 pages.
Communication, dated Nov. 9, 2011, issued in corresponding EP Application No. 11155568.6, 5 pages.
Notice of Reasons for Rejection, dated Sep. 24, 2013, issued in corresponding JP 2010-043530, 5 pages in English and Japanese.

* cited by examiner

*Primary Examiner* — John A. McPherson
(74) *Attorney, Agent, or Firm* — Sughrue Mion, PLLC

(57) ABSTRACT

The present invention provides a colored curable composition including a phthalocyanine pigment, a dioxazine pigment, a dye, a polymerization initiator, a polymerizable compound and a solvent; and a colored curable composition including a phthalocyanine pigment, a dye multimer having a polymerizable group and a group derived from a dipyrromethene dye, a polymerization initiator, a polymerizable compound and a solvent.

10 Claims, No Drawings

COLORED CURABLE COMPOSITION, COLOR FILTER AND METHOD OF PRODUCING COLOR FILTER, SOLID-STATE IMAGE SENSOR AND LIQUID CRYSTAL DISPLAY DEVICE

CROSS-REFERENCE TO RELATED APPLICATION

This application claims priority under 35 USC 119 from Japanese Patent Application No. 2010-043529 filed Feb. 26, 2010 and Japanese Patent Application No. 2010-043530 filed Feb. 26, 2010, the disclosure of which is incorporated by reference herein.

BACKGROUND OF THE INVENTION

1. Field of the Invention

The present invention relates to a colored curable composition, a color filter and a method of producing a color filter, a solid-state image sensor and a liquid crystal display device.

2. Description of the Related Art

As a method of producing a color filter used in liquid crystal display devices (LCDs) or solid-state image sensors (CCD or CMOS image sensors), a pigment dispersion method has been widely known.

A pigment dispersion method is a method of producing a color filter by photolithography using a colored photosensitive composition in which a pigment is dispersed in various kinds of photosensitive composition. This method, in which patterning is performed by photolithography, is known to be suitable for producing large-sized, high-definition color filters with high positional accuracy. When producing color filters by a pigment dispersion method, a coating film is formed by applying a photosensitive composition on a glass support with a spin coater or a roll coater, exposing the coating film to light and developing the same to form color pixels. A color filter is thus obtained by repeating these processes a number of times according to the number of colors used in the color filter.

One exemplary colored photosensitive composition in which a pigment is used is a blue colored composition for color filters in which a phthalocyanine pigment is included, as described in Japanese Patent Application Laid-Open (JP-A) No. 2001-33616.

When producing display devices, such as liquid crystal display devices or solid-state image sensors, by forming a color filter using a pigment, a pigment having a small particle size is desired in view of improving contrast. Problems in contrast are caused by light scattering due to a pigment or rotation of the polarizing axis by double refraction or the like. When micronization of a pigment is not sufficient, light is scattered or absorbed by the pigment, whereby light transmissivity is decreased and contrast is lowered and, moreover, curing sensitivity at the time of pattern exposure may be decreased.

In particular, in the field of color filters for solid-state image sensors, in which even higher definition has been required in recent years, further improvements in resolution has been difficult in a conventional pigment dispersion system, i.e., there are problems in that unevenness in color may occur due to coarse pigment particles, and the like. As a result, a pigment dispersion system is not suitable for applications that require a highly fine pattern for solid-state image sensors with a pixel size of from 1.5 to 3.0 μm square.

In response to such circumstances, techniques in which a dye is used instead of a pigment have been proposed. However, dyes have problems such as light resistance and heat resistance being inferior compared with pigments, which may cause problems in performance of color filters. There is also a problem in that a dye may precipitate due to its low solubility with respect to a photosensitive composition, and poor stability with time in the form of a liquid formulation or a coating film.

In view of such problems, a colored curable composition has been proposed in which a dye including a dipyrromethene compound and a phthalocyanine dye are used in combination, the composition exhibiting superior storage stability and being capable of forming a color filter that exhibits a high light resistance (see, for example, JP-A No. 2008-292970).

Further, a colored curable composition, in which a dye and a pigment are combined, is known (see, for example, United States Patent Application Publication No. 2008/0171271).

SUMMARY OF THE INVENTION

A first aspect of the invention provides a colored curable composition containing a phthalocyanine pigment, a dioxazine pigment, a dye, a polymerization initiator, a polymerizable compound, and a solvent.

A second aspect of the invention provides a colored curable composition comprising a phthalocyanine pigment, a dye multimer having a polymerizable group and a group derived from a dipyrromethene dye, a polymerization initiator, a polymerizable compound, and a solvent.

<First Aspect>

The first aspect of the present invention provides a colored curable composition containing a phthalocyanine pigment, a dioxazine pigment, a dye, a polymerization initiator, a polymerizable compound, and a solvent.

As described above, it is known that a colored curable composition in which a dye is used provides effects such as formation of a color filter that exhibits superior light fastness etc. by selecting a suitable dye. However, it is also true that these effects need to be further enhanced in order to realize even higher fineness or improved performances of color filters.

The first aspect of the present invention has been made in view of the above circumstances, and an object thereof is to provide a colored curable composition capable of forming a colored cured film that exhibit superior light fastness.

A further object of the first aspect of the present invention is to provide a color filter that exhibits superior light fastness and a method for producing the color filter; and a solid-state image sensor and a liquid crystal display device including the color filter.

According to the first aspect of the invention, a colored curable composition capable of forming a colored cured film that exhibits superior light fastness can be provided.

According to the first aspect of the invention, a color filter that exhibits superior light fastness and a method of producing the same, and a solid-state image sensor and a liquid crystal display device including the color filter can be provided.

<Colored Curable Composition>

First, the colored curable composition of the first aspect of the invention will be described.

The colored curable composition of the first aspect of the invention includes a phthalocyanine pigment, a dioxazine pigment, a dye, a polymerization initiator, a polymerizable compound, and a solvent.

In order to obtain favorable spectroscopic characteristics of a blue or green colored cured film (in particular, a blue colored cured film), the combined use of a phthalocyanine pigment and a dye as a colorant in the colored curable composition is effective. However, since a dye is prone to decomposition when exposed to light, colored curable compositions containing a dye generally exhibits poor light fastness.

In view of the above, the present inventors have made extensive studies and, as a result, arrived at the invention based on the findings that decomposition of a dye can be suppressed and light fastness of a blue cured film can be improved when a dioxazine pigment is used in addition to a phthalocyanine pigment and a dye as a colorant in the colored curable composition.

Accordingly, when the colored curable composition of the first aspect of the invention is used, a colored cured film that exhibits improved light fastness can be obtained.

The reason why decomposition of a dye is suppressed is presumed to be that light that allows the dye to decompose is absorbed by the dioxazine pigment. However, the first aspect of the invention is not limited to this speculation.

Hereinafter, the components of the colored curable composition of the first aspect of the invention will be described.

<Phthalocyanine Pigment>

The colored curable composition of the first aspect of the invention contains a phthalocyanine pigment.

The phthalocyanine pigment used in the first aspect of the invention is not particularly limited as long as it is a pigment having a phthalocyanine backbone. The central metal included in the phthalocyanine pigment is not particularly limited and may be any metal as long as it can form a phthalocyanine backbone. Among them, magnesium, titanium, iron, cobalt, nickel, copper, zinc and aluminum are preferably used as the central metal.

Specific examples of the phthalocyanine pigment used in the first aspect of the invention include C.I. Pigment Blue 15, C.I. Pigment Blue 15:1, C.I. Pigment Blue 15:2, C.I. Pigment Blue 15:3, C.I. Pigment Blue 15:4, C.I. Pigment Blue 15:5, C.I. Pigment Blue 15:6, C.I. Pigment Blue 16, C.I. Pigment Blue 17:1, C.I. Pigment Blue 75, C.I. Pigment Blue 79, C.I. Pigment Green 7, C.I. Pigment Green 36, C.I. Pigment Green 37, chloroaluminum phthalocyanine, hydroxyaluminum phthalocyanine, aluminum phthalocyanine oxide and zinc phthalocyanine. Among them, C.I. Pigment Blue 15, C.I. Pigment Blue 15:6, C.I. Pigment Blue 15:1 and C.I. Pigment Blue 15:2 are preferable, and C.I. Pigment Blue 15:6 is particularly preferable in view of light fastness and tinctorial strength.

The content of the phthalocyanine pigment in the colored curable composition of the first aspect of the invention is preferably in the range of from 5% by mass to 60% by mass, more preferably from 10% by mass to 60% by mass, and most preferably from 35% by mass to 50% by mass, with respect to the total solid components of the colored curable composition, in view of adjusting color hues of a color filter.

<Dioxazine Pigment>

The colored curable composition of the first aspect of the invention includes a dioxazine pigment.

Examples of the dioxazine pigment include C.I. Pigment Violet 19, C.I. Pigment Violet 23, C.I. Pigment Violet 32, and C.I. Pigment Violet 37. Among them, C.I. Pigment Violet 23 is preferable.

The content of the dioxazine pigment in the colored curable composition of the first aspect of the invention is in the range of from 0.1% by mass to 40% by mass, more preferably from 0.1% by mass to 20% by mass, and particularly preferably from 0.3% by mass to 10% by mass, with respect to the total solid components in the colored curable composition.

If the content of the dioxazine pigment is 0.1% by mass or more, it is possible to more effectively improve the light fastness.

If the content of the dioxazine pigment is 40% by mass or less, it is possible to more effectively adjust the color hues.

Further, in the colored curable composition of the first aspect of the invention, the mass ratio of the dioxazine pigment to the dye to be described hereinafter (dioxazine pigment/dye) is preferably in the range of from 0.01 to 2.00, more preferably from 0.05 to 1.50, and particularly preferably from 0.35 to 0.80.

If the mass ratio (dioxazine pigment/dye) is 0.01 or greater, it is possible to more effectively improve the light fastness.

If the mass ratio (dioxazine pigment/dye) is 2.00 or less, it is possible to more effectively adjust the color hues.

<Dye>

The colored curable composition of the first aspect of the invention includes a dye.

The dye is not particularly limited, and any known dyes that have been conventionally used in color filters may be used. Examples of such dyes include dyes described in JP-A Nos. 64-90403, 64-91102, 1-94301 and 6-11614, Japanese Patent Registration No. 2592207, U.S. Pat. Nos. 4,808,501, 5,667,920, 505,950 and 5,667,920, JP-A Nos. 5-333207, 6-35183, 6-51115 and 6-194828, and the like. Examples of the chemical structure of the dye include a pyrazole azo dye, an anilino azo dye, a triphenylmethane dye, an anthraquinone dye, a benzylidene dye, an oxonol dye, a pyrazolotriazole azo dye, a pyridone azo dye, a cyanine dye, a phenothiazine dye, and a pyrrolopyrazole azomethine dye.

Among them, from the viewpoint that the absorption wavelength is close to that of a dioxazine pigment, a complex including a compound represented by the following formula (I) and a metal atom or a metal compound (hereinafter, also referred to as a "specific complex") is preferable.

(Dipyrromethene Compound)

First, the compound represented by the formula (I) that constitutes the specific complex (dipyrromethene compound) is described.

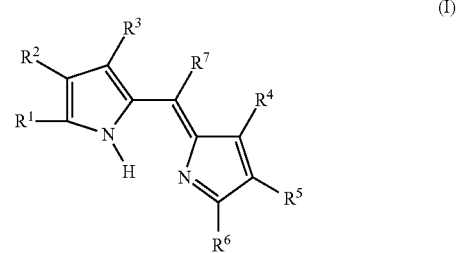

In the formula (I), each of $R^1$ to $R^6$ independently represents a hydrogen atom or a substituent, and $R^7$ represents a hydrogen atom, a halogen atom, an alkyl group, an aryl group or a heterocyclic group.

It is preferred that $R^1$ and $R^6$ are not bonded to each other to form a ring.

Examples of the substituent represented by $R^1$ to $R^6$ in the formula (I) include the following monovalent groups (hereinafter, these monovalent groups may be collectively referred to as "Substituent R").

A halogen atom (for example, a fluorine atom, a chlorine atom or a bromine atom), an alkyl group (a linear, branched or cyclic alkyl group having preferably 1 to 48 carbon atoms, more preferably 1 to 24 carbon atoms, such as a methyl group, an ethyl group, a propyl group, an isopropyl group, a butyl group, a t-butyl group, a pentyl group, a hexyl group, a heptyl group, an octyl group, a 2-ethylhexyl group, a dodecyl group, a hexadecyl group, a cyclopropyl group, a cyclopentyl group, a cyclohexyl group, a 1-norbornyl group or a 1-adamantyl group), an alkenyl group (an alkenyl group having preferably 2 to 48 carbon atoms, more preferably 2 to 18 carbon atoms, such as a vinyl group, an allyl group or a 3-buten-1-yl group), an aryl group (an aryl group having preferably 6 to 48 carbon atoms, more preferably 6 to 24 carbon atoms, such as a phenyl group or a naphthyl group), a heterocyclic group (a heterocyclic group having preferably 1 to 32 carbon atoms, more preferably 1 to 18 carbon atoms, such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group or a benzotriazol-1-yl group), a silyl group (a silyl group having preferably 3 to 38 carbon atoms, more preferably 3 to 18 carbon atoms, such as a trimethylsilyl group, a triethylsilyl group, a tributylsilyl group, a t-butyldimethylsilyl group or a t-hexyldimethylsilyl group), a hydroxyl group, a cyano group, a nitro group, an alkoxy group (an alkoxy group having preferably 1 to 48 carbon atoms, more preferably 1 to 24 carbon atoms, such as a methoxy group, an ethoxy group, a 1-butoxy group, a 2-butoxy group, an isopropoxy group, a t-butoxy group, a dodecyloxy group, or a cycloalkyloxy group, for example a cyclopentyloxy group or a cyclohexyloxy group), an aryloxy group (an aryloxy group having preferably 6 to 48 carbon atoms, more preferably 6 to 24 carbon atoms, such as a phenoxy group or a 1-naphthoxy group), a heterocyclic oxy group (a heterocyclic oxy group having preferably 1 to 32 carbon atoms, more preferably 1 to 18 carbon atoms, such as a 1-phenyltetrazole-5-oxy group or a 2-tetrahydropyranyloxy group), a silyloxy group (a silyloxy group having preferably 1 to 32 carbon atoms, more preferably 1 to 18 carbon atoms, such as a trimethylsilyloxy group, a t-butyldimethylsilyloxy group or a diphenylmethylsilyloxy group), an acyloxy group (an acyloxy group having preferably 2 to 48 carbon atoms, more preferably 2 to 24 carbon atoms, such as an acetoxy group, a pivaloyloxy group, a benzoyloxy group or a dodecanoyloxy group), an alkoxycarbonyloxy group (an alkoxycarbonyloxy group having preferably 2 to 48 carbon atoms, more preferably 2 to 24 carbon atoms, such as an ethoxycarbonyloxy group, a t-butoxycarbonyloxy group, or a cycloalkyloxycarbonyloxy group, for example, a cyclohexyloxycarbonyloxy group), an aryloxycarbonyloxy group (an aryloxycarbonyloxy group having preferably 7 to 32 carbon atoms, more preferably 7 to 24 carbon atoms, such as a phenoxycarbonyloxy group), a carbamoyloxy group (a carbamoyloxy group having preferably 1 to 48 carbon atoms, more preferably 1 to 24 carbon atoms, such as an N,N-dimethylcarbamoyloxy group, an N-butylcarbamoyloxy group, an N-phenylcarbamoyloxy group or an N-ethyl-N-phenylcarbamoyloxy group), a sulfamoyloxy group (a sulfamoyloxy group having preferably 1 to 32 carbon atoms, more preferably 1 to 24 carbon atoms, such as an N,N-diethylsulfamoyloxy group or an N-propylsulfamoyloxy group), an alkylsulfonyloxy group (an alkylsulfonyloxy group having preferably 1 to 38 carbon atoms, more preferably 1 to 24 carbon atoms, such as a methylsulfonyloxy group, a hexadecylsulfonyloxy group or a cyclohexylsulfonyloxy group), an arylsulfonyloxy group (an arylsulfonyloxy group having preferably 6 to 32 carbon atoms, more preferably 6 to 24 carbon atoms, such as a phenylsulfonyloxy group), an acyl group (an acyl group having preferably 1 to 48 carbon atoms, more preferably 1 to 24 carbon atoms, such as a formyl group, an acetyl group, a pivaloyl group, a benzoyl group, a tetradecanoyl group or a cyclohexanoyl group), an alkoxycarbonyl group (an alkoxycarbonyl group having preferably 2 to 48 carbon atoms, more preferably 2 to 24 carbon atoms, such as a methoxycarbonyl group, an ethoxycarbonyl group, an octadecyloxycarbonyl group, a cyclohexyloxycarbonyl group or a 2,6-di-tert-butyl-4-methylcyclohexyloxycarbonyl group), an aryloxycarbonyl group (an aryloxycarbonyl group having preferably 7 to 32 carbon atoms, more preferably 7 to 24 carbon atoms, such as a phenoxycarbonyl group), a carbamoyl group (a carbamoyl group having preferably 1 to 48 carbon atoms, more preferably 1 to 24 carbon atoms, such as a carbamoyl group, an N,N-diethylcarbamoyl group, an N-ethyl-N-octylcarbamoyl group, an N,N-dibutylcarbamoyl group, an N-propylcarbamoyl group, an N-phenylcarbamoyl group, an N-methyl-N-phenylcarbamoyl group or an N,N-dicyclohexylcarbamoyl group), an amino group (an amino group having preferably 32 or less carbon atoms, more preferably 24 or less carbon atoms, such as an amino group, a methylamino group, an N,N-dibutylamino group, a tetradecylamino group, a 2-ethylhexylamino group or a cyclohexylamino group), an anilino group (an anilino group having preferably 6 to 32 carbon atoms, more preferably 6 to 24 carbon atoms, such as an anilino group or an N-methylanilino group), a heterocyclic amino group (a heterocyclic amino group having preferably 1 to 32 carbon atoms, more preferably 1 to 18 carbon atoms, such as a 4-pyridylamino group), a carbonamido group (a carbonamido group having preferably 2 to 48 carbon atoms, more preferably 2 to 24 carbon atoms, such as an acetamido group, a benzamido group, a tetradecanamido group, a pivaloylamido group or a cyclohexanamido group), an ureido group (an ureido group having preferably 1 to 32 carbon atoms, more preferably 1 to 24 carbon atoms, such as an ureido group, an N,N-dimethylureido group or an N-phenylureido group), an imido group (an imido group having preferably 36 or less carbon atoms, more preferably 24 or less carbon atoms, such as an N-succinimido group or an N-phthalimido group), an alkoxycarbonylamino group (an alkoxycarbonylamino group having preferably 2 to 48 carbon atoms, more preferably 2 to 24 carbon atoms, such as a methoxycarbonylamino group, an ethoxycarbonylamino group, a t-butoxycarbonylamino group, an octadecyloxycarbonylamino group or a cyclohexyloxycarbonylamino group), an aryloxycarbonylamino group (an aryloxycarbonylamino group having preferably 7 to 32 carbon atoms, more preferably 7 to 24 carbon atoms, such as a phenoxycarbonylamino group), a sulfonamido group (a sulfonamido group having preferably 1 to 48 carbon atoms, more preferably 1 to 24 carbon atoms, such as a methanesulfonamido group, a butanesulfonamido group, a benzenesulfonamido group, a hexadecanesulfonamido group or a cyclohexanesulfonamido group), a sulfamoylamino group (a sulfamoylamino group having preferably 1 to 48 carbon atoms, more preferably 1 to 24 carbon atoms, such as an N,N-dipropylsulfamoylamino group or an N-ethyl-N-dodecylsulfamoylamino group), an azo group (an azo group having preferably 1 to 32 carbon atoms, more preferably 1 to 24 carbon atoms, such as a phenylazo group or a 3-pyrazolylazo group), an alkylthio group (an alkylthio group having preferably 1 to 48 carbon atoms, more preferably 1 to 24 carbon atoms, such as a methylthio group, an ethylthio group, an octylthio group or a cyclohexylthio group), an arylthio group (an arylthio group having preferably 6 to 48 carbon atoms, more preferably 6 to 24 carbon atoms, such as a phenylthio group), a heterocyclic thio group (a heterocyclic thio group having preferably 1 to 32 carbon atoms, more preferably 1 to 18 carbon atoms, such as a 2-benzothiazolylthio group, a 2-pyridylthio group or a 1-phenyltetrazolylthio group), an alkylsulfinyl group (an alkylsulfinyl group having preferably 1 to 32 carbon atoms, more preferably 1 to 24 carbon atoms, such as a dodecanesulfinyl group), an arylsulfinyl group (an arylsulfinyl group having preferably 6 to 32 carbon atoms, more preferably 6 to 24 carbon atoms, such as a phenylsulfinyl group), an alkylsulfonyl group (an alkylsulfonyl group having preferably 1 to 48 carbon atoms, more preferably 1 to 24 carbon atoms, such as a methylsulfonyl group, an ethylsulfonyl group, a propylsulfonyl group, a butylsulfonyl group, an isopropylsulfonyl group, a 2-ethylhexylsulfonyl group, a hexadecylsulfonyl group, an octylsulfonyl group or a cyclohexylsulfonyl group), an arylsulfonyl group (an arylsulfonyl group having preferably 6 to 48 carbon atoms, more preferably 6 to 24 carbon atoms, such as a phenylsulfonyl group or a 1-naphthylsulfonyl group), a sulfamoyl group (a sulfamoyl group having preferably 32 or less carbon atoms, more preferably 24 or less carbon atoms, such as a sulfamoyl group, an N,N-dipropylsulfamoyl group, an N-ethyl-N-dodecylsulfamoyl group, an N-ethyl-N-phenylsulfamoyl group or an N-cyclohexylsulfamoyl group), a sulfo group, a phosphonyl group (a phosphonyl group having preferably 1 to 32 carbon atoms, more preferably 1 to 24 carbon atoms, such as a phenoxyphosphonyl group, an octyloxyphosphonyl group or a phenylphosphonyl group) and a phosphinoylamino group (a phosphinoylamino group having preferably 1 to 32 carbon atoms, more preferably 1 to 24 carbon atoms, such as a diethoxyphosphinoylamino group or a dioctyloxyphosphinoylamino group).

When the above-mentioned monovalent groups are a group that can be further substituted, the group may be further substituted by any one of the above-mentioned groups. When the monovalent group has two or more substituents, these substituents may be the same or different from each other.

In the formula (I), combinations of $R^1$ and $R^2$, $R^2$ and $R^3$, $R^4$ and $R^5$, and $R^5$ and $R^6$ may independently bond to each other to form a 5-, 6- or 7-membered ring. Examples of the ring formed from the above combinations include saturated or unsaturated rings. Examples of the 5-, 6- or 7-membered saturated or unsaturated rings include a pyrrole ring, a furan ring, a thiophene ring, a pyrazole ring, an imidazole ring, a triazole ring, an oxazole ring, a thiazole ring, a pyrrolidine ring, a piperidine ring, a cyclopentene ring, a cyclohexene ring, a benzene ring, a pyridine ring, a pyrazine ring and a pyridazine ring, preferably a benzene ring and a pyridine ring.

When the 5-, 6- or 7-membered ring is a group that can be further substituted, the group may be substituted by any one of the groups mentioned as Substituent R, and when the ring is substituted by two or more substituents, these substituents may be the same or different from each other.

In the formula (I), when $R^7$ represents a halogen atom, an alkyl group, an aryl group or a heterocyclic group, preferable ranges thereof are the same as the preferable ranges of a halogen atom, an alkyl group, an aryl group or a heterocyclic group represented by $R^1$ to $R^6$.

Among these groups, $R^1$ and $R^6$ in the formula (I) preferably represent an alkylamino group, an arylamino group, a carbonamido group, an ureido group, an imido group, an alkoxycarbonylamino group or a sulfonamido group, more preferably a carbonamido group, an ureido group, an alkoxycarbonylamino group or a sulfonamido group, and particularly preferably a carbonamido group or an ureido group.

Among these groups, $R^2$ and $R^5$ in the formula (I) preferably represent an alkoxycarbonyl group, an aryloxycarbonyl group, a carbamoyl group, an alkylsulfonyl group, an arylsulfonyl group, a nitrile group, an imido group or a carbamoylsulfonyl group, more preferably an alkoxycarbonyl group, an aryloxycarbonyl group, a carbamoyl group, an alkylsulfonyl group, a nitrile group, an imido group or a carbamoylsulfonyl group, still more preferably an alkoxycarbonyl group, an aryloxycarbonyl group, a carbamoyl group, a nitrile group, an imido group or a carbamoylsulfonyl group, and particularly preferably an alkoxycarbonyl group, an aryloxycarbonyl group or a carbamoyl group.

Among these groups, $R^3$ and $R^4$ in the formula (I) preferably represent a substituted or unsubstituted alkyl group, a substituted or unsubstituted aryl group, or a substituted or unsubstituted heterocyclic group, more preferably a substituted or unsubstituted alkyl group, or a substituted or unsubstituted aryl group.

When $R^3$ and $R^4$ in the formula (I) represent an alkyl group, examples of the alkyl group preferably include a linear, branched or cyclic, substituted or unsubstituted alkyl group having 1 to 12 carbon atoms, more specifically, for example, a methyl group, an ethyl group, an n-propyl group, an isopropyl group, a cyclopropyl group, an n-butyl group, an i-butyl group, a t-butyl group, a cyclobutyl group, a cyclopentyl group, a cyclohexyl group and a benzyl group, more preferably a branched or cyclic, substituted or unsubstituted alkyl group having 1 to 12 carbon atoms, still more specifically, for example, an isopropyl group, a cyclopropyl group, an i-butyl group, a t-butyl group, a cyclobutyl group, a cyclopentyl group and a cyclohexyl group, even more preferably a secondary or tertiary substituted or unsubstituted alkyl group having 1 to 12 carbon atoms, and more specifically, for example, an isopropyl group, a cyclopropyl group, an i-butyl group, a t-butyl group, a cyclobutyl group and a cyclohexyl group.

When $R^3$ and $R^4$ in the formula (I) represent an aryl group, examples of the aryl group preferably include a substituted or unsubstituted phenyl group and a substituted or unsubstituted naphthyl group, more preferably a substituted or unsubstituted phenyl group.

When $R^3$ and $R^4$ represent a heterocyclic group, examples of the heterocyclic group preferably include a substituted or unsubstituted 2-thienyl group, a substituted or unsubstituted 4-pyridyl group, a substituted or unsubstituted 3-pyridyl group, a substituted or unsubstituted 2-pyridyl group, a substituted or unsubstituted 2-furyl group, a substituted or unsubstituted 2-pyrimidinyl group, a substituted or unsubstituted 2-benzothiazolyl group, a substituted or unsubstituted 1-imidazolyl group, a substituted or unsubstituted 1-pyrazolyl group and a substituted or unsubstituted benzotriazol-1-yl group, more preferably a substituted or unsubstituted 2-thienyl group, a substituted or unsubstituted 4-pyridyl group, a substituted or unsubstituted 2-furyl group, a substituted or unsubstituted 2-pyrimidinyl group and a substituted or unsubstituted 1-pyridyl group.

—Metal Atom or Metal Compound—

Next, a metal atom or a metal compound that constitutes the specific complex will be described.

The metal atom or the metal compound used in the invention may be any metal atom or metal compound as long as it can form a complex, and examples thereof include divalent metal atoms, divalent metal oxides, divalent metal hydroxides and divalent metal chlorides, for example, Zn, Mg, Si, Sn, Rh, Pt, Pd, Mo, Mn, Pb, Cu, Ni, Co, Fe and the like, as well as metal chlorides including AlCl, InCl, FeCl, $TiCl_2$, $SnCl_2$, $SiCl_2$ and $GeCl_2$, metal oxides including TiO and VO, and metal hydroxides including $Si(OH)_2$.

Among them, Fe, Zn, Mg, Si, Pt, Pd, Mo, Mn, Cu, Ni, Co, TiO and VO are preferable, Fe, Zn, Mg, Si, Pt, Pd, Cu, Ni, Co and VO are more preferable, and Fe, Zn, Cu, Co and VO (V=O) are most preferable, in view of stability, spectroscopic properties, heat resistance, light fastness, manufacturability etc. of the complex.

Preferred examples of the complex containing a compound represented by the formula (I) and a metal atom or a metal compound include a complex that includes:

a compound represented by the formula (I) in which each of $R^1$ and $R^6$ independently represents a hydrogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an amino group, an anilino group, a heterocyclic amino group, a carbonamido group, an ureido group, an imido group, an alkoxycarbonylamino group, an aryloxycarbonylamino group, a sulfonamido group, an azo group, an alkylthio group, an arylthio group, a heterocyclic thio group, an alkylsulfonyl group, an arylsulfonyl group or a phosphinoylamino group; each of $R^2$ and $R^5$ independently represents a hydrogen atom, a halogen atom, an alkyl group, an alkenyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imido group, an alkoxycarbonylamino group, a sulfonamido group, an azo group, an alkylthio group, an arylthio group, a heterocyclic thio group, an alkylsulfonyl group, an arylsulfonyl group or a sulfamoyl group; each of $R^3$ and $R^4$ independently represents a hydrogen atom, a halogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an anilino group, a carbonamido group, an ureido group, an imido group, an alkoxycarbonylamino group, a sulfonamido group, an azo group, an alkylthio group, an arylthio group, a heterocyclic thio group, an alkylsulfonyl group, an arylsulfonyl group, a sulfamoyl group or a phosphinoylamino group; and $R^7$ represents a hydrogen atom, a halogen atom, an alkyl group, an aryl group or a heterocyclic group, and a metal atom or a metal compound selected from Zn, Mg, Si, Pt, Pd, Mo, Mn, Cu, Ni, Co, TiO or VO.

More preferred examples of the complex containing a compound represented by the formula (I) and a metal atom or a metal compound include a complex that includes:

a compound represented by the formula (I) in which each of $R^1$ and $R^6$ independently represents a hydrogen atom, an alkyl group, an alkenyl group, an aryl group, a heterocyclic group, a cyano group, an acyl group, an alkoxycarbonyl group, a carbamoyl group, an amino group, a heterocyclic amino group, a carbonamido group, an ureido group, an imido group, an alkoxycarbonylamino group, an aryloxycarbonylamino group, a sulfonamido group, an azo group, an alkylsulfonyl group, an arylsulfonyl group or a phosphinoylamino group; each of $R^2$ and $R^5$ independently represents an alkyl group, an alkenyl group, an aryl group, a heterocyclic group, a cyano group, a nitro group, an acyl group, an alkoxycarbonyl group, an aryloxycarbonyl group, a carbamoyl group, an imido group, an alkylsulfonyl group, an arylsulfonyl group or a sulfamoyl group; each of $R^3$ and $R^4$ independently represents a hydrogen atom, an alkyl group, an alkenyl group, an aryl group, a heterocyclic group, a cyano group, an acyl group, an alkoxycarbonyl group, a carbamoyl group, a carbonamido group, an ureido group, an imido group, an alkoxycarbonylamino group, a sulfonamido group, an alkylthio group, an arylthio group, a heterocyclic thio group, an alkylsulfonyl group, an arylsulfonyl group or a sulfamoyl group; and $R^7$ represents a hydrogen atom, a halogen atom, an alkyl group, an aryl group or a heterocyclic group, and a metal atom or a metal compound selected from Zn, Mg, Si, Pt, Pd, Cu, Ni, Co or VO.

Particularly preferred examples of the complex containing a compound represented by the formula (I) and a metal atom or a metal compound include a complex that includes:

a compound represented by formula (I) in which each of $R^1$ and $R^6$ independently represents a hydrogen atom, an alkyl group, an aryl group, a heterocyclic group, an amino group, a heterocyclic amino group, a carbonamido group, a ureido group, an imido group, an alkoxycarbonylamino group, a sulfonamido group, an azo group, an alkylsulfonyl group, an arylsulfonyl group or a phosphinoylamino group; each of $R^2$ and $R^5$ independently represents an alkyl group, an aryl group, a heterocyclic group, a cyano group, an acyl group, an alkoxycarbonyl group, a carbamoyl group, an alkylsulfonyl group or an arylsulfonyl group; each of $R^3$ and $R^4$ independently represents a hydrogen atom, an alkyl group, an aryl group or a heterocyclic group; and $R^7$ represents a hydrogen atom, an alkyl group, an aryl group or a heterocyclic group, and a metal atom or a metal compound selected from Zn, Cu, Co or VO.

In the formula (I), $R^3$ and $R^4$ are particularly preferably a phenyl group in view of achieving excellent robustness. The reason for this is considered to be that: (1) when $R^3$ and $R^4$ are a phenyl group, the spectrum of the compound shifts to the longer wavelength side to increase the range overlapping the spectrum of the phthalocyanine pigment that is used in combination (approximately 550 nm) that enables easy transfer of energy; and (2) the robustness of this compound by itself is increased due to the presence of sterically bulky substituents.

Further, in the formula (I), $R^2$ and/or $R^5$ preferably represent a 2,6-di-tert-butyl-4-methylcyclohexyloxycarbonyl group in view of excellent solubility in a solvent.

(Compound Represented by the Formula (II-1))

One of the preferable examples of the specific complex used in the first aspect of the invention is a compound represented by the following formula (II-1).

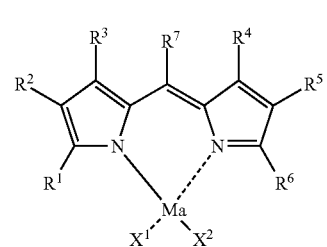

(II-1)

In the formula (II-1), each of $R^1$ to $R^6$ independently represents a hydrogen atom or a substituent, $R^7$ represents a hydrogen atom, a halogen atom, an alkyl group, an aryl group or a heterocyclic group, Ma represents a metal atom or a metal compound, $X^2$ represents a group to neutralize a charge of Ma, and $X^1$ represents a group capable of being bonded to Ma. $X^1$ and $X^2$ may be bonded to each other to form a 5-, 6- or 7-membered ring.

It is preferred that $R^1$ and $R^6$ are not bonded to each other to form a ring.

$R^1$ to $R^6$ in the formula (II-1) have the same definitions as that of $R^1$ to $R^6$ in the formula (I), respectively, and preferable embodiments thereof are also the same.

Ma in the formula (II-1) represents a metal atom or a metal compound having the same definitions as that of the metal atom or the metal compound that constitutes the above-mentioned specific complex, and preferable ranges thereof are also the same.

$R^7$ in the formula (II-1) has the same definition as that of $R^7$ in the formula (I), and preferable embodiments thereof are also the same.

$X^1$ in the formula (II-1) may be any group as long as it is capable of being bonded to Ma, and examples thereof include water, alcohols (for example, methanol, ethanol and propanol) and the like, as well as groups derived from the compounds described in "Metal Chelates" Volume 1 (1995), Volume 2 (1996) and Volume 3 (1997), authored by Takeichi Sakaguchi and Kyohei Ueno and published by Nankodo, and the like. Among them, in view of producibility, water, carboxylic acid compounds and alcohols are preferable, and water and carboxylic acid compounds are more preferable.

$X^2$ in the formula (II-1) represents a group to neutralize a charge of Ma, and examples thereof include a halogen atom, a hydroxyl group, a carboxylic group, a phosphoric group and a sulfonic group. Among them, in view of producibility, a halogen atom, a hydroxyl group, a carboxylic group and a sulfonic group are preferable, and a hydroxyl group and a carboxylic group are more preferable.

$X^1$ and $X^2$ in the formula (II-1) may be bonded to each other to form a 5-, 6- or 7-membered ring together with Ma. The 5-, 6- or 7-membered ring may be either a saturated ring or an unsaturated ring. Further, the 5-, 6- or 7-membered ring may be formed only of carbon atoms and hydrogen atoms, or may be a heterocyclic ring having at least one atom selected from a nitrogen atom, an oxygen atom or a sulfur atom.

(Compound Represented by the Formula (II-2))

One of the preferable examples of the specific complex used in the first aspect of the invention is a compound represented by the following formula (II-2).

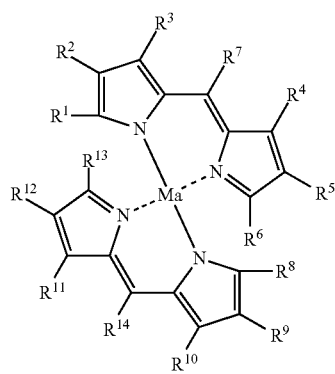

(II-2)

In the formula (II-2), each of $R^1$ to $R^6$ and $R^8$ to $R^{13}$ independently represents a hydrogen atom or a substituent, each of $R^7$ and $R^{14}$ independently represents a hydrogen atom, a halogen atom, an alkyl group, an aryl group or a heterocyclic group, and Ma represents a metal atom or a metal compound.

It is preferred that $R^1$ and $R^8$ or $R^1$ and $R^{13}$ are not bonded to each other to form a ring, and it is preferred that $R^6$ and $R^8$ or $R^6$ and $R^{13}$ are not bonded to each other to form a ring.

$R^1$ to $R^6$ in the formula (II-2) have the same definitions as that of $R^1$ to $R^6$ in the formula (I), respectively, and preferable embodiments thereof are also the same.

The substituents represented by $R^8$ to $R^{13}$ in the formula (II-2) have the same definitions as that of the substituents represented by $R^1$ to $R^6$ in the compound represented by the formula (I), respectively, and preferable embodiments thereof are also the same. When the substituents represented by $R^8$ to $R^{13}$ of the compound represented by the formula (II-2) are a group that can be further substituted, the group may be substituted by any group mentioned as Substituent R, and when the group is substituted by two or more substituents, these substituents may be the same or different from each other.

$R^7$ in the formula (II-2) has the same definitions as that of $R^7$ in the formula (I), and preferable embodiments thereof are also the same.

$R^{14}$ in the formula (II-2) represents a hydrogen atom, a halogen atom, an alkyl group, an aryl group or a heterocyclic group, and preferable ranges of $R^{14}$ are the same as the preferable ranges of $R^7$. When $R^{14}$ represents a group that can be further substituted, the group may be substituted by any group mentioned as Substituent R, and when the group is substituted by two or more substituents, these substituents may be the same or different from each other.

Ma in the formula (II-2) represents a metal atom or a metal compound having the same definitions as the metal atom or the metal compound that constitutes the specific complex as mentioned above, and preferable ranges thereof are also the same.

Combinations of $R^8$ and $R^9$, $R^9$ and $R^{10}$, $R^{11}$ and $R^{12}$, and $R^{12}$ and $R^{13}$ in the formula (II-2) may independently be bonded to each other to form a 5-, 6- or 7-membered saturated or unsaturated ring. The saturated or unsaturated ring has the same definitions as that of the saturated or unsaturated ring formed by $R^1$ and $R^2$, $R^2$ and $R^3$, $R^4$ and $R^5$, or $R^5$ and $R^6$, and preferable examples thereof are also the same.

(Compound Represented by the Formula (III))

One of the preferable examples of the specific complex in the first aspect of the invention is a compound represented by the following formula (III).

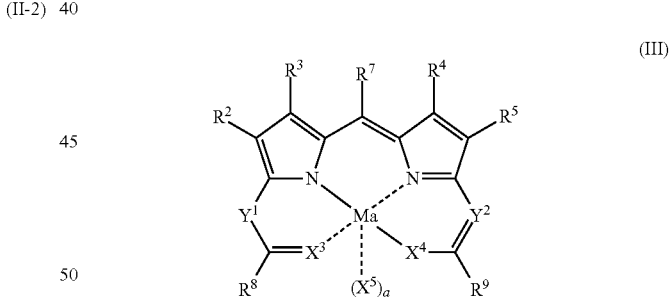

(III)

In the formula (III), each of $R^2$ to $R^5$ independently represents a hydrogen atom or a substituent, $R^7$ represents a hydrogen atom, a halogen atom, an alkyl group, an aryl group or a heterocyclic group, Ma represents a metal atom or a metal compound, $X^3$ represents NR (wherein R represents a hydrogen atom, an alkyl group, an alkenyl group, an aryl group, a heterocyclic group, an acyl group, an alkylsulfonyl group or an arylsulfonyl group), a nitrogen atom, an oxygen atom or a sulfur atom, $X^4$ represents NRa (wherein Ra represents a hydrogen atom, an alkyl group, an alkenyl group, an aryl group, a heterocyclic group, an acyl group, an alkylsulfonyl group or an arylsulfonyl group), an oxygen atom or a sulfur atom, $Y^1$ represents NRc (wherein Rc represents a hydrogen atom, an alkyl group, an alkenyl group, an aryl group, a heterocyclic group, an acyl group, an alkylsulfonyl group or an arylsulfonyl group), a nitrogen atom or a carbon atom, $Y^2$ represents a nitrogen atom or a carbon atom, each of $R^8$ and $R^9$ independently represents an alkyl group, an alkenyl group, an aryl group, a heterocyclic group, an alkoxy group, an aryloxy group, an alkylamino group, an arylamino group or a heterocyclic amino group, $R^8$ and $Y^1$ may be bonded to each other to form a 5-, 6- or 7-membered ring, $R^9$ and $Y^2$ may be bonded to each other to form a 5-, 6- or 7-membered ring, $X^5$ represents a group capable of being bonded to Ma, and a represents 0, 1 or 2.

$R^2$ to $R^5$ and $R^7$ in the formula (III) have the same definitions as that of $R^2$ to $R^5$ and $R^7$ in the formula (I), respectively, and preferable embodiments thereof are also the same.

Ma in the formula (III) represents a metal or a metal compound having the same definitions as the metal atom or the metal compound that constitutes the specific complex as mentioned above, and preferable ranges thereof are also the same.

In the formula (III), each of $R^8$ and $R^9$ independently represents an alkyl group (a linear, branched or cyclic alkyl group having preferably 1 to 36 carbon atoms, more preferably 1 to 12 carbon atoms, such as a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group or a 1-adamantyl group), an alkenyl group (an alkenyl group having preferably 2 to 24 carbon atoms, more preferably 2 to 12 carbon atoms, such as a vinyl group, an allyl group or a 3-buten-1-yl group), an aryl group (an aryl group having preferably 6 to 36 carbon atoms, more preferably 6 to 18 carbon atoms, such as a phenyl group or a naphthyl group), a heterocyclic group (a heterocyclic group having preferably 1 to 24 carbon atoms, more preferably 1 to 12 carbon atoms, such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group or a benzotriazol-1-yl group), an alkoxy group (an alkoxy group having preferably 1 to 36 carbon atoms, more preferably 1 to 18 carbon atoms, such as a methoxy group, an ethoxy group, a propyloxy group, a butoxy group, a hexyloxy group, a 2-ethylhexyloxy group, a dodecyloxy group or a cyclohexyloxy group), an aryloxy group (an aryloxy group having preferably 6 to 24 carbon atoms, more preferably 6 to 18 carbon atoms, such as a phenoxy group or a naphthyloxy group), an alkylamino group (an alkylamino group having preferably 1 to 36 carbon atoms, more preferably 1 to 18 carbon atoms, such as a methylamino group, an ethylamino group, a propylamino group, a butylamino group, a hexylamino group, a 2-ethylhexylamino group, an isopropylamino group, a t-butylamino group, a t-octylamino group, a cyclohexylamino group, an N,N-diethylamino group, an N,N-dipropylamino group, an N,N-dibutylamino group or an N-methyl-N-ethylamino group), an arylamino group (an aryl amino group having preferably 6 to 36 carbon atoms, more preferably 6 to 18 carbon atoms, such as a phenylamino group, a naphthylamino group, an N,N-diphenylamino group or an N-ethyl-N-phenylamino group), or a heterocyclic amino group (a heterocyclic amino group having preferably 1 to 24 carbon atoms, more preferably 1 to 12 carbon atoms, such as a 2-aminopyrrole group, a 3-aminopyrazole group, a 2-aminopyridine group or a 3-aminopyridine group).

In the formula (III), when the alkyl group, alkenyl group, aryl group, heterocyclic group, alkoxy group, aryloxy group, alkylamino group, arylamino group or heterocyclic amino group represented by $R^8$ or $R^9$ are a group that can be further substituted, the group may be substituted by any group mentioned as Substituent R, and when the group is substituted by two or more substituents, these substituents may be the same or different from each other.

In the formula (III), $X^3$ represents NR, a nitrogen atom, an oxygen atom or a sulfur atom, $X^4$ represents NRa, an oxygen atom or a sulfur atom, wherein each of R and Ra independently represents a hydrogen atom, an alkyl group (a linear, branched or cyclic alkyl group having preferably 1 to 36 carbon atoms, more preferably 1 to 12 carbon atoms, such as a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group or a 1-adamantyl group), an alkenyl group (an alkenyl group having preferably 2 to 24 carbon atoms, more preferably 2 to 12 carbon atoms, such as a vinyl group, an allyl group or a 3-buten-1-yl group), an aryl group (an aryl group having preferably 6 to 36 carbon atoms, more preferably 6 to 18 carbon atoms, such as a phenyl group or a naphthyl group), a heterocyclic group (a heterocyclic group having preferably 1 to 24 carbon atoms, more preferably 1 to 12 carbon atoms, such as a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group or a benzotriazol-1-yl group), an acyl group (an acyl group having preferably 1 to 24 carbon atoms, more preferably 2 to 18 carbon atoms, such as an acetyl group, a pivaloyl group, a 2-ethylhexyl group, a benzoyl group or a cyclohexanoyl group), an alkylsulfonyl group (an alkylsulfonyl group having preferably 1 to 24 carbon atoms, more preferably 1 to 18 carbon atoms, such as a methylsulfonyl group, an ethylsulfonyl group, an isopropylsulfonyl group or a cyclohexylsulfonyl group), or an arylsulfonyl group (an arylsulfonyl group having preferably 6 to 24 carbon atoms, more preferably 6 to 18 carbon atoms, such as a phenylsulfonyl group or a naphthylsulfonyl group).

The alkyl group, alkenyl group, aryl group, heterocyclic group, acyl group, alkylsulfonyl group or arylsulfonyl group represented by R or Ra may be further substituted by any group mentioned as Substituent R, and when the group is substituted by two or more substituents, these substituents may be the same or different from each other.

In the formula (III), $Y^1$ represents NRc, a nitrogen atom or a carbon atom, $Y^2$ represents a nitrogen atom or a carbon atom, and Rc has the same definitions as that of R for $X^3$.

In the formula (III), $R^8$ and $Y^1$ may be bonded to each other to form a 5-membered ring (for example, cyclopentane, pyrrolidine, tetrahydrofuran, dioxolane, tetrahydrothiophene, pyrrole, furan, thiophene, indole, benzofuran or benzothiophene), a 6-membered ring (for example, cyclohexane, piperidine, piperazine, morpholine, tetrahydropyran, dioxane, pentamethylenesulfide, dithiane, benzene, piperidine, piperazine, pyridazine, quinoline or quinazoline) or a 7-membered ring (for example, cycloheptane or hexamethyleneimine), together with the carbon atom.

In the formula (III), $R^9$ and $Y^2$ may be bonded to each other to form a 5-, 6- or 7-membered ring together with the carbon atom. Examples of the 5-membered, 6-membered and 7-membered rings include the rings formed by $R^8$, $Y^1$ and the carbon atom, as mentioned above, in which one bond in the ring is changed to a double bond.

In the formula (III), when the 5-, 6- or 7-membered ring formed by $R^8$ and $Y^1$ or $R^9$ and $Y^2$ is a ring that can be further substituted, the ring may be substituted by any group mentioned as Substituent R, and when the ring is substituted by two or more substituents, these substituents may be the same or different from each other.

In the formula (III), $X^5$ represents a group capable of being bonded to Ma, and examples thereof include the groups for $X^1$ in the formula (II-1); and a represents 0, 1 or 2.

Preferable embodiments of the compound represented by the formula (III) include a compound in which:

$R^2$ to $R^5$, $R^7$ and Ma each represent the preferable embodiments for the complex containing a compound represented by the formula (I) and a metal atom or a metal compound, $X^3$ represents NR (wherein R represents a hydrogen atom or an alkyl group), a nitrogen atom or an oxygen atom, $X^4$ represents NRa (wherein Ra represents a hydrogen atom, an alkyl group or a heterocyclic group) or an oxygen atom, $Y^1$ represents NRc (wherein Rc represents a hydrogen atom or an alkyl group), a nitrogen atom or a carbon atom, $Y^2$ represents a nitrogen atom or a carbon atom, $X^5$ represents a group that is bonded via an oxygen atom, each of $R^8$ and $R^9$ independently represents an alkyl group, an aryl group, a heterocyclic group, an alkoxy group or an alkylamino group, or $R^8$ and $Y^1$ are bonded to each other to form a 5- or 6-membered ring and $R^9$ and $Y^2$ are bonded to each other to form a 5- or 6-membered ring, and a represents 0, 1 or 2.

More preferable embodiments of the compound represented by the formula (III) include a compound in which:

$R^2$ to $R^5$, $R^7$ and Ma each represent the preferable embodiments for the complex containing a compound represented by the formula (I) and a metal atom or a metal compound, $X^3$ and $X^4$ represent an oxygen atom, $Y^1$ represents NH, $Y^2$ represents a nitrogen atom, $X^5$ represents a group that is bonded via an oxygen atom, each of $R^8$ and $R^9$ independently represents an alkyl group, an aryl group, a heterocyclic group, an alkoxy group or an alkylamino group, or $R^8$ and $Y^1$ are bonded to each other to form a 5- or 6-membered ring and $R^9$ and $Y^2$ are bonded to each other to form a 5- or 6-membered ring, and a represents 0 or 1.

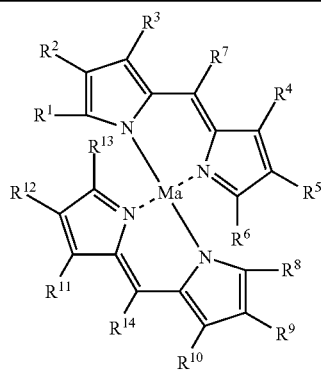

| Compound No. | $R^1 = R^6 = R^8 = R^{13}$ | $R^2 = R^5 = R^9 = R^{12}$ | $R^3 = R^4 = R^{10} = R^{11}$ | $R^7 = R^{14}$ | Ma |
|---|---|---|---|---|---|
| Ia-3 | —NH$_2$ | C$_4$H$_9$(t) | —CH$_3$ | —H | Zn |
| | | —COO—⟨cyclohexyl with C$_4$H$_9$(t), C$_4$H$_9$(t), CH$_3$⟩ | | | |
| Ia-4 | same as above | same as above | same as above | same as above | V = O |
| Ia-5 | —NHCOCH$_3$ | same as above | same as above | same as above | Zn |
| Ia-6 | same as above | same as above | same as above | same as above | Cu |
| Ia-7 | same as above | same as above | same as above | —CH$_3$ | Zn |
| Ia-8 | —NHCOCH$_2$OCH$_2$COOH | same as above | same as above | same as above | Zn |
| Ia-9 | same as above | same as above | same as above | same as above | Zn |
| Ia-10 | same as above | same as above | —C$_3$H$_7$(iso) | —H | Zn |
| Ia-11 | same as above | same as above | same as above | —CH$_3$ | Zn |
| Ia-12 | same as above | same as above | —C$_4$H$_9$(t) | —H | Cu |
| Ia-13 | —NH$_2$ | same as above | same as above | —CH$_3$ | Zn |
| Ia-14 | same as above | same as above | same as above | —H | Zn |
| Ia-15 | same as above | same as above | —⟨cyclohexyl⟩ | same as above | Zn |
| Ia-16 | —NHCOCH$_3$ | same as above | —CH$_2$S—CH(CH$_3$)COOH | —CH$_3$ | Cu |
| Ia-17 | —NH$_2$ | same as above | —⟨phenyl⟩ | —H | Zn |
| Ia-18 | same as above | same as above | same as above | same as above | Cu |
| Ia-19 | same as above | same as above | same as above | same as above | V = O |

-continued

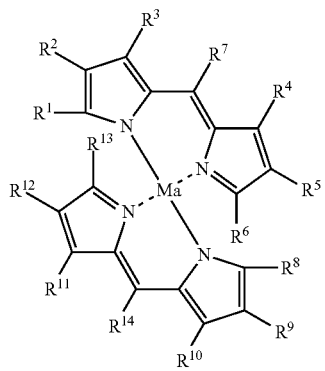

| Compound No. | $R^1 = R^6 = R^8 = R^{13}$ | $R^2 = R^5 = R^9 = R^{12}$ | $R^3 = R^4 = R^{10} = R^{11}$ | $R^7 = R^{14}$ | Ma |
|---|---|---|---|---|---|
| Ia-20 | same as above | same as above | same as above | —CH$_3$ | Zn |
| Ia-21 | —NHCOCH$_3$ | same as above | same as above | same as above | Zn |
| Ia-22 | —NHCOCH$_2$OCH$_2$COOH | same as above | same as above | —H | Zn |
| Ia-23 | same as above | same as above | same as above | —CH$_3$ | Zn |

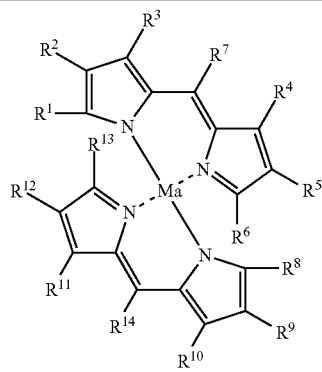

| Compound No. | $R^1 = R^6 = R^8 = R^{13}$ | $R^2 = R^5 = R^9 = R^{12}$ | $R^3 = R^4 = R^{10} = R^{11}$ | $R^7 = R^{14}$ | Ma |
|---|---|---|---|---|---|
| Ia-24 | —NHCOCH$_2$OCH$_2$COOH | ![2,6-di-tert-butyl-4-methylcyclohexyl ester group with C$_4$H$_9$(t), —COO—, CH$_3$, C$_4$H$_9$(t)] | phenyl | —CH$_3$ | Cu |
| Ia-25 | same as above | same as above | 4-chlorophenyl | same as above | Zn |
| Ia-26 | same as above | same as above | 2-methylphenyl | same as above | Zn |
| Ia-27 | 2-(—NHCO—)benzoic acid (—NHCO— attached to benzene ring bearing COOH) | same as above | —CH$_3$ | —H | Cu |

-continued

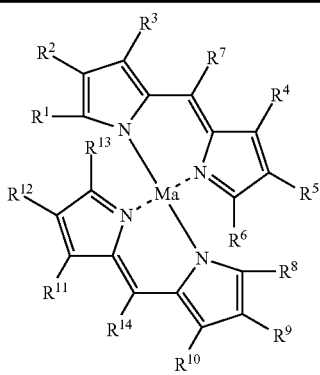

| Compound No. | $R^1 = R^6 = R^8 = R^{13}$ | $R^2 = R^5 = R^9 = R^{12}$ | $R^3 = R^4 = R^{10} = R^{11}$ | $R^7 = R^{14}$ | Ma |
|---|---|---|---|---|---|
| Ia-28 | same as above | same as above | same as above | —CH$_3$ | Zn |
| Ia-29 | —NHCO—C$_6$H$_4$—SO$_3$H | same as above | same as above | same as above | Cu |
| Ia-30 | same as above | same as above | —CH$_2$—CH(C$_2$H$_5$)C$_4$H$_9$ | same as above | Cu |
| Ia-31 | N-maleimidyl | same as above | phenyl | same as above | Zn |
| Ia-32 | methyl-N-maleimidyl (CH$_3$ substituted) | same as above | same as above | same as above | Zn |
| Ia-33 | —NHSO$_2$CH$_3$ | same as above | —CH$_3$ | same as above | Zn |
| Ia-34 | —CH$_2$O—C$_6$H$_4$—N(SO$_2$) (thiomorpholine-1,1-dioxide) | same as above | same as above | same as above | Zn |

IIa-1
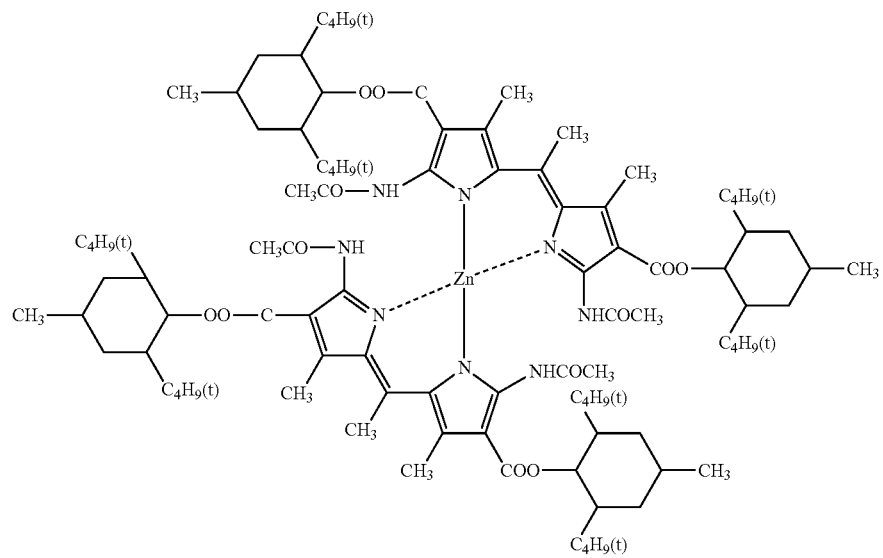
IIa-2 IIa-7
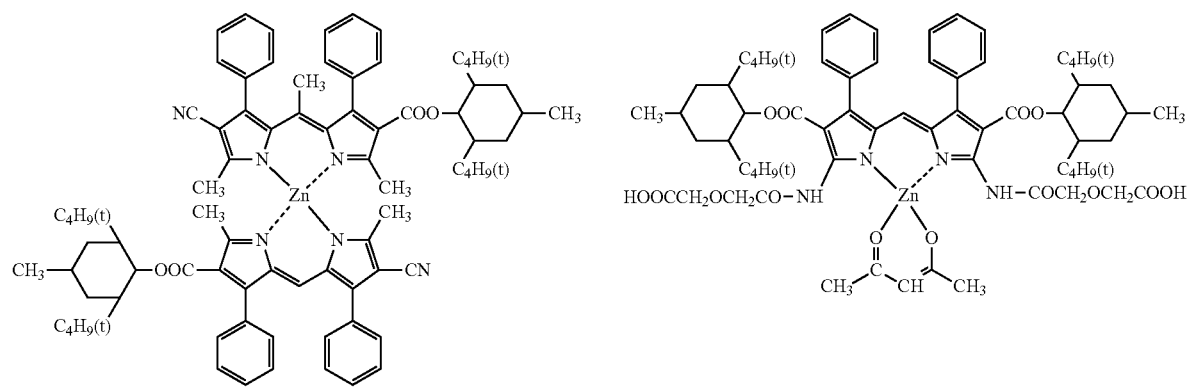
IIa-8 IIa-10
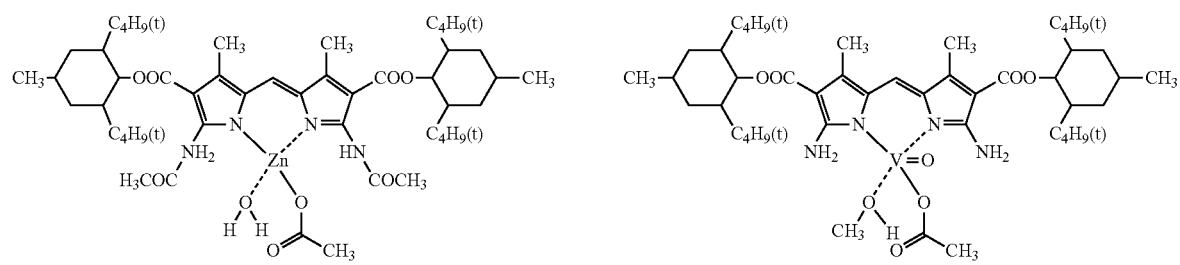
IIa-11 IIa-12
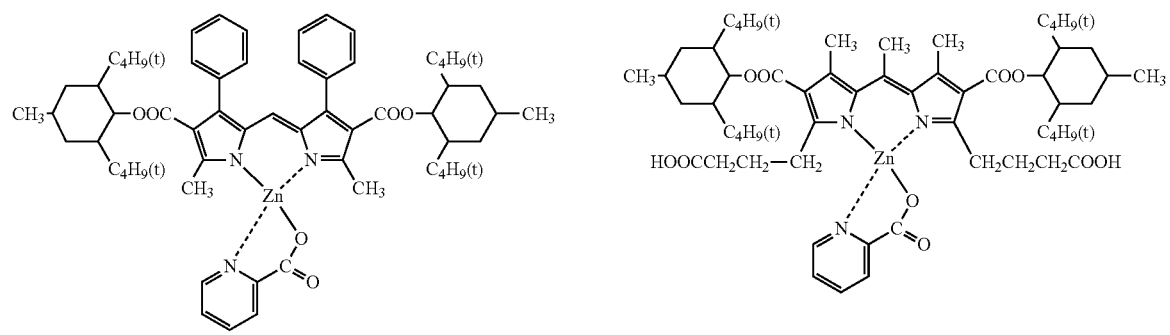

-continued
IIa-13
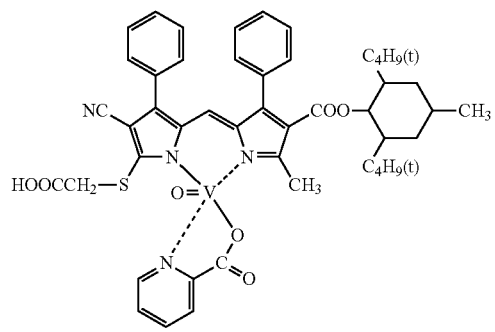
IIa-14
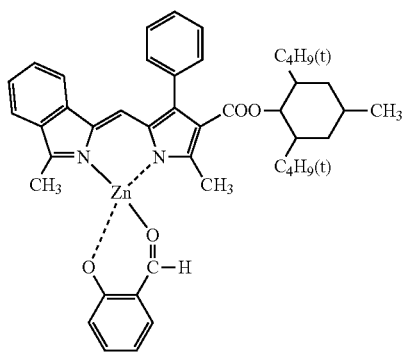
IIa-15
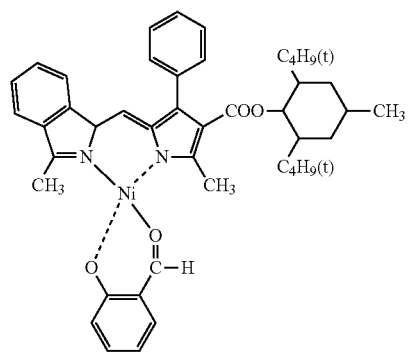
IIa-16
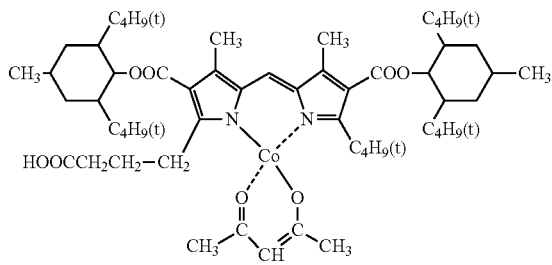
IIa-17
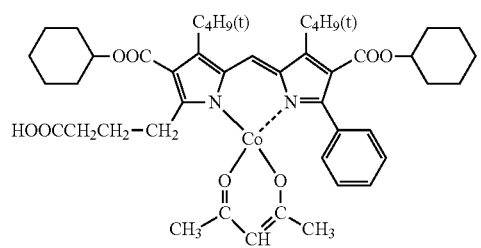
IIa-18
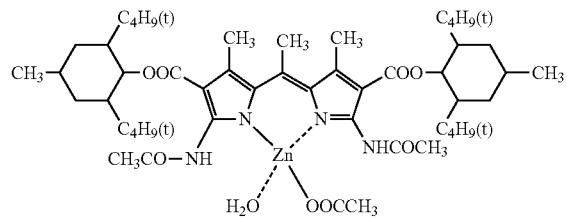
IIa-19
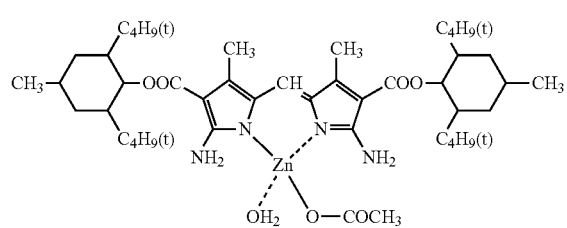
IIa-20
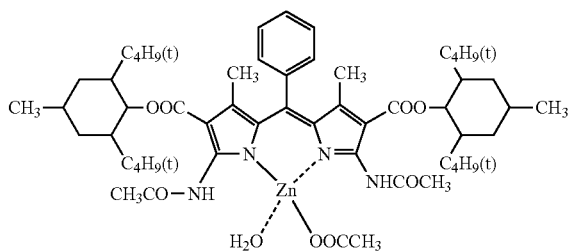
I-1
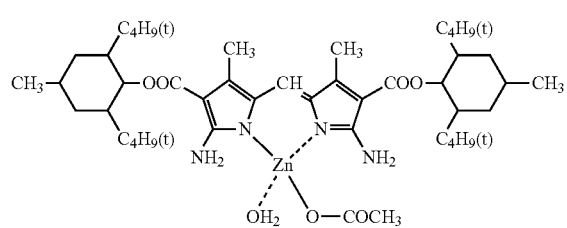
I-2
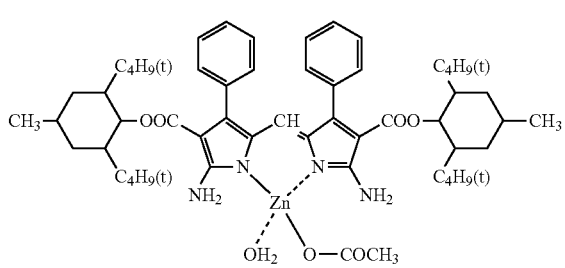

-continued
I-3
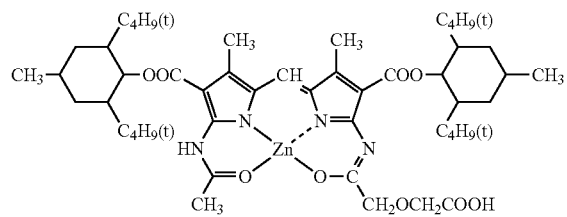
I-4
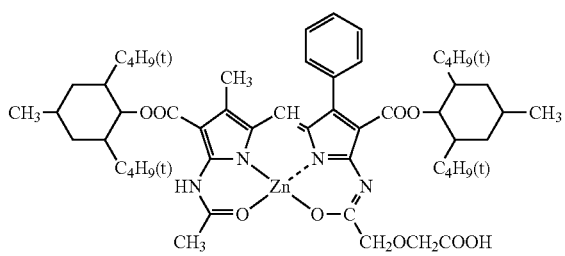
I-5
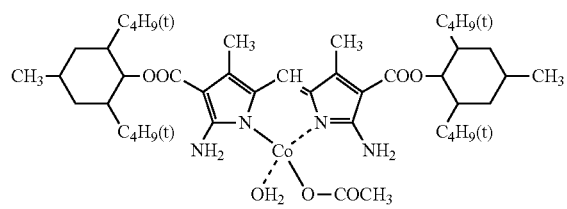
I-6
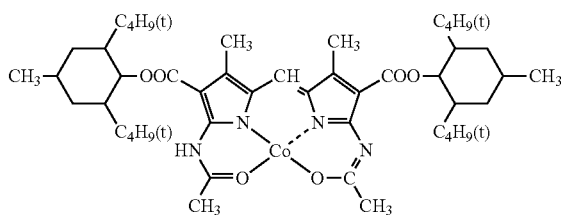
I-7
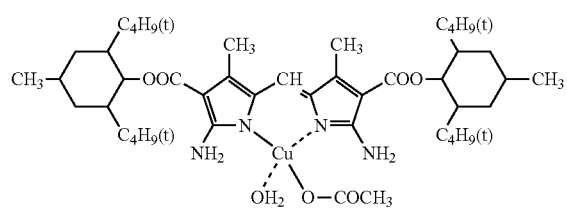
I-8
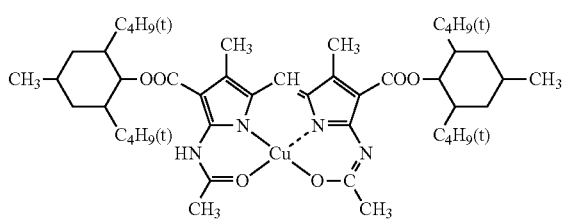
I-9
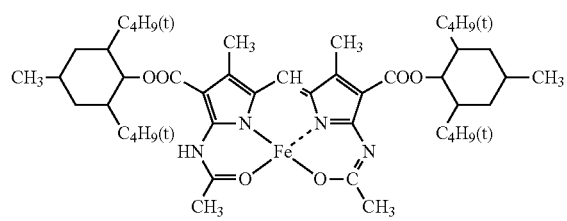
I-10
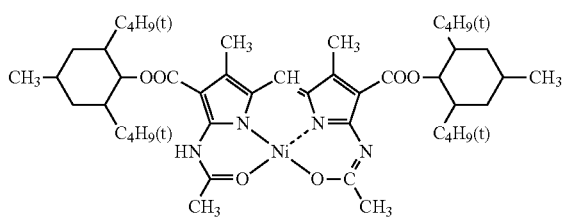
I-11
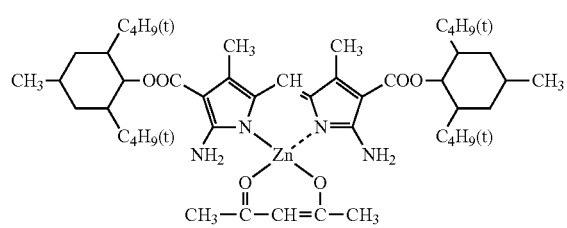
I-12
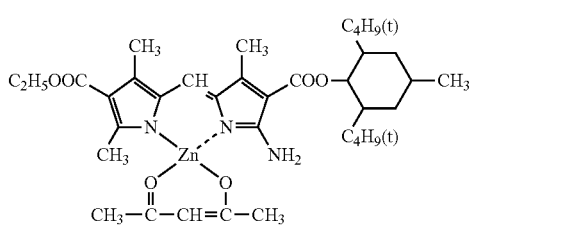
I-13
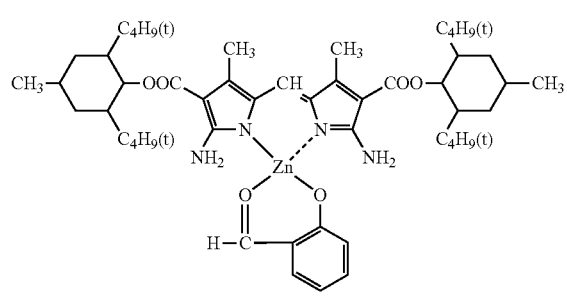
I-14
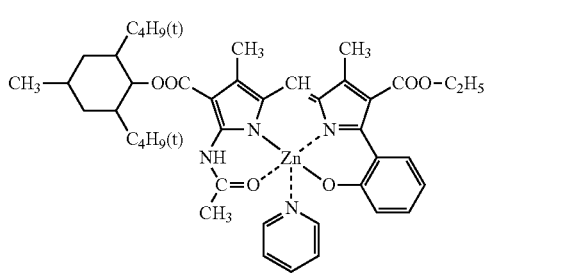

-continued
I-15
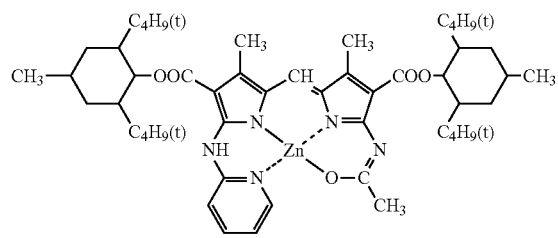
I-16
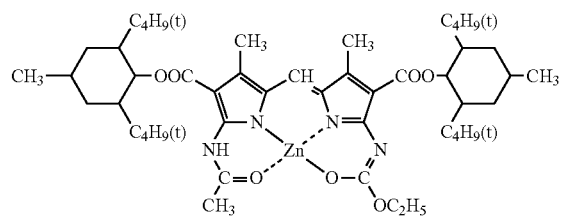
I-17
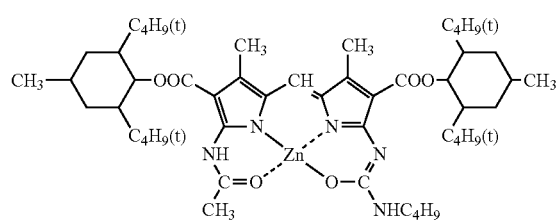
I-18
I-19
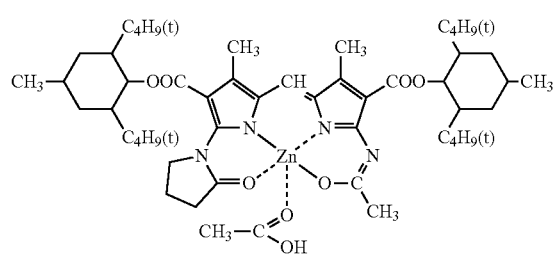
I-20
I-21
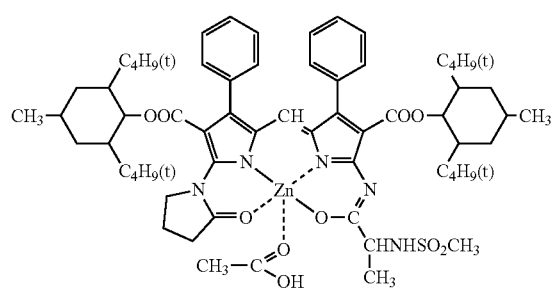
I-22
I-23
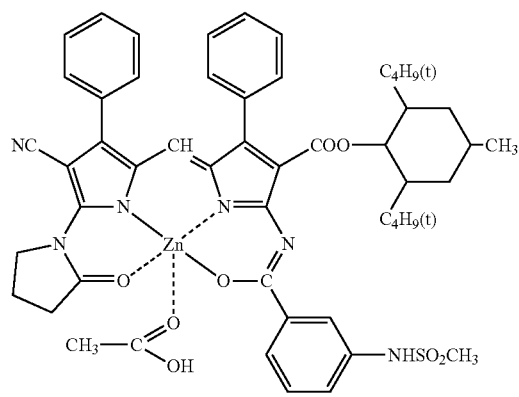
I-24
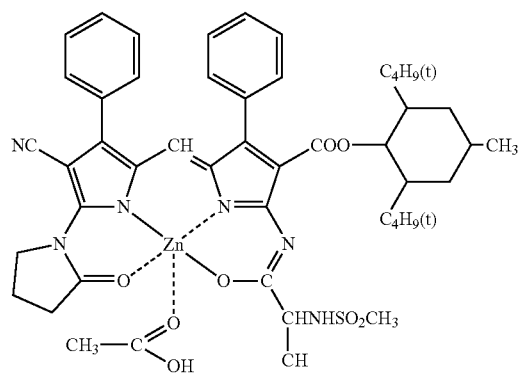

-continued
I-25
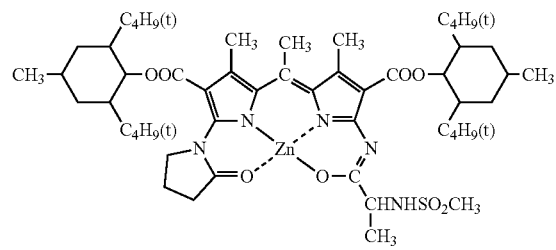
I-26
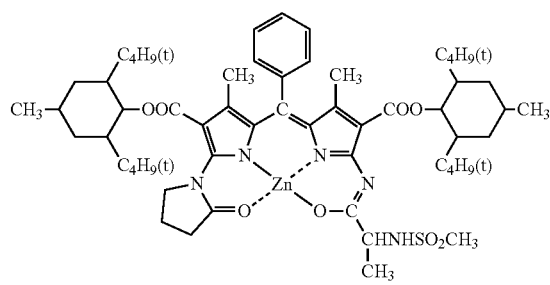
I-27
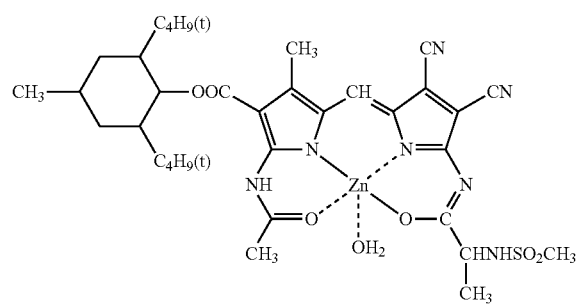
I-28
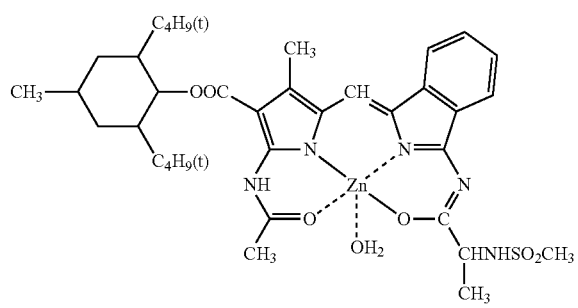
I-29
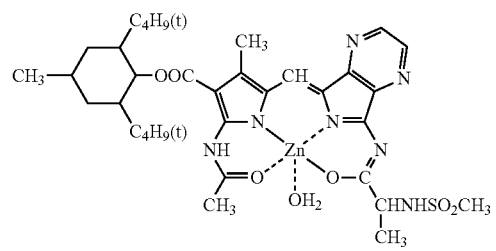
I-30
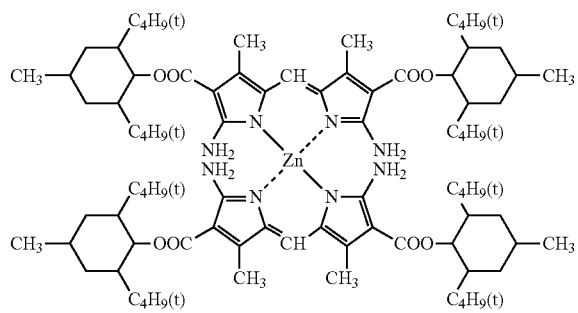
I-31
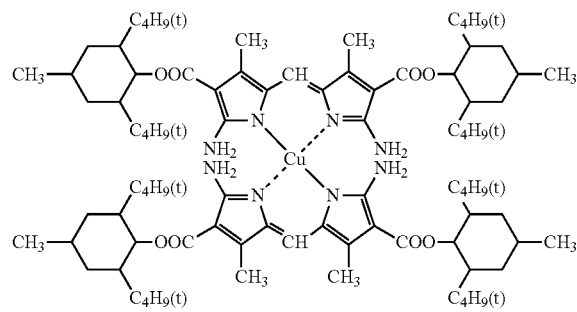
I-32
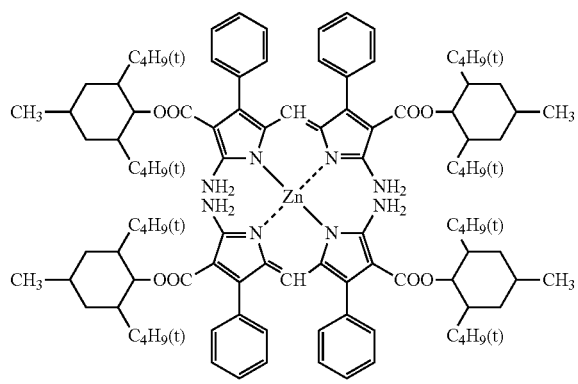

-continued
I-33
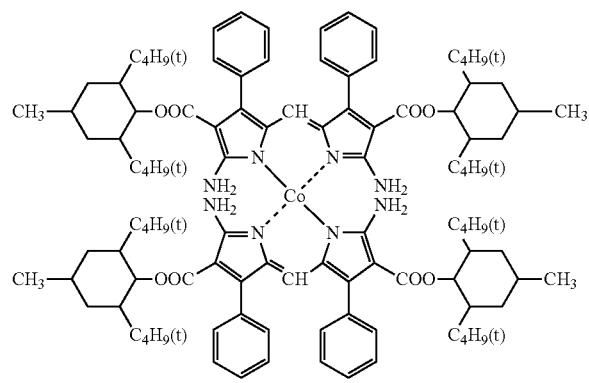
I-34
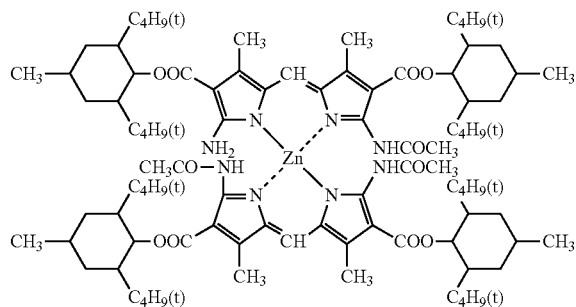
I-35
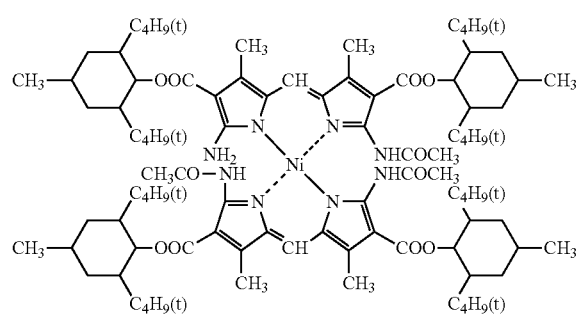
I-36
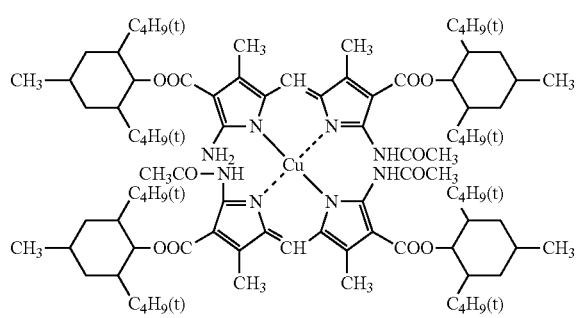
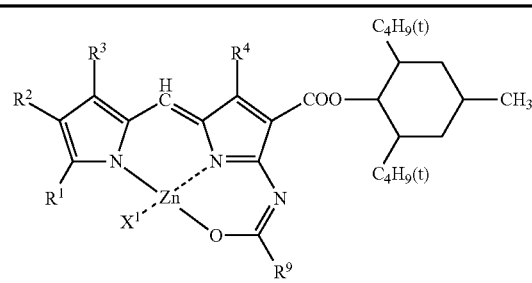
| Compound No. | R¹ | R² | R³ | R⁴ | R⁹ | X¹ |
|---|---|---|---|---|---|---|
| II-1 | —CH$_3$ | —COOC$_2$H$_5$ | —CH$_3$ | —CH$_3$ | —CH$_3$ | H$_2$O |
| II-2 | same as above | same as above | same as above | same as above | —CHNHSO$_2$CH$_3$ <br> \| <br> CH$_3$ | same as above |
| II-3 | same as above | same as above | same as above | same as above | (3-NHSO$_2$CH$_3$-phenyl) | same as above |
| II-4 | (3-NHSO$_2$CH$_3$-phenyl) | —COOCH$_3$ | same as above | (phenyl) | —CH$_3$ | same as above |

-continued

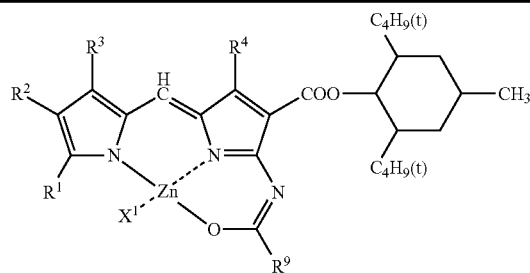

| Compound No. | $R^1$ | $R^2$ | $R^3$ | $R^4$ | $R^9$ | $X^1$ |
|---|---|---|---|---|---|---|
| II-5 | ![3-NHSO2CH3-phenyl] | —COOC$_2$H$_5$ | same as above | same as above | —CH$_2$OCH$_2$COOH | same as above |
| II-6 | same as above | same as above | same as above | same as above | —CH$_3$ | same as above |

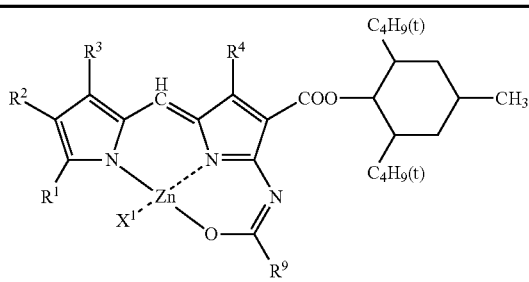

| Compound No. | $R^1$ | $R^2$ | $R^3$ | $R^4$ | $R^9$ | $X^1$ |
|---|---|---|---|---|---|---|
| II-7 | —CH$_3$ | —COOC$_2$H$_5$ | phenyl | phenyl | —CH$_3$ | H$_2$O |
| II-8 | 3-pyridyl | same as above | same as above | same as above | same as above | same as above |
| II-9 | 3-NHSO$_2$CH$_3$-phenyl | —CN | —CH$_3$ | —CH$_3$ | same as above | same as above |
| II-10 | 3-NHSO$_2$CH$_3$-phenyl | same as above | same as above | same as above | 3-NHSO$_2$CH$_3$-phenyl | same as above |
| II-11 | same as above | same as above | phenyl | phenyl | —CH$_3$ | same as above |

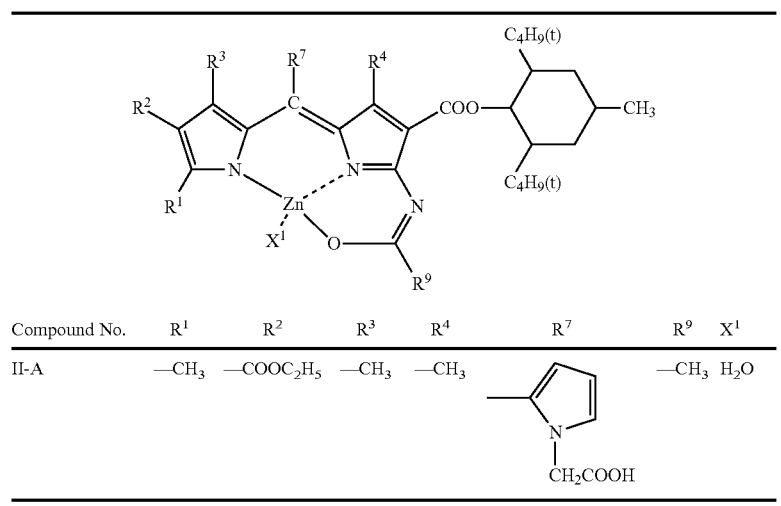

| Compound No. | R¹ | R² | R³ | R⁴ | R⁷ | R⁹ | X¹ |
|---|---|---|---|---|---|---|---|
| II-A | —CH₃ | —COOC₂H₅ | —CH₃ | —CH₃ | (2-methylpyrrol-1-yl with N—CH₂COOH) | —CH₃ | H₂O |

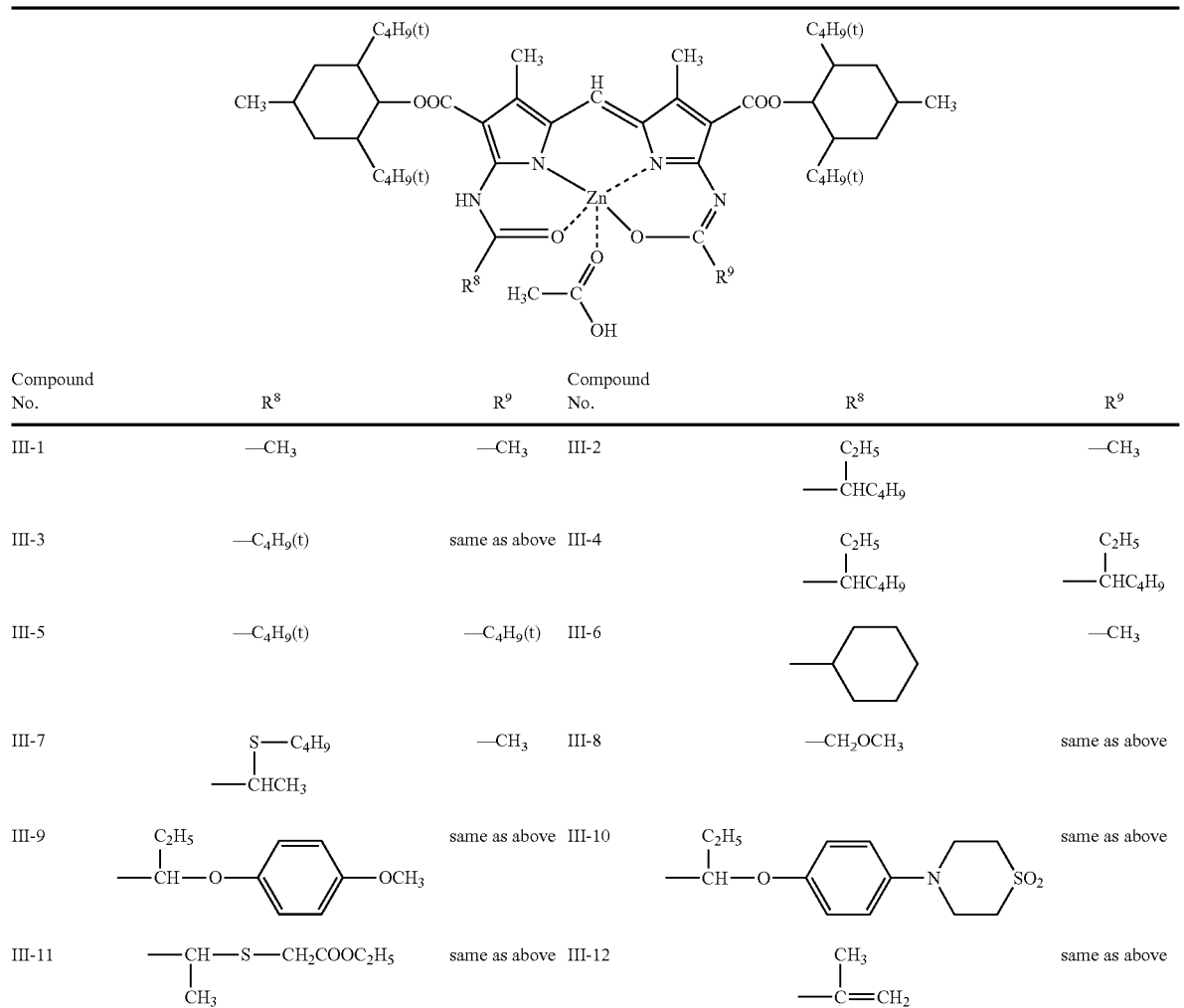

| Compound No. | R⁸ | R⁹ | Compound No. | R⁸ | R⁹ |
|---|---|---|---|---|---|
| III-1 | —CH₃ | —CH₃ | III-2 | —CH(C₂H₅)C₄H₉ | —CH₃ |
| III-3 | —C₄H₉(t) | same as above | III-4 | —CH(C₂H₅)C₄H₉ | —CH(C₂H₅)C₄H₉ |
| III-5 | —C₄H₉(t) | —C₄H₉(t) | III-6 | —cyclohexyl | —CH₃ |
| III-7 | —CH(CH₃)S—C₄H₉ | —CH₃ | III-8 | —CH₂OCH₃ | same as above |
| III-9 | —CH(C₂H₅)—O—C₆H₄—OCH₃ | same as above | III-10 | —CH(C₂H₅)—O—C₆H₄—N(SO₂)(morpholine) | same as above |
| III-11 | —CH(CH₃)—S—CH₂COOC₂H₅ | same as above | III-12 | —C(CH₃)=CH₂ | same as above |

-continued

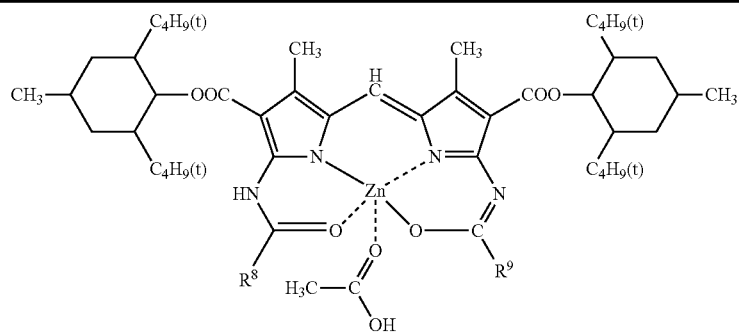

| Compound No. | R⁸ | R⁹ | Compound No. | R⁸ | R⁹ |
|---|---|---|---|---|---|
| III-13 | —C(CH₃)(CH₃)—COOCH₃ | same as above | III-14 | —CO—CH(CH₃)—COCH₃ | same as above |
| III-15 | —CH₂OCH₂COOC₂H₅ | same as above | III-16 | —CH₂NHSO₂CH₃ | same as above |
| III-17 | —CHNHSO₂CH₃ | same as above | III-18 | —CH(C₂H₅)NHSO₂CH₃ | same as above |
| III-19 | —CH(C₄H₉)NHSO₂CH₃ | same as above | III-20 | —CH(CH(CH₃)₂)NHSO₂CH₃ | same as above |
| III-21 | —CH(CH₃)NHSO₂—C₄H₉ | same as above | III-22 | —CH(CH₃)NHSO₂—C₆H₄—CH₃ | same as above |
| III-23 | —CH(CH₃)NHSO₂—C₆H₄—NHSO₂CH₃ | same as above | III-24 | —CH(CH₃)NHSO₂—N(C₂H₅)₂ | same as above |

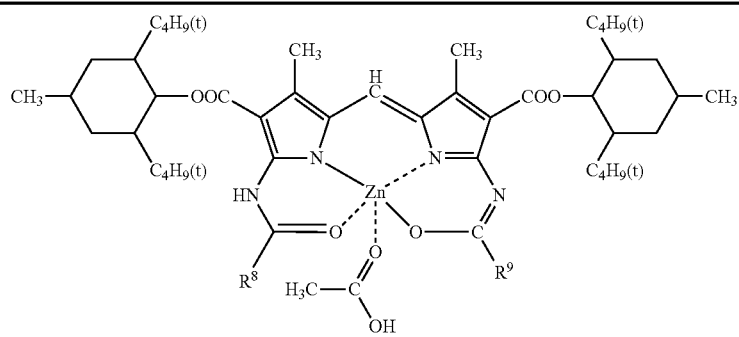

| Compound No. | R⁸ | R⁹ | Compound No. | R⁸ | R⁹ |
|---|---|---|---|---|---|
| III-25 | —CH(CH₃)-phthalimide | —CH₃ | III-26 | —CH₂CH₂COOC₂H₅ | —CH₃ |
| III-27 | —CH(CH₃)-S-(2-COOCH₃-phenyl) | same as above | III-28 | —CH(CH₃)-S-(2-pyridyl) | same as above |
| III-29 | —CH₂NHSO₂CH₃ | —CH₂NHSO₂CH₃ | III-30 | —CH₂—CH(CH₃)NHSO₂CH₃ | —CH₂—CH(CH₃)NHSO₂CH₃ |
| III-31 | —CH₂NHSO₂CH₃ | —CH(C₂H₅)C₄H₉ | III-32 | —CH₂—CH(CH₃)NHSO₂CH₃ | —C₄H₉(t) |
| III-33 | —C₆H₅ | —CH₃ | III-34 | —C₆H₅ | —CH₂—CH(CH₃)NHSO₂CH₃ |

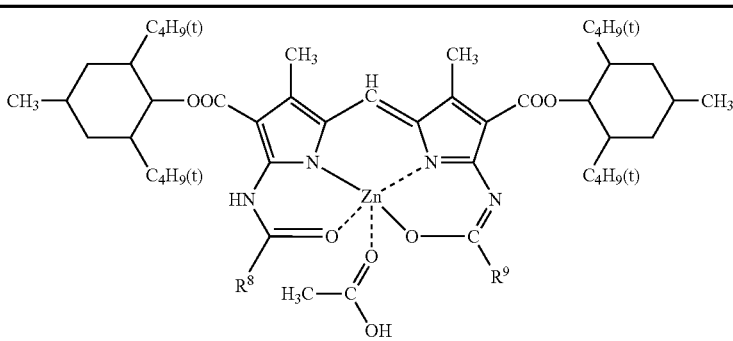

| Compound No. | R⁸ | R⁹ | Compound No. | R⁸ | R⁹ |
|---|---|---|---|---|---|
| III-35 | —C₆H₄-C₄H₉(t) (para) | —CH₃ | III-36 | —C₆H₄-NHSO₂CH₃ (meta) | —CH₃ |

-continued
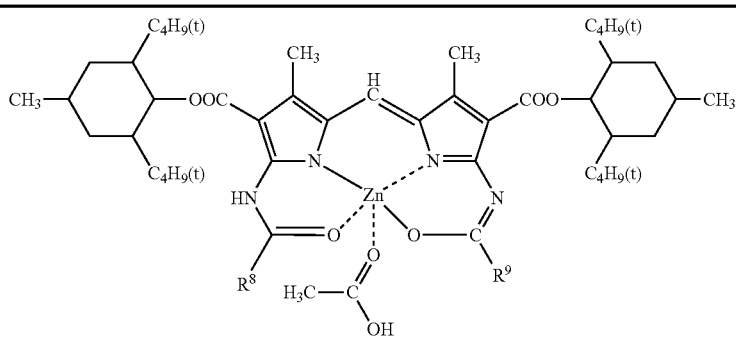
| Compound No. | R⁸ | R⁹ | Compound No. | R⁸ | R⁹ |
|---|---|---|---|---|---|
| III-37 | ![2-NHSO2CH3 phenyl] | same as above | III-38 | ![3-NHSO2Ph phenyl] | same as above |
| III-39 | ![2-OH phenyl] | same as above | III-40 | ![2-OCH3 phenyl] | same as above |
| III-41 | ![3-SO2NH2 phenyl] | same as above | III-42 | ![3-SO2N(CH3)2 phenyl] | same as above |
| III-43 | ![4-SCH3 phenyl] | same as above | III-44 | ![4-SO2CH3 phenyl] | same as above |
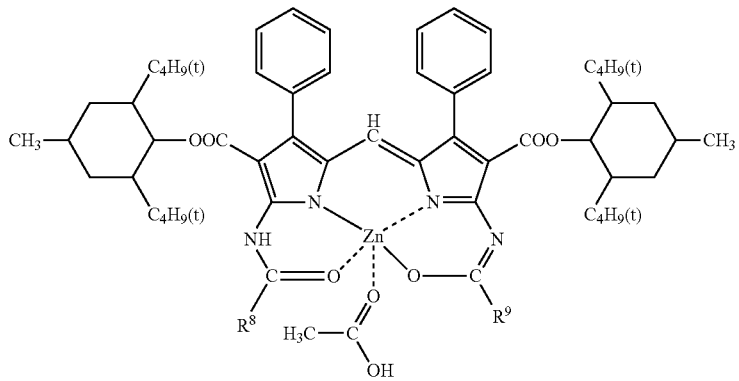
| Compound No. | R⁸ | R⁹ | Compound No. | R⁸ | R⁹ |
|---|---|---|---|---|---|
| III-45 | —CH₃ | —CH₃ | III-46 | —CH(C₂H₅)C₄H₉ | —CH(C₂H₅)C₄H₉ |

-continued
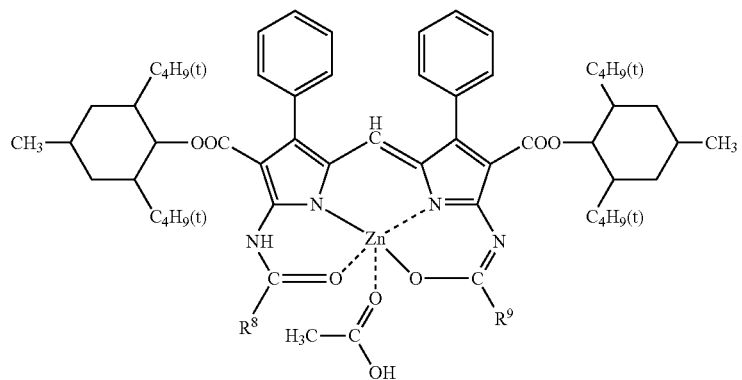
| Compound No. | R⁸ | R⁹ | Compound No. | R⁸ | R⁹ |
|---|---|---|---|---|---|
| III-47 | —C₄H₉(t) | —C₄H₉(t) | III-48 | cyclohexyl | cyclohexyl |
| III-49 | —CH₂NHSO₂CH₃ | —CH₃ | III-50 | —CH₂NHSO₂CH₃ | —CH₂NHSO₂CH₃ |
| III-51 | —CH(CH₃)NHSO₂CH₃ | same as above | III-52 | —CH(CH₃)NHSO₂CH₃ | —CH(CH₃)NHSO₂CH₃ |
| III-53 | —CH(C₄H₉)NHSO₂CH₃ | same as above | III-54 | 3-(NHSO₂CH₃)-phenyl | —CH₃ |
| III-55 | 3-(NHSO₂CH₃)-phenyl | 3-(NHSO₂CH₃)-phenyl | III-56 | 3-(NHSO₂CH₃)-phenyl | same as above (3-(SO₂NHCOCH₃)-phenyl) |

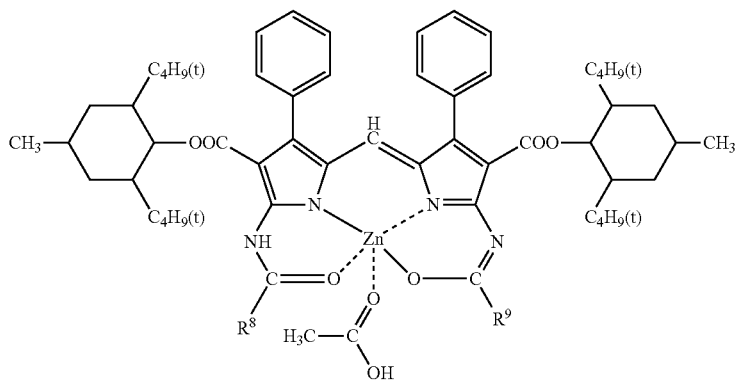
| Compound No. | R⁸ | R⁹ | Compound No. | R⁸ | R⁹ |
|---|---|---|---|---|---|
| III-57 | 2,4,6-trimethylphenyl | —CH₃ | III-58 | 2,4,6-trimethylphenyl | 2,4,6-trimethylphenyl |
| III-59 | 2-(2-hydroxyethoxy)phenyl | same as above | III-60 | 3-(methoxycarbonyl)phenyl | —CH₃ |
| III-61 | 2,5-dimethoxyphenyl | same as above | III-62 | 2-(methylsulfonylamino)phenyl | same as above |
| III-63 | 2-pyridyl | same as above | III-64 | 2-pyridyl | 2-pyridyl |
| III-64-2 | phenyl | phenyl | | | |

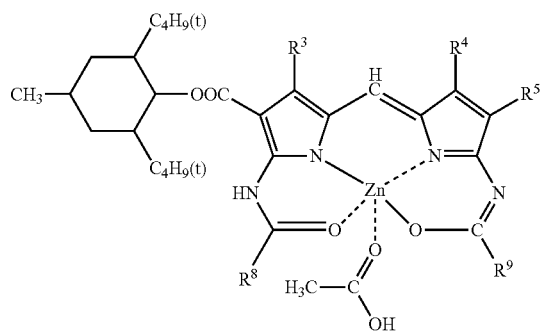
| Compound No. | R³ | R⁴ | R⁵ | R⁸ | R⁹ |
|---|---|---|---|---|---|
| III-65 | —CH₃ | —CH₃ | —COOC₂H₅ | —CH₃ | —CH₃ |
| III-66 | same as above | same as above | same as above | —CH(CH₃)NHSO₂CH₃ | —CH(CH₃)NHSO₂CH₃ |
| III-67 | same as above | same as above | same as above | -C₆H₄-NHSO₂CH₃ (m) | -C₆H₄-NHSO₂CH₃ (m) |
| III-68 | -C₆H₅ | same as above | same as above | —CH₃ | —CH₃ |
| III-69 | -C₆H₄- | -C₆H₅ | same as above | same as above | same as above |
| III-70 | —CH₃ | -C₆H₅ | —COO-(2,6-di-t-C₄H₉-4-CH₃-C₆H₂) | same as above | —CH₂NHSO₂-C₆H₄-CH₃ |

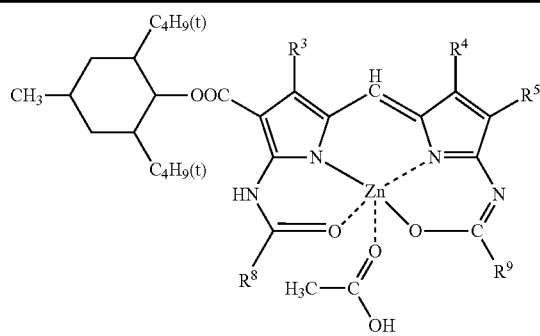

| Compound No. | $R^3$ | $R^4$ | $R^5$ | $R^8$ | $R^9$ |
|---|---|---|---|---|---|
| III-71 | phenyl | phenyl | —CO—N(CH$_3$)CH$_3$ | —CH$_3$ | —CH$_2$NHSO$_2$—C$_6$H$_4$—CH$_3$ |
| III-72 | same as above | same as above | —CO—N(C$_3$H$_7$(iso))C$_3$H$_7$(iso) | same as above | same as above |
| III-73 | same as above | same as above | —CONH—cyclohexyl | same as above | same as above |
| III-74 | same as above | same as above | —CONH—(2,4,6-trimethylphenyl) | same as above | same as above |
| III-75 | same as above | same as above | —CON(CH$_3$)—phenyl | same as above | same as above |

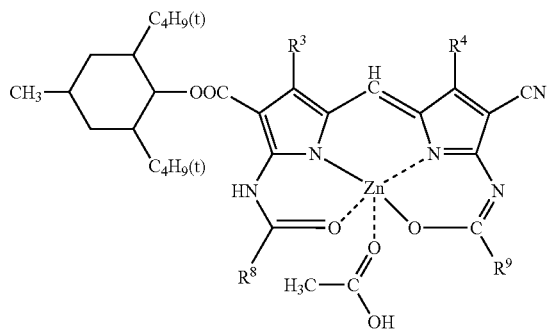

| Compound No. | $R^3$ | $R^4$ | $R^8$ | $R^9$ |
|---|---|---|---|---|
| III-76 | —CH$_3$ | —CH$_3$ | —CH$_3$ | —CH$_3$ |
| III-77 | same as above | same as above | —CH(CH$_3$)NHSO$_2$CH$_3$ | same as above |

-continued

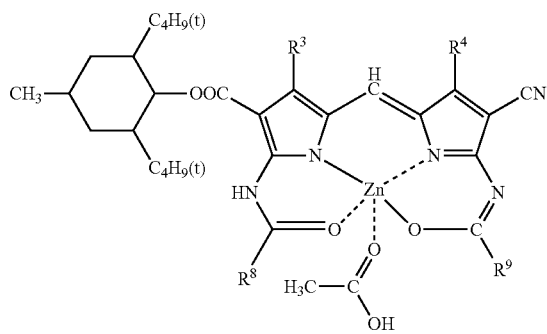

| Compound No. | R³ | R⁴ | R⁸ | R⁹ |
|---|---|---|---|---|
| III-78 | same as above | same as above | same as above | —CHNHSO₂CH₃ <br> \| <br> CH₃ |
| III-79 | same as above | same as above | —CHNHSO₂CH₃ <br> \| <br> CH₃ | —CHNHSO₂CH₃ <br> \| <br> CH₃ |
| III-80 | same as above | —C₆H₅ (phenyl) | —CH₃ | —CH₃ |
| III-81 | same as above | same as above | same as above | —CHNHSO₂CH₃ <br> \| <br> CH₃ |
| III-82 | same as above | same as above | —CHNHSO₂CH₃ <br> \| <br> CH₃ | same as above |

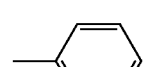

| Compound No. | R³ | R⁴ | R⁸ | R⁹ |
|---|---|---|---|---|
| III-83 | —CH₃ | —C₆H₅ (phenyl) | —CHNHSO₂CH₃ <br> \| <br> CH₃ | —CHNHSO₂CH₃ <br> \| <br> CH₃ |
| III-84 | same as above | same as above | same as above | —C₆H₄-NHSO₂CH₃ |
| III-85 | same as above | same as above | —C₄H₉(t) | same as above |

-continued

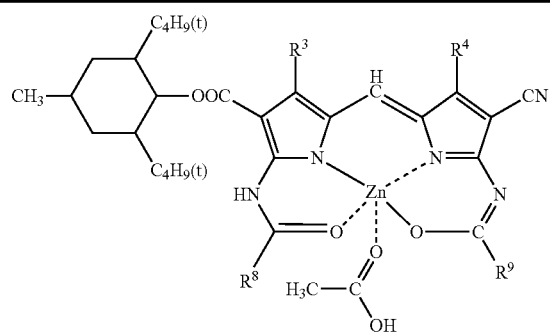

| Compound No. | R³ | R⁴ | R⁸ | R⁹ |
|---|---|---|---|---|
| III-86 | ![phenyl] | —CH₃ | —CH₃ | —CH₃ |
| III-87 | same as above | same as above | —CH₂NHSO₂CH₃ | —CH₂NHSO₂CH₃ |
| III-88 | ![phenyl] | ![phenyl] | —CH₃ | —CH₃ |
| III-89 | —CH₃ | ![3-NHSO₂CH₃-phenyl] | same as above | same as above |

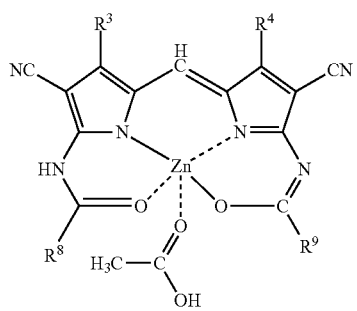

| Compound No. | R³ | R⁴ | R⁸ | R⁹ |
|---|---|---|---|---|
| III-90 | —CH₃ | —CH₃ | —CH₃ | —CH₃ |
| III-91 | same as above | same as above | same as above | —CHNHSO₂CH₃ \| C₄H₉ |
| III-92 | same as above | same as above | —CHNHSO₂CH₃ \| C₄H₉ | same as above |
| III-93 | ![phenyl] | ![phenyl] | —CH₃ | —CH₃ |
| III-94 | same as above | same as above | —C₄H₉(t) | —C₄H₉(t) |

-continued
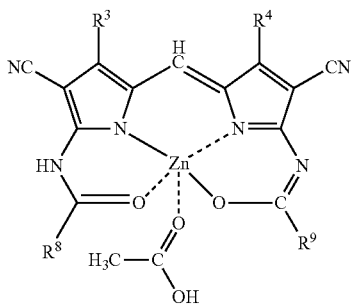
| Compound No. | R³ | R⁴ | R⁸ | R⁹ |
|---|---|---|---|---|
| III-95 | same as above | same as above | —CH(C₄H₉)NHSO₂CH₃ | same as above |
| III-96 | same as above | same as above | 3-(NHSO₂C₈H₁₇)-C₆H₄— | —CH₃ |
| III-97 | 3-(NHSO₂CH₃)-C₆H₄— | 3-(NHSO₂CH₃)-C₆H₄— | —CH₃ | —CH₃ |
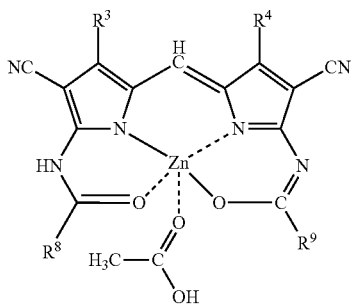
| Compound No. | R³ | R⁴ | R⁸ | R⁹ |
|---|---|---|---|---|
| III-98 | 2-CH₃-C₆H₄— | 2-CH₃-C₆H₄— | —CH₃ | —CH₃ |
| III-99 | 2,4-Cl₂-C₆H₃— | 2,4-Cl₂-C₆H₃— | same as above | same as above |

-continued
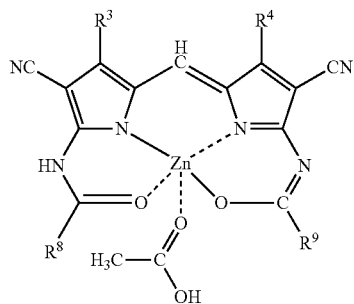
| Compound No. | R³ | R⁴ | R⁸ | R⁹ |
|---|---|---|---|---|
| III-100 | —C₆H₄—OCH₃ (para) | —C₆H₄—OCH₃ (para) | same as above | same as above |
| III-101 | 2-pyridyl | 2-pyridyl | same as above | same as above |
| III-102 | —CH(CH₃)C₂H₅ | —CH(CH₃)C₂H₅ | —CH(C₄H₉)NHSO₂CH₃ | —CH(C₄H₉)NHSO₂CH₃ |
| III-103 | 3-pyridyl | 3-pyridyl | 3-(NHSO₂C₈H₁₇)phenyl | 3-(NHSO₂C₈H₁₇)phenyl |
| Compound No. | R⁷ | R⁸ | R⁹ |
|---|---|---|---|
| III-A | 1-(CH₂COOH)-2-pyrrolyl | —C₄H₉(t) | —C₄H₉(t) |

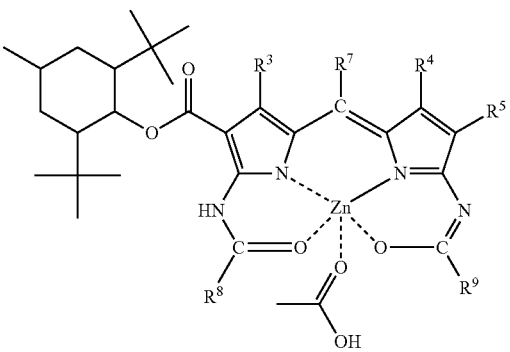

| Compound No. | $R^3$ | $R^4$ | $R^5$ | $R^7$ | $R^8$ | $R^9$ |
|---|---|---|---|---|---|---|
| III-B | —$CH_3$ | —$CH_3$ | —$COOC_2H_5$ | (pyrrole-$CH_2COOH$) | —$CH_3$ | —$CH_3$ |

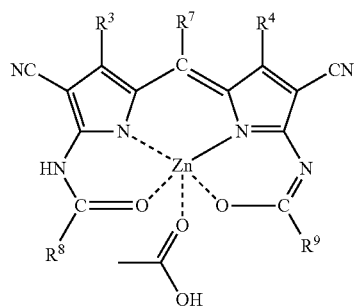

| Compound No. | $R^3$ | $R^4$ | $R^7$ | $R^8$ | $R^9$ |
|---|---|---|---|---|---|
| III-C | —$CH_3$ | —$CH_3$ | (pyrrole-$CH_2COOH$) | —$CH_3$ | —$CH_3$ |

In view of the thickness of the film, the molar absorption coefficient of the specific complex of the first aspect of the invention is preferably as high as possible. Further, in view of improving color purity, the maximum absorption wavelength (λmax) is preferably in the range of from 520 nm to 580 nm, more preferably from 530 nm to 570 nm. The maximum absorption wavelength and the molar absorption coefficient can be measured by a spectrophotometer (UV-2400PC, trade name, manufactured by Shimadzu Corporation).

In view of solubility, the melting point of the specific complex of the first aspect of the invention is preferably not too high.

The specific complex of the first aspect of the invention may be synthesized by the methods described in U.S. Pat. Nos. 4,774,339 and 5,433,896, JP-A Nos. 2001-240761 and 2002-155052, Japanese Patent No. 3614586, Aust. J. Chem, 1965, 11, 1835-1845, J. H. Boger et al, Heteroatom Chemistry, Vol. 1, No. 5, 389 (1990), and the like.

With respect to the synthesis method of the specific complex in accordance with the first aspect of the invention, the method described in paragraphs [0131] to [0157] of JP-A No. 2008-292970 may be specifically applied.

As the specific complex in accordance with the first aspect of the invention, Complex A, in which $R^1$ to $R^6$ in the compound represented by the formula (I) are substituted by at least the following Substituent a (preferably Substituent a and Substituent b), is also preferred.

Substituent a: a group having an ethylenically unsaturated bond at the end thereof (more preferably, a group having an acryloyl group or a methacryloyl group at the end thereof).

Substituent b: a group having a —$CO_2M$ group (M represents a hydrogen atom, an organic base or metal atom that is necessary for neutralizing a charge of —$CO_2^-$, or a simple anion (that is, $CO_2M$ represents $CO_2^-$) at the end thereof.

Further, Complex B, in which $R^2$ to $R^5$, $R^8$ and $R^9$ in the compound represented by the formula (III) are substituted at least by the Substituent a (preferably, substituted by the Substituent a and the Substituent b), is also preferred as the specific complex in accordance with the first aspect of the invention.

The dye in accordance with the first aspect of the invention may be a dye multimer obtained by polymerizing the Complex A or the Complex B. The dye multimer may also be obtained by copolymerizing the Complex A or the Complex B with a further monomer component (for example, acrylic acid or methacrylic acid).

The Complex B is preferably a compound represented by the following formula (2).

(Compound Represented by the Formula (2))

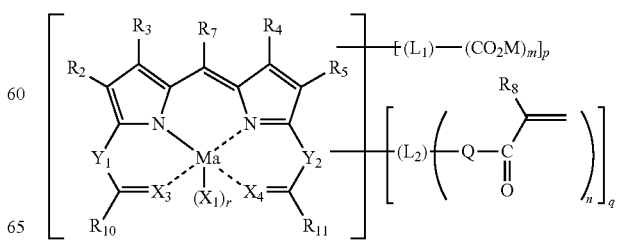

(2)

In the formula (2), each of $R_2$ to $R_5$ independently represents a hydrogen atom or a substituent; $R_7$ represents a hydrogen atom, a halogen atom, an alkyl group, an aryl group or a heterocyclic group; each of $R_{10}$ and $R_{11}$ independently represents an alkyl group, an alkenyl group, an aryl group, a heterocyclic group, an alkoxy group, an aryloxy group, an amino group, an anilino group or a heterocyclic amino group; a substituent represented by any of $R_2$ to $R_5$, $R_{10}$ or $R_{11}$ is a divalent linking group bonded to $-L_1-$ or $-L_2-$, or a substituent represented by any of R, to $R_5$, $R_{10}$ or $R_{11}$ is a single bond and $-L_1-$ or $-L_2-$ directly substitutes the dipyrromethene skeleton; Ma represents a metal or a metal compound; $X_1$ represents a group to neutralize a charge of Ma; r represents 0 or 1; each of $X_3$ and $X_4$ independently represents NR (R represents a hydrogen atom, an alkyl group, an alkenyl group, an aryl, group, a heterocyclic group, an acyl group, an alkylsulfonyl group or an arylsulfonyl group), a nitrogen atom, an oxygen atom or a sulfur atom; each of $Y_1$ and $Y_2$ independently represents NR (R represents a hydrogen atom, an alkyl group, an alkenyl group, an aryl group, a heterocyclic group, an acyl group, an alkylsulfonyl group or an arylsulfonyl group) or an oxygen atom; $R_{10}$ and $Y_1$ may be bonded to each other to form a five, six or seven-membered ring; $R_{11}$ and $Y_2$ may be bonded to each other to form a five, six or seven-membered ring; M represents a hydrogen atom, or an organic base or a metal atom to neutralize a charge of $—CO_2^-$, or an anion (i.e., $CO_2M$ represents $CO_2^-$); $L_1$ represents a single bond or a (m+1)-valent linking group; m represents 1, 2 or 3; p represents 1 or 2; $R_3$ represents a hydrogen atom or a methyl group; Q represents an oxygen atom or $NR_9$ ($R_9$ represents a hydrogen atom, an alkyl group, an alkenyl group, an aryl group, a heterocyclic group, an acyl group, an alkylsulfonyl group or an arylsulfonyl group); $L_2$ represents a single bond or an (n+1)-valent linking group; n represents 1, 2 or 3; q represents 1 or 2; when p is 2, the two of $\{(L_1)\text{-}(CO_2M)_m\}$ may be the same or different from each other; when q is 2, the two of $\{(L_2)\text{-}(Q\text{-}COC(R_8)=CH_2)n\}$ may be the same or different from each other; when m is 2 or 3, the two or three of $(CO_2M)$ may be the same or different from each other; and when n is 2 or 3, the two or three of $(Q\text{-}COC(R_8)=CH_2)$ may be the same or different from each other.

The compound represented by the formula (2) has a structure in which a polymerizable group and a carboxyl group are introduced into the same molecule.

The compound represented by the formula (2) inhibits color transfer by having a polymerizable group when the compound is formed into a colored cured film, and improves pattern formation suitability by having a carboxyl group.

Further, the compound represented by the formula (2) may also be a tautomer.

In the formula (2), $R_2$ to $R_5$ have the same definitions as that of $R^2$ to $R^5$ in the formula (I), respectively, and the preferable ranges thereof are also the same.

In the formula (2), $R_7$ has the same definitions as that of $R^7$ in the formula (I), and preferable ranges thereof are also the same.

In the formula (2), each of $R_{10}$ and $R_{11}$ independently represents an alkyl group, an alkenyl group, an aryl group, a heterocyclic group, an alkoxy group, an aryloxy group, an amino group, an anilino group or a heterocyclic amino group.

Among them, $R_{10}$ and $R_{11}$ preferably represent an alkyl group, an alkenyl group, an aryl group, a heterocyclic group, an alkoxy group, an aryloxy group or a heterocyclic amino group, more preferably an alkyl group, an alkenyl group, an alkoxy group or an aryloxy group.

In the formula (2), any one of $R_2$ to $R_5$, $R_{10}$ and $R_{11}$ is a divalent linking group and is bonded to $-L_1-$ or $-L_2-$, or any one of $R_2$ to $R_5$, $R_{10}$ and $R_{11}$ is a single bond and $-L_1-$ or $-L_2-$ directly substitutes the dipyrromethene backbone.

In the formula (2), the site at which $-L_1-$ is bonded is preferably at least one of $R_3$, $R_4$, $R_{10}$ and $R_{11}$, more preferably at least one of $R_{10}$ and $R_{11}$, in view of synthesis suitability.

In the formula (2), the site at which $-L_2-$ is bonded is preferably at least one of $R_3$, $R_4$, $R_{10}$ and $R_{11}$, more preferably at least one of $R_{10}$ and in view of synthesis suitability.

In the formula (2), Ma, $X_1$ and r have the same definitions as that of Ma, $X^5$ and a in the formula (III), respectively, and the preferable ranges thereof are also the same.

In the formula (2), M represents a hydrogen atom, an organic base or a metal atom that is necessary for neutralizing a charge of $—CO_2^-$, or a simple anion (that is, $CO_2M$ represents $CO_2^-$).

Among them, M is more preferably a hydrogen atom or a simple anion (that is, $CO_2M$ represents $CO_2^-$).

In the formula (2), $L_1$ represents a single bond or a (m+1)-valent linking group.

Examples of the (m+1)-valent linking group represented by $L_1$ include an alkyl group having 1 to 10 carbon atoms (hereinafter, in the specific examples of the group represented by $L_1$, it refers to a group obtained by removing one to m hydrogen atoms from the group, and exemplary alkyl groups include a divalent alkylene group (m=1), a trivalent alkanetriyl group (m=2), and a tetravalent alkanetetrayl group (m=3)), an aryl group having 6 to 12 carbon atoms, an alkylthioether group having 1 to 10 carbon atoms, an arylthioether group having 6 to 12 carbon atoms, an alkylether group having 1 to 10 carbon atoms, an arylether group having 6 to 12 carbon atoms, an alkylamino group having 1 to 10 carbon atoms, an arylamino group having 6 to 12 carbon atoms, an alkylamido group having 1 to 10 carbon atoms, an arylamido group having 6 to 12 carbon atoms, an alkylcarbamoyl group having 1 to 10 carbon atoms, an arylcarbamoyl group having 6 to 12 carbon atoms, an alkylsulfonamido group having 1 to 10 carbon atoms, an arylsulfonamido group having 6 to 12 carbon atoms, an alkylsulfamoyl group having 1 to 10 carbon atoms, and an arylsulfamoyl group having 6 to 12 carbon atoms. Specific examples of L1 include the following groups.

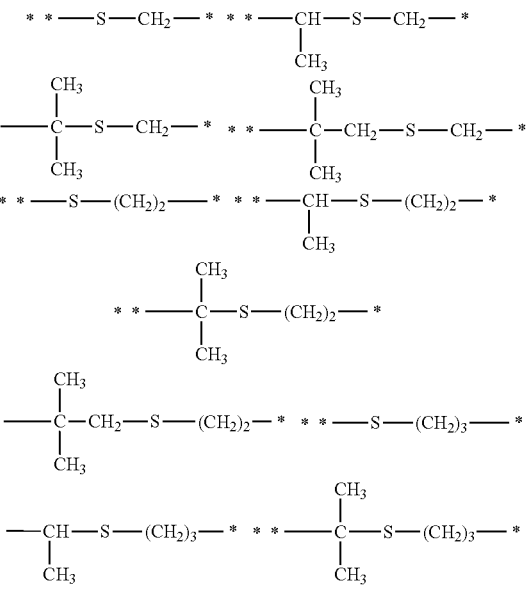

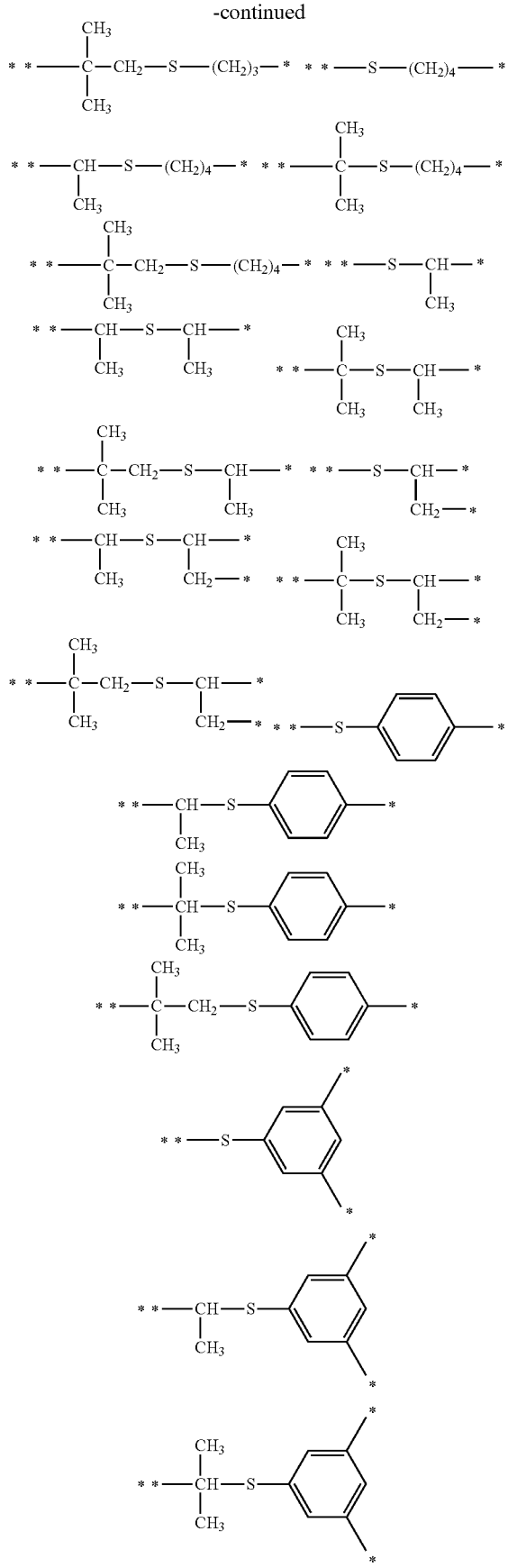
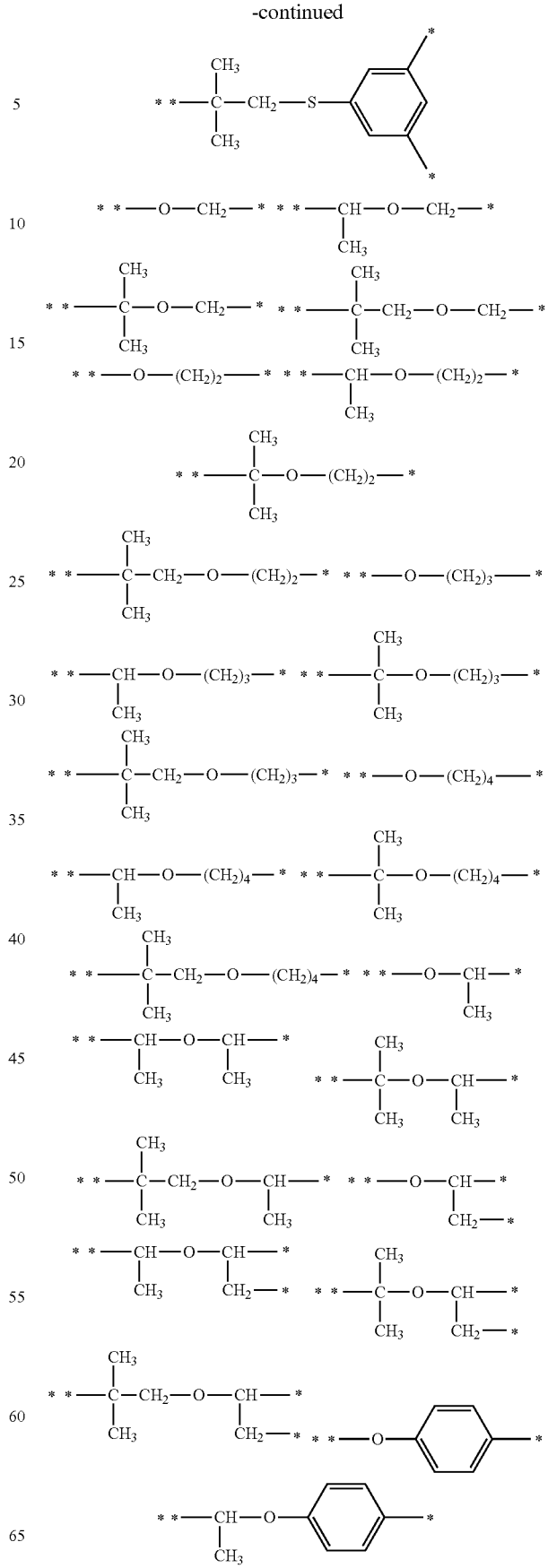

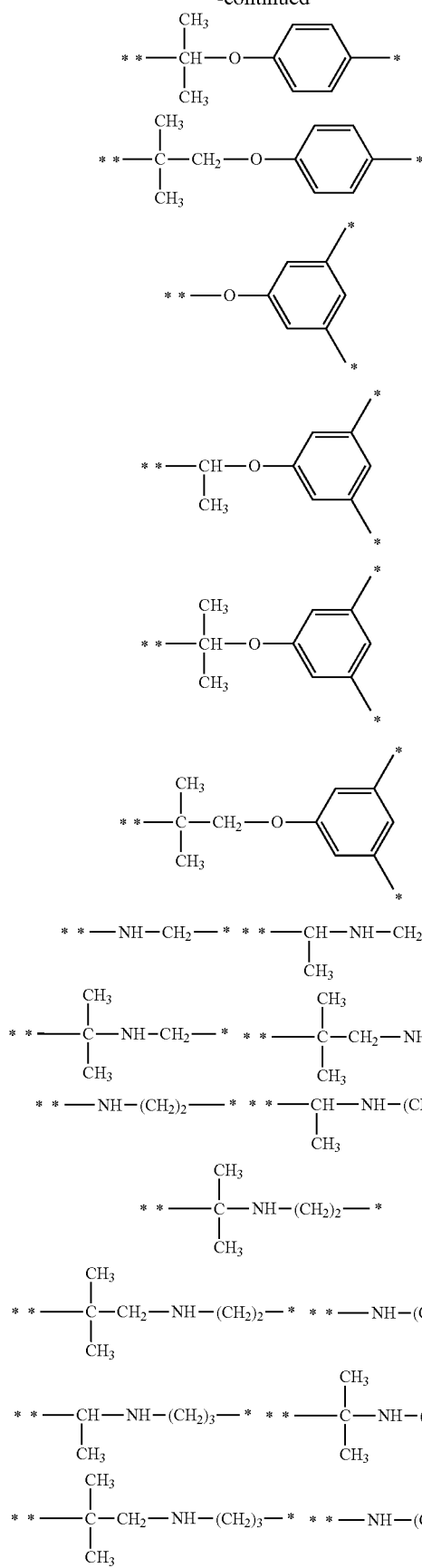
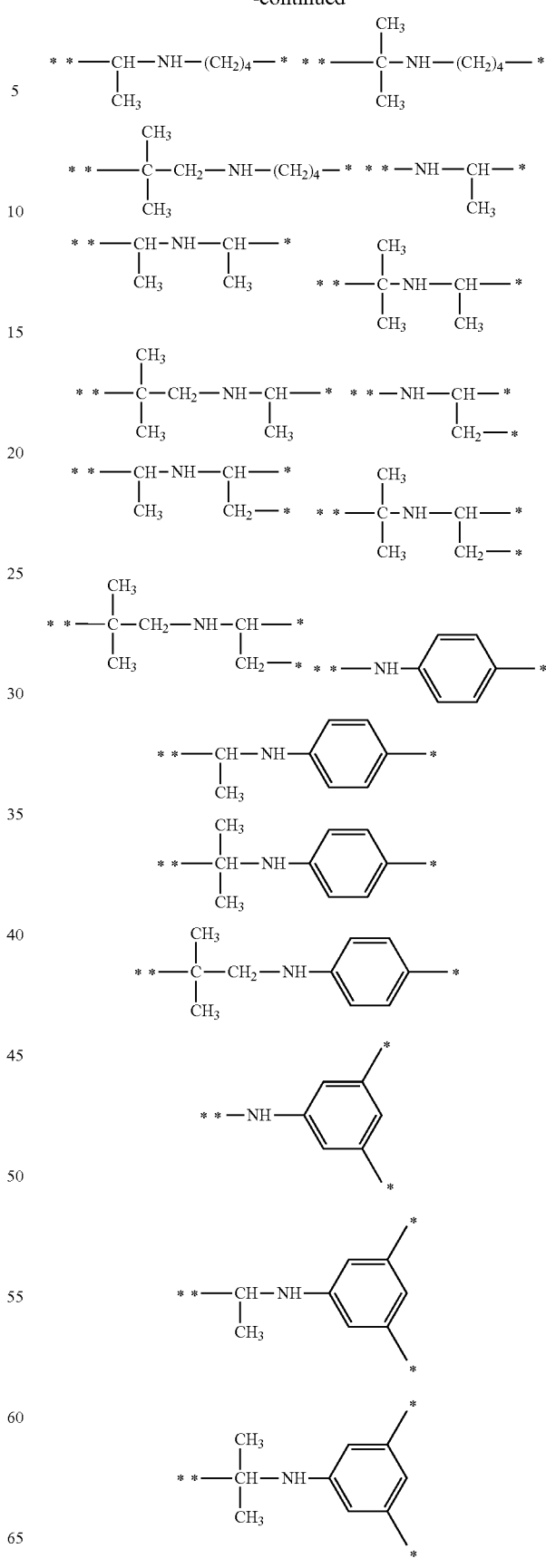

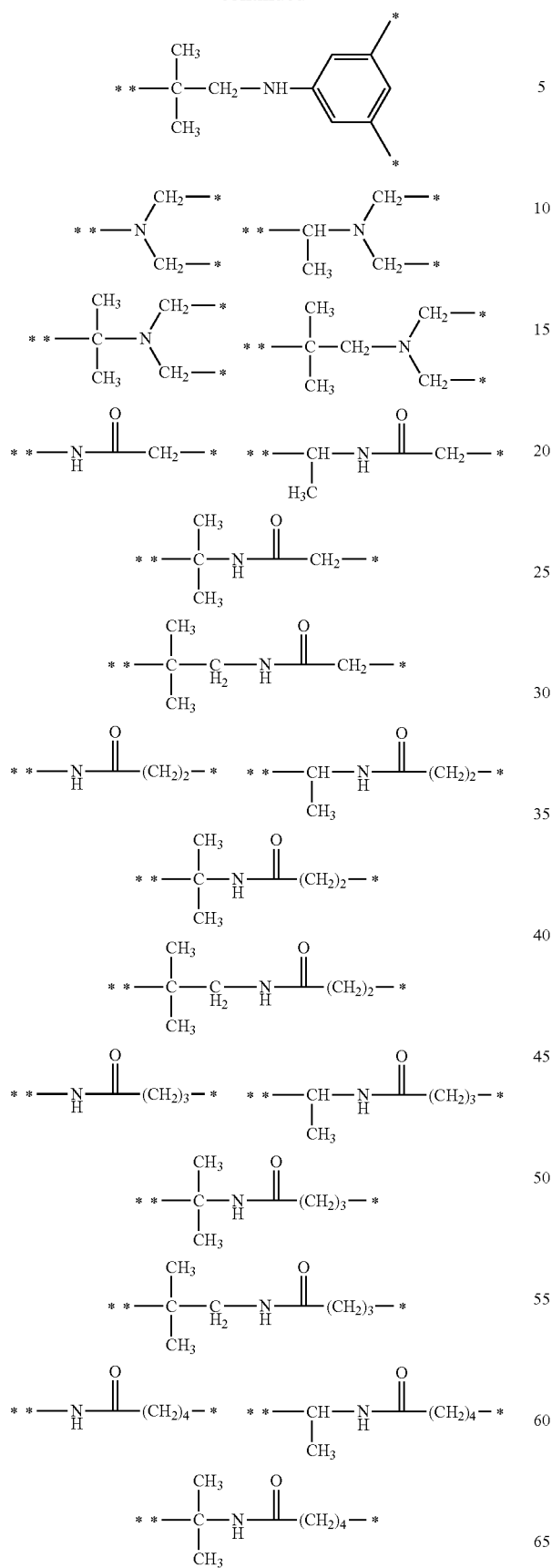
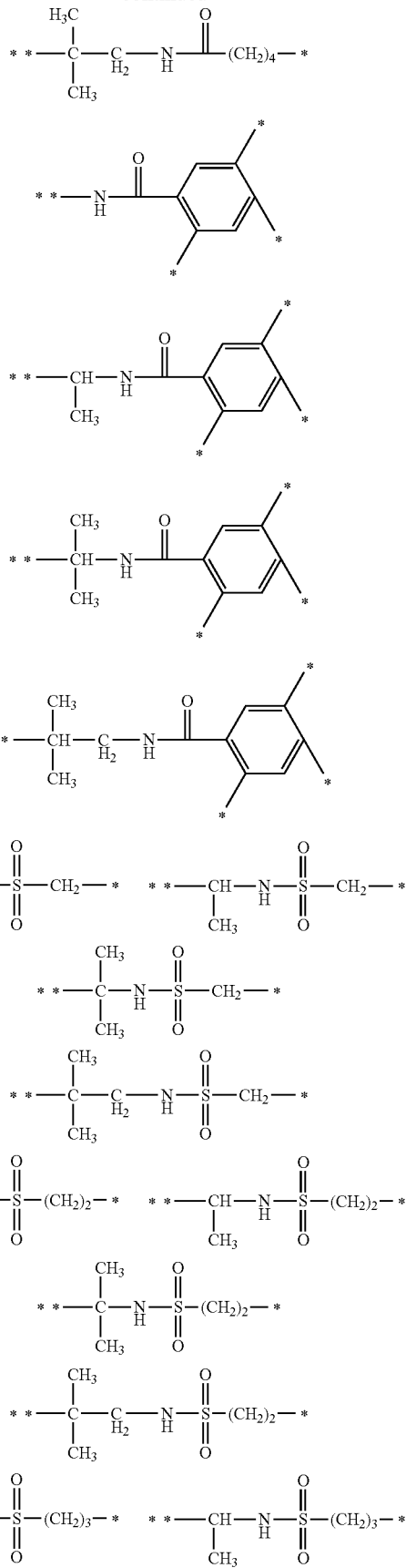

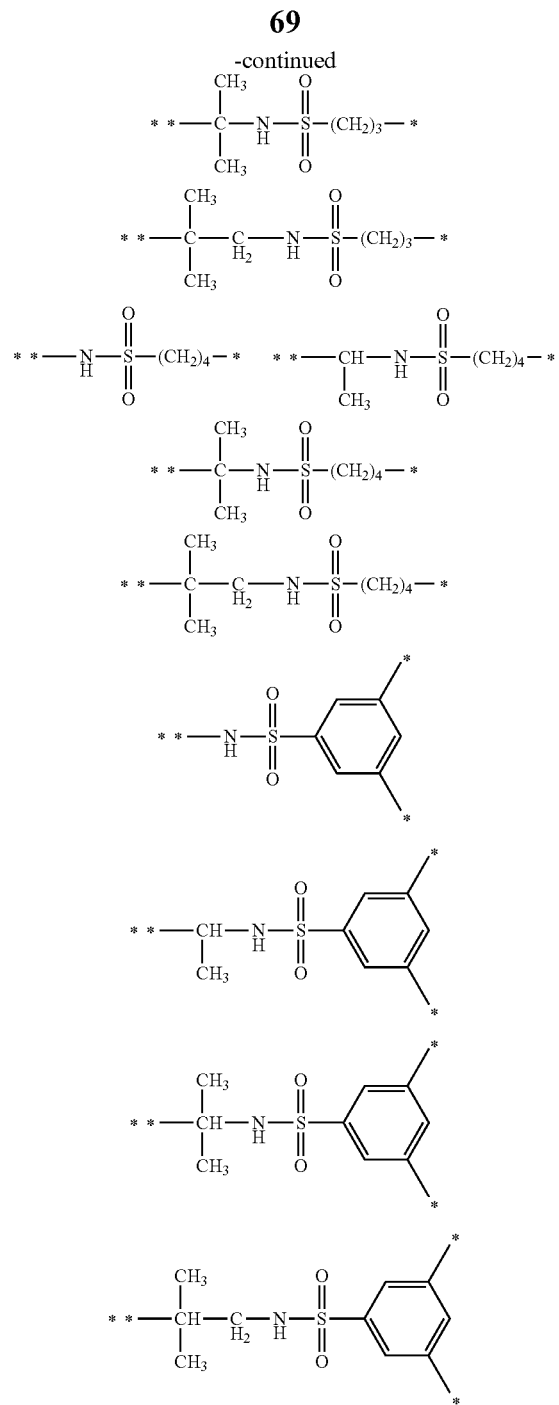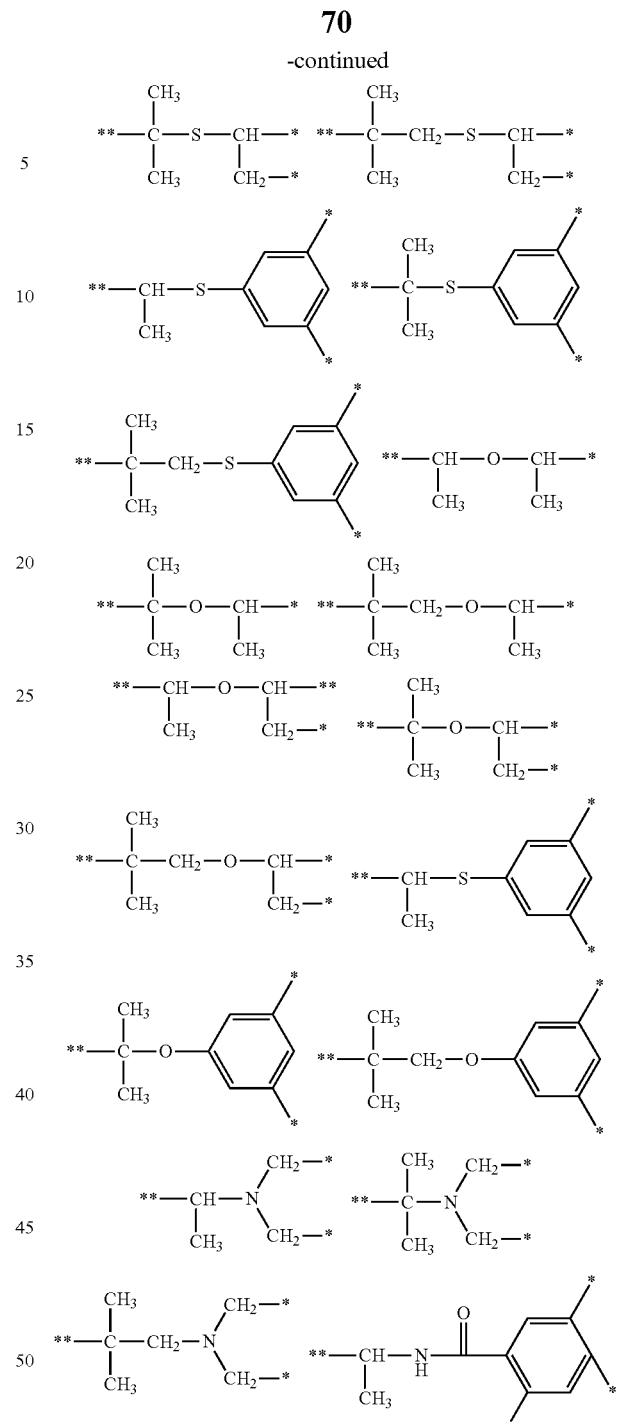
$L_1$ is more preferably selected from the following linking groups.
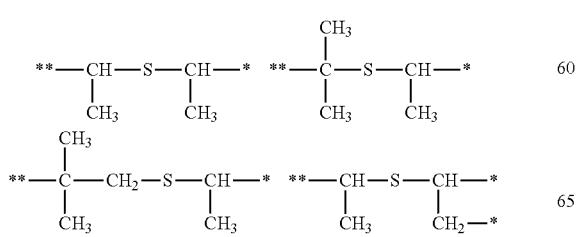

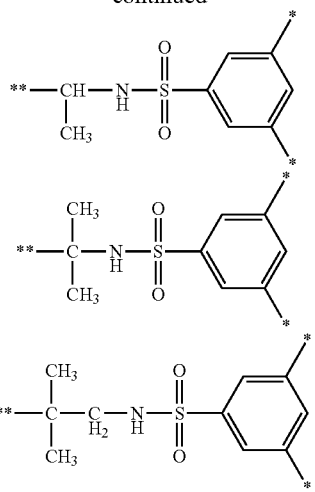

In the above linking groups, * represents a position to be linked to —COOM, and ** represents a position to be linked to the dipyrromethene backbone directly or via any one of $R_1$ to $R_6$.

In the formula (2), m represents 1, 2 or 3, preferably 1 or 2, more preferably 1.

In the formula (2), p represents 1 or 2, preferably 1.

In the formula (2), $R_8$ represents a hydrogen atom or a methyl group.

In the formula (2), Q represents an oxygen atom or $NR_9$ ($R_9$ represents a hydrogen atom, an alkyl group, an alkenyl group, an aryl group, a heterocyclic group, an acyl group, an alkylsulfonyl group or an aryl sulfonyl group).

In the formula (2), $L_2$ represents a single bond or a (n+1)-valent linking group.

The (n+1)-valent linking groups represented by $L_2$ include an alkyl group having 1 to 10 carbon atoms, an aryl group having 6 to 12 carbon atoms, an alkylthioether group having 1 to 10 carbon atoms, an arylthioether group having 6 to 12 carbon atoms, an alkylether group having 1 to 10 carbon atoms, an arylether group having 6 to 12 carbon atoms, an alkylamino group having 1 to 10 carbon atoms, an arylamino group having 6 to 12 carbon atoms, an alkylamide group having 1 to 10 carbon atoms, an arylamide group having 6 to 12 carbon atoms, an alkylcarbamoyl group having 1 to 10 carbon atoms, an arylcarbamoyl group having 6 to 12 carbon atoms, an alkylsulfoneamide group having 1 to 10 carbon atoms, an arylsulfoneamide group having 6 to 12 carbon atoms, an alkylsulfamoyl group having 1 to 10 carbon atoms, and an arylsulfamoyl group having 6 to 12 carbon atoms. Specific examples of the (n+1)-valent linking groups represented by $L_2$ include the following groups.

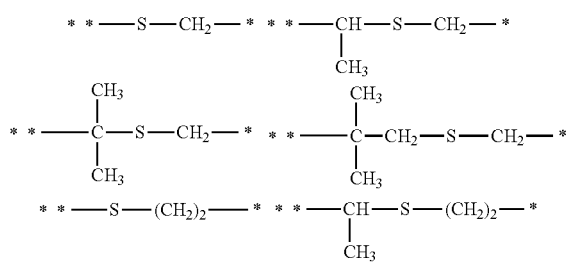

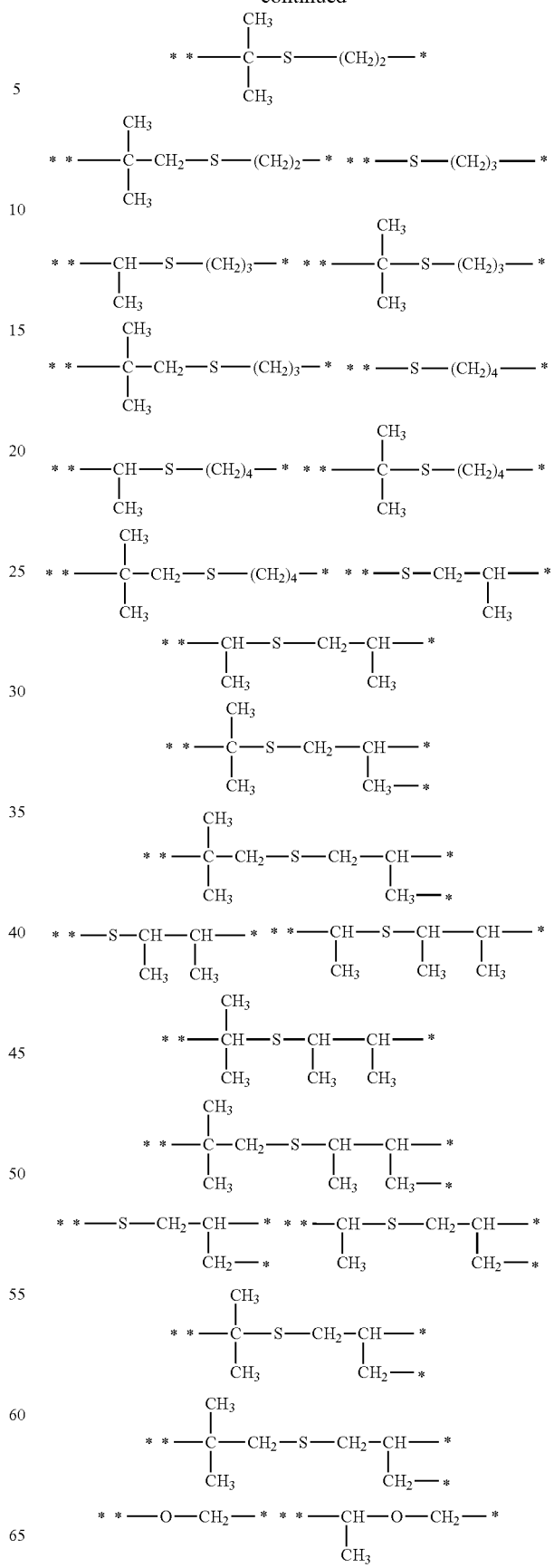

-continued
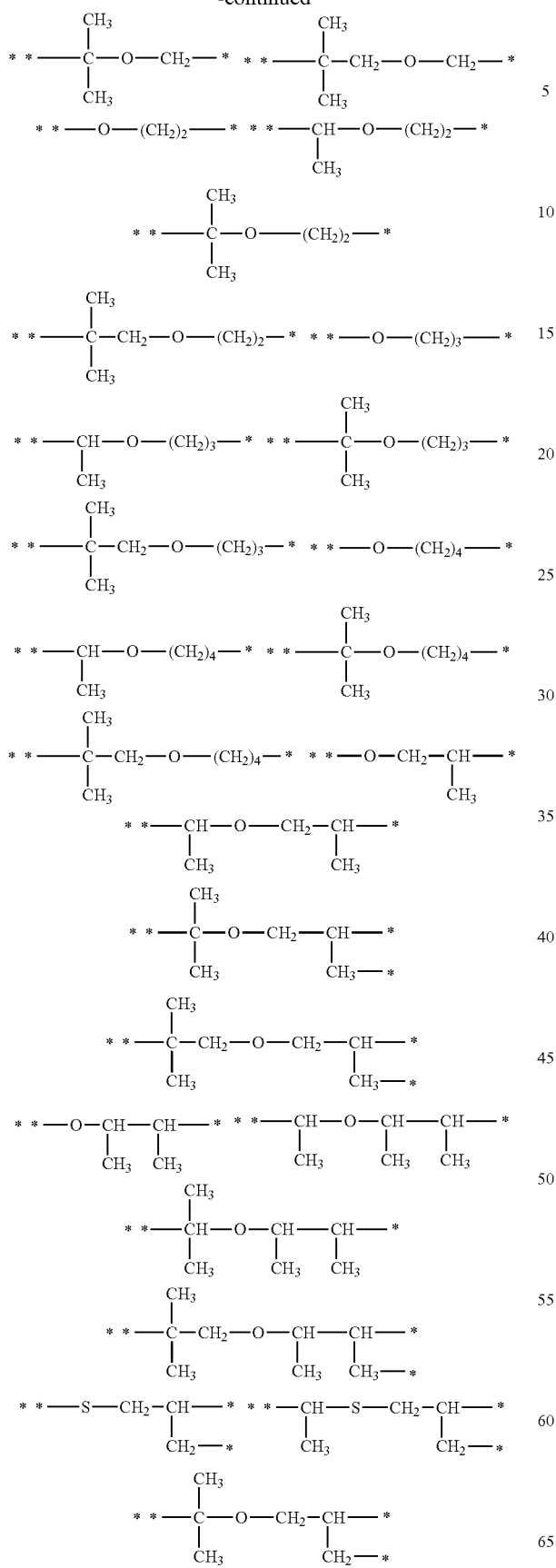
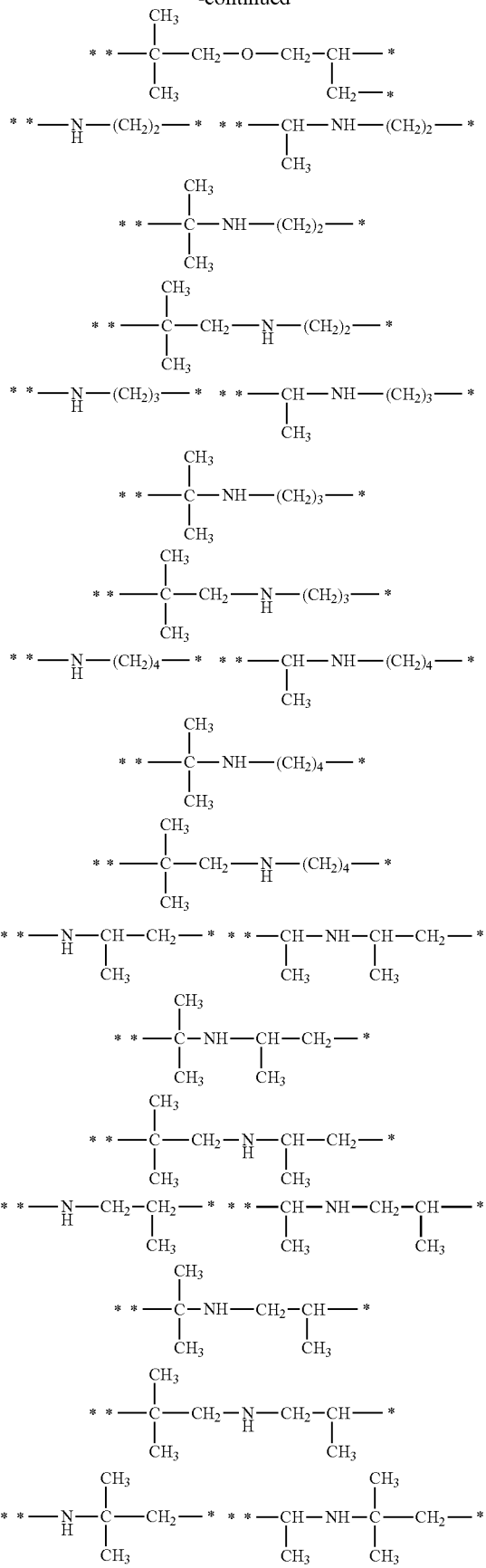

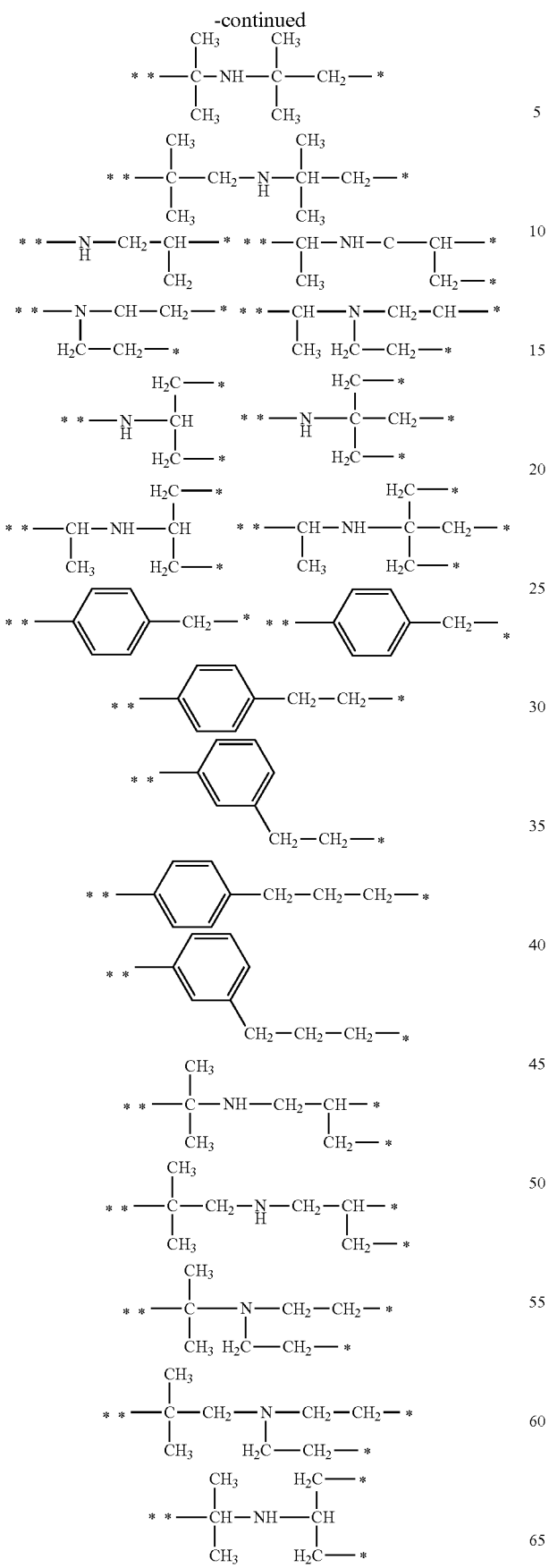
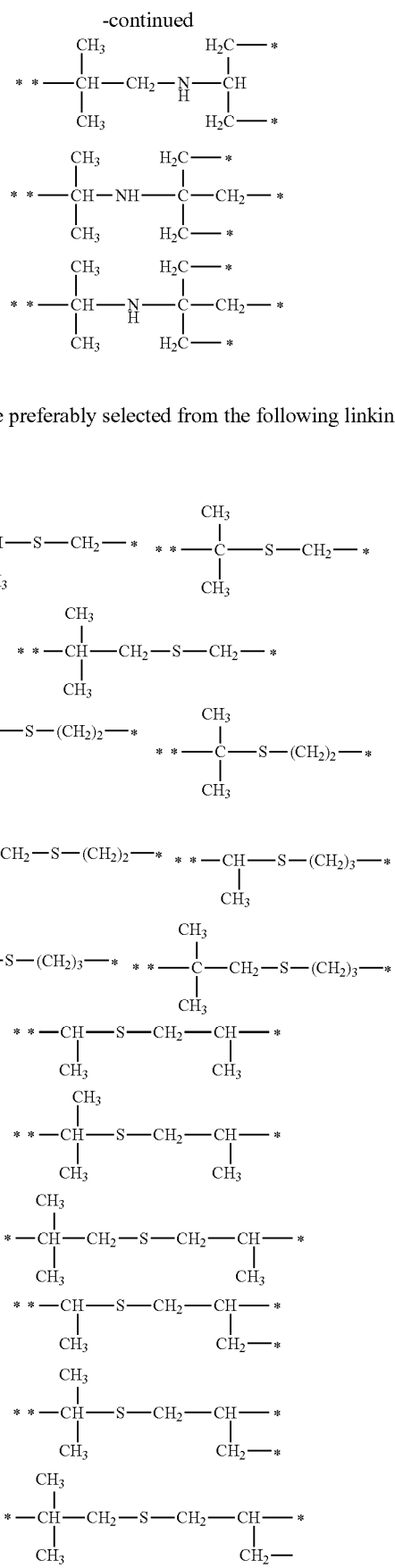
$L_2$ is more preferably selected from the following linking groups.

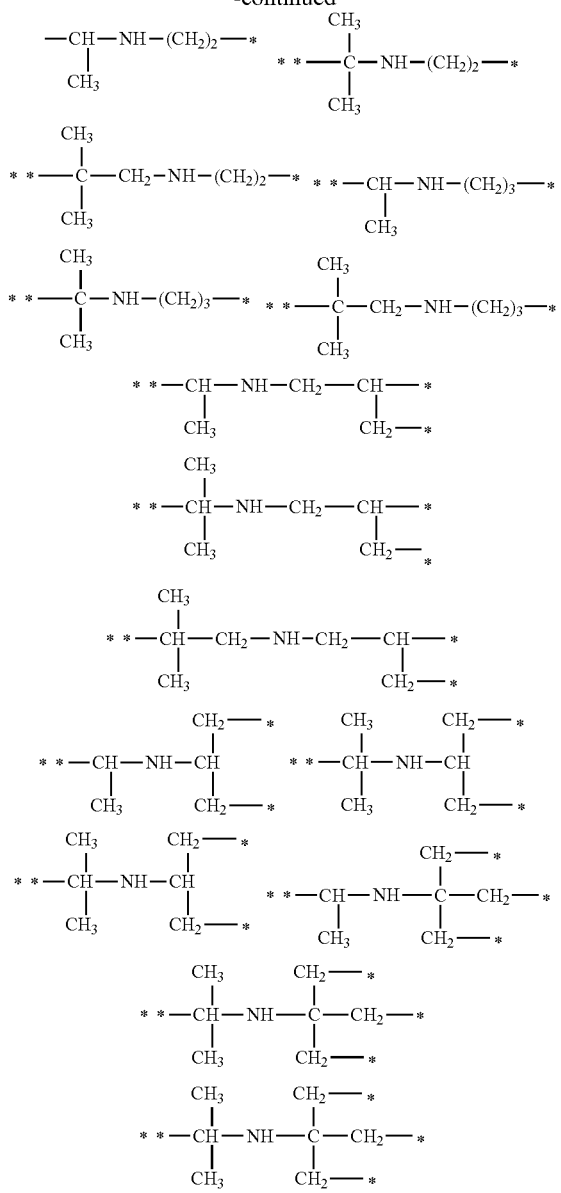

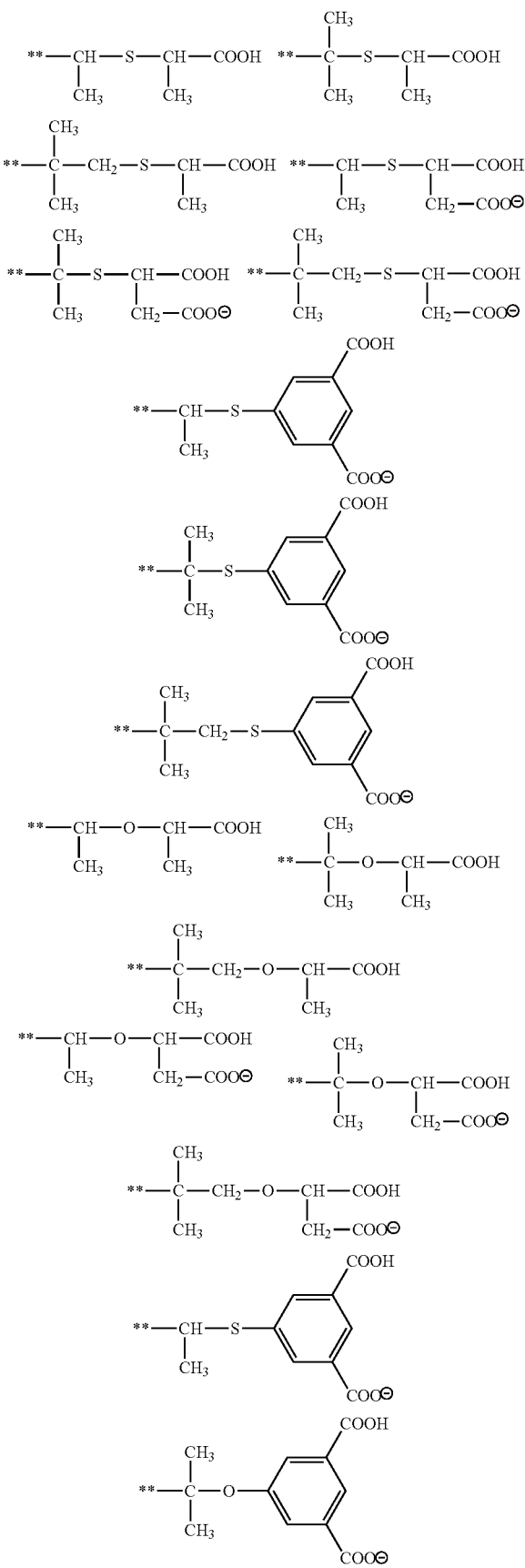

In the above linking groups, * represents a position to be linked to -Q-, and ** represents a position to be linked to the dipyrromethene backbone directly or via any one of $R_1$ to $R_6$.

In the formula (2), n represents 1, 2 or 3, preferably 2 or 3, more preferably 2.

In the formula (2), q represents 1 or 2, preferably 1.

In the formula (2), when p is 2, the two of $\{(L_1)\text{-}(CO_2M)_m\}$ may be the same or different from each other; when q is 2, the two of $\{(L_2)\text{-}(Q\text{-}COC(R_8)=CH_2)n\}$ may be the same or different from each other; when m is 2 or 3, the two or three of $(CO_2M)$ may be the same or different from each other; and when n is 2 or 3, the two or three of $(Q\text{-}COC(R_8)=CH_2)$ may be the same or different from each other.

In the formula (2), the group represented by $\text{-}(L_1)\text{-}(CO_2M)_m$ is preferably selected from the following groups.

-continued
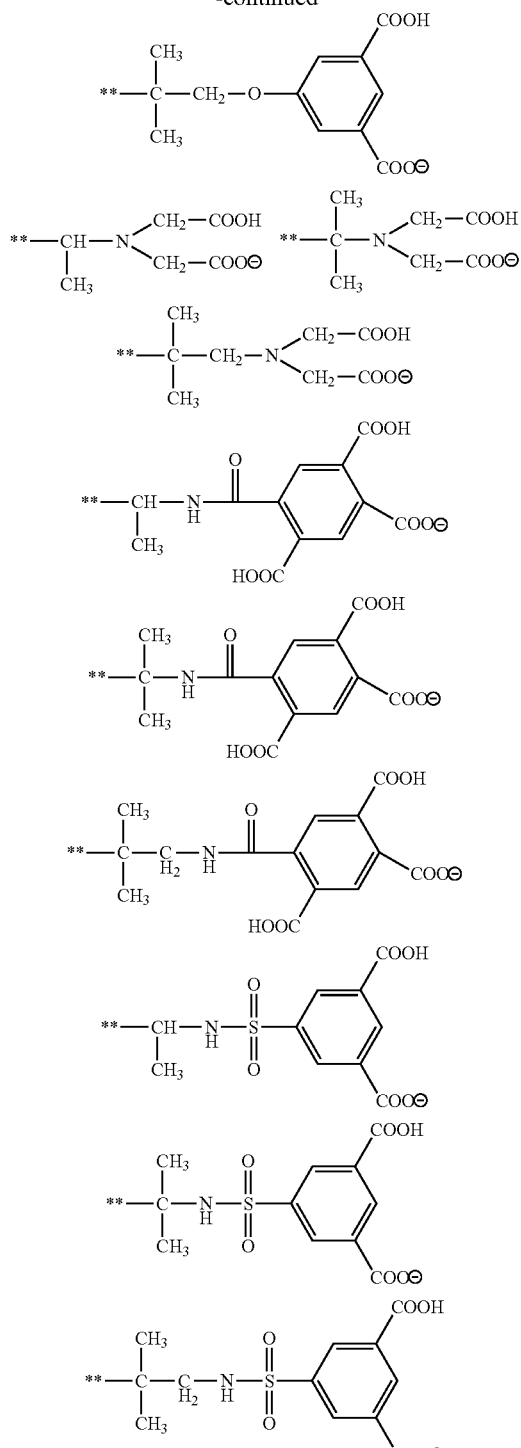
In the above groups, ** represents a position to be linked to the dipyrromethene backbone directly or via any one of $R_1$ to $R_6$.
In the formula (2), the group represented by $\{(L_2)\text{-}(Q\text{-}COC(R_8)=CH_2)n\}$ is preferably selected from the following groups.
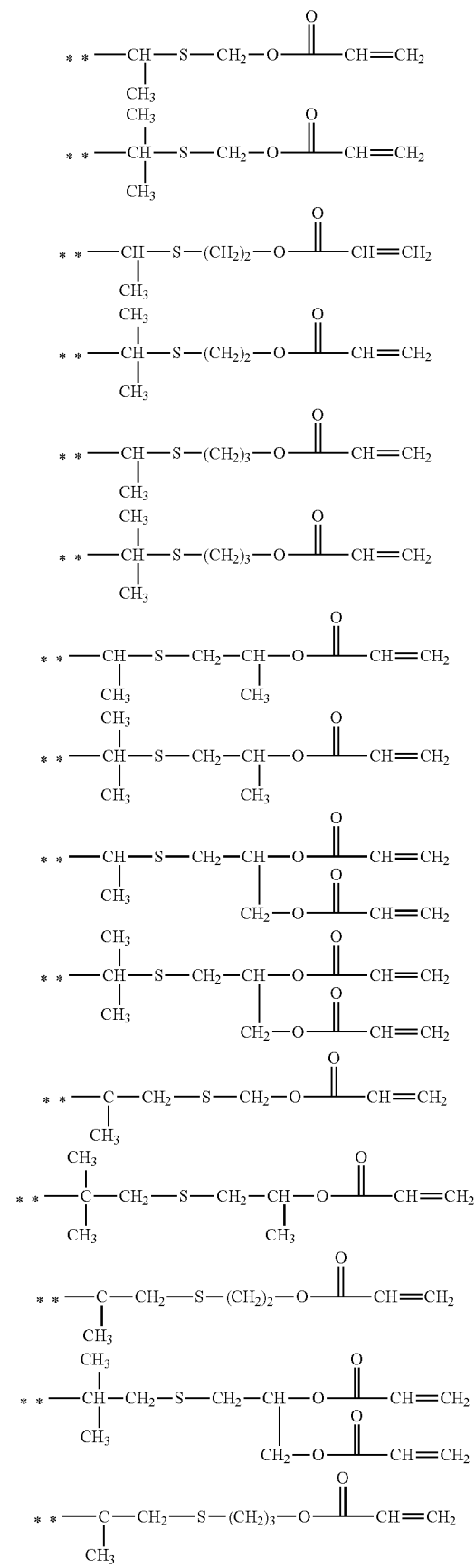

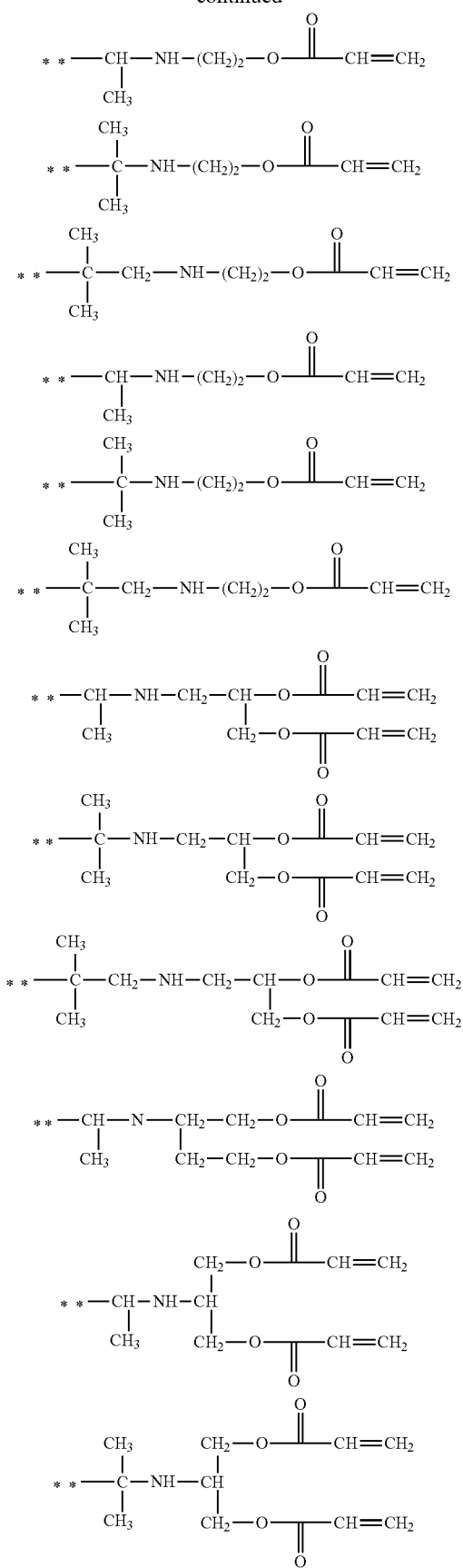
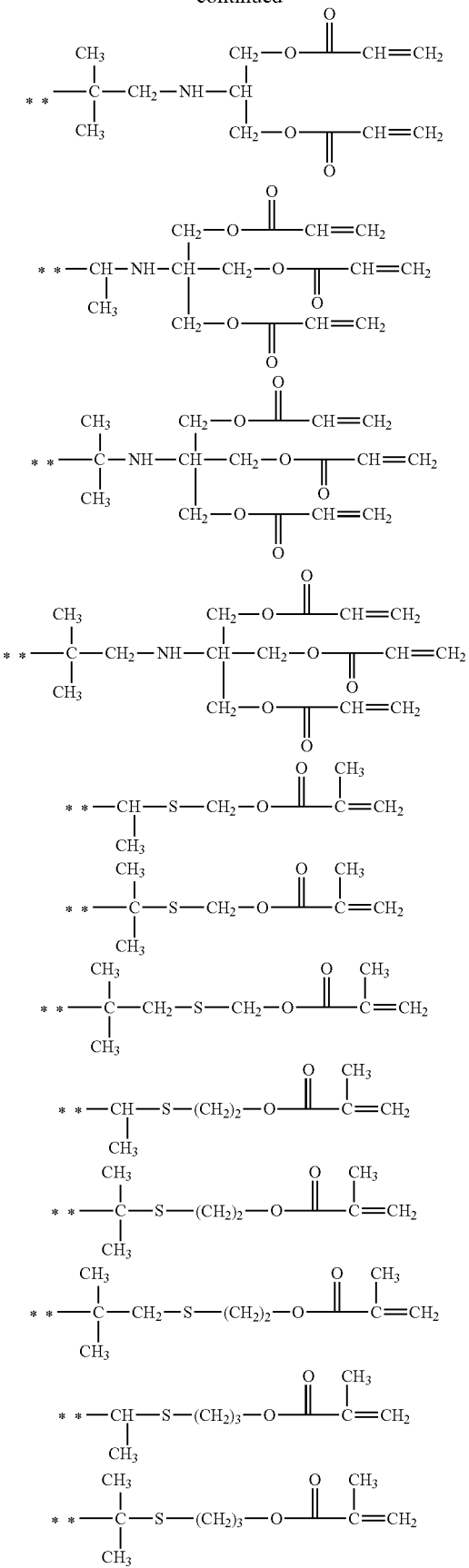

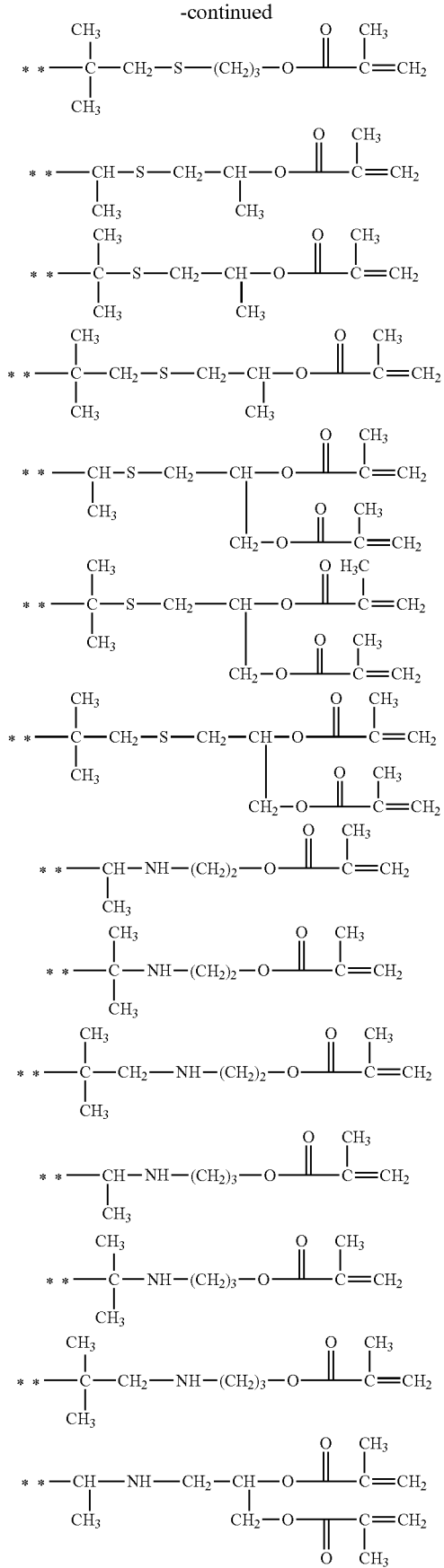
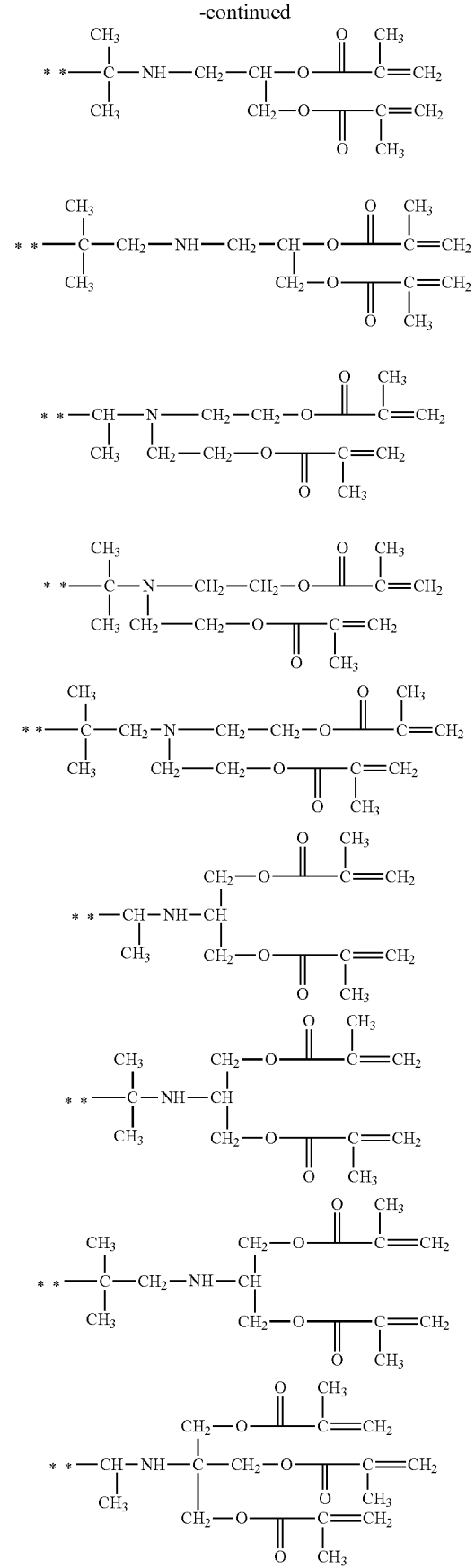

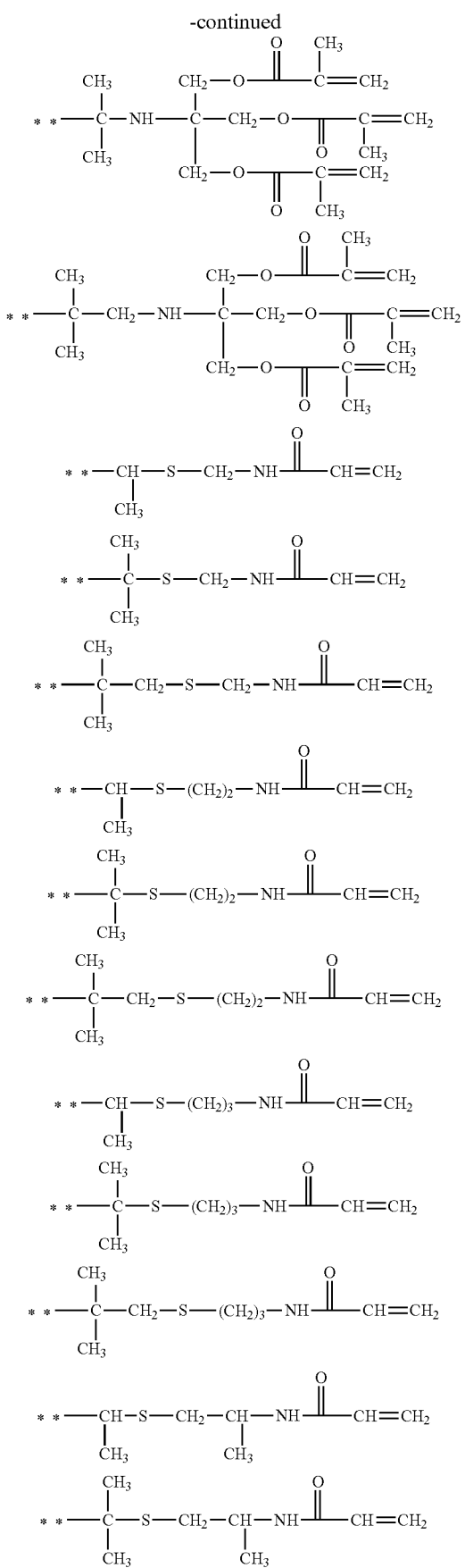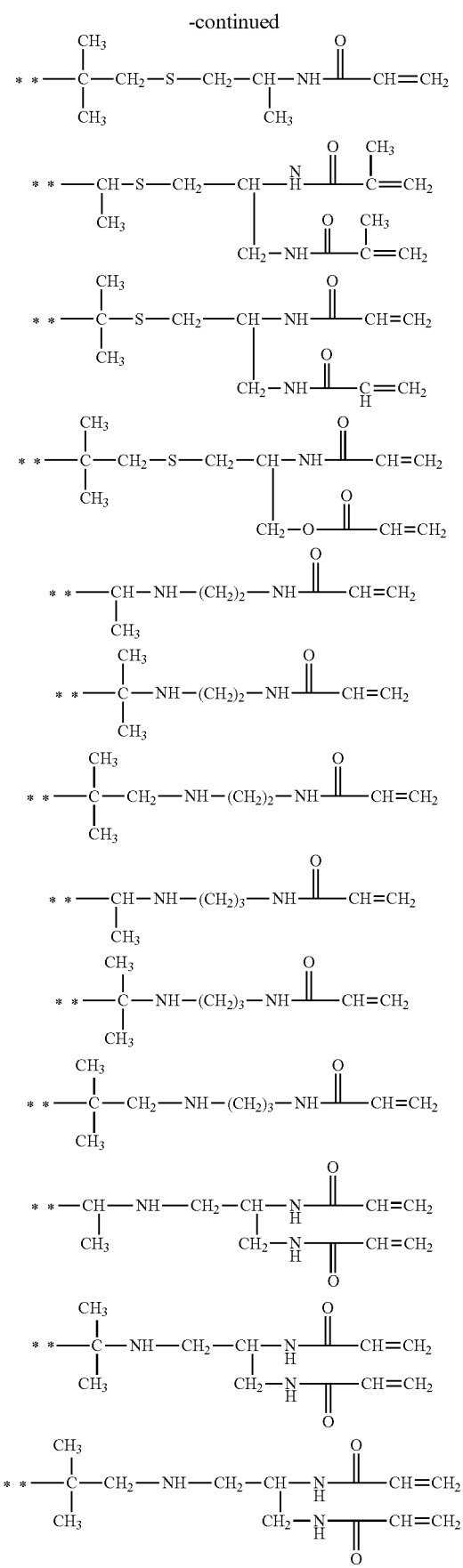

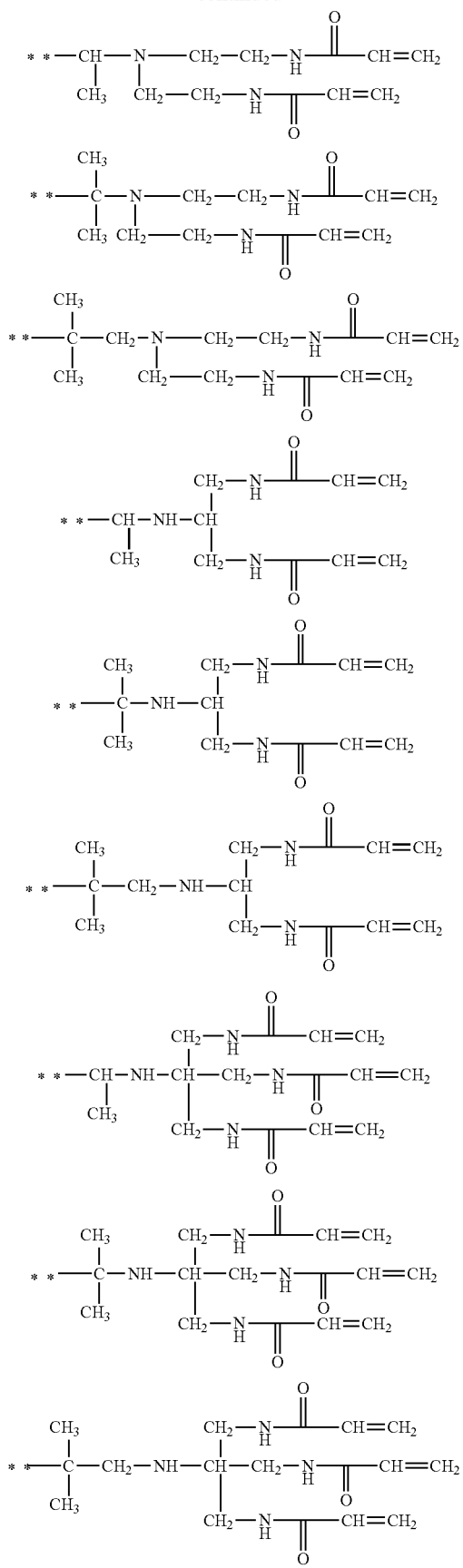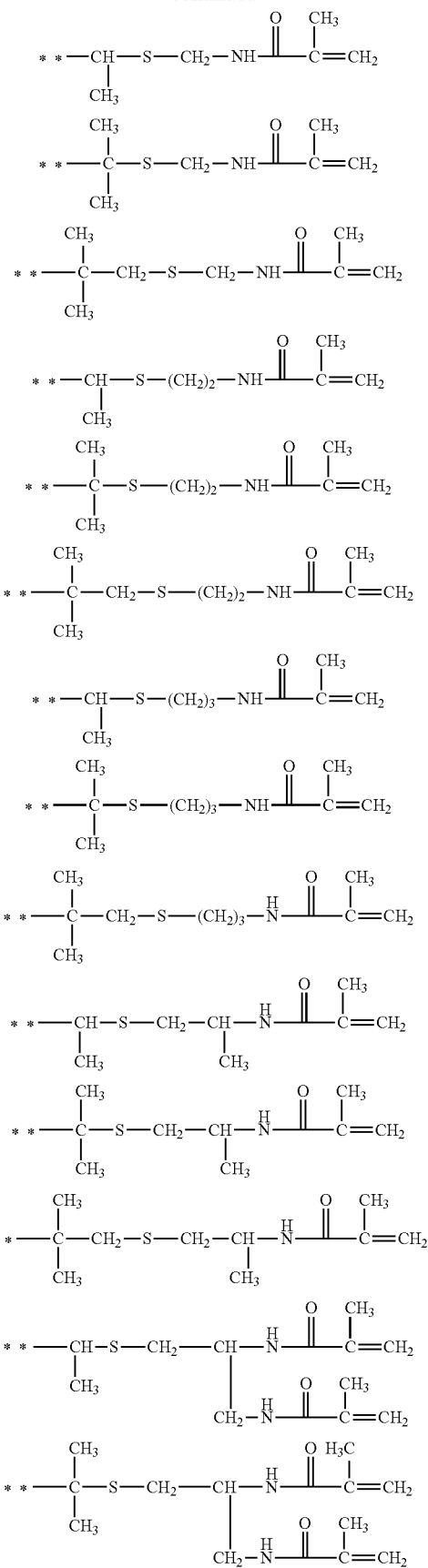

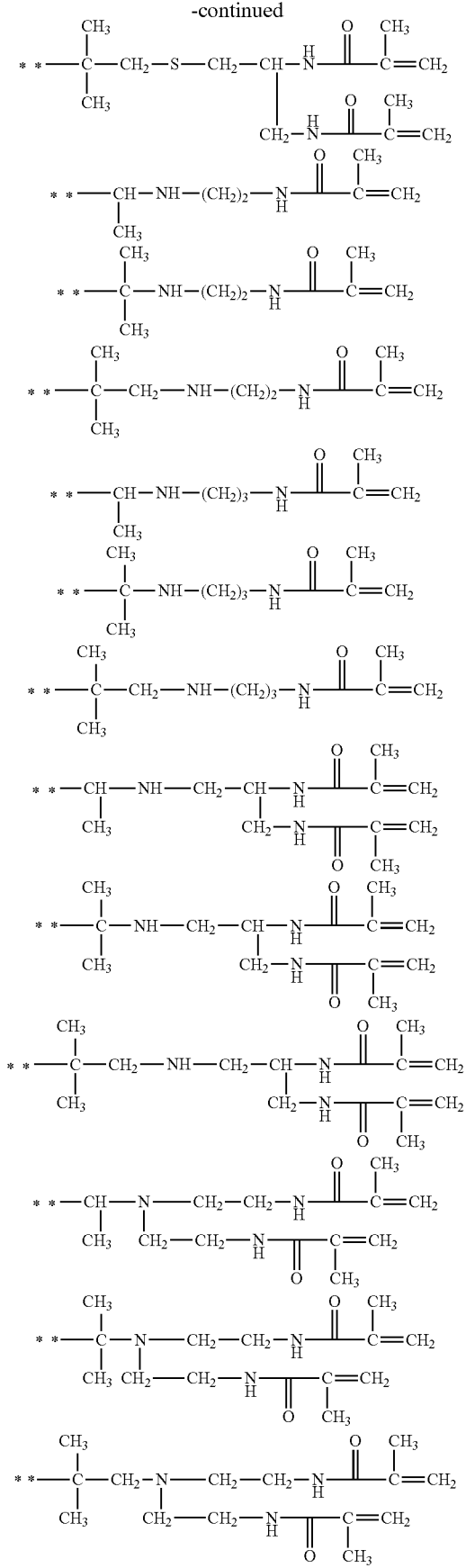

In the above groups, ** represents a position to be linked to the dipyrromethene backbone directly or via any one of $R_1$ to $R_6$.

In the formula (2), each of $X_3$ and $X_4$ independently represents NR (R represents a hydrogen atom, an alkyl group, an alkenyl group, an aryl group, a heterocyclic group, an acyl group, an alkylsulfonyl group or an arylsulfonyl group), a nitrogen atom, an oxygen atom or a sulfur atom.

Among them, $X_3$ and $X_4$ are preferably NR (R represents a hydrogen atom, an alkyl group or an alkenyl group), a nitrogen atom, an oxygen atom or a sulfur atom, more preferably NR (R represents a hydrogen atom), a nitrogen atom, an oxygen atom or a sulfur atom.

In the formula (2), each of $Y_1$ and $Y_2$ independently represents NR (R represents a hydrogen atom, an alkyl group, an alkenyl group, an aryl group, a heterocyclic group, an acyl group, an alkylsulfonyl group or an arylsulfonyl group) or an oxygen atom.

Among them, $Y_1$ and $Y_2$ are preferably NR (R represents a hydrogen atom, an alkyl group or an alkenyl group) or an oxygen atom, more preferably NR (R represents a hydrogen atom) or an oxygen atom.

In the formula (2), $R_{10}$ and $Y_1$ may be bonded to each other to form a five, six or seven-membered ring, and $R_{11}$ and $Y_2$ may be bonded to each other to form a five, six or seven-membered ring. The five, six or seven-membered ring may be the ring as previously described.

The compound represented by the formula (2) preferably has at least one substituent selected from the above preferred examples, more preferably more substituents are selected from the above preferred examples, and most preferably all of the substituents are selected from the above preferred examples.

The following are specific examples of the compound represented by the formula (2). However, the invention is not limited to these examples.

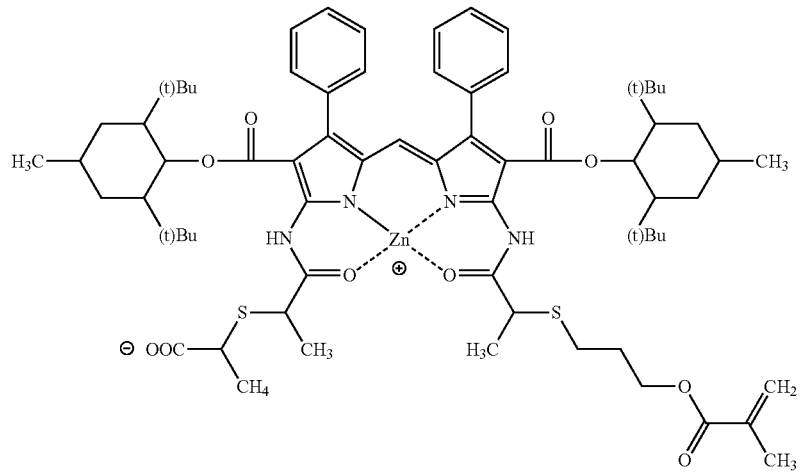

(a-1)

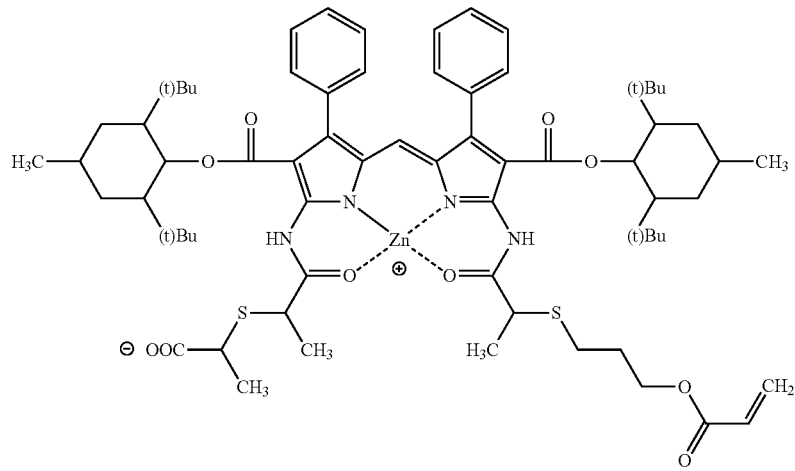

(a-2)

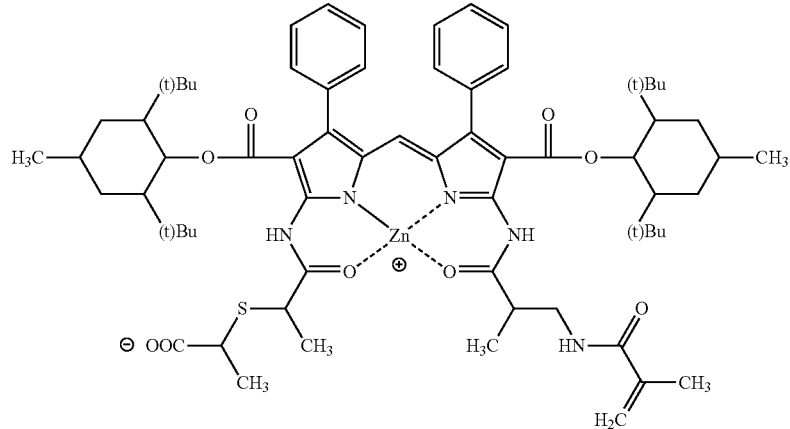

(a-3)

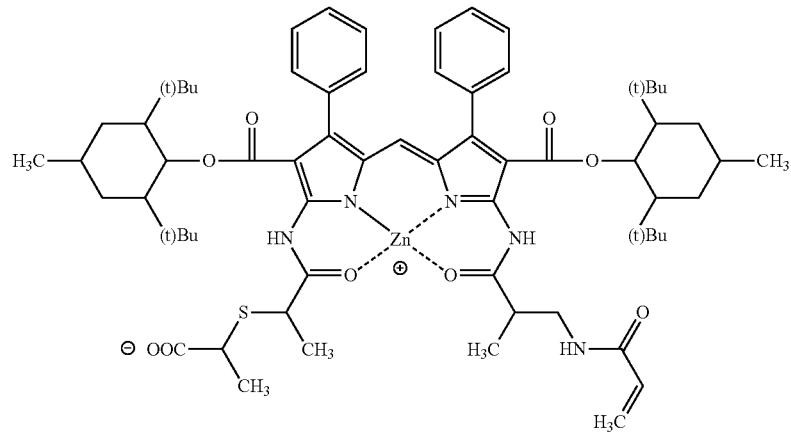
(a-4)
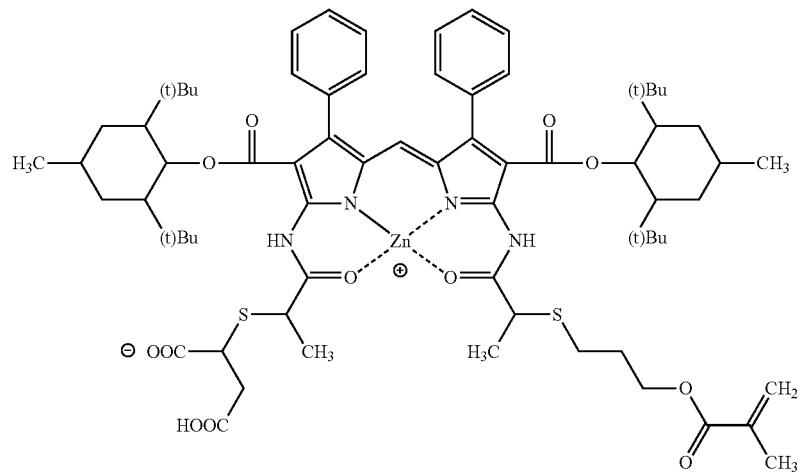
(a-5)
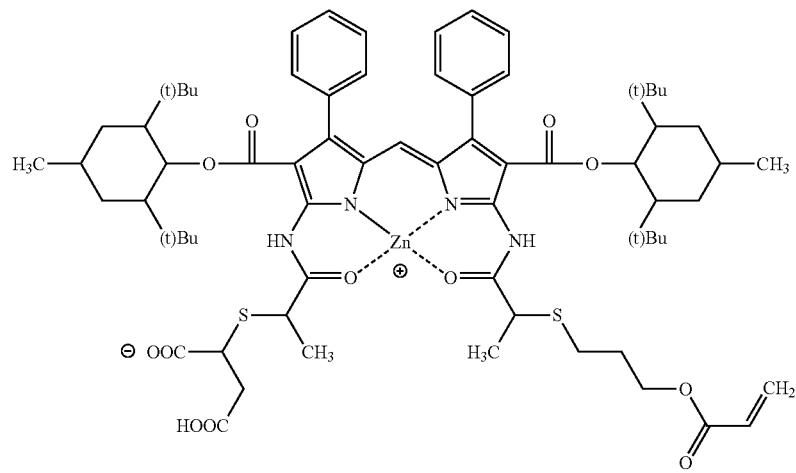
(a-6)

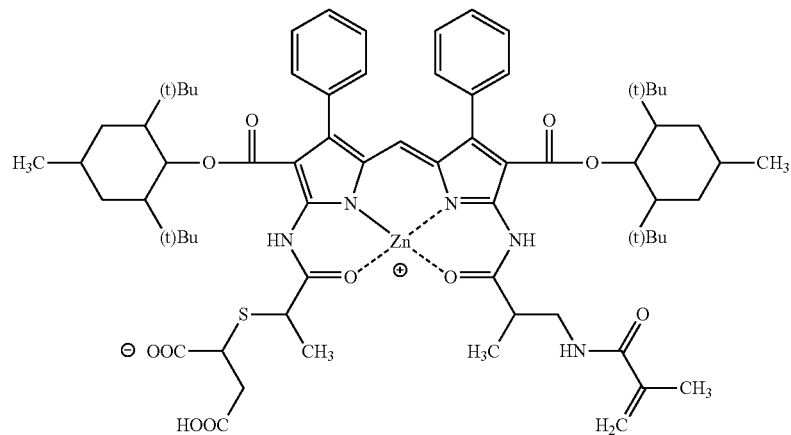
(a-7)
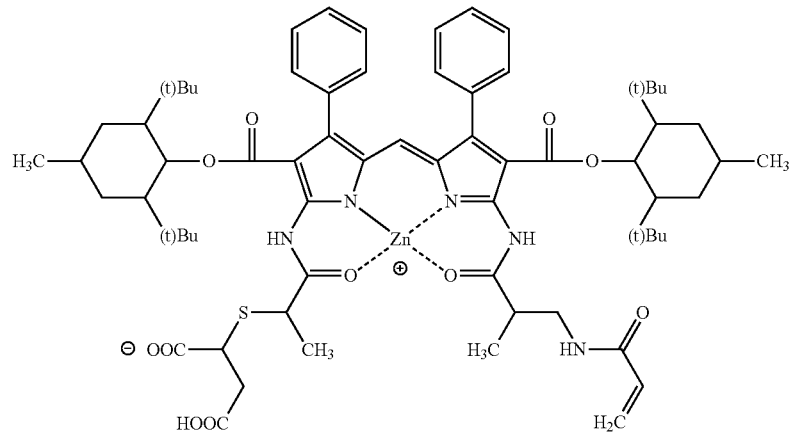
(a-8)
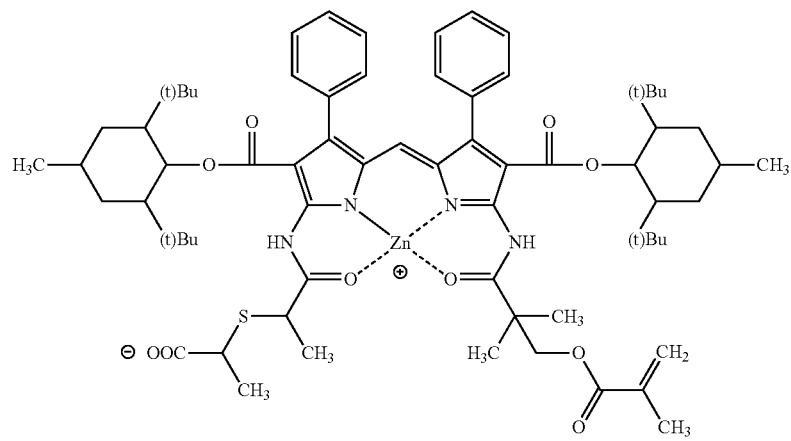
(a-9)

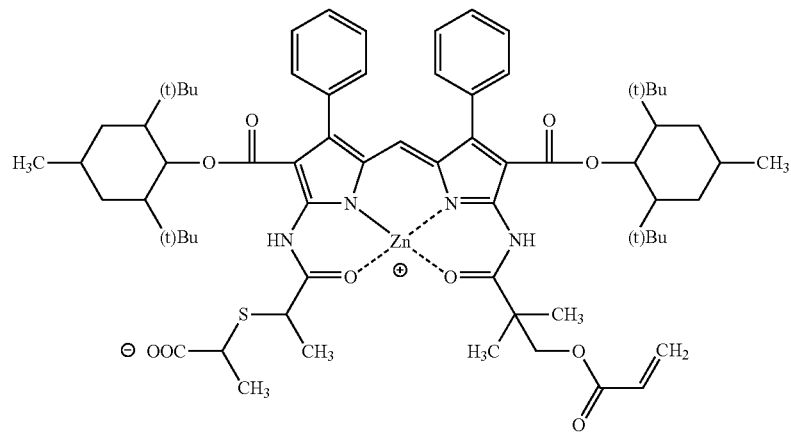
(a-10)
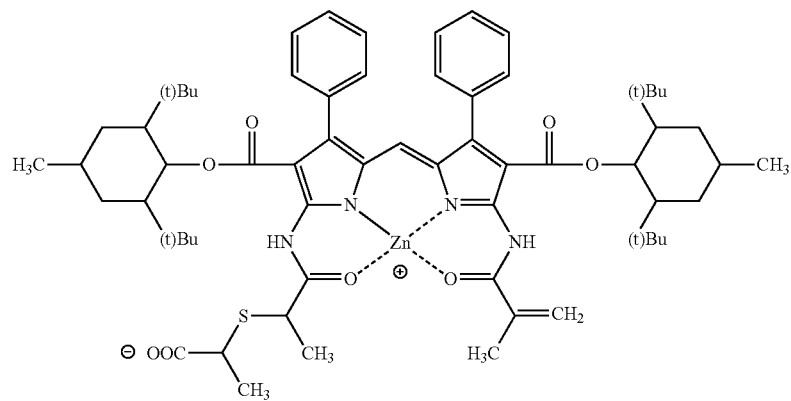
(a-11)
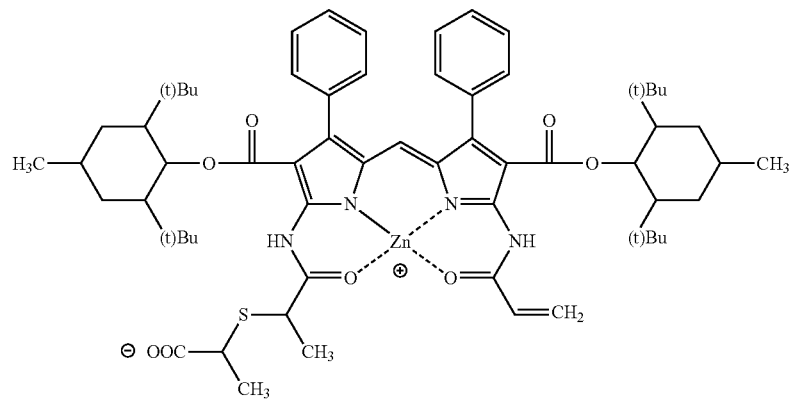
(a-12)

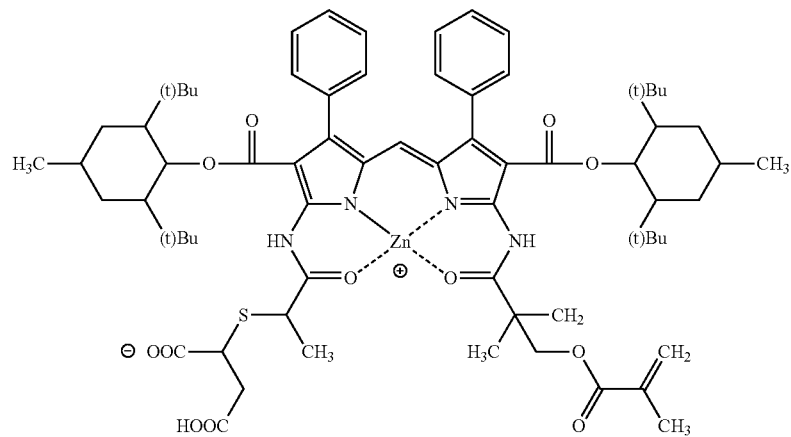
(a-13)
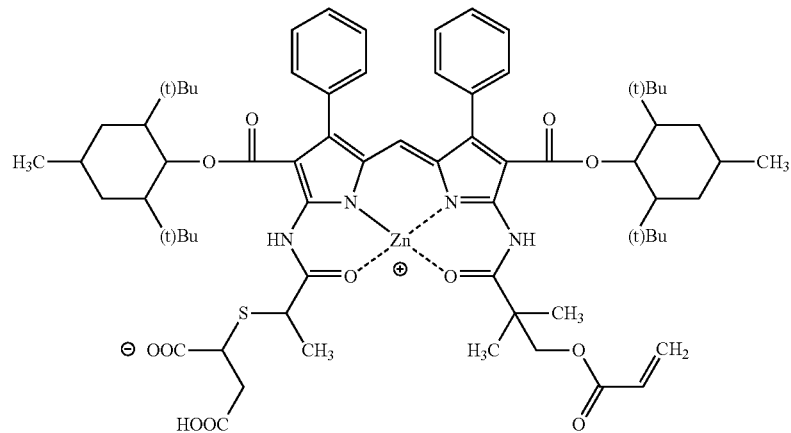
(a-14)
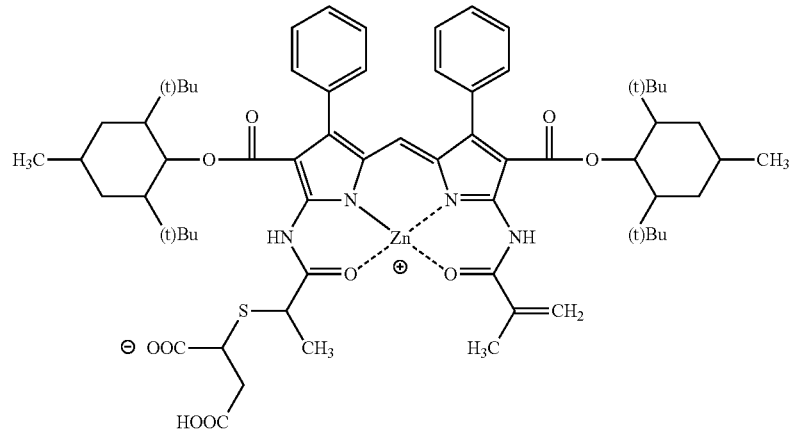
(a-15)

-continued
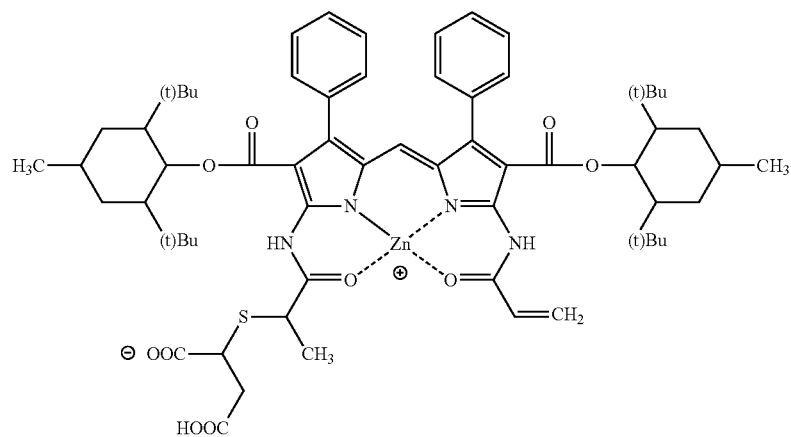
(a-16)
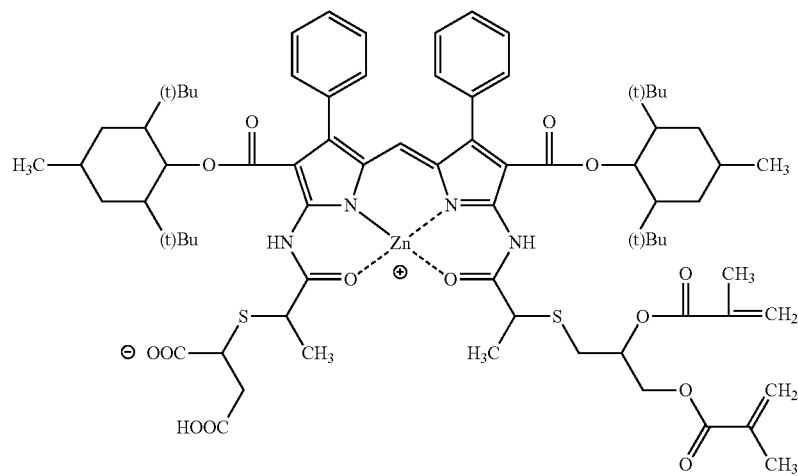
(a-17)
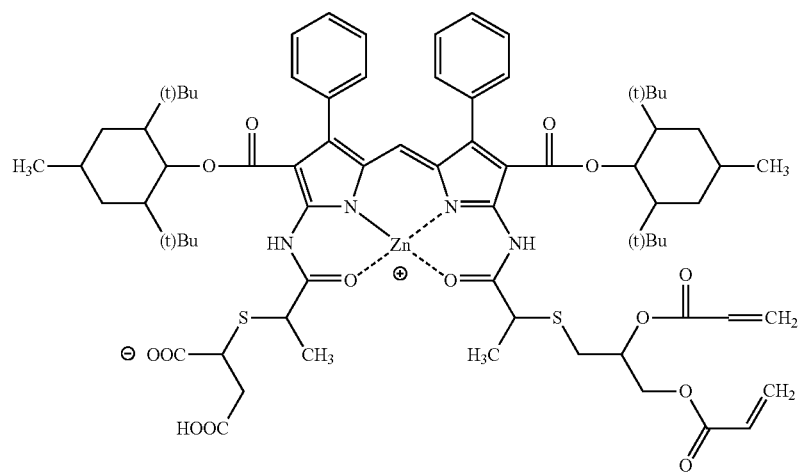
(a-18)

(a-19)
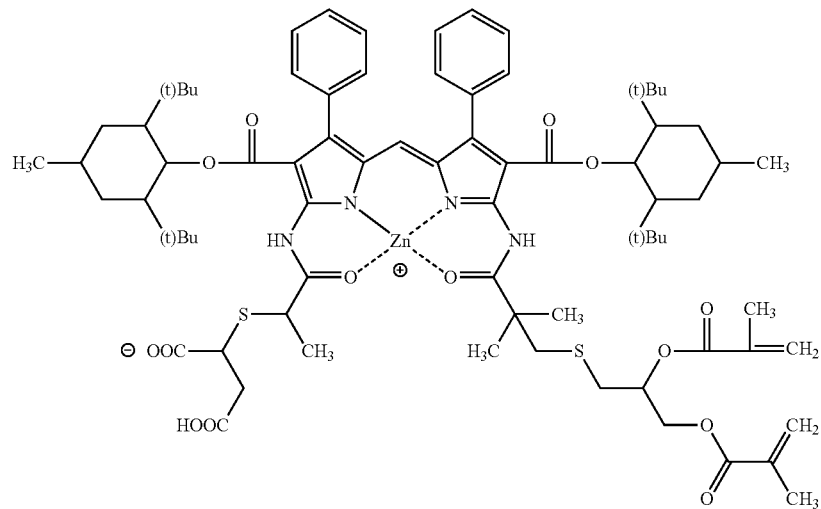
(a-20)
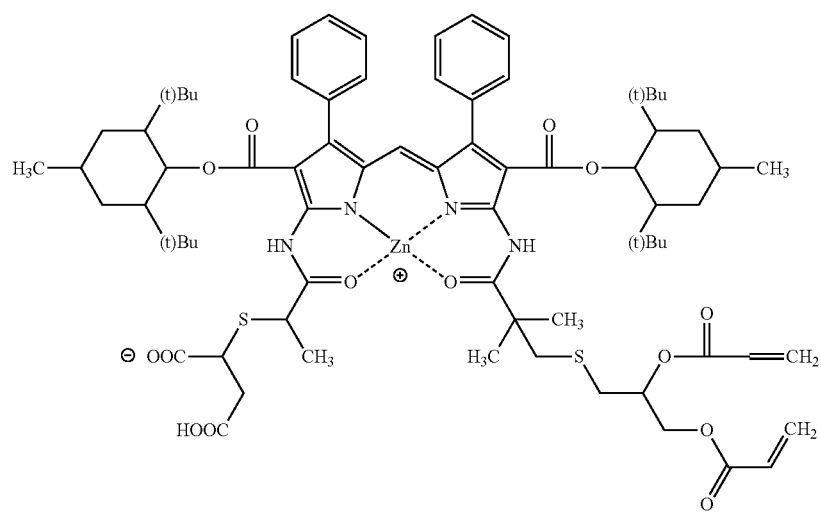
(a-21)
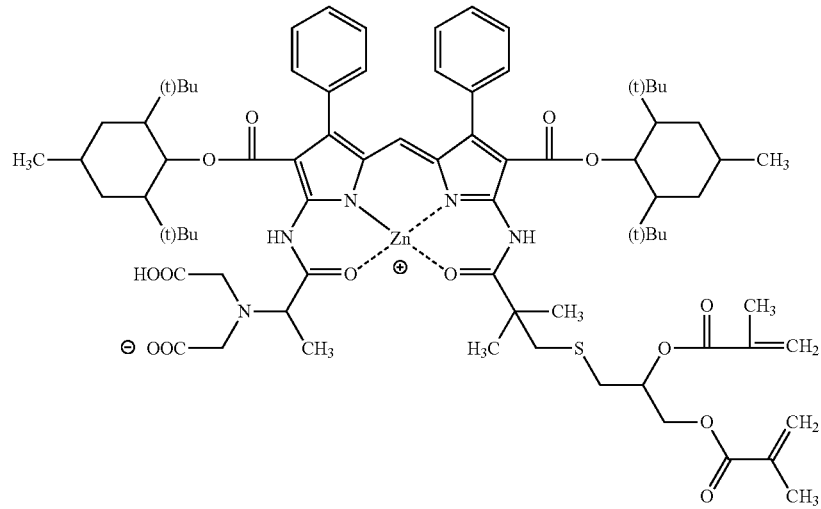

-continued
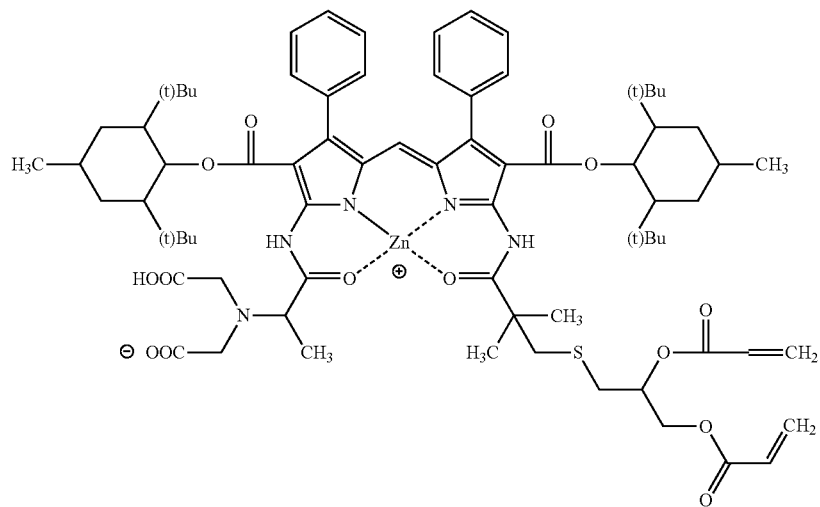
(a-22)
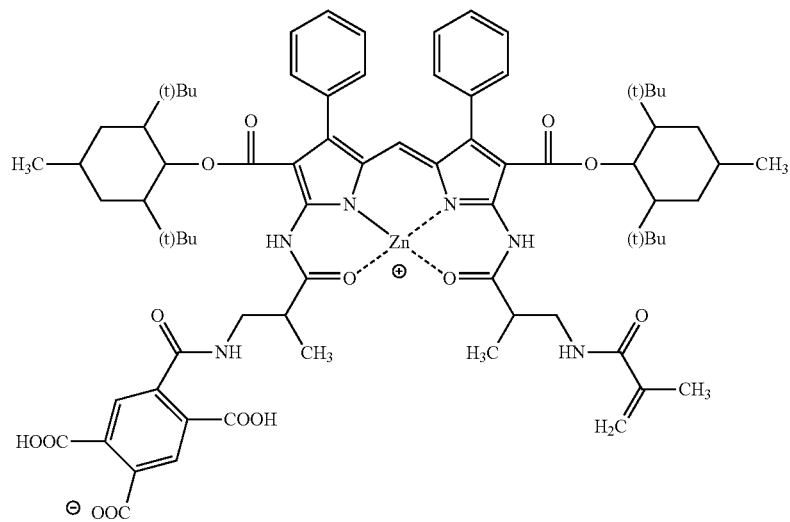
(a-23)
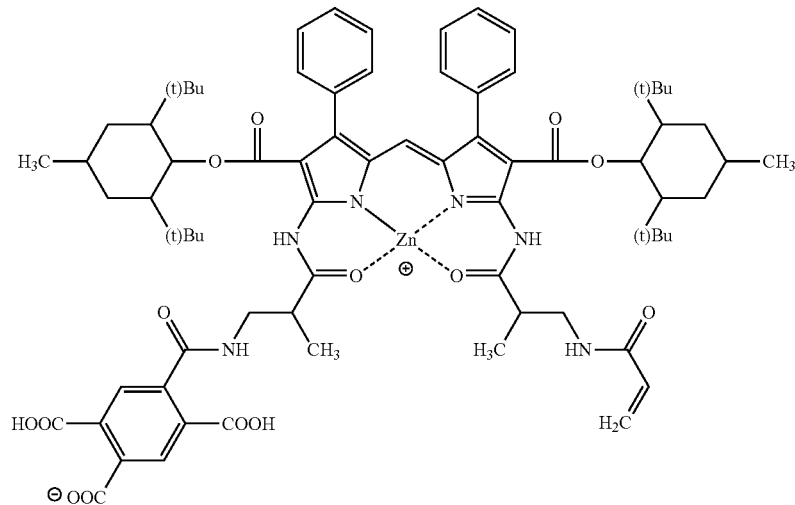
(a-24)

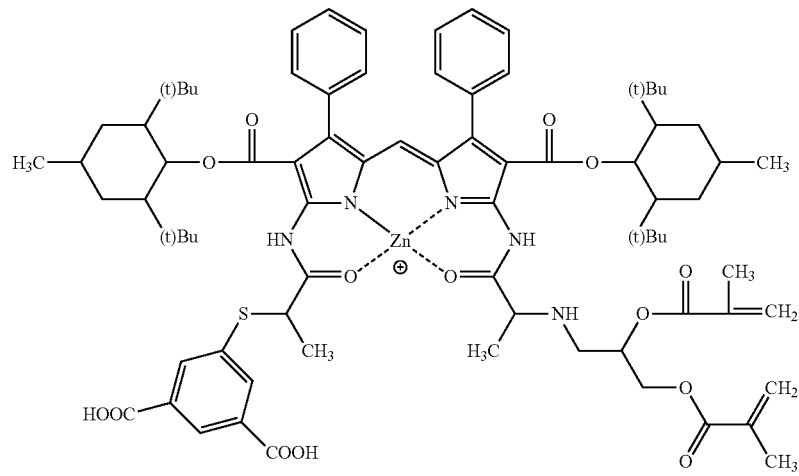
(a-25)
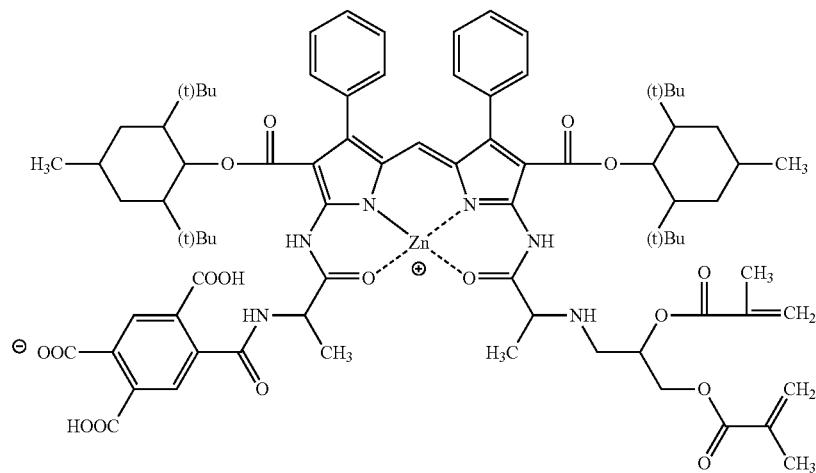
(a-26)
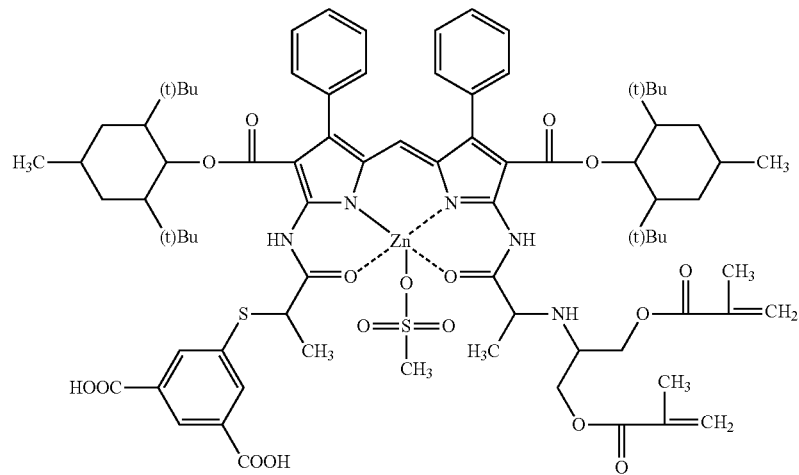
(a-27)

(a-28)
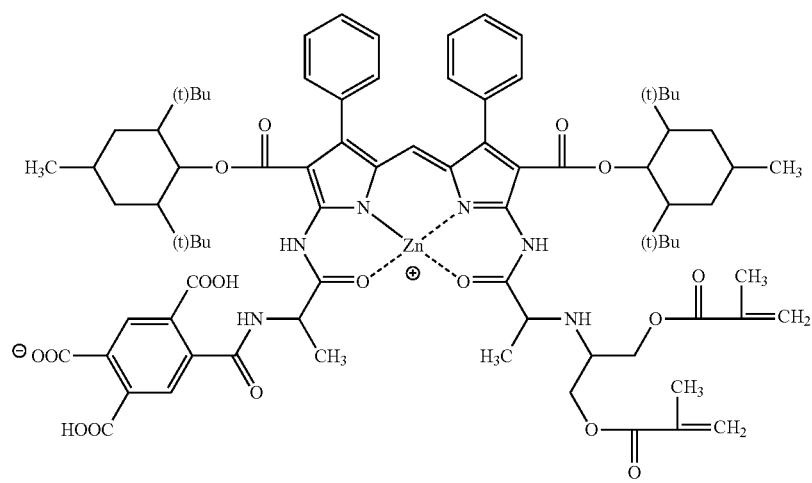
(a-29)
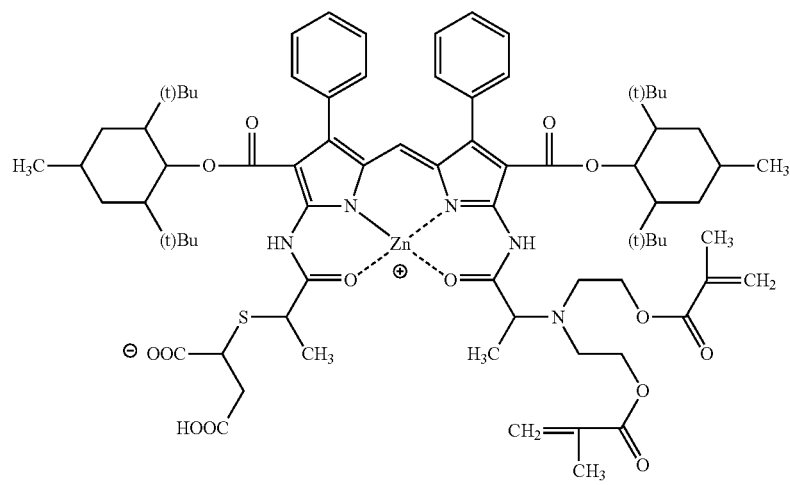
(a-30)
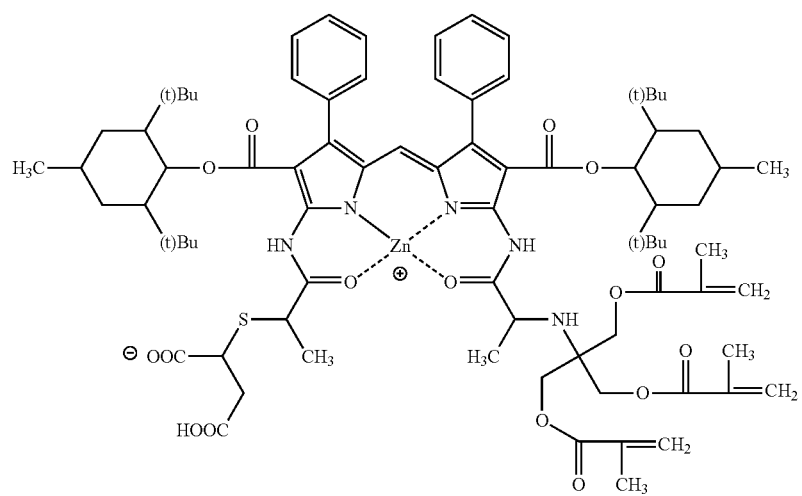

-continued
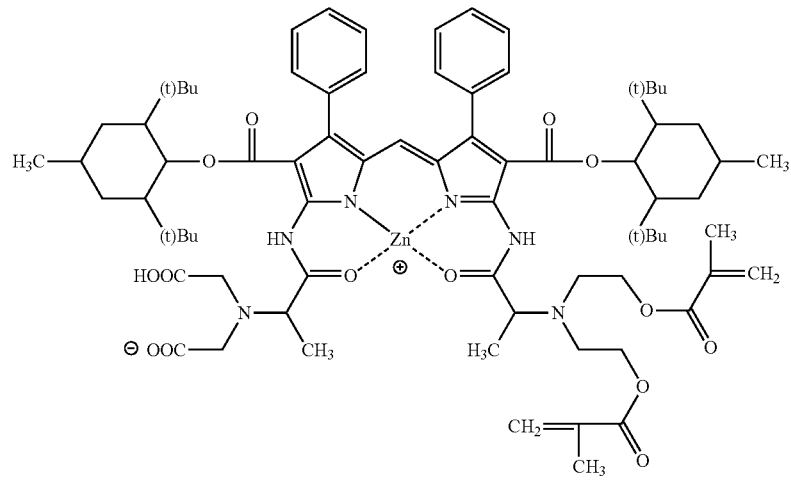
(a-31)
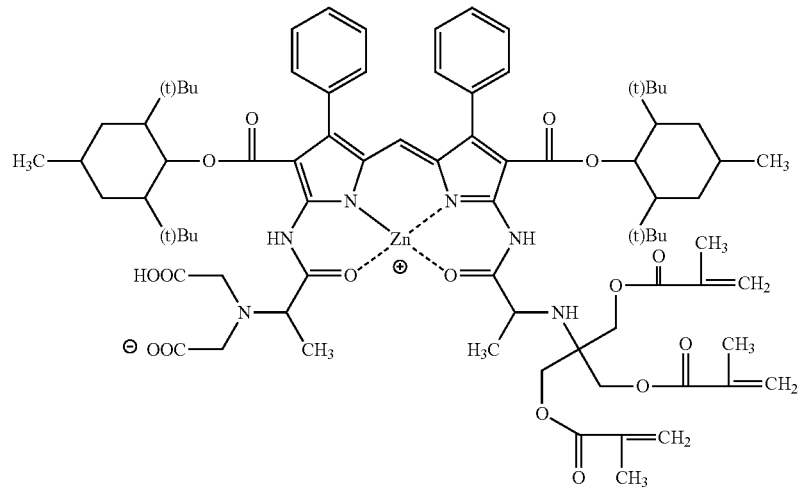
(a-32)
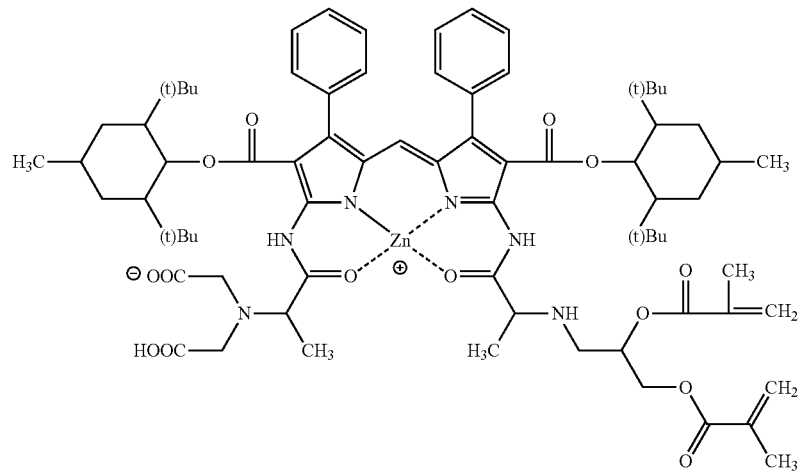
(a-33)

-continued
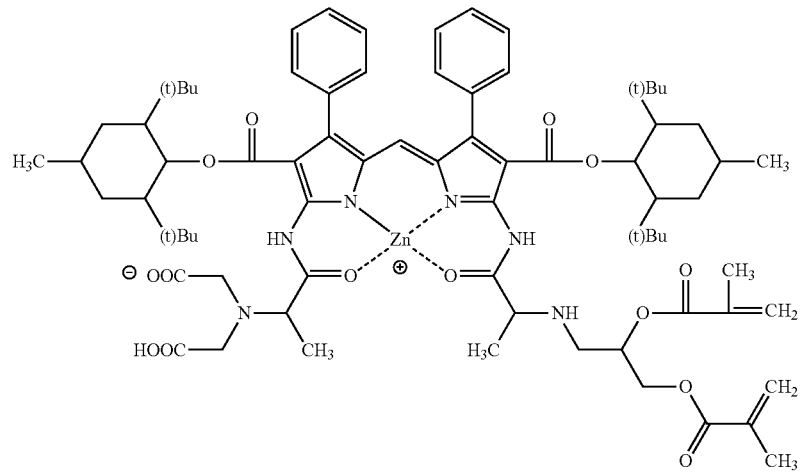
(a-34)
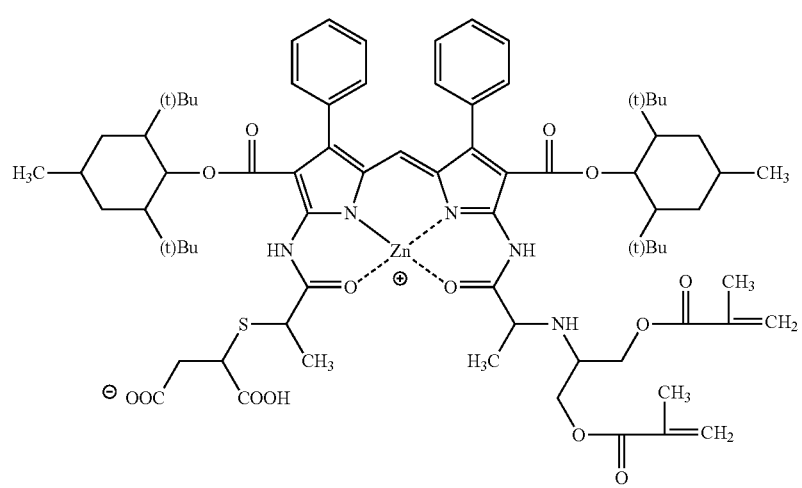
(a-35)
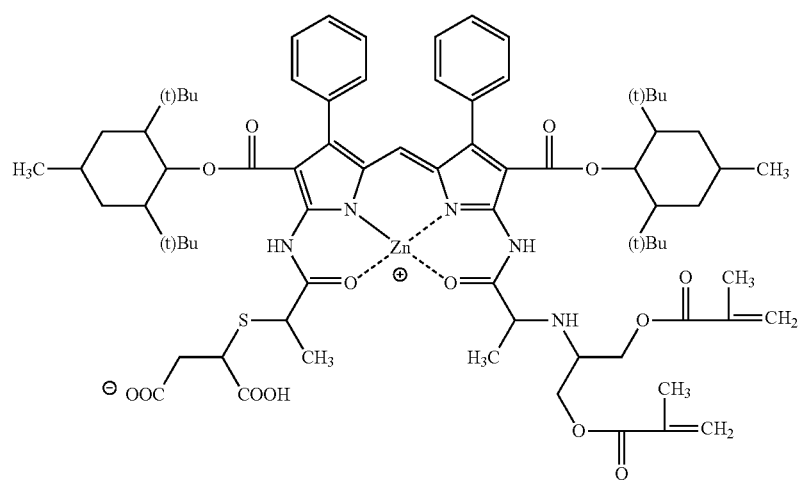
(a-36)

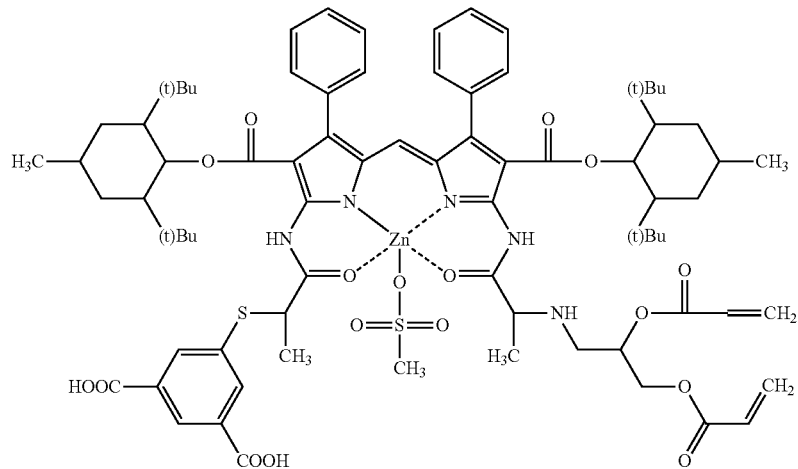
(a-37)
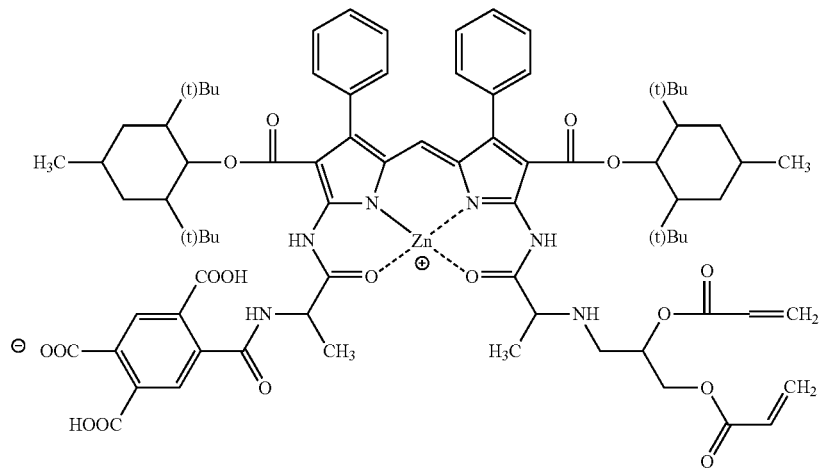
(a-38)
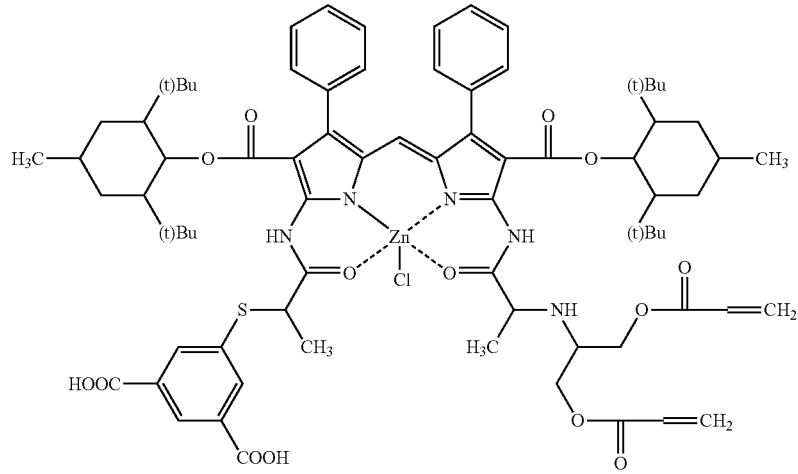
(a-39)

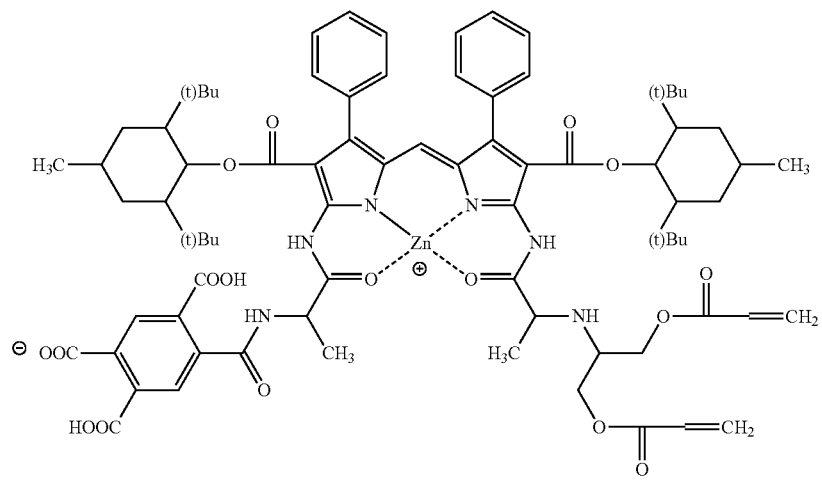
(a-40)
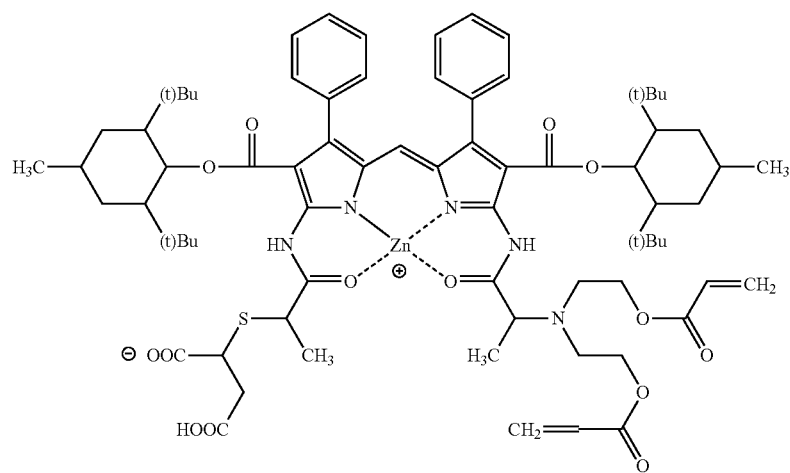
(a-41)
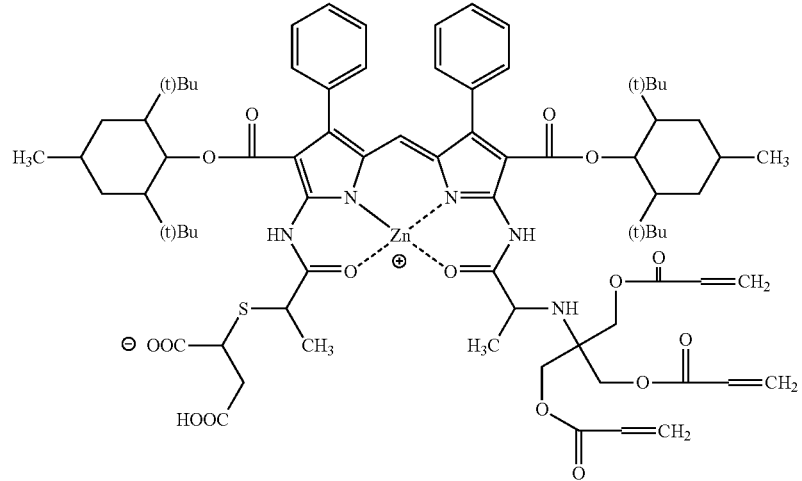
(a-42)

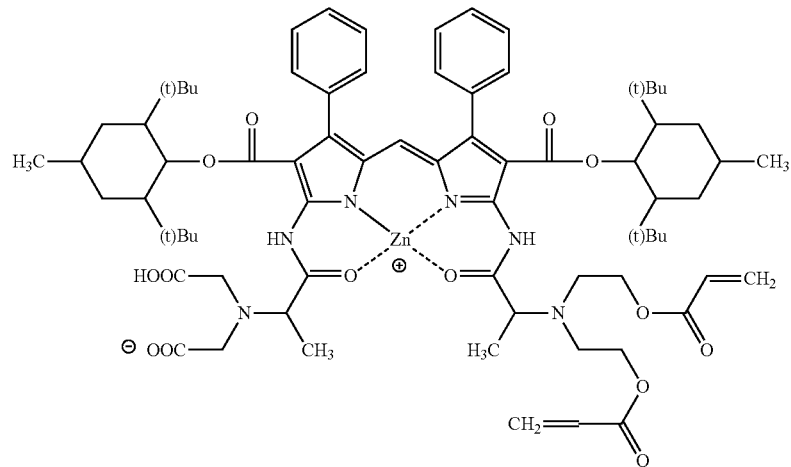
(a-43)
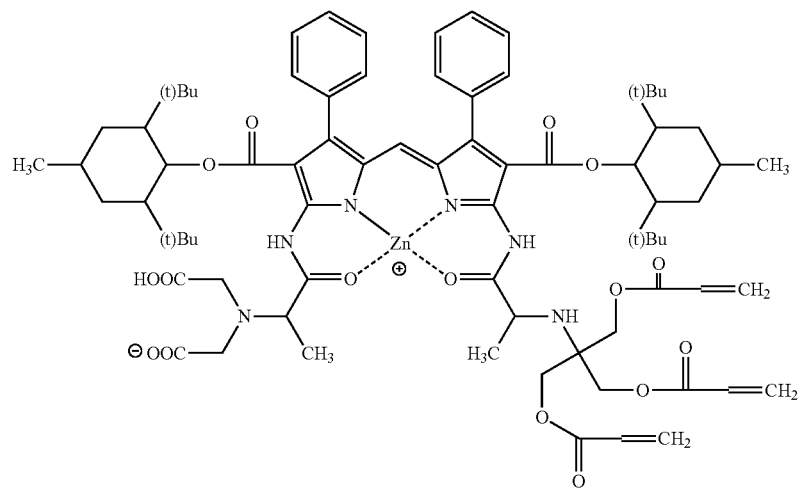
(a-44)
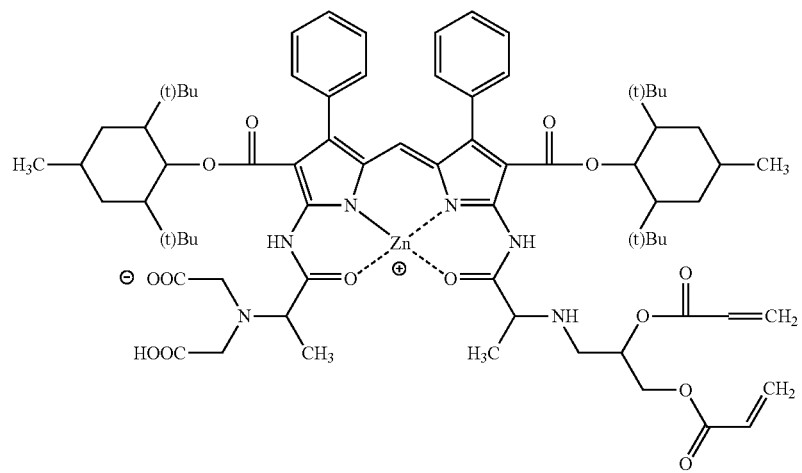
(a-45)

-continued
(a-46)
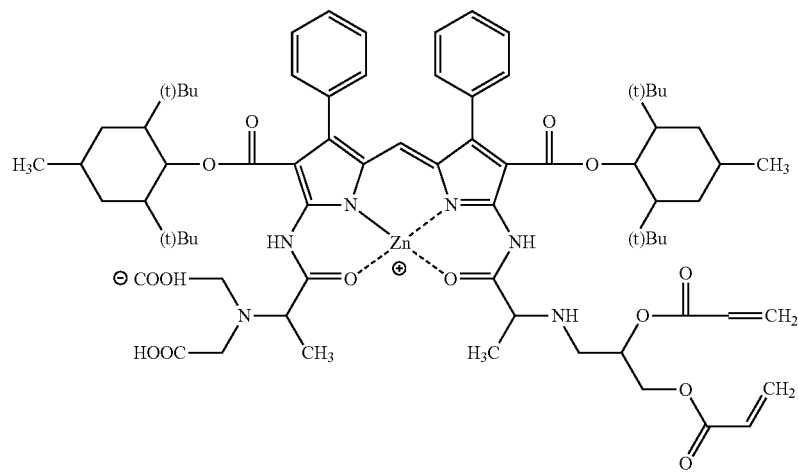
(a-47)
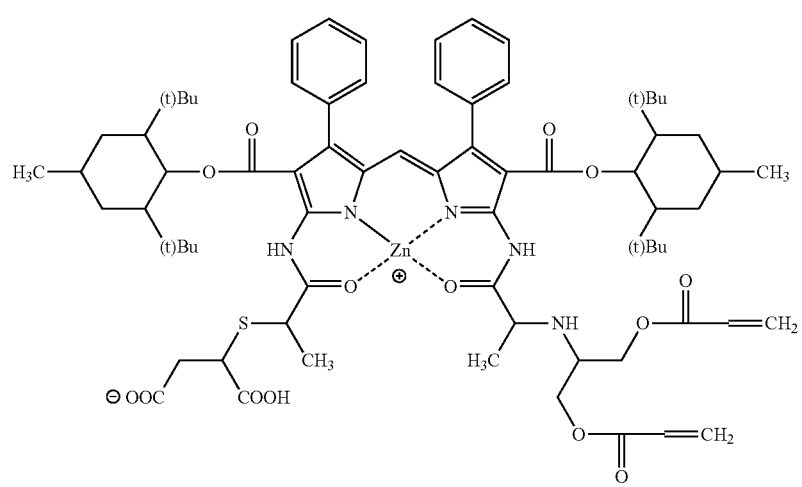
(a-48)
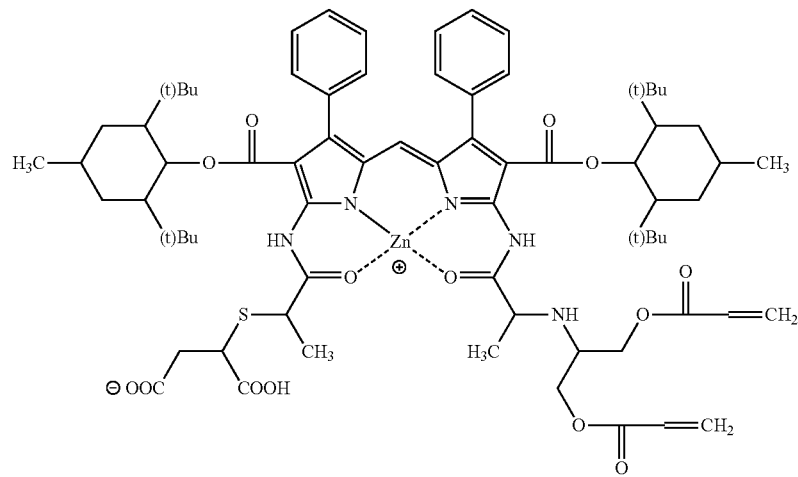

(b-1)
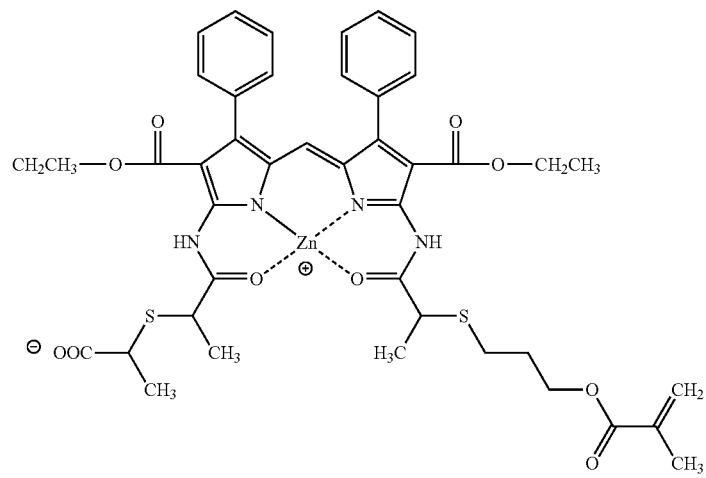
(b-2)
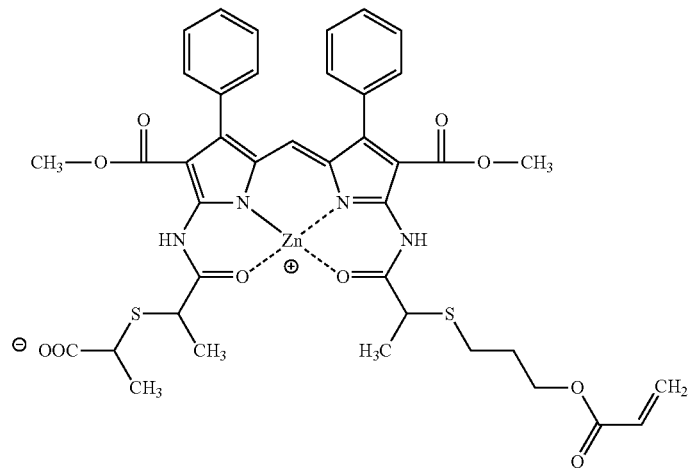
(b-3)
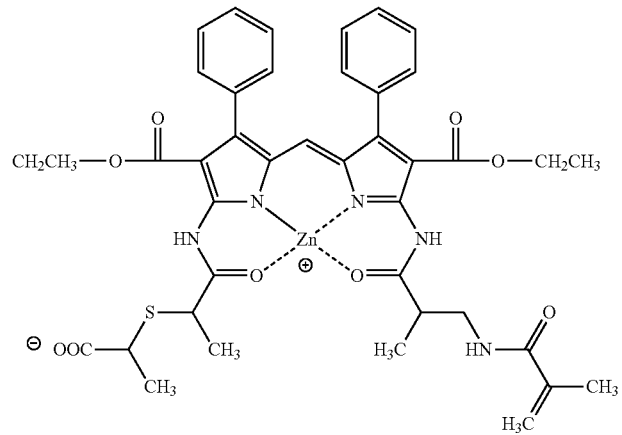

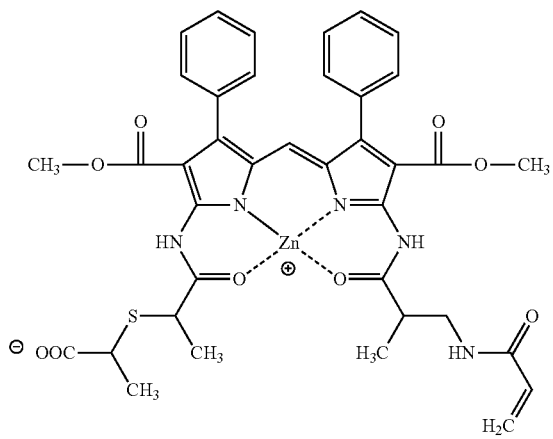
(b-4)
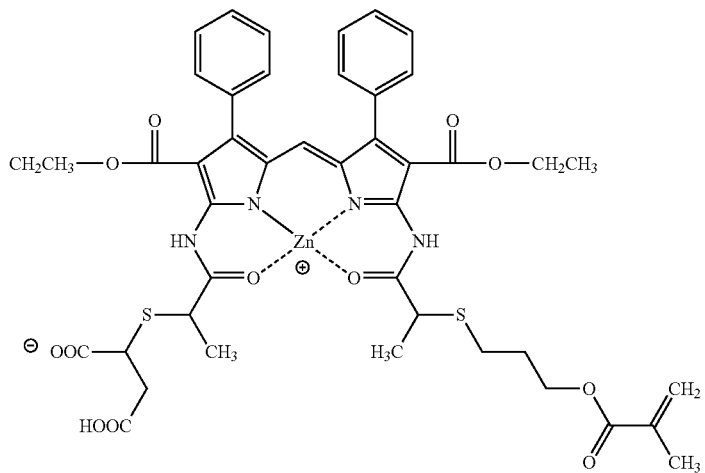
(b-5)
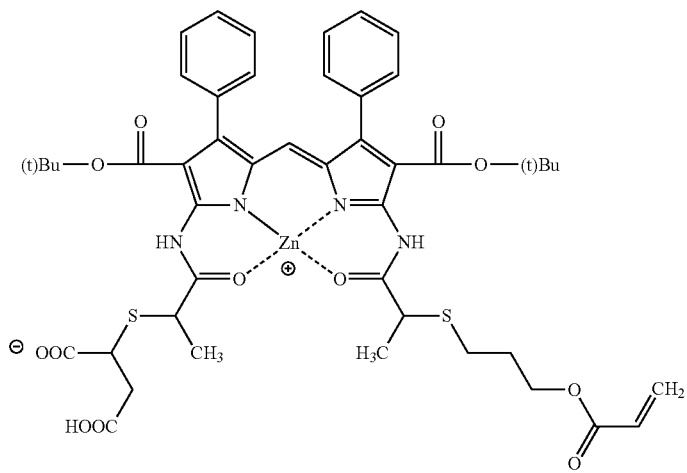
(b-6)

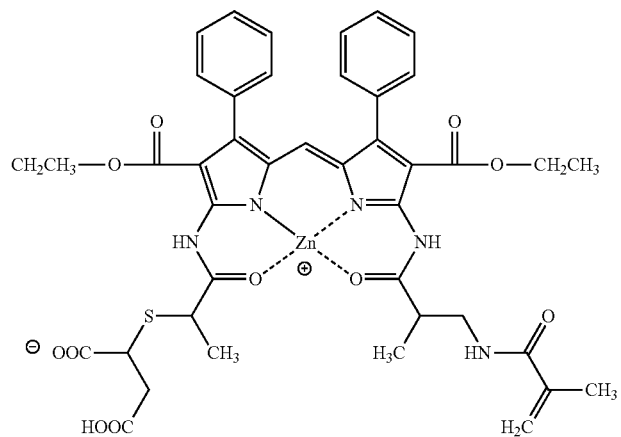
(b-7)
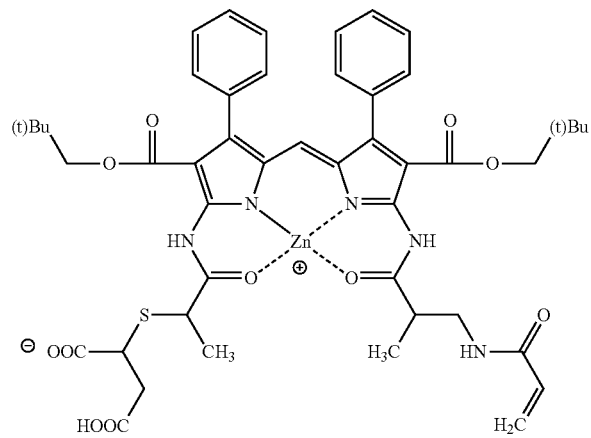
(b-8)
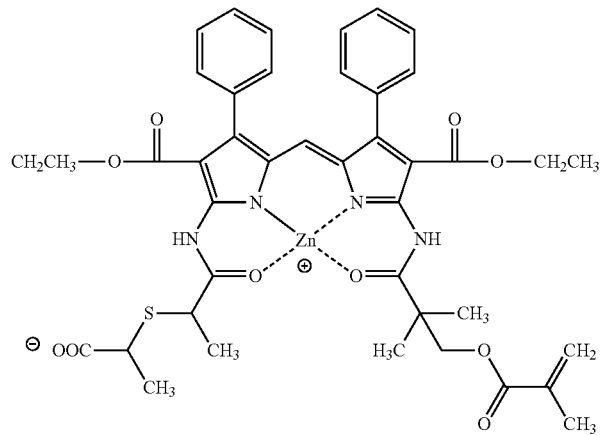
(b-9)

-continued
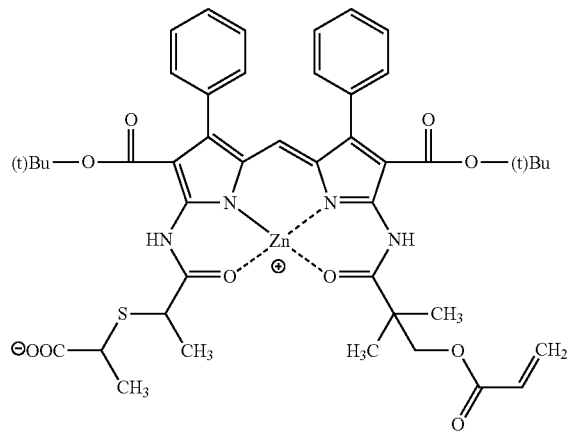
(b-10)
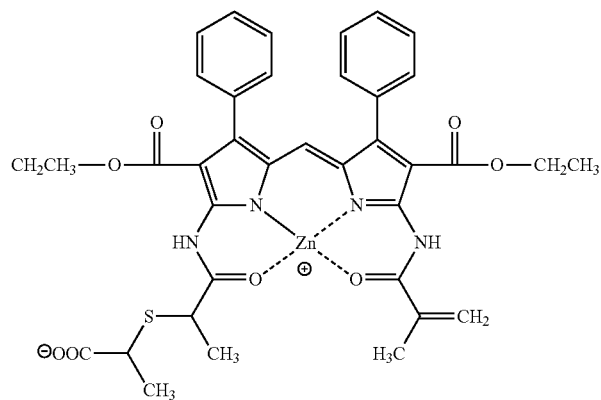
(b-11)
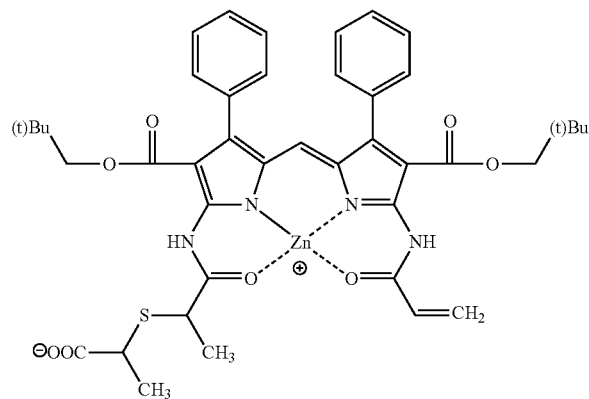
(b-12)

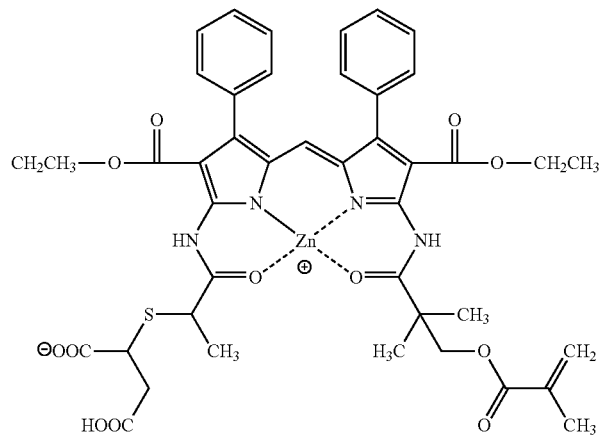
(b-13)
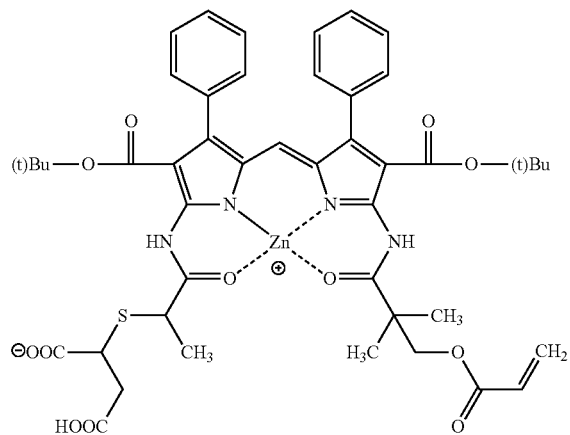
(b-14)
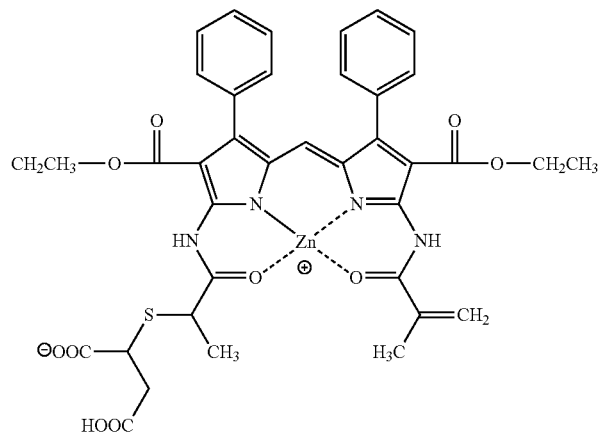
(b-15)

(b-16)
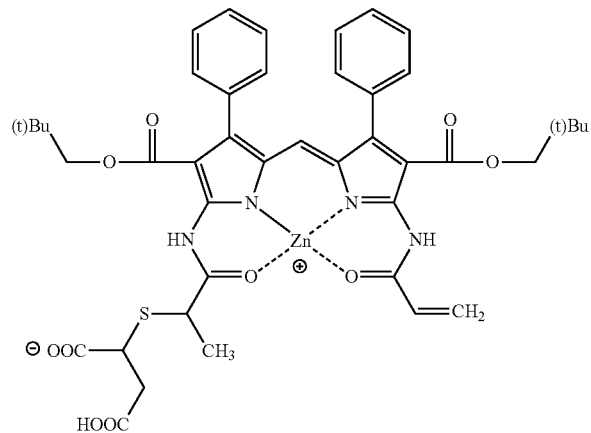
(b-17)
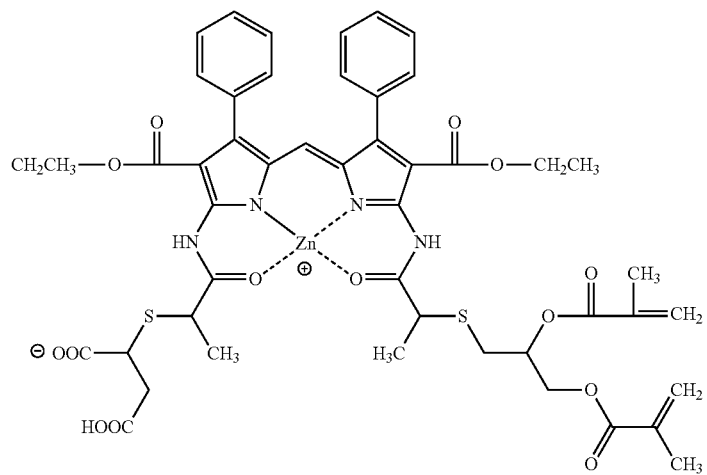
(b-18)
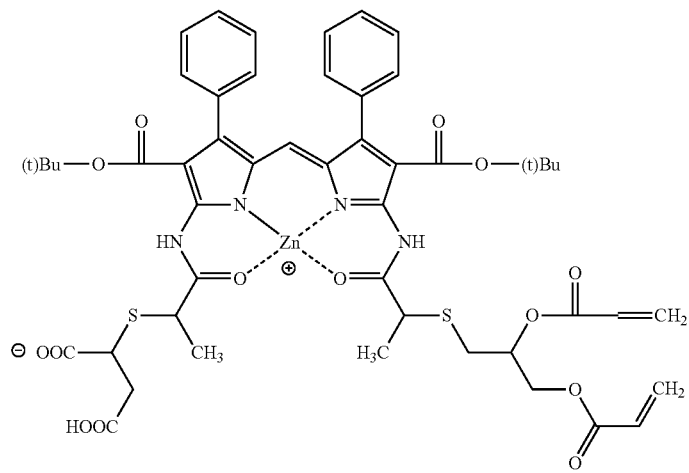

(b-19)
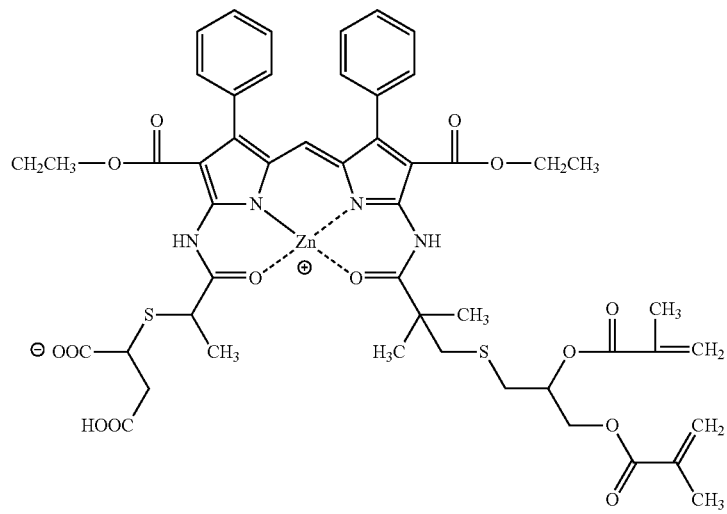
(b-20)
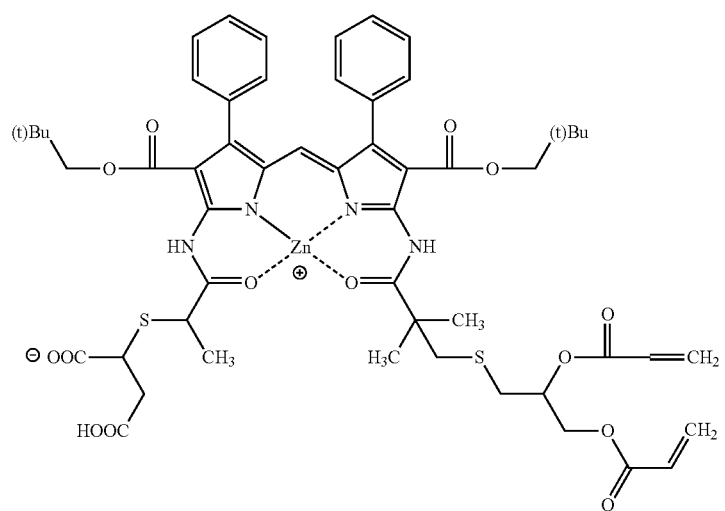
(b-21)
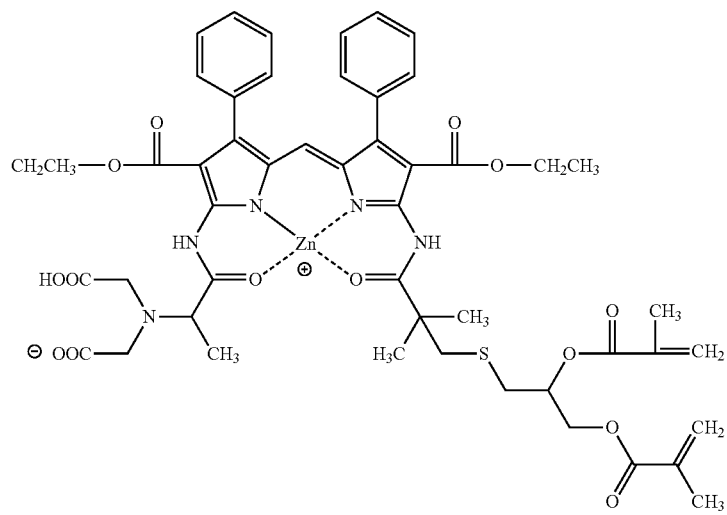

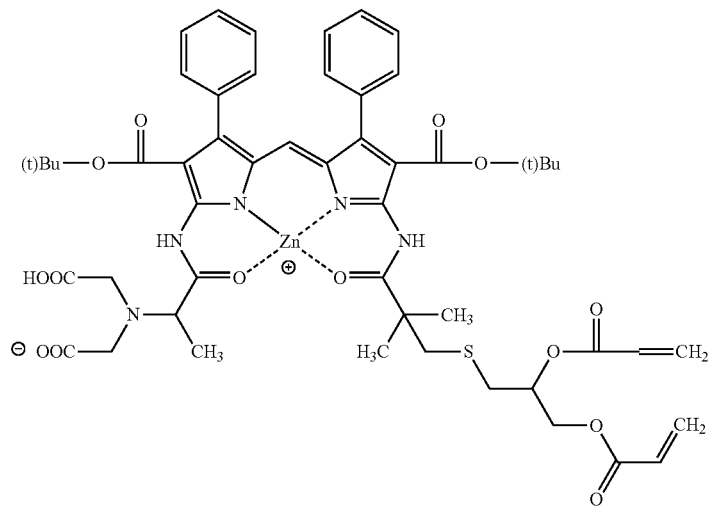
(b-22)
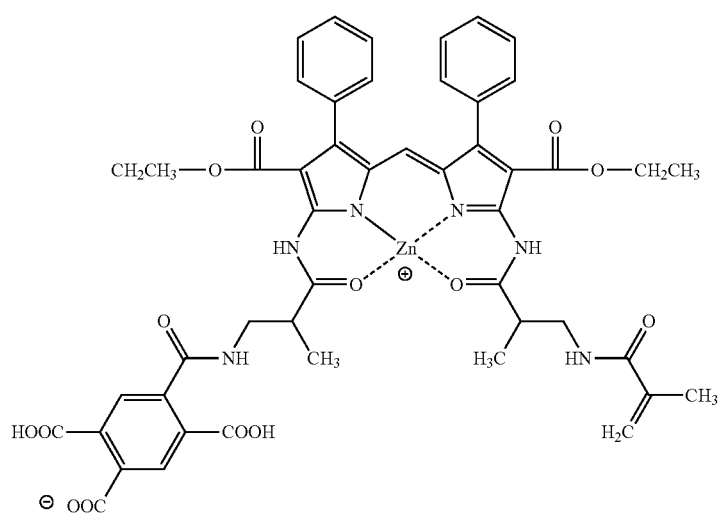
(b-23)
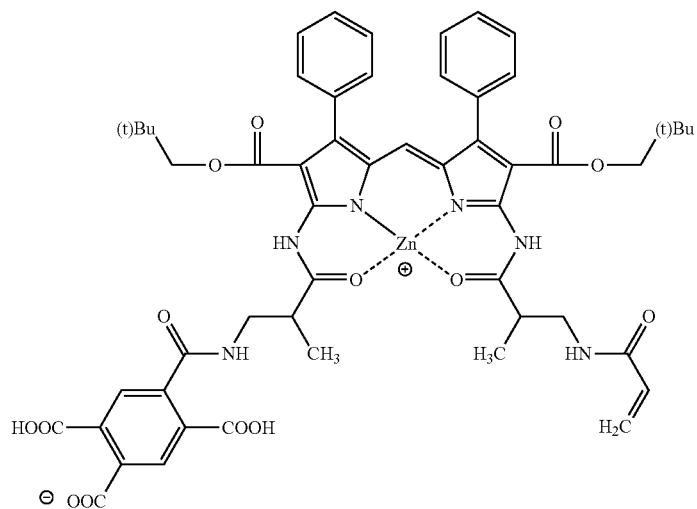
(b-24)

-continued
(b-25)
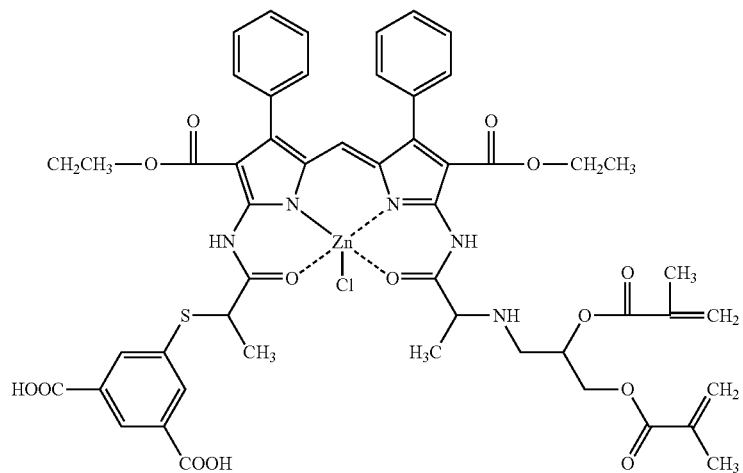
(b-26)
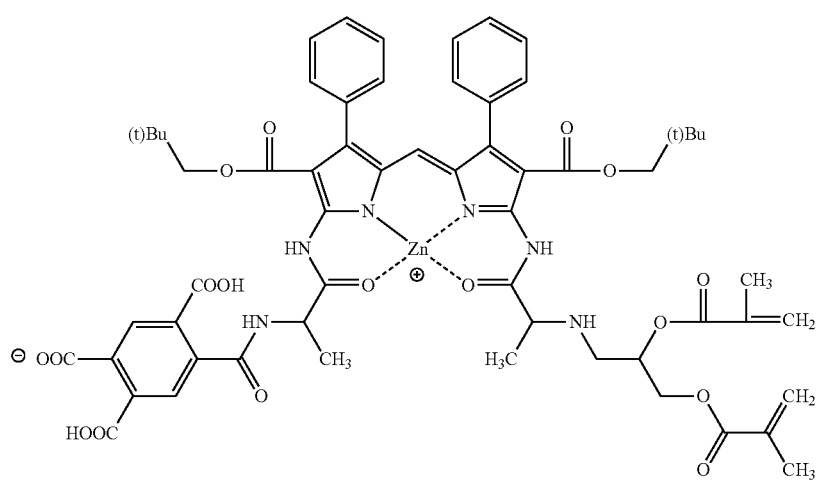
(b-27)
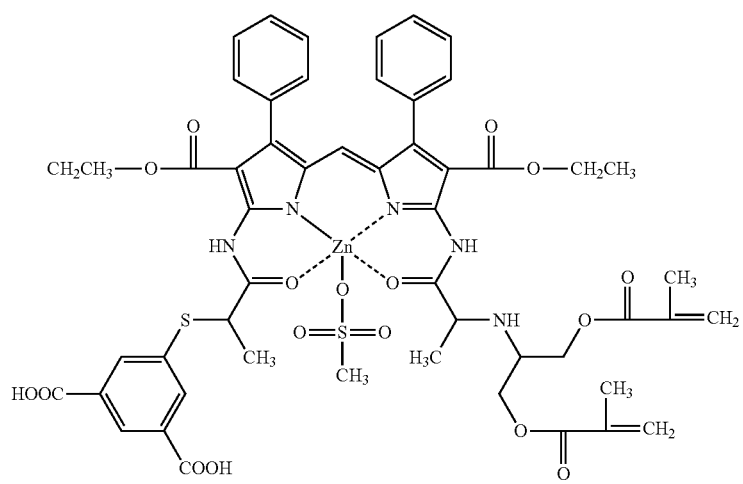

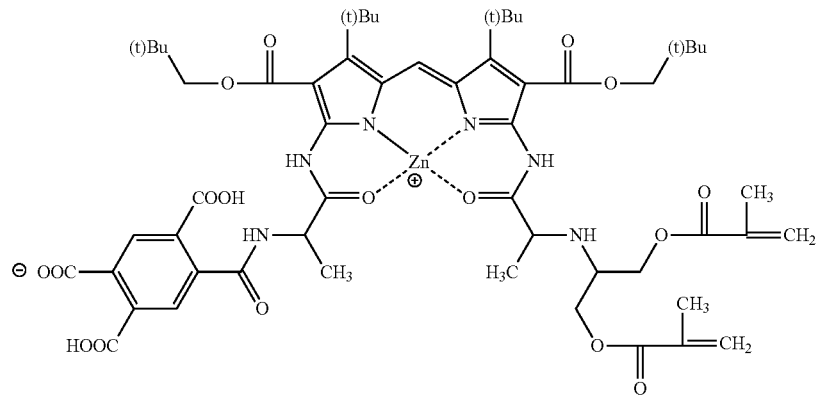
(b-28)
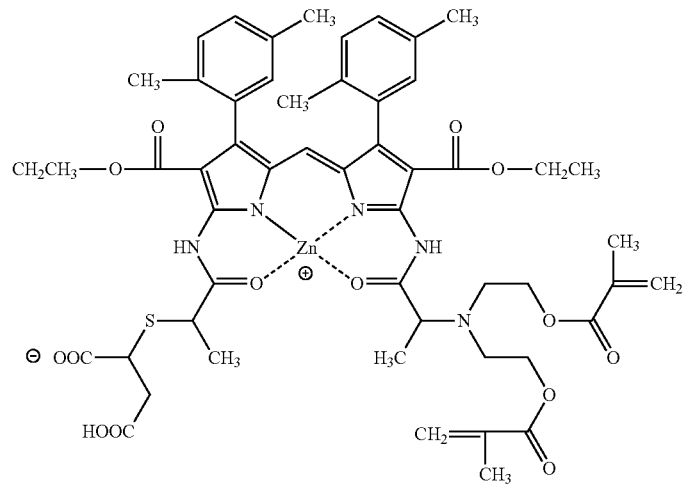
(b-29)
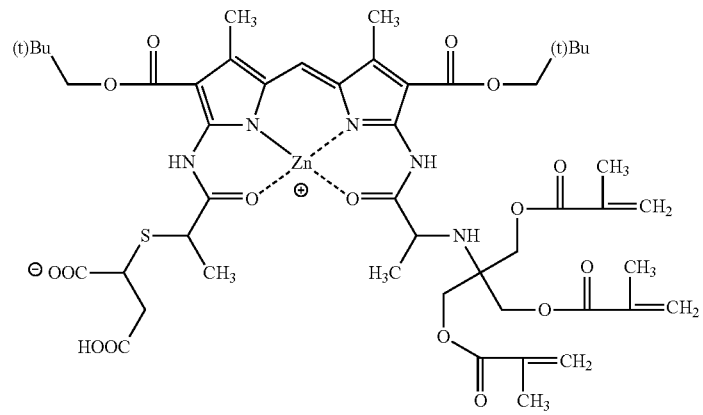
(b-30)

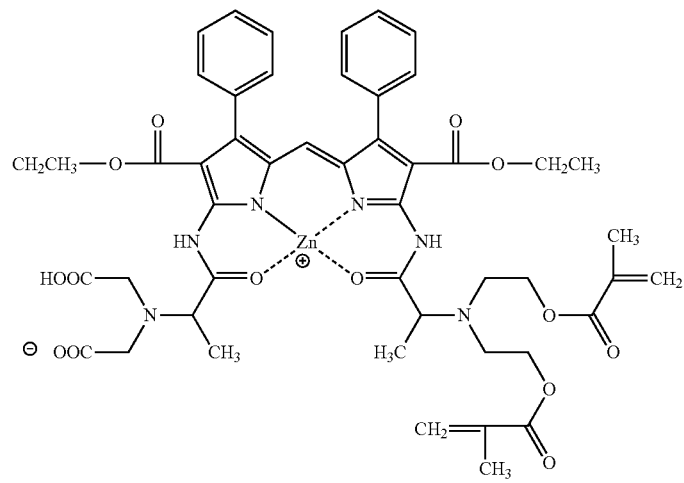
(b-31)
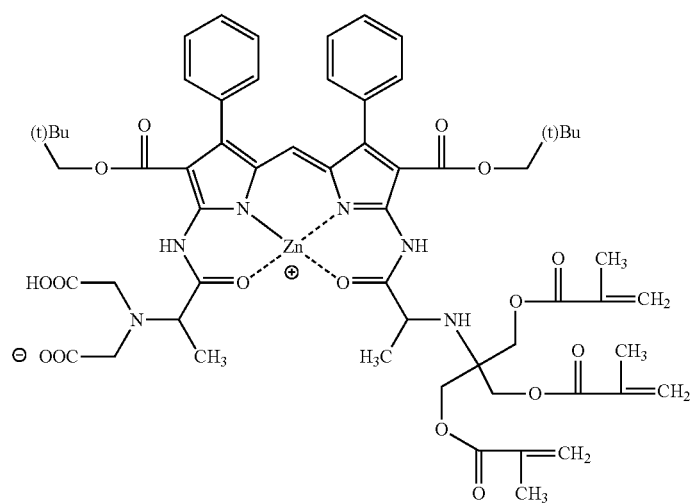
(b-32)
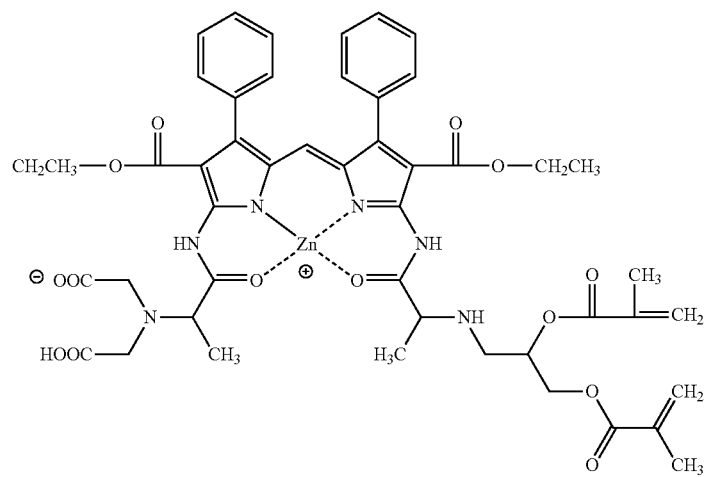
(b-33)

(b-34)
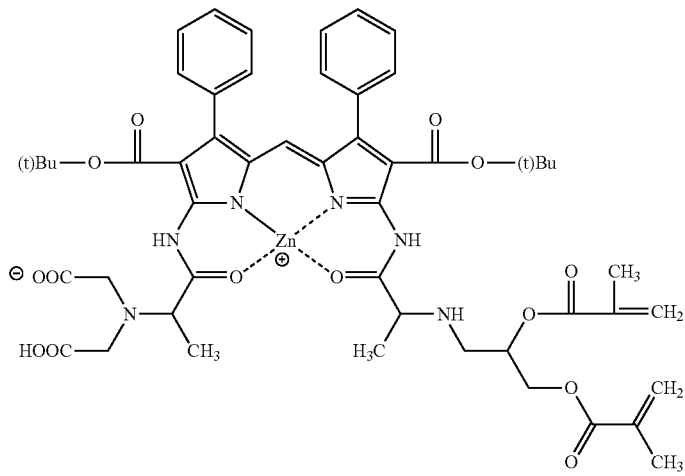
(b-35)
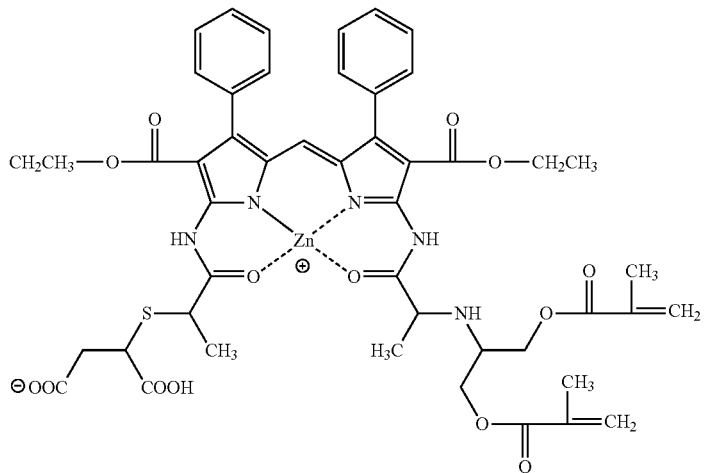
(b-36)
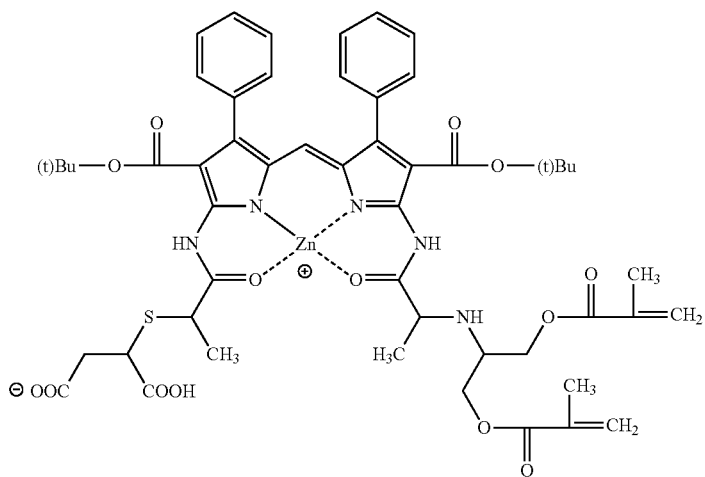

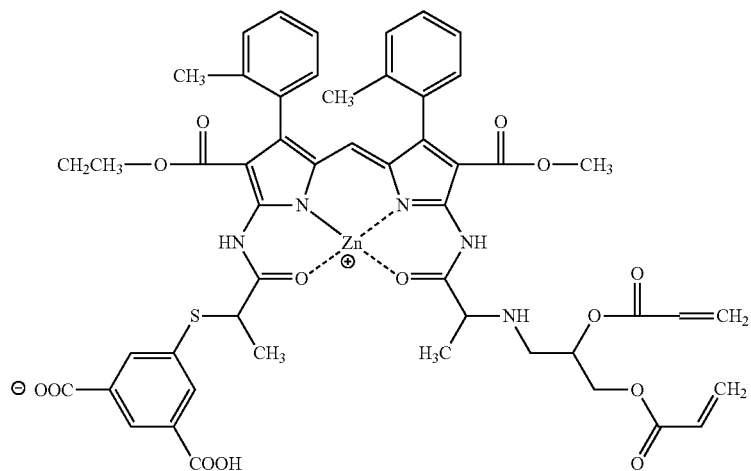
(b-37)
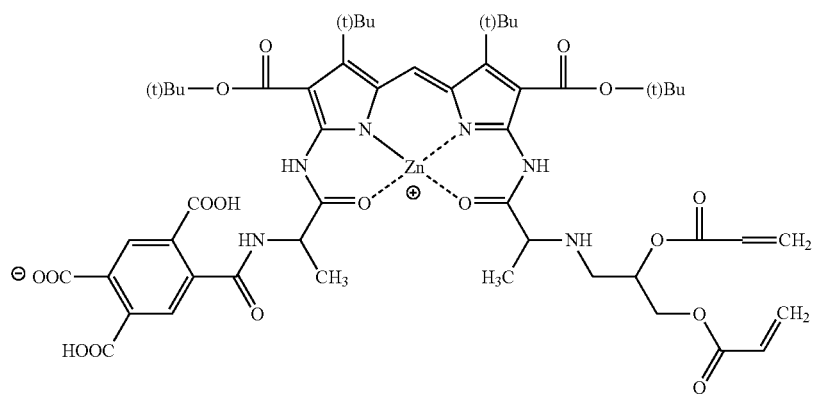
(b-38)
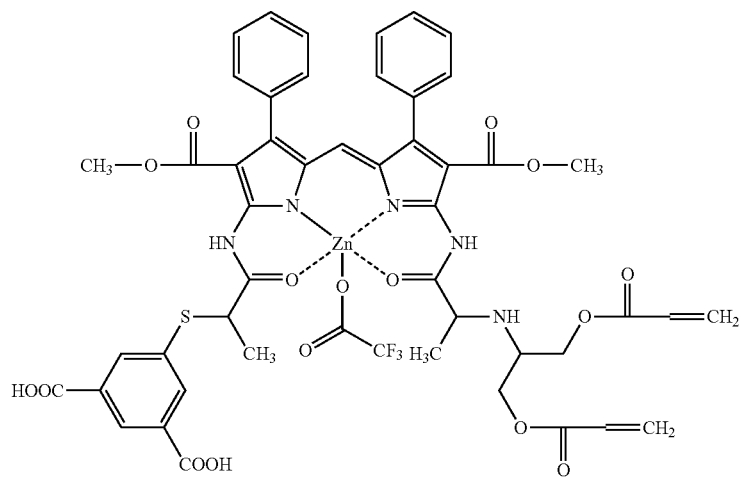
(b-39)

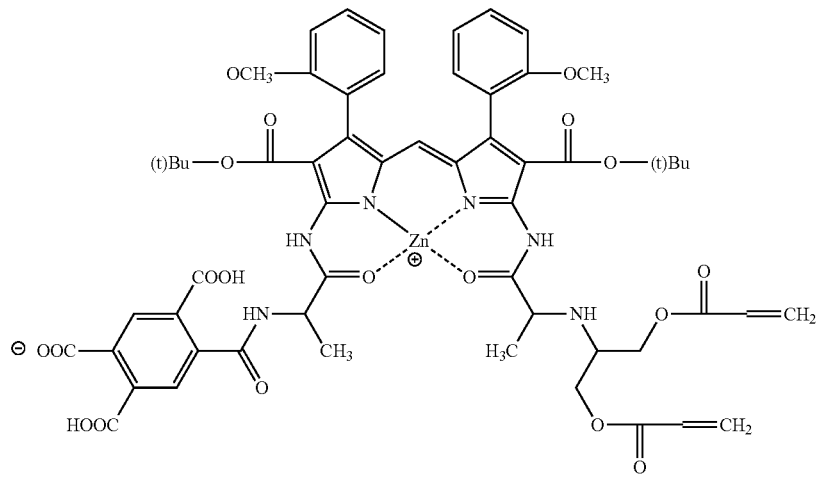
(b-40)
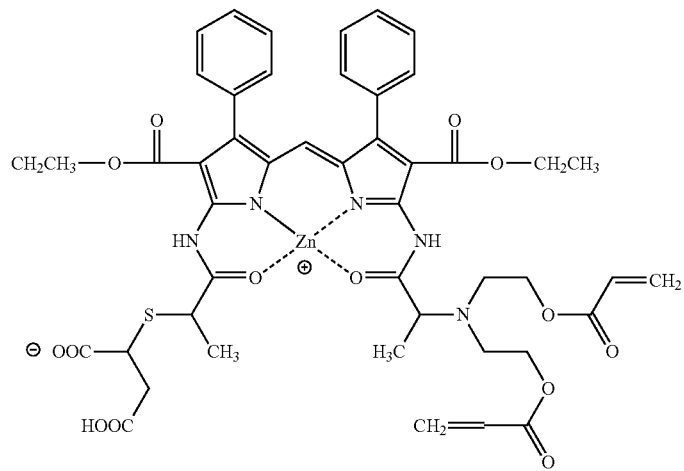
(b-41)
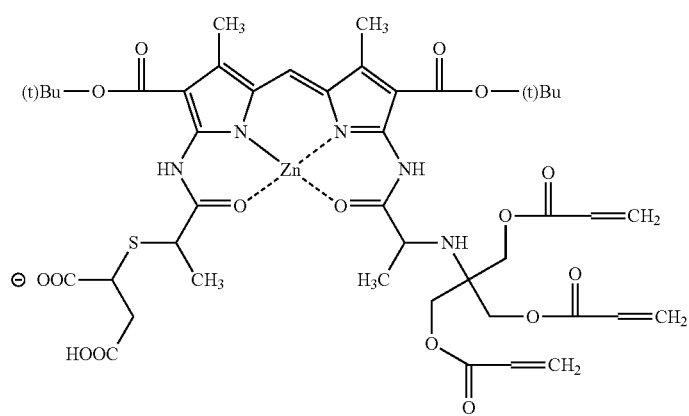
(b-42)

-continued
(b-43)
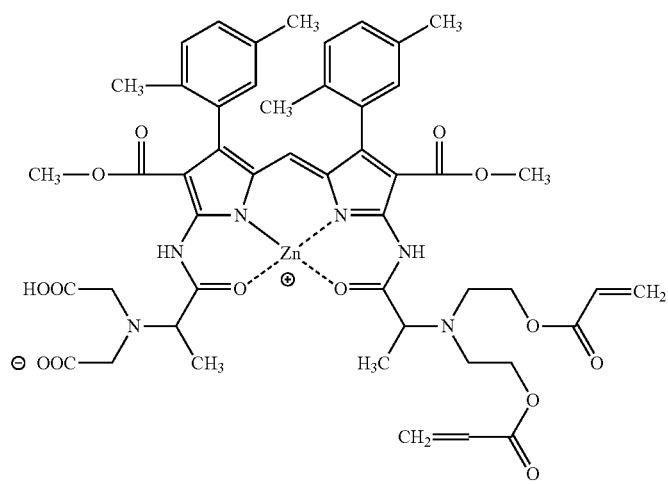
(b-44)
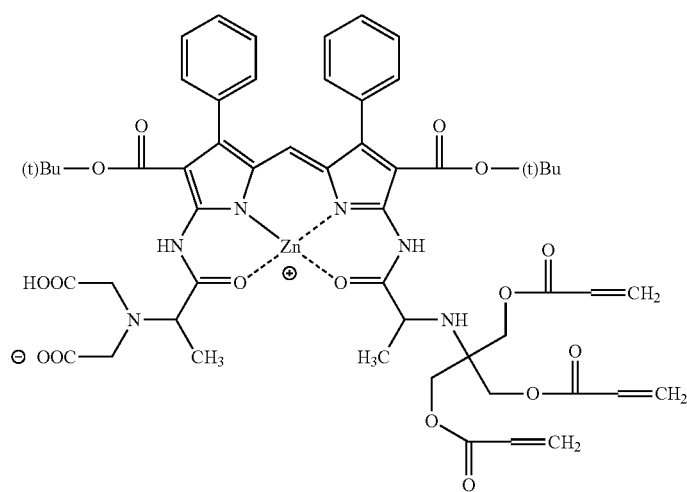
(b-45)
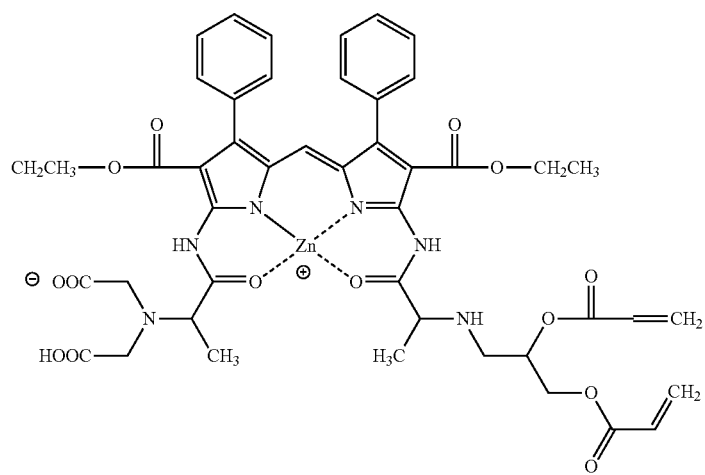

(b-46)
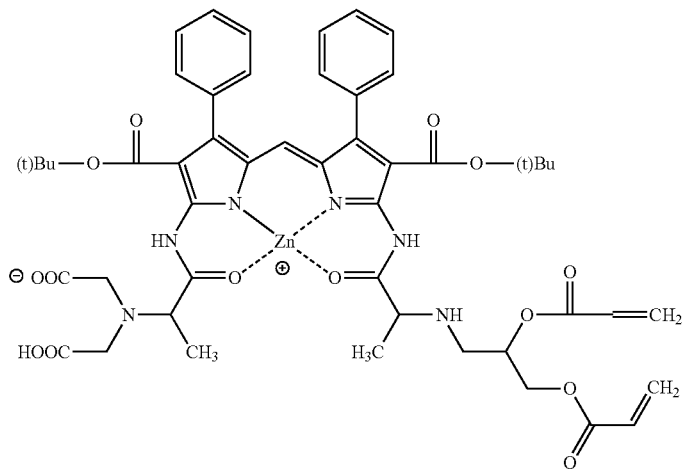
(b-47)
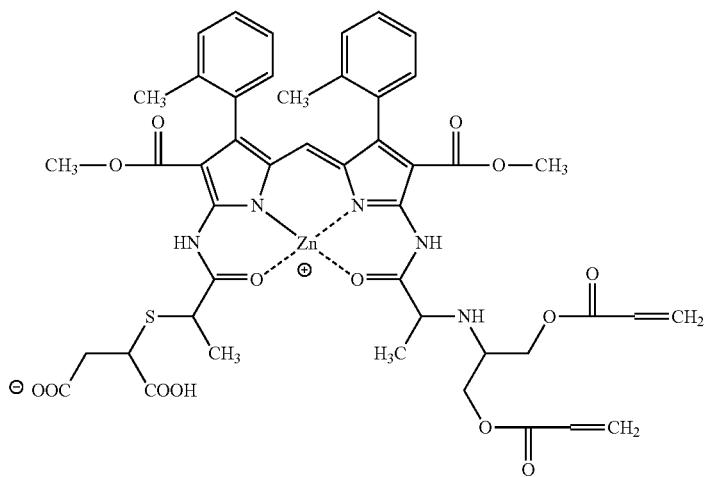
(b-48)
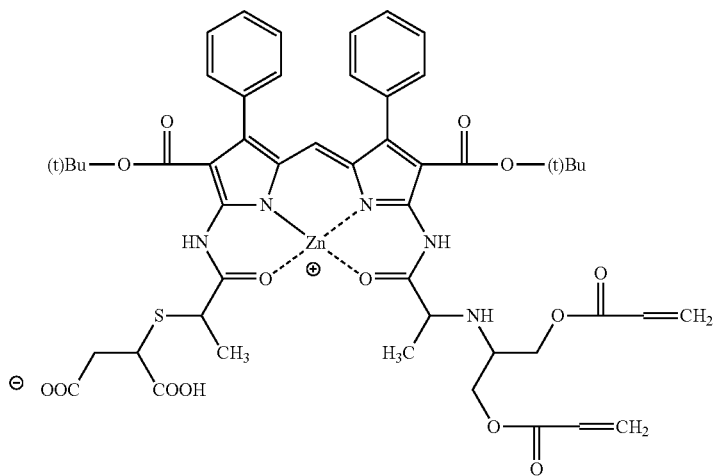

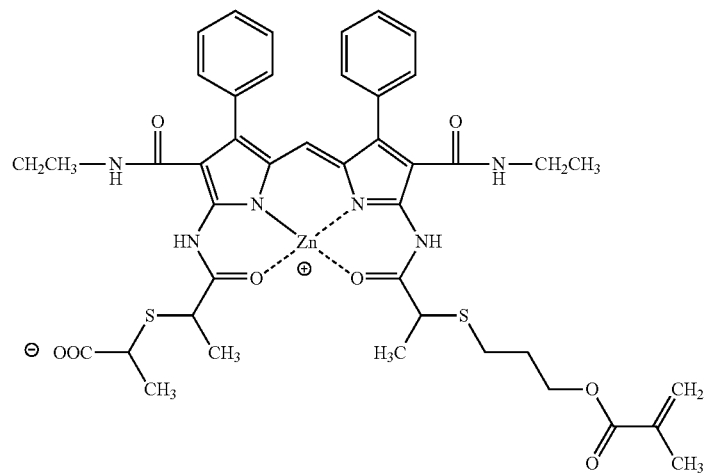
(c-1)
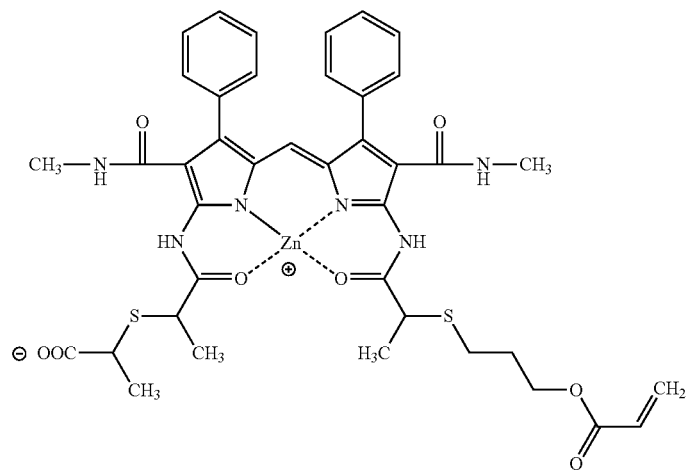
(c-2)
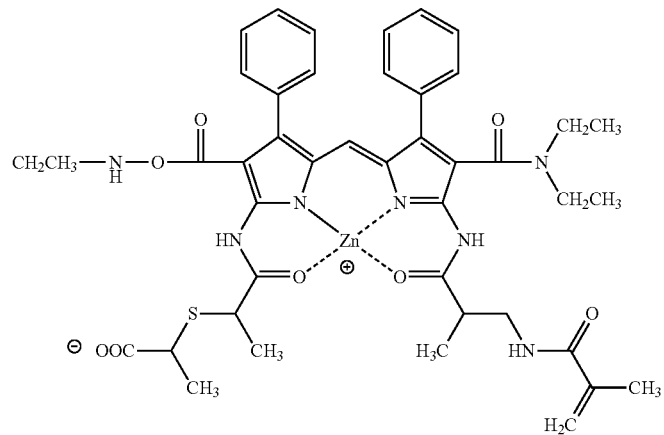
(c-3)

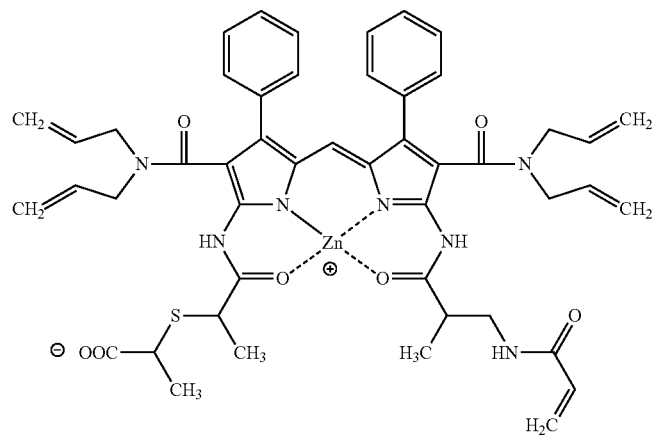
(c-4)
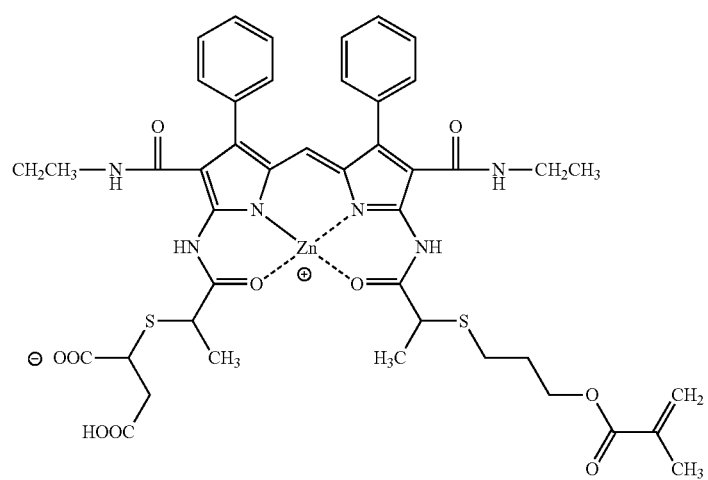
(c-5)
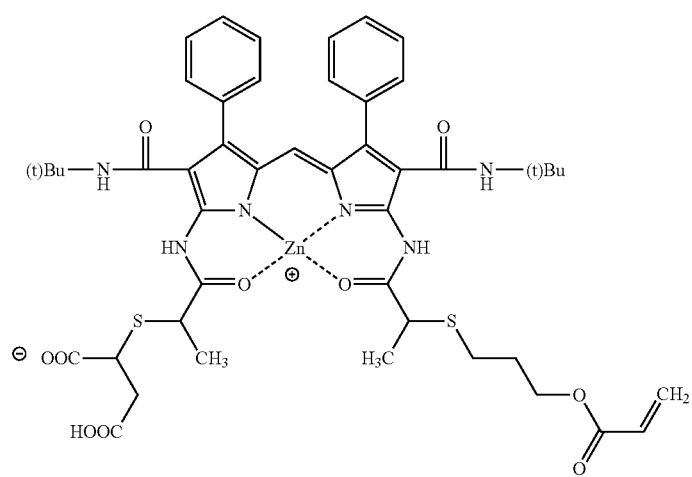
(c-6)

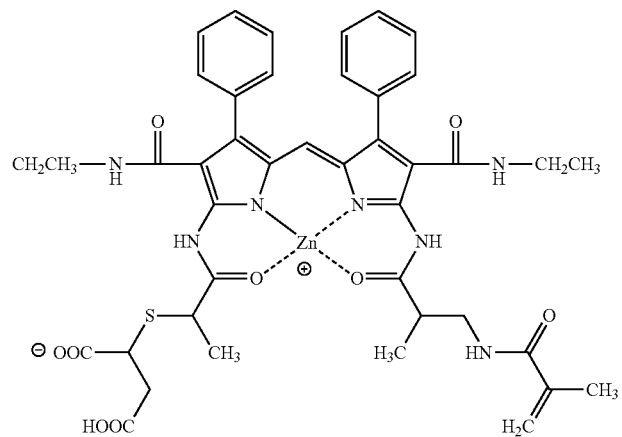
(c-7)
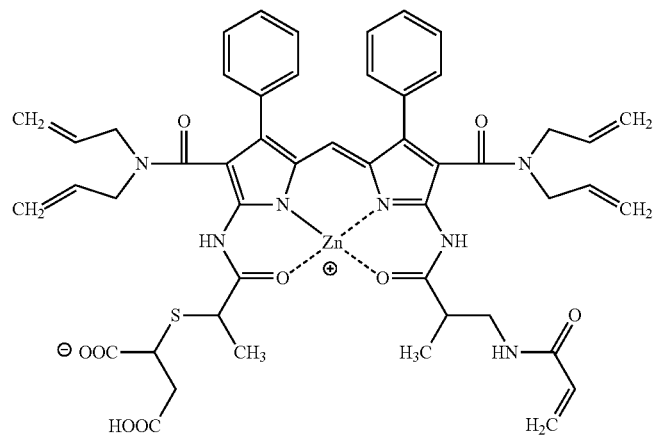
(c-8)
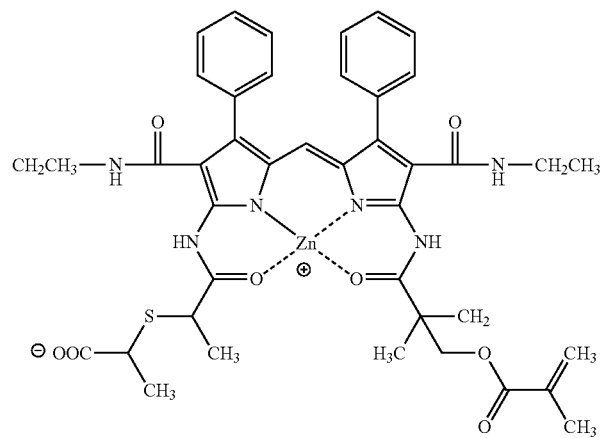
(c-9)

(c-10)
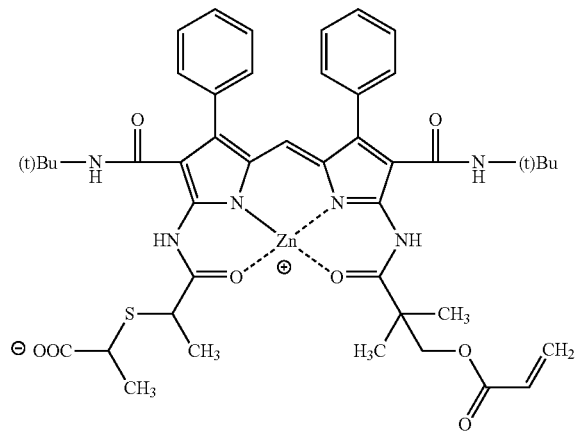
(c-11)
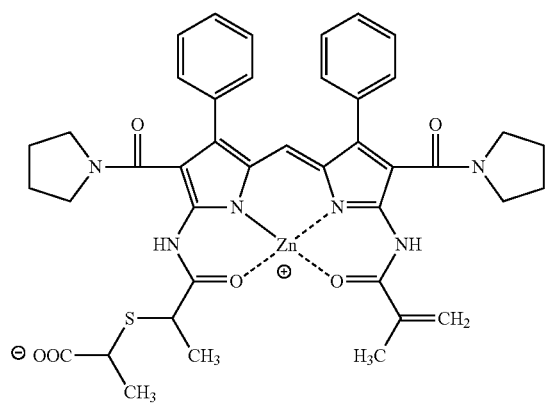
(c-12)
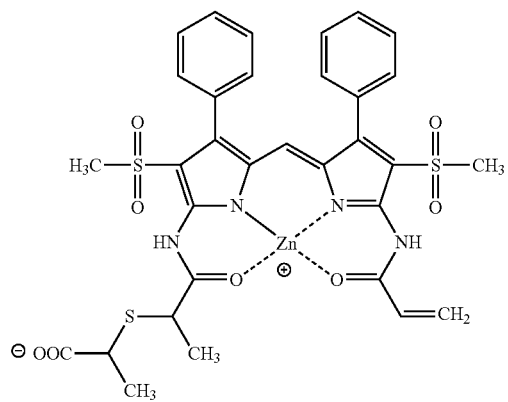

(c-13)
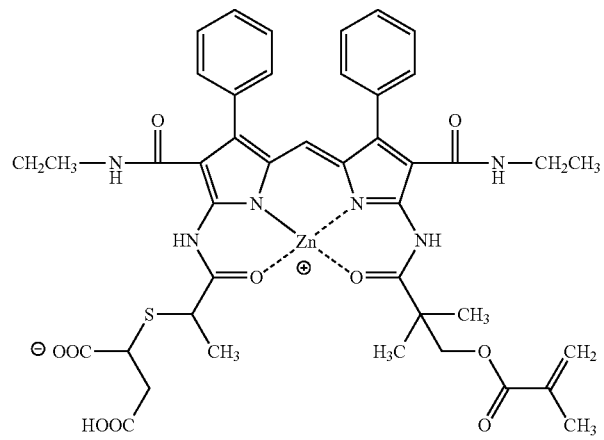
(c-14)
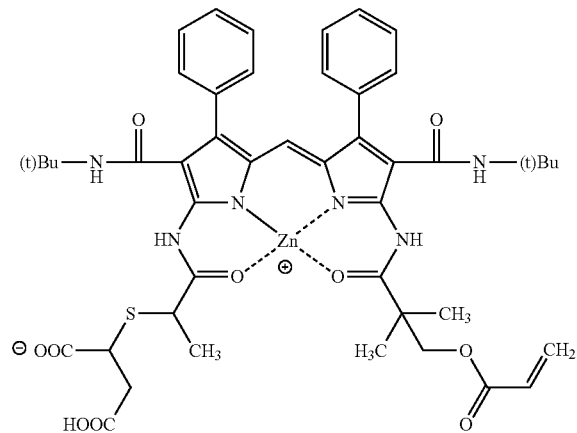
(c-15)
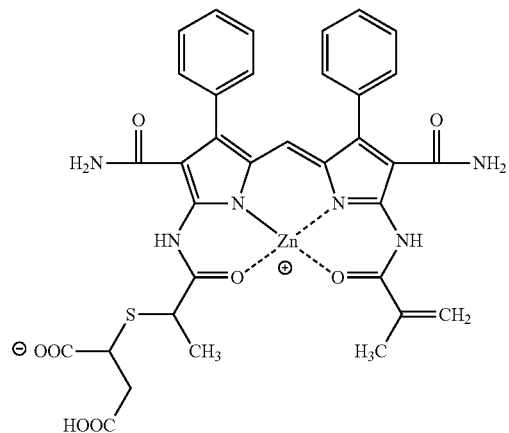

(c-16)
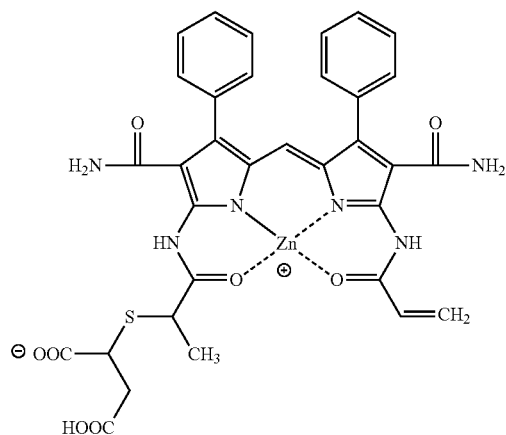
(c-17)
(c-18)
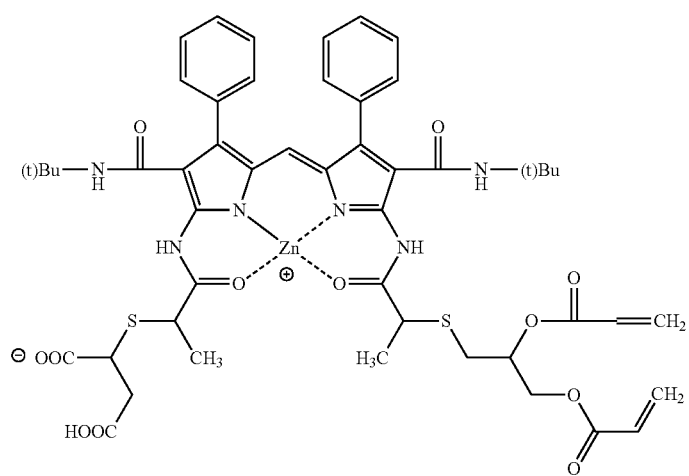

(c-19)
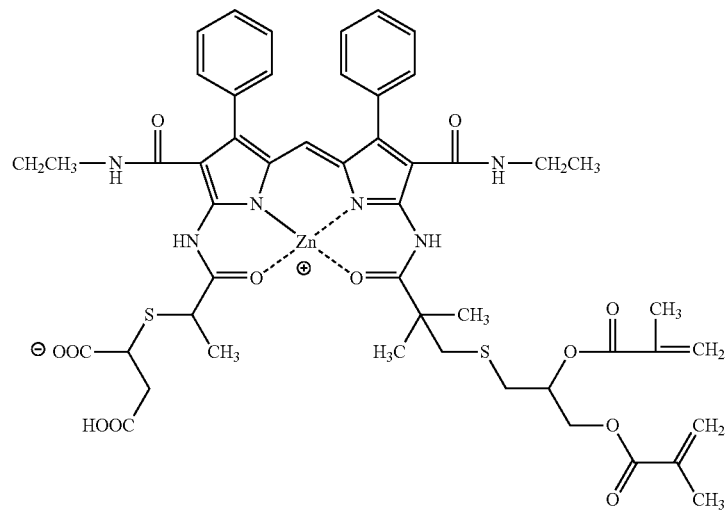
(c-20)
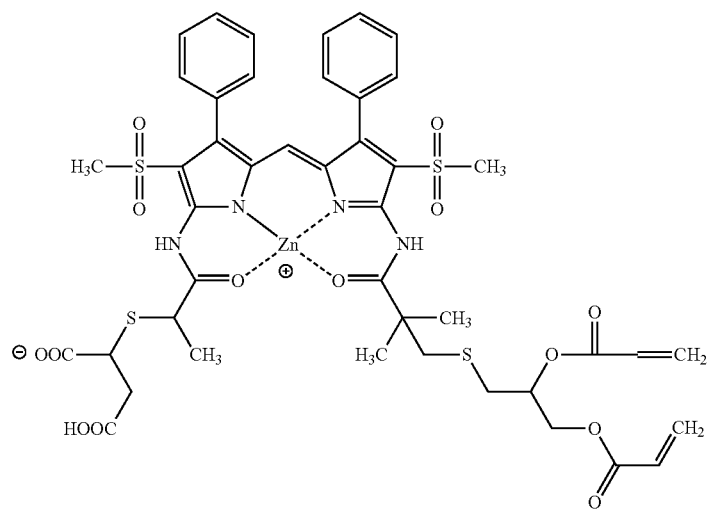
(c-21)
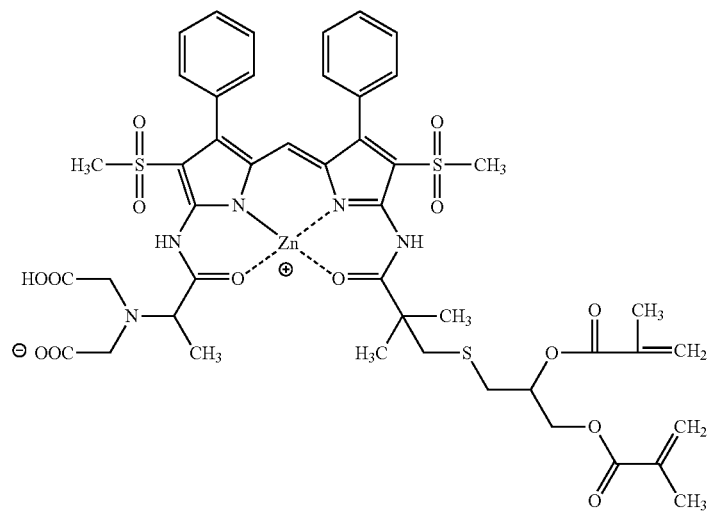

-continued
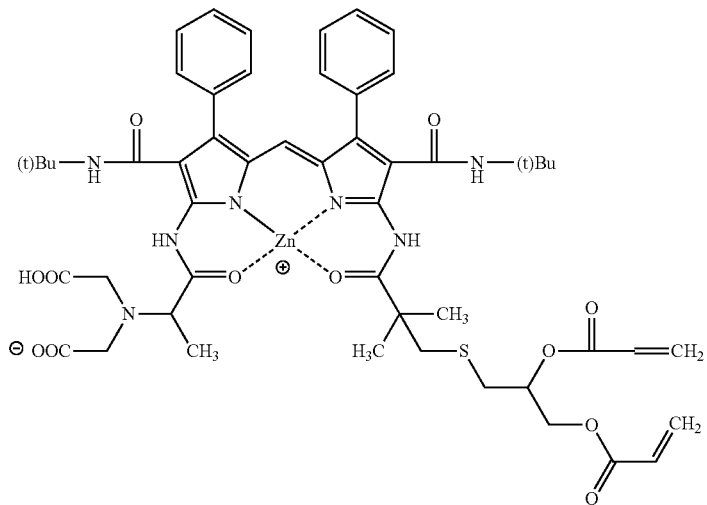
(c-22)
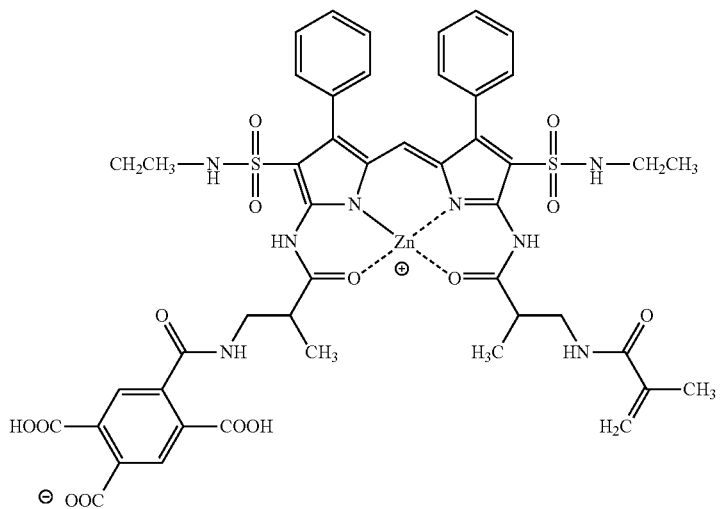
(c-23)
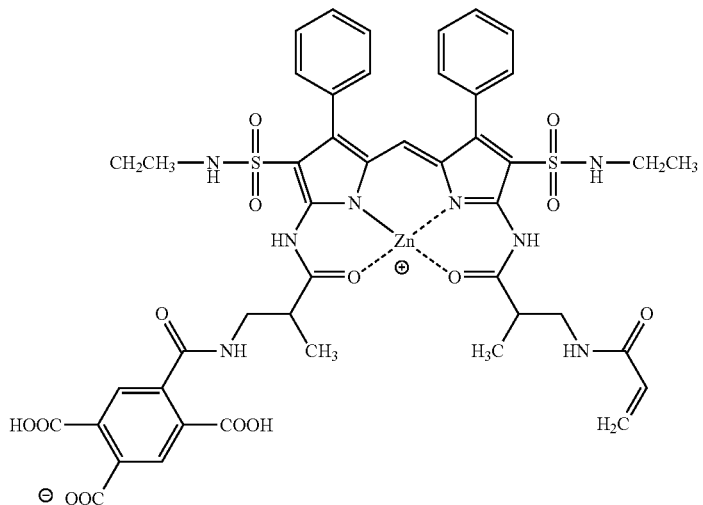
(c-24)

-continued
(c-25)
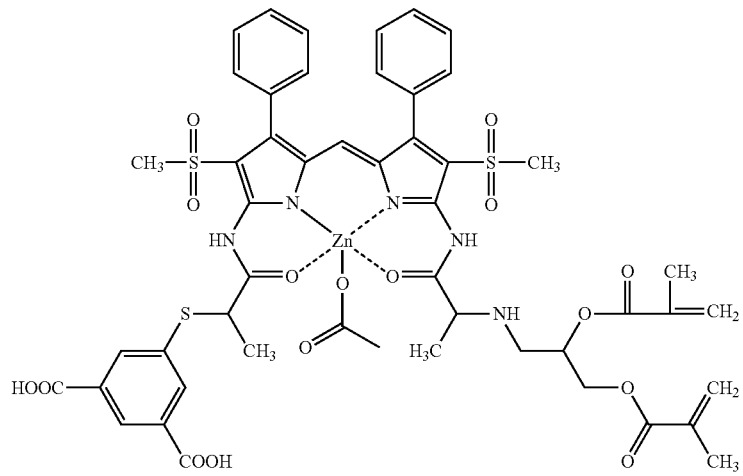
(c-26)
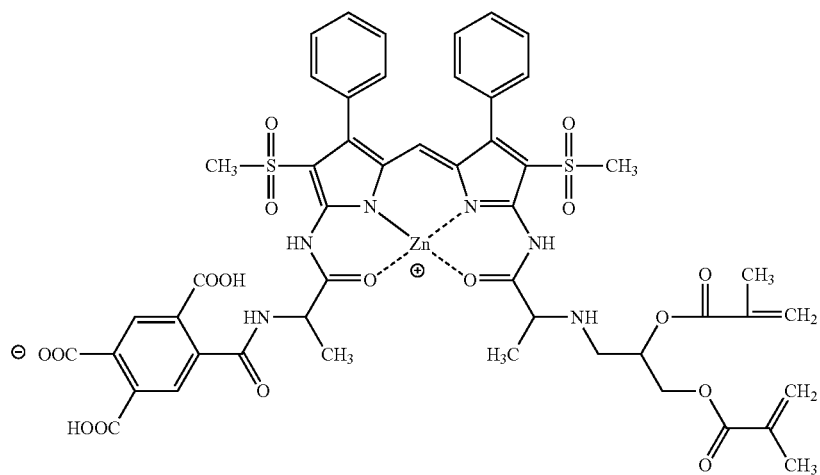
(c-27)
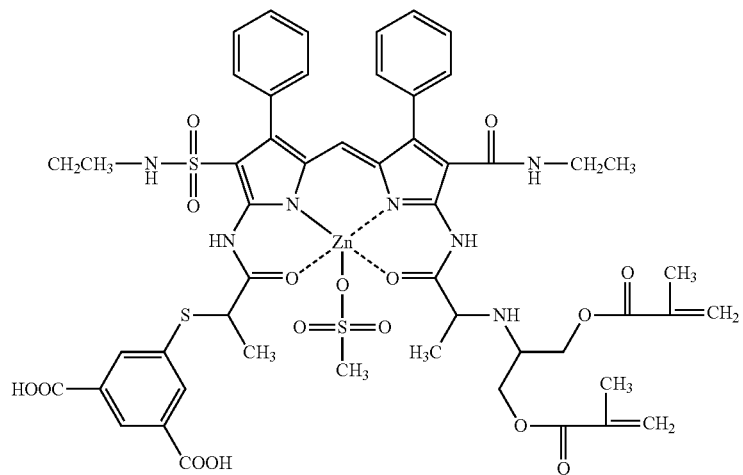

-continued
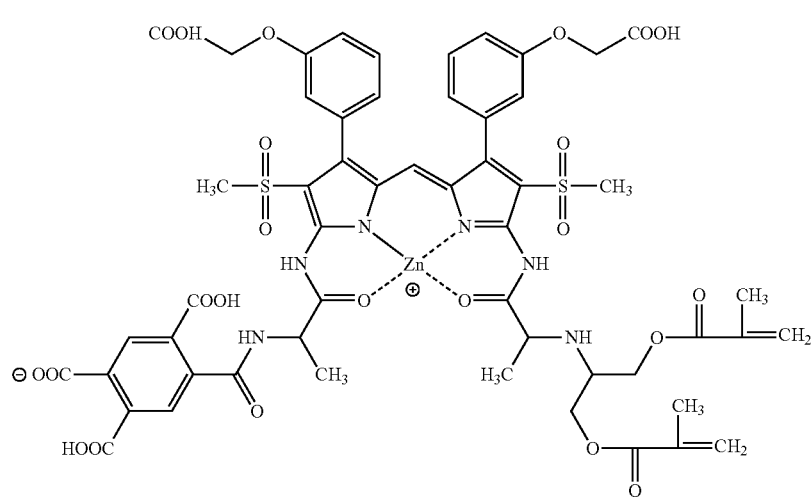
(c-28)
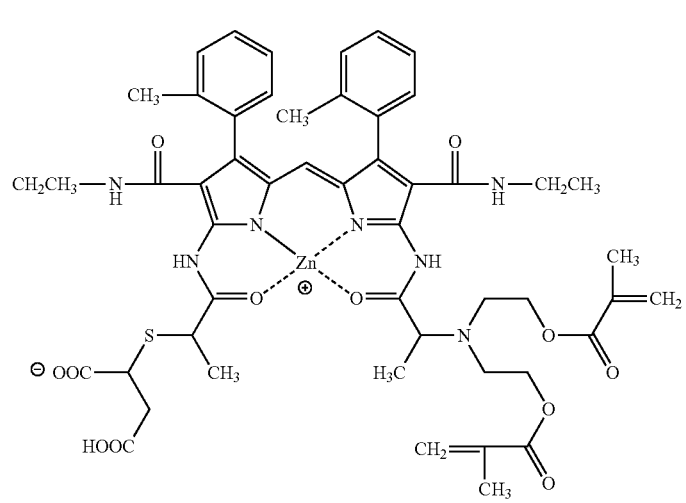
(c-29)
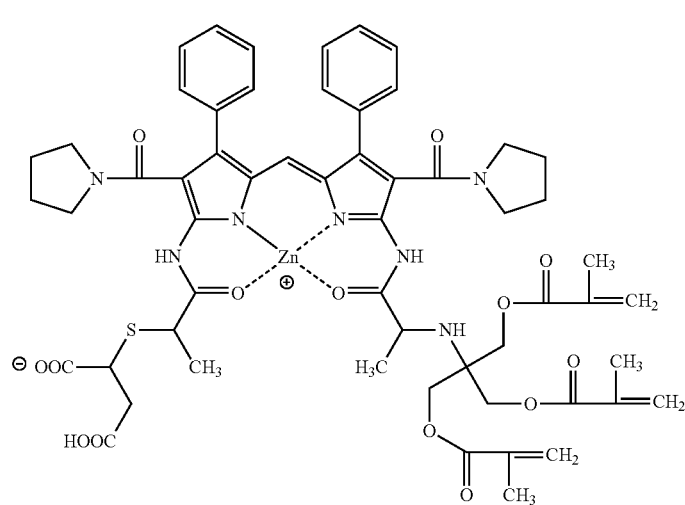
(c-30)

(c-31)
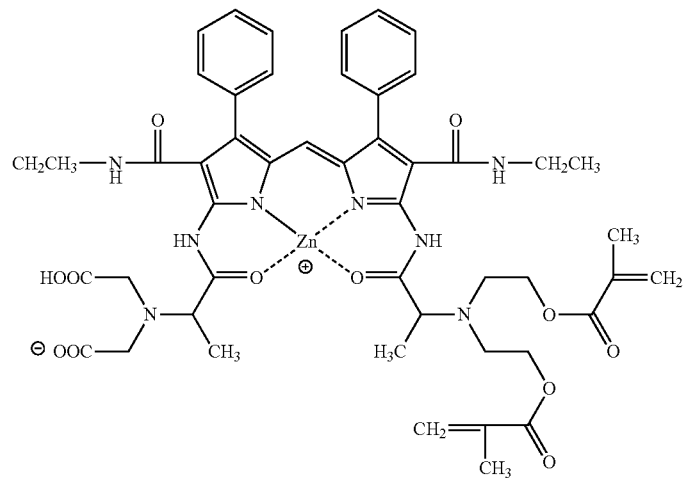
(c-32)
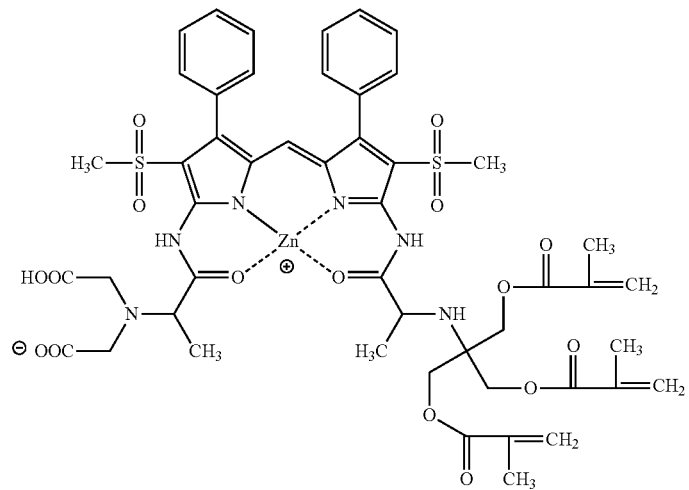
(c-33)
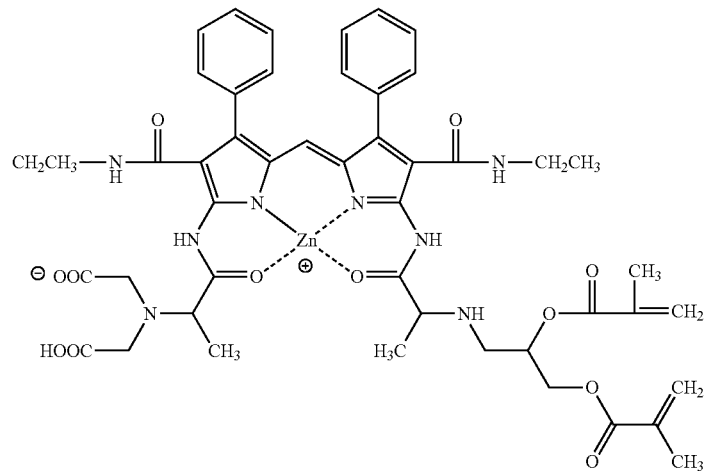

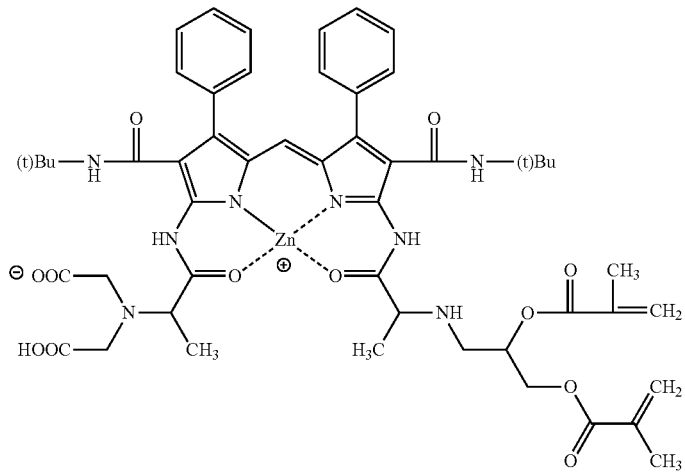
(c-34)
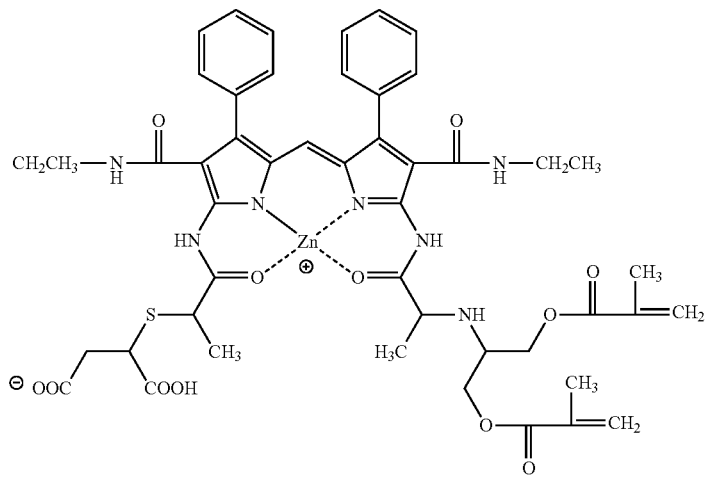
(c-35)
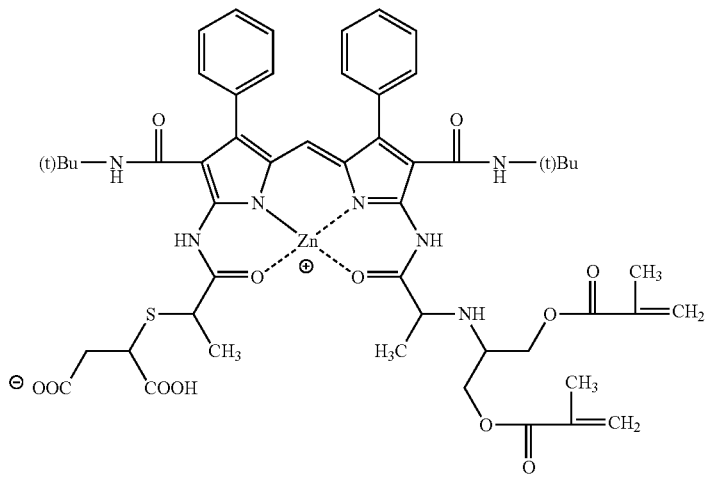
(c-36)

(c-37)
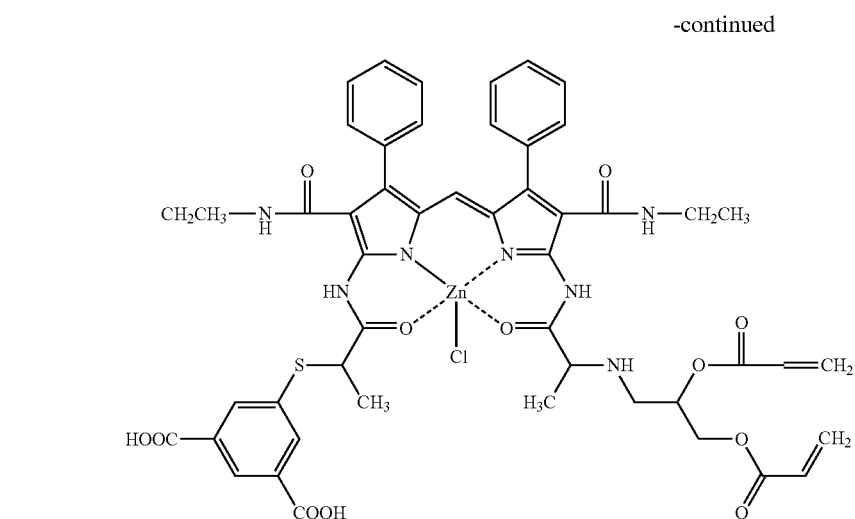
(c-38)
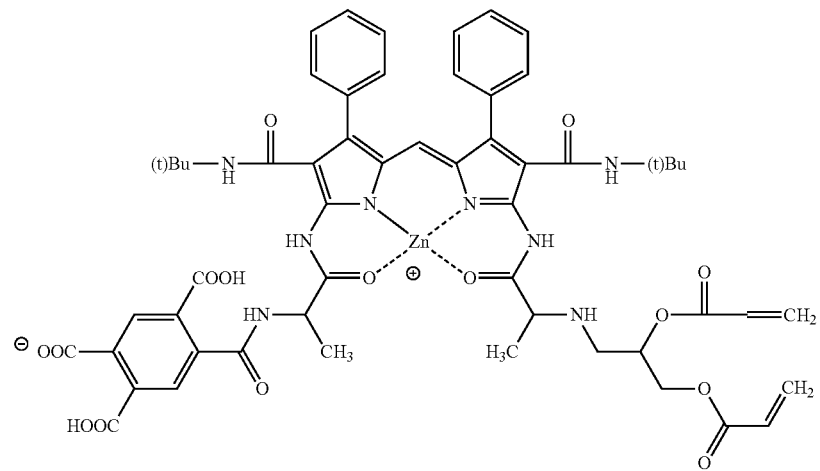
(c-39)
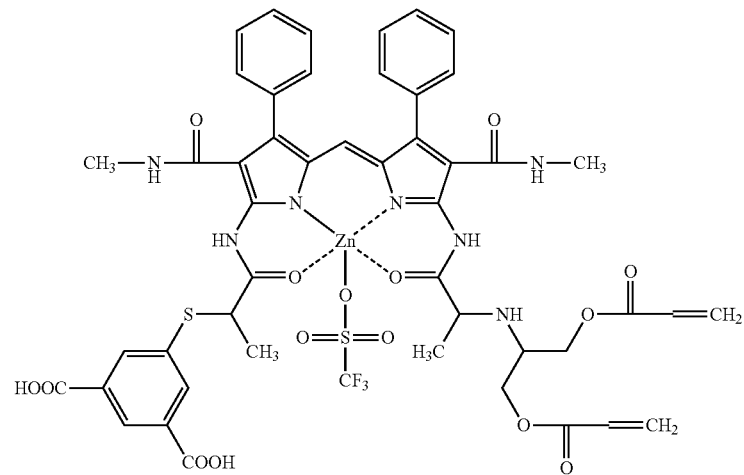

(c-40)
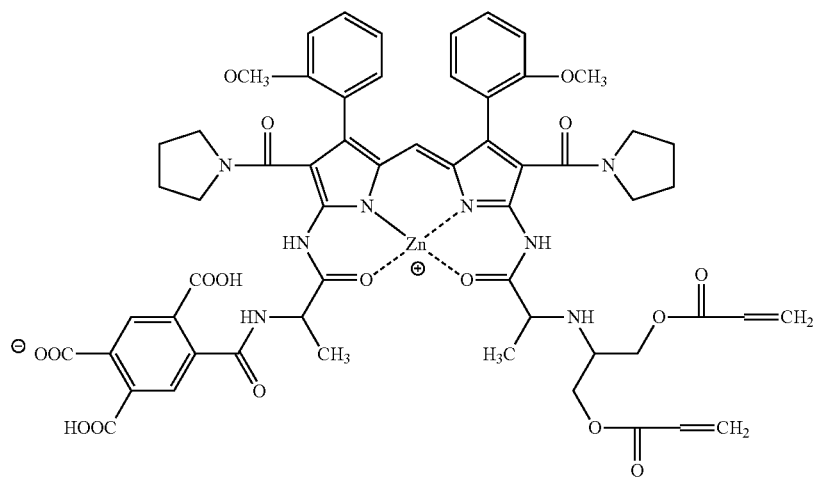
(c-41)
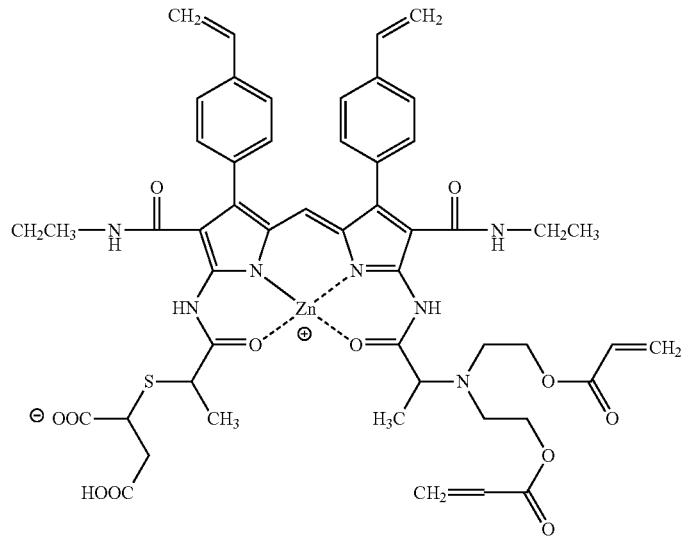
(c-42)
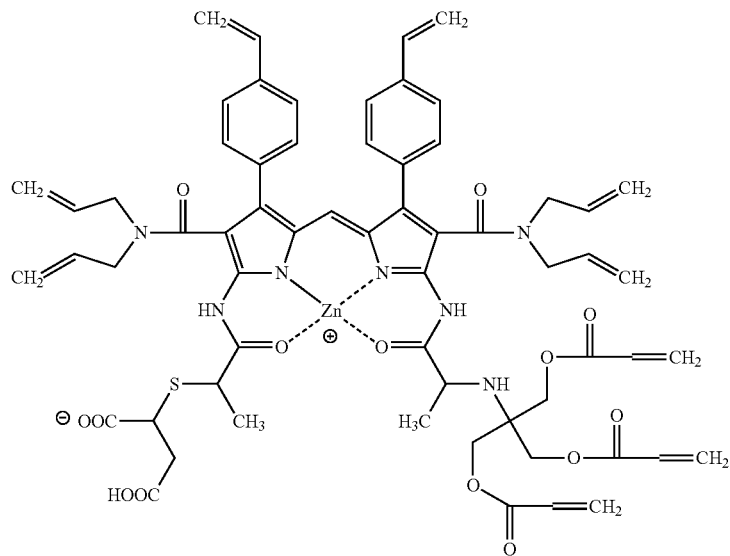

-continued
(c-43)
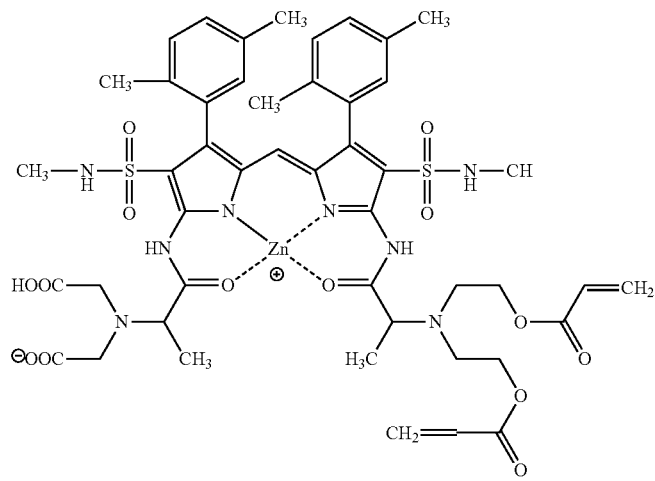
(c-44)
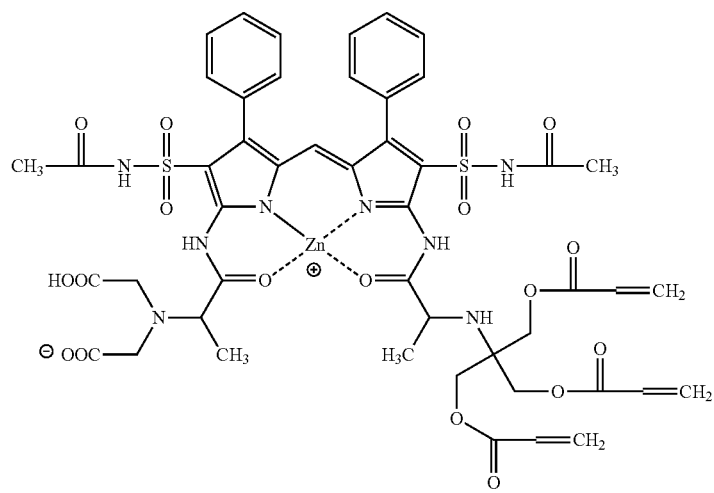
(c-45)
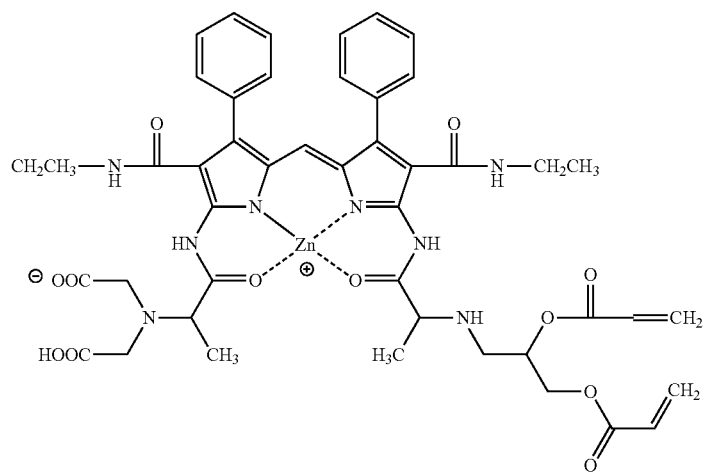

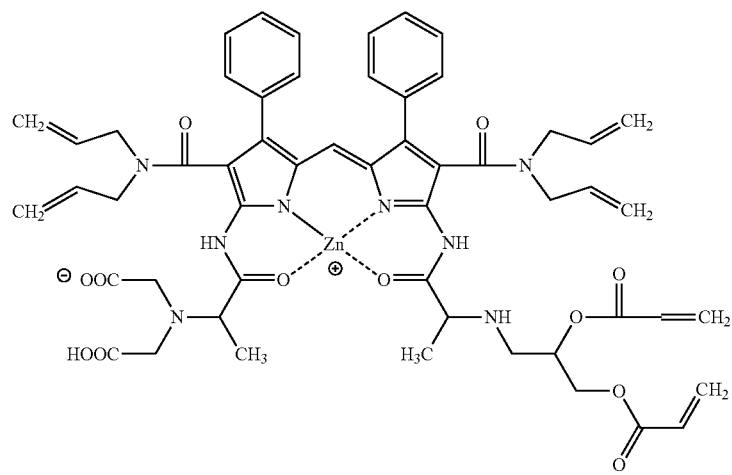
(c-46)
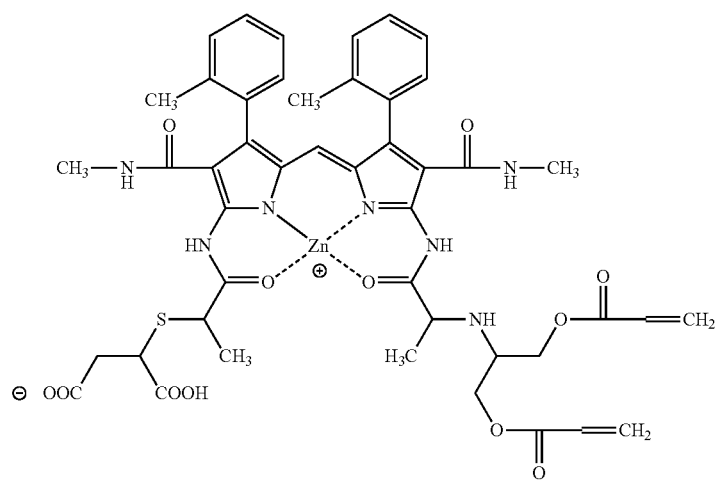
(c-47)
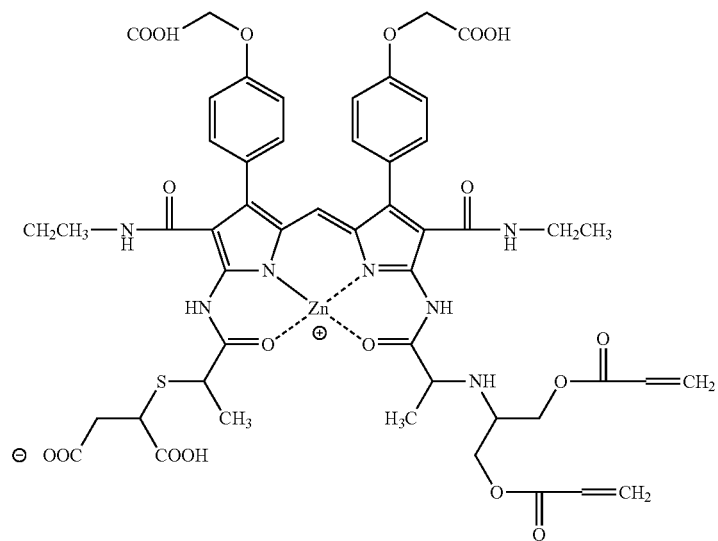
(c-48)

-continued

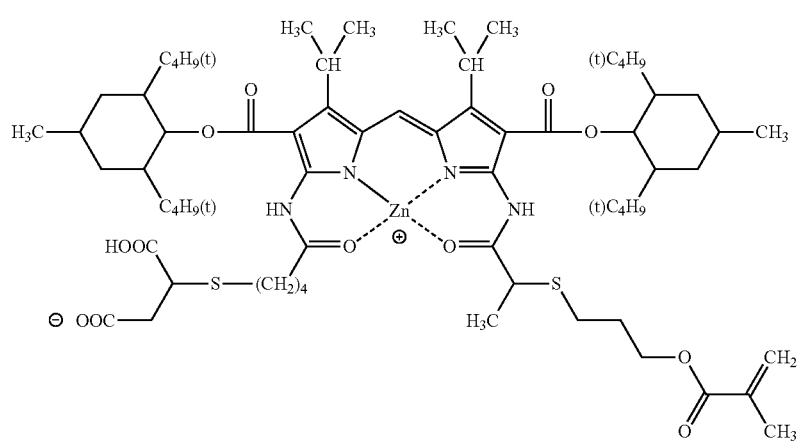
(d-1)

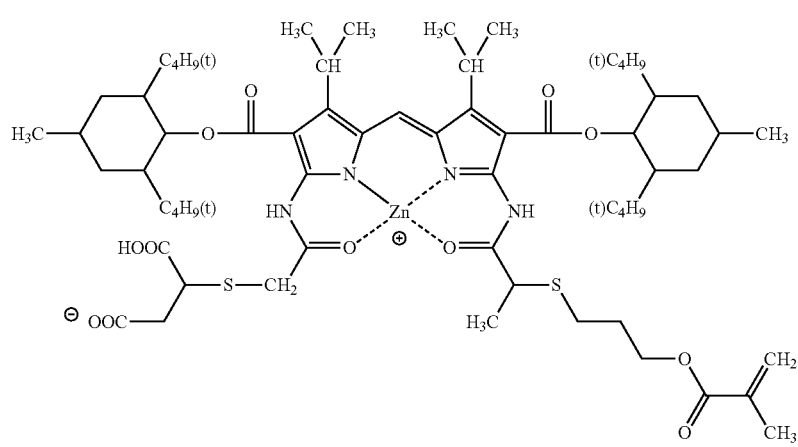
(d-2)

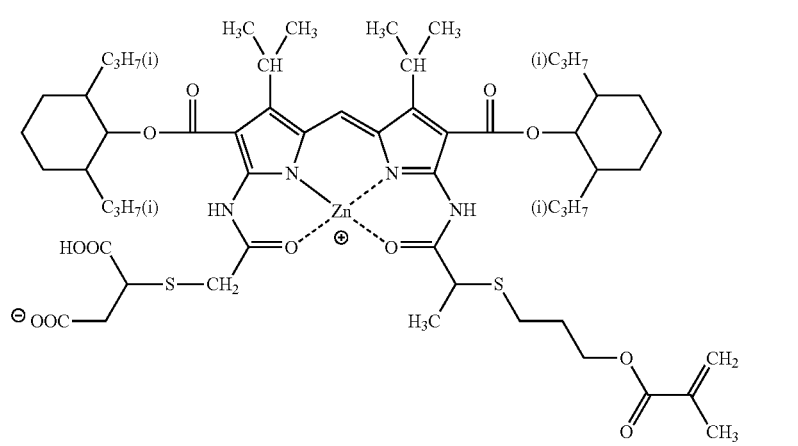
(d-3)

Among the above-mentioned exemplary compounds, in view of developability, exemplary compounds a-5 to a-8, a-13 to a-48, b-5 to b-8, b-13 to b-48, c-5 to c-8, and c-13 to c-48 are preferable, and b-5 to b-8, b-13 to b-48, c-5 to c-8, c-13 to c-48, d-1, d-2, and d-3 are more preferable.

These dye compounds can be easily synthesized according to a method described in JP-A No. 2008-292970 or the like. Further, the dye compounds can also be synthesized by selecting starting materials with reference to the synthesis examples described in the following Examples.

Although the total concentration of the compound represented by the formula (2) in the colored curable composition varies depending on the molecular weight and the molar absorption coefficient, it is preferably in the range of from 0.5% by mass to 80% by mass, more preferably from 0.5% by mass to 70% by mass, and particularly preferably from 1% by mass to 70% by mass, with respect to the total solid components of the composition.

The above explanation of the dye used in the first aspect of the invention mainly relates to the specific complexes (for example, compounds represented by the formula (II-1), formula (II-2), formula (III) or formula (2)), but the dye used in the first aspect of the invention is not limited to these specific complexes.

The content of the dye in the colored curable composition is preferably in the range of from 5% by mass to 40% by mass, more preferably from 10% by mass to 30% by mass, and particularly preferably from 15% by mass to 25% by mass, with respect to the total solid components of the colored curable composition, in view of adjusting color hues.

Further, the mass ratio of the phthalocyanine pigment to the dye (dye/phthalocyanine pigment) in the colored curable composition of the first aspect of the invention is preferably in the range of from 0.1 to 5.0, more preferably from 0.5 to 3.0, and particularly preferably from 0.7 to 1.5.

If the mass ratio (dye/phthalocyanine pigment) is 0.1 or more, it is possible to more effectively adjust color hues.

If the mass ratio (dye/phthalocyanine pigment) is 5.0 or less, it is possible to more effectively improve light fastness.

The colored curable composition of the first aspect of the invention may use a colorant having a different structure than that of the above-mentioned phthalocyanine pigment, dioxazine pigment or the dye. There is no particular limitation on such a dye having a different structure, and any known dyes that have been conventionally used in color filters may be used. Examples thereof include dyes described in JP-A Nos. 2002-14220, 2002-14221, 2002-14222 and 2002-14223, and U.S. Pat. Nos. 5,667,920 and 5,059,500.

Examples of the chemical structure of the dye include a pyrazole azo dye, an anilino azo dye, a triphenylmethane dye, an anthraquinone dye, an anthrapyridone dye, a benzylidene dye, an oxonol dye, a pyrazolotriazole azo dye, a pyridone azo dye, a cyanine dye, a phenothiazine dye, a pyrrolopyrazole azomethine dye, a xanthene dye, a phthalocyanine dye, a benzopyrane dye, and an indigo dye.

With respect to the colored curable composition of the first aspect of the invention, the total content of the phthalocyanine pigment, the dioxazine pigment and the dye in the total colorant components (including a pigment and a dye) is preferably in the range of from 80% by mass to 100% by mass, more preferably from 90% by mass to 100% by mass.

<Polymerizable Compound>

The colored curable composition of the first aspect of the invention contains a polymerizable compound.

One example of the polymerizable compound is an addition-polymerizable compound having at least one ethylenically unsaturated double bond. Specifically, the polymerizable compound is selected from compounds having at least one, preferably two or more, terminal ethylenically unsaturated bonds. Such compounds are widely known in this industrial field, and may be used in the first aspect of the invention without particular limitation. These compounds may have any chemical form of, for example, a monomer, a prepolymer (that is, a dimer, trimer or oligomer) or a mixture thereof, or a (co)polymer thereof. The polymerizable compounds in the first aspect of the invention may be used alone or in a combination of two or more thereof.

Examples of the monomer and the (co)polymer thereof include an unsaturated carboxylic acid (for example, acrylic acid, methacrylic acid, itaconic acid, crotonic acid, isocrotonic acid or maleic acid) and an ester and an amide thereof and a (co)polymer thereof, and preferable examples include an ester of an unsaturated carboxylic acid and an aliphatic polyhydric alcohol compound, an amide of an unsaturated carboxylic acid and an aliphatic polyvalent amine compound, and a (co)polymer thereof. Further, an adduct of an unsaturated carboxylic acid ester or amide having a nucleophilic substituent such as a hydroxyl group, an amino group or a mercapto group with a monofunctional or multifunctional isocyanate or epoxy, a dehydration condensate with a monofunctional or multifunctional carboxylic acid, and the like are preferably used. Moreover, an adduct of an unsaturated carboxylic acid ester or amide having an electrophilic substituent such as an isocyanate group or an epoxy group with a monofunctional or multifunctional alcohol, amine or thiol, and a substituted reaction product of an unsaturated carboxylic acid ester or amide having a leaving group such as a halogen group or a tosyloxy group with a monofunctional or multifunctional alcohol, amine or thiol are also preferable. Further examples include compounds in which the unsaturated carboxylic acid is replaced with unsaturated phosphonic acid, styrene, vinyl ether or the like.

Compounds described in paragraphs [0095] to [0108] of JP-A No. 2009-288705 are also suitably used in the first aspect of the invention.

As the polymerizable compound, the polymerizable monomer is preferably a compound having at least one addition-polymerizable ethylenically unsaturated group and having a boiling point of 100° C. or higher under a normal pressure. Examples thereof include monofunctional acrylates or methacrylates such as polyethylene glycol mono(meth)acrylate, polypropylene glycol mono(meth)acrylate and phenoxyethyl (meth)acrylate; multifunctional acrylates and methacrylates such as polyethylene glycol di(meth)acrylate, trimethylol ethane tri(meth)acrylate, neopentyl glycol di(meth)acrylate, pentaerythritol tri(meth)acrylate, pentaerythritol tetra(meth)acrylate, dipentaerythritol penta(meth)acrylate, dipentaerythritol hexa(meth)acrylate, hexanediol (meth)acrylate, trimethylol propane tri(acryloyloxypropyl)ether, tri(acryloyloxyethyl)isocyanurate, compounds obtained by adding ethylene oxide or propylene oxide to a multifunctional alcohol such as glycerin or trimethylol ethane and then methacrylating the same, urethane acrylates as described in Japanese Examined Patent Publication (JP-B) Nos. 48-41708 and 50-6034, and JP-A No. 51-37193, polyester acrylates described in JP-A No. 48-64183, JP-B Nos. 49-43191 and 52-30490, and polyfunctional acrylates or methaycrylates, such as epoxy acrylates obtained by reaction of an epoxy resin and (meth)acrylic acid, or mixtures thereof.

In addition, radical-polymerizable monomers represented by the following formulae (MO-1) to (MO-5) are also suitably used. In these formulae, when T represents an oxyalkylene group, its end at the carbon atom side is bonded to R.

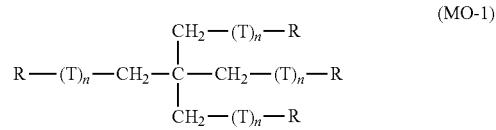

(MO-1)

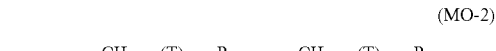

(MO-2)

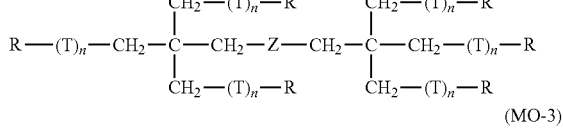

(MO-3)

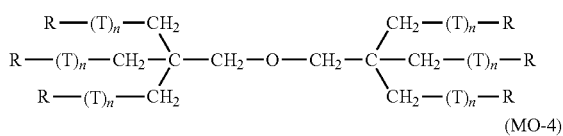

(MO-4)

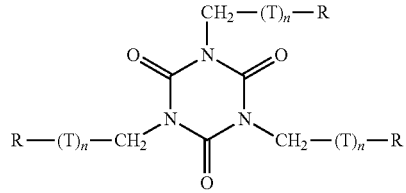

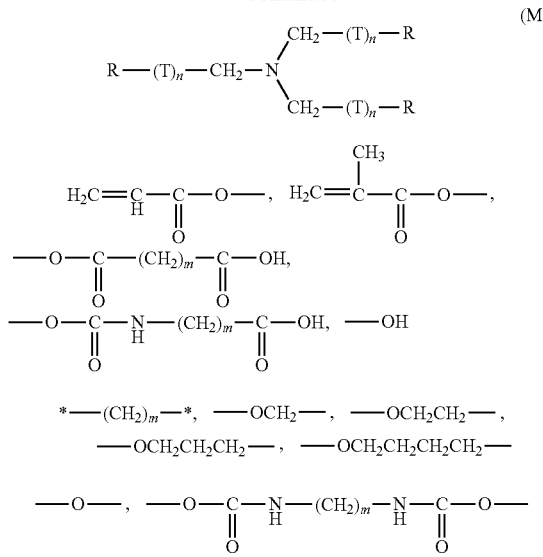

In the above-mentioned formulae, n represents 0 to 14, and m represents 1 to 8. Two or more of R and T existing in one molecule may be the same or different from each other, respectively.

As the specific examples of the radical-polymerizable monomer represented by the formulae (MO-1) to (MO-5), the compounds described in paragraphs [0248] to [0251] of JP-A No. 2007-269779 may be suitably used in the first aspect of the invention.

The content of the above-described polymerizable compound in the colored curable composition is preferably in the range of from 5% by mass to 90% by mass, more preferably from 10% by mass to 80% by mass, and particularly preferably from 15% by mass to 50% by mass, with respect to the solid content of the composition. If the content of the polymerizable compound is within the above-specified range, sufficient curability and dissolvability of unexposed portions may be retained, and sufficient curability of exposed portions may be maintained, whereby significant reduction in dissolvability of unexposed portions may be prevented.

<Polymerization Initiator>

The colored curable composition of the first aspect of the invention includes a polymerization initiator.

The polymerization initiator is not particularly limited as long as it can cause polymerization of a polymerizable compound as mentioned above, and is preferably selected in view of physical properties, initiation efficiency, absorption wavelength, availability, costs and the like.

The polymerization initiator is preferably a photopolymerization initiator. Examples of the photopolymerization initiator include at least one active halogen compound selected from halomethyloxadiazole compounds and halomethyl-s-triazine compounds, a 3-aryl-substituted coumarin compound, a lophine dimer, a benzophenone compound, an acetophenone compound and a derivative thereof, a cyclopentadiene-benzene-iron complex and a salt thereof, and an oxime compound. Specific examples of the photopolymerization initiator include those described in the paragraphs [0070] to [0077] of JP-A No. 2004-295116.

Among these, an oxime compound (hereinafter, also referred to as an "oxime photopolymerization initiator") is preferable in view of causing rapid polymerization reaction or the like.

The oxime photopolymerization initiator is not particularly limited, and examples thereof include the oxime compounds described in, for example, JP-A No. 2000-80068 (paragraphs [0004] to [0296]), WO02/100903A1, JP-A No. 2001-233842, JP-A No. 2006-342166 (paragraphs [0004] to [0264]), and the like.

Specific examples of the oxime photopolymerization initiator include, but are not limited to, 2-(O-benzoyloxime)-1-[4-(phenylthio)phenyl]-1,2-butanedione, 2-(O-benzoyloxime)-1-[4-(phenylthio)phenyl]-1,2-pentanedione, 2-(O-benzoyloxime)-1-[4-(phenylthio)phenyl]-1,2-hexanedione, 2-(O-benzoyloxime)-1-[4-(phenylthio)phenyl]-1,2-heptanedione, 2-(O-benzoyloxime)-1-[4-(phenylthio)phenyl]-1,2-octanedione, 2-(O-benzoyloxime)-1-[4-(methylphenylthio)phenyl]-1,2-butanedione, 2-(O-benzoyloxime)-1-[4-(ethylphenylthio)phenyl]-1,2-butanedione, 2-(O-benzoyloxime)-1-[4-(butylphenylthio)phenyl]-1,2-butanedione, 1-(O-acetyloxime)-1-[9-ethyl-6-(2-methylbenzoyl)-9H-carbazol-3-yl]ethanone, 1-(O-acetyloxime)-1-[9-methyl-6-(2-methylbenzoyl)-9H-carbazol-3-yl]ethanone, 1-(O-acetyloxime)-1-[9-propyl-6-(2-methylbenzoyl)-9H-carbazol-3-yl]ethanone, 1-(O-acetyloxime)-1-[9-ethyl-6-(2-ethylbenzoyl)9H-carbazol-3-yl]ethanone, and 1-(O-acetyloxime)-1-[9-ethyl-6-(2-butylbenzoyl)-9H-carbazol-3-yl]ethanone.

Among them, oxime-O-acyl compounds, such as 2-(O-benzoyloxime)-1-[4-(phenylthio)phenyl]-1,2-octanedione and 1-(O-acetyloxime)-1-[9-ethyl-6-(2-methylbenzoyl)-9H-carbazol-3-yl]ethanone, are particularly preferable in view of obtaining a pattern having a favorable shape (in particular, favorable rectangularity of a pattern for solid-state image sensors) with a smaller exposure dose, and specific examples thereof include CGI-124 and CGI-242 (all trade names, manufactured by BASF Japan).

Further, as the polymerization initiator, an oxime photopolymerization initiator represented by the following formula (OX-1), as described in JP-A No. 2007-269779 (paragraphs [0016] to [0082]), is also preferable.

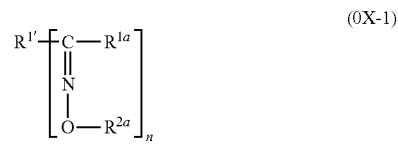

In the formula (OX-1), $R^{1'}$ represents a substituent including an aromatic ring or a heteroaromatic ring. $R^{1a}$ represents an alkyl group having at least one substituent selected from the following Group (A). $R^{2a}$ represents an alkanoyl group, an alkenoyl group, an aryloyl group, an alkoxycarbonyl group, an aryloxycarbonyl group, a heterocyclic oxycarbonyl group, a heteroaryloxycarbonyl group, an alkylthiocarbonyl group, an arylthiocarbonyl group, a heterocyclic thiocarbonyl group, a heteroarylthiocarbonyl group, —CO—CO-Rd (Rd represents an aromatic ring or heteroaromatic ring that may have a substituent). n represents an integer of 1 to 6.

<Group (A)> a cyano group, an alkenyl group, an alkynyl group, —NArAr', —SAr, —COOH, —CONRaRb, —NRa—CO—Rb, —O—CO—NRaRb, —NRa—CO—ORb, —NRa—CO—NRaRb, —SO-Rc, —SO$_2$—Rc, —O—SO$_2$—Rc, —SO$_2$—NRaRb, —NRa—SO$_2$—Ra, —CO—NRa—CORb, —CO—NRa—SO$_2$—Rb, —SO$_2$—NRa—CO—Rb, —SO$_2$—NRa—SO$_2$—Rc, —Si(Ra)$_l$(ORb)$_m$, and a heterocyclic group. Each of Ar and Ar' independently represents an aromatic ring or heteroaromatic ring that may have a substituent, each of Ra and Rb independently represents a hydrogen atom or an alkyl group, aromatic ring or heteroaromatic ring, which may have a substituent, Rc represents an alkyl group, an aromatic ring or a heteroaromatic ring, which may have a substituent, and each of l and m independently represents an integer of 0 to 3, which satisfy l+m=3.

In the first aspect of the invention, in view of sensitivity, stability over time and coloring during post-heating, a compound represented by the following formula (OX-2) is more preferable as the oxime compound.

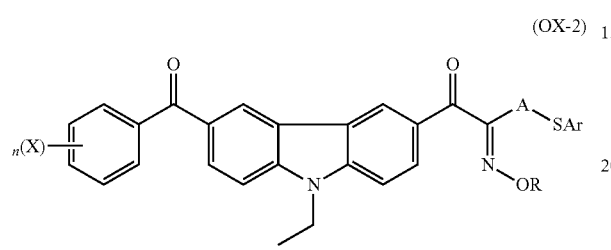

(OX-2)

In the formula (OX-2), each of R and X independently represents a monovalent substituent, A represents a divalent organic group, Ar represents an aryl group, and n represents an integer of 1 to 5.

From the viewpoint of increasing sensitivity, R is preferably an acyl group and preferable specific examples thereof include an acetyl group, a propionyl group, a benzoyl group and a toluoyl group.

From the viewpoint of increasing sensitivity and suppressing coloration due to heating over time, A is preferably an unsubstituted alkylene group, an alkylene group substituted by an alkyl group (for example, a methyl group, an ethyl group, a tert-butyl group or a dodecyl group), an alkylene group substituted by an alkenyl group (for example, a vinyl group or an allyl group), or an alkylene group substituted by an aryl group (for example, a phenyl group, a p-tolyl group, a xylyl group, a cumenyl group, a naphthyl group, an anthryl group, a phenanthryl group or a styryl group).

From the viewpoint of increasing sensitivity and suppressing coloration due to heating over time, Ar is preferably a substituted or unsubstituted phenyl group. When the phenyl group is substituted, the substituent is preferably a halogen group such as a fluorine atom, a chlorine atom, a bromine atom or an iodine atom.

From the viewpoint of improving solubility in a solvent and absorption efficiency at a longer wavelength range, X is preferably an alkyl group that may be substituted, an aryl group that may be substituted, an alkenyl group that may be substituted, an alkynyl group that may be substituted, an alkoxy group that may be substituted, an aryloxy group that may be substituted, an alkylthioxy group that may be substituted, an arylthioxy group that may be substituted, or an amino group that may be substituted.

In the formula (OX-2), n preferably represents an integer of 1 to 2.

The following are specific examples of the compound represented by the formula (OX-2), but the invention is not limited thereto.

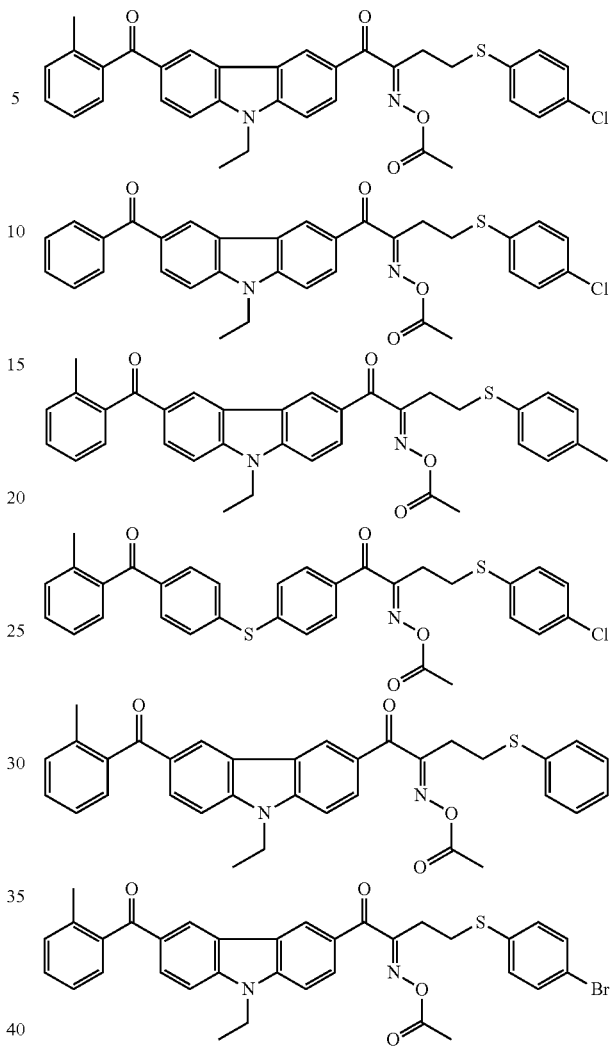

Besides the above-mentioned photopolymerization initiators, other known photopolymerization initiators described in the paragraph [0079] of JP-A No. 2004-295116 may be used for the colored curable composition of the first aspect of the invention.

The photopolymerization initiator may be used alone or in a combination of two or more kinds.

The content of the photopolymerization initiator (when two or more kinds of photopolymerization initiators are used, the total content thereof) in the total solid content of the colored curable composition is preferably in the range of from 3% by mass to 20% by mass, more preferably from 4% by mass to 19% by mass, and particularly preferably from 5% by mass to 18% by mass, in view of more effectively achieving the effect of the first aspect of the invention.

<Solvent>

The colored curable composition of the first aspect of the invention includes a solvent.

The solvent is not particularly limited as long as it can satisfy the solubility of the coexisting components or the coatability of the colored curable composition, and is preferably selected particularly in view of solubility of a binder with respect to the solvent, coatability and safety.

Examples of the solvent include esters including ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, alkyl oxyacetates (for example, methyl oxyacetate, ethyl oxyacetate and butyl oxyacetate (specifically, methyl methoxyacetate, ethyl methoxyacetate, butyl methoxyacetate, methyl ethoxyacetate and ethyl ethoxyacetate)), alkyl 3-oxypropionates (for example, methyl 3-oxypropionate and ethyl 3-oxypropionate (specifically, methyl 3-methoxypropionate, ethyl 3-methoxypropionate, methyl 3-ethoxypropionate and ethyl 3-ethoxypropionate)), and alkyl 2-oxypropionates (for example, methyl 2-oxypropionate, ethyl 2-oxypropionate and propyl 2-oxypropionate (specifically, methyl 2-methoxypropionate, ethyl 2-methoxypropionate, propyl 2-methoxypropionate, methyl 2-ethoxypropionate and ethyl 2-ethoxypropionate)), methyl 2-oxy-2-methylpropionate and ethyl 2-oxy-2-methylpropionate (specifically, methyl 2-methoxy-2-methylpropionate and ethyl 2-ethoxy-2-methylpropionate)), methyl pyruvate, ethyl pyruvate, propyl pyruvate, methyl acetoacetate, ethyl acetoacetate, methyl 2-oxobutanoate, and ethyl 2-oxobutanate.

Examples of the ethers include diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate and propylene glycol monopropyl ether acetate.

Examples of the ketones include methyl ethyl ketone, cyclohexanone, 2-heptanone and 3-heptanone.

Preferable examples of the aromatic hydrocarbons include toluene and xylene.

It is also preferable to mix two or more kinds of solvents in view of the solubility of each component, the solubility of an alkali-soluble binder when it is included, and the coating surface properties. When a mixed solution of the solvent is used, it is particularly preferably a mixture of at least two solvents selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether, and propylene glycol methyl ether acetate.

The solvent is preferably used in the colored curable composition in an amount that makes the total solid component concentration to be from 10% by mass to 80% by mass, more preferably from 15% by mass to 60% by mass.

<Dispersant>

The colored curable composition of the first aspect of the invention preferably contains a dispersant.

As the dispersant, a known pigment dispersant or surfactant may be used.

Many kinds of compounds may be used as the dispersant, and examples thereof include cationic surfactants such as a phthalocyanine derivative (commercial product, trade name: EFKA-745 (manufactured by Efka), SOLSPERSE 5000 (trade name, manufactured by Lubrizol Japan Ltd.); an organosiloxane polymer KP341 (trade name, manufactured by Shin-Etsu Chemical Co., Ltd.), (meth)acrylic acid (co)polymers POLYFLOW Nos. 75, 90 and 95 (all trade names, manufactured by Kyoeisha Chemical Co., Ltd.) and W001 (trade name, manufactured by Yusho Co., Ltd.); nonionic surfactants such as polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate and sorbitan fatty acid esters; anionic surfactants such as W004, W005 and W017 (all trade names, manufactured by Yusho Co., Ltd.); polymer dispersants such as EFKA-46, EFKA-47, EFKA-47EA, EFKA POLYMER 100, EFKA POLYMER 400, EFKA POLYMER 401 and EFKA POLYMER 450 (all trade names, manufactured by Morishita & Co., Ltd.) and DISPERSE AID 6, DISPERSE AID 8, DISPERSE AID 15 and DISPERSE AID 9100 (all trade names, manufactured by San Nopco Ltd.); SOLSPERSE dispersants such as SOLSPERSE 3000, 5000, 9000, 12000, 13240, 13940, 17000, 24000, 26000 and 28000 (all trade names, manufactured by Lubrizol Japan Ltd.); ADEKA PLURONIC L31, F38, L42, L44, L61, L64, F68, L72, P95, F77, P84, F87, P94, L101, P103, F108, L121 and P-123 (all trade names, manufactured by Adeka Corporation), and ISONET S-20 (trade name, manufactured by Sanyo Chemical Industries, Ltd.)

When the colored curable composition of the first aspect of the invention includes a dispersant, the content of the dispersant in the colored curable composition is preferably from 1% by mass to 80% by mass, more preferably from 5% by mass to 70% by mass, and most preferably from 10% by mass to 60% by mass, with respect to the pigment.

<Pigment Derivative>

The colored curable composition of the first aspect of the invention may contain a pigment derivative.

The pigment derivative present in the first aspect of the invention is a compound in which an acidic group, a basic group or an aromatic group as a substituent is introduced into a side chain of an organic pigment.

In the first aspect of the invention, by allowing a pigment derivative having a moiety having affinity with the dispersant to be adsorbed to a surface of the pigment, and using the same as an adsorption point of the dispersant, the pigment can be dispersed in the colored composition as fine particles, and reaggregation thereof can be prevented. In other words, the pigment derivative has an effect of accelerating the adsorption of the dispersant by modifying the pigment surface.

When the dispersant has an acidic group, dispersibility of the pigment can be further improved and fine particles of the pigment can be more effectively dispersed by using a basic pigment derivative having a basic group as a pigment derivative. Further, by using a colored composition including a basic pigment derivative, a color filter that exhibits suppressed color density unevenness and favorable color properties can be formed.

The pigment derivative used in the first aspect of the invention is, specifically, a compound having an organic pigment as a mother skeleton, and a substituent such as an acidic group, a basic group or an aromatic group being introduced to a side chain of the mother skeleton. Specific examples of the organic pigment to serve as a mother skeleton include a quinacridone pigment, a phthalocyanine pigment, an azo pigment, a quinophthalone pigment, an isoindoline pigment, an isoindolinone pigment, a quinoline pigment, a diketopyrrolopyrrole pigment, and a benzimidazolone pigment. Pale yellow aromatic polycyclic compounds such as a naphthalene compound, an anthraquinone compound, a triazine compound and a quinoline compound, which are typically not included in dyes, are also usable as a mother skeleton.

Further, examples of the pigment derivative in the first aspect of the invention also include those described in JP-A Nos. 11-49974, 11-189732, 10-245501, 2006-265528, 8-295810, 11-199796, 2005-234478, 2003-240938, 2001-356210, and the like.

When a pigment derivative is used in the colored composition of the first aspect of the invention, the amount of the pigment derivative to be used is preferably in the range of from 1% by mass to 80% by mass, more preferably from 3% by mass to 65% by mass, yet more preferably from 5% by mass to 50% by mass, with respect to the mass of the pigment. When the content of the pigment derivative is within the above-specified range, the pigment can be favorable dispersed while suppressing the viscosity at a low level, whereby dispersion stability after the dispersion can be improved. In addition, by using the thus obtained colored composition, color filters that exhibit high transmissivity, excellent color properties and high contrast can be obtained.

<Other Components>

The colored curable composition of the first aspect of the invention may further contain other components such as a resin or a crosslinking agent, in addition to the above-mentioned components, to such an extent that the effect of the invention is not deteriorated.

—Resin—

As a resin to be used in the colored curable composition, an alkali-soluble binder is suitably used.

The alkali-soluble binder is not particularly limited as long as it has alkali solubility, and may be preferably selected in view of heat resistance, developability, availability and the like.

Preferable examples of the alkali-soluble binder include a linear organic high molecular weight polymer that is soluble in an organic solvent and is developable with a weak alkali aqueous solution. Examples of such linear organic high molecular weight polymers include polymers having carboxylic acid in a side chain, such as methacrylic acid copolymers, acrylic acid copolymers, itaconic acid copolymers, crotonic acid copolymers, maleic acid copolymers and partially-esterified maleic acid copolymers as described in JP-A No. 59-44615, JP-B Nos. 54-34327, 58-12577 and 54-25957 and JP-A Nos. 59-53836 and 59-71048. Acidic cellulose derivatives having carboxylic acids in side chains are also useful.

In addition to the above-mentioned binders, adducts of polymers having hydroxyl groups with acid anhydrides, polyhydroxystyrene resins, polysiloxane resins, poly(2-hydroxyethyl(meth)acrylate), polyvinyl pyrrolidone, polyethylene oxides, polyvinyl alcohols, and the like are also useful as the alkali-soluble binder in the first aspect of the invention. The linear organic high molecular weight polymer may be a copolymerization product of a hydrophilic monomer. Examples thereof include alkoxyalkyl (meth)acrylates, hydroxyalkyl (meth)acrylates, glycerol (meth)acrylates, (meth)acrylamides, N-methylolacrylamides, secondary or tertiary alkylacrylamides, dialkylaminoalkyl (meth)acrylates, morpholine (meth)acrylates, N-vinylpyrrolidone, N-vinylcaprolactam, vinylimidazole, vinyltriazole, methyl (meth)acrylates, ethyl (meth)acrylates, branched or linear propyl (meth)acrylates, branched or linear butyl (meth)acrylates, and phenoxyhydroxy propyl(meth)acrylates. Other examples of the hydrophilic monomer include monomers containing a tetrahydrofurfuryl group, a phosphoric acid group, a phosphoric acid ester group, a quaternary ammonium salt group, an ethyleneoxy chain, a propyleneoxy chain, a sulfonic acid group or a group derived from a salt thereof, or a morpholinoethyl group.

The alkali-soluble binder may have a polymerizable group in a side chain thereof in order to improve crosslinking efficiency. For example, polymers having an allyl group, a (meth) acryl group, an allyloxyalkyl groups or the like in a side chain thereof, and the like are also useful. Examples of the polymer having a polymerizable group include commercial products such as KS RESIST-106 (trade name, manufactured by Osaka Organic Chemical Industry Ltd.) and CYCLOMER-P series (all trade names, manufactured by Daicel Chemical Industries, Ltd.) Further, in order to improve the strength of a cured film, an alcohol-soluble nylon and a polyether of 2,2-bis-(4-hydroxyphenyl)propane and epichlorohydrin are also useful.

The alkali-soluble binder to be used is preferably a polymer (a), which obtained by polymerizing a compound represented by the following formula (E-1) (hereinafter, also referred to as an "ether dimer").

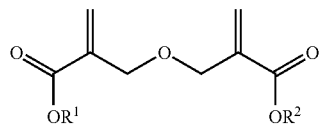

(E-1)

In the formula (E-1), each of $R^1$ and $R^2$ independently represents a hydrogen atom or a hydrocarbon group having 1 to 25 carbon atoms which may have a substituent.

When the colored curable composition of the first aspect of the invention contains the polymer (a), heat resistance and transparency of a cured film formed from the composition can be further improved.

In the formula (E-1) representing an ether dimer, the hydrocarbon group having 1 to 25 carbon atoms which may have a substituent, represented by $R^1$ and $R^2$, is not particularly limited, and examples thereof include a linear or branched alkyl group such as a methyl group, an ethyl group, an n-propyl group, an isopropyl group, an n-butyl group, an isobutyl group, a t-butyl group, a t-amyl group, a stearyl group, a lauryl group or a 2-ethylhexyl group; an aryl group such as a phenyl group; a cycloaliphatic group such as a cyclohexyl group, a t-butyl cyclohexyl group, a dicyclopentadienyl group, a tricyclodecanyl group, an isobornyl group, an adamantyl group or a 2-methyl-2-adamantyl group; an alkoxy-substituted alkyl group such as a 1-methoxyethyl group or a 1-ethoxyethyl group; and an aryl group-substituted alkyl group such as a benzyl group.

Among them, a group including a primary or secondary carbon, such as a methyl group, an ethyl group, a cyclohexyl group or a benzyl group that is less likely to detach due to acid or heat, is preferable in view of heat resistance.

The substituents represented by $R^1$ and $R^2$ may be the same or different from each other.

Specific examples of the ether dimer include:
dimethyl-2,2'-[oxybis(methylene)]bis-2-propenoate,
diethyl-2,2'-[oxybis(methylene)]bis-2-propenoate,
di(n-propyl)-2,2'[oxybis(methylene)]bis-2-propenoate,
di(isopropyl)-2,2'-[oxybis(methylene)]bis-2-propenoate,
di(n-butyl)-2,2'-[oxybis(methylene)]bis-2-propenoate,
di(isobutyl)-2,2'[oxybis(methylene)]bis-2-propenoate,
di(t-butyl)-2,2'[oxybis(methylene)]bis-2-propenoate,
di(t-amyl)-2,2'-[oxybis(methylene)]bis-2-propenoate,
di(stearyl)-2,2'[oxybis(methylene)]bis-2-propenoate,
di(lauryl)-2,2'-[oxybis(methylene)]bis-2-propenoate,
di(2-ethylhexyl)-2,2'[oxybis(methylene)]bis-2-propenoate,
di(1-methoxyethyl)-2,2'4-[oxybis(methylene)]bis-2-propenoate,
di(1-ethoxyethyl)-2,2'-[oxybis(methylene)]bis-2-propenoate,
dibenzyl-2,2'-[oxybis(methylene)]bis-2-propenoate,
diphenyl-2,2'1-[oxybis(methylene)]bis-2-propenoate,
dicyclohexyl-2,2'4-[oxybis(methylene)]bis-2-propenoate,
di(t-butylcyclohexyl)-2,2'4-[oxybis(methylene)]bis-2-propenoate,
di(dicyclopentadienyl)-2,2'-[oxybis(methylene)]bis-2-propenoate, di(tricyclodecanyl)-2,2'1-[oxybis(methylene)]bis-2-propenoate,
di(isobornyl)-2,2'-[oxybis(methylene)]bis-2-propenoate,
diadamantyl-2,2'-[oxybis(methylene)]bis-2-propenoate, and
di(2-methyl-2-adamantyl)-2,2'4-[oxybis(methylene)]bis-2-propenoate.

Among them, dimethyl-2,2'-[oxybis(methylene)]bis-2-propenoate, diethyl-2,2'-[oxybis(methylene)]bis-2-propenoate, dicyclohexyl-2,2'-[oxybis(methylene)]bis-2-propenoate, and dibenzyl-2,2'[oxybis(methylene)]bis-2-propenoate are preferable. These ether dimers may be used alone or in a combination of two or more kinds thereof.

A polymer having an epoxy group is also suitable as the alkali-soluble binder.

An epoxy group can be introduced into the alkali-soluble binder by, for example, using a monomer having an epoxy group (hereinafter, also referred to as a "monomer for introducing an epoxy group") for polymerization as a monomer component. Examples of such monomers having an epoxy group include glycidyl (meth)acrylate, 3,4-epoxycyclohexylmethyl (meth)acrylate and o-, m- or p-vinylbenzylglycidyl ether. These monomers for introducing an epoxy group may be used alone or in a combination of two or more kinds thereof. When the monomer components used for obtaining an alkali-soluble binder include a monomer for introducing an epoxy group, the content thereof is not particularly limited but preferably in the range of from 5% by mass to 70% by mass, more preferably from 10% by mass to 60% by mass, with respect to the total mass of the monomer components.

A polymer having an acidic group is also suitable as the alkali-soluble binder.

The acidic group is not particularly limited, and examples thereof include a carboxy group, a phenolic hydroxyl group, and a carboxylic acid anhydride group. These acidic groups may be used alone or in a combination of two or more kinds thereof. In order to introduce an acidic group into the alkali-soluble binder, for example, a monomer having an acidic group and/or a monomer capable of imparting an acidic group after polymerization (hereinafter, also referred to as a "monomer for introducing an acid group") may be used for polymerization as a monomer component.

When an acidic group is introduced by means of the monomer capable of imparting an acidic group after polymerization as a monomer component, for example, a treatment for imparting an acidic group, such as described hereinafter, needs to be carried out after the polymerization.

Examples of the monomer having an acidic group include a monomer having a carboxy group, such as (meth)acrylic acid or itaconic acid; a monomer having a phenolic hydroxyl group, such as N-hydroxyphenylmaleimide; and a monomer having a carboxylic acid anhydride group, such as maleic anhydride or itaconic anhydride. Particularly among them, (meth)acrylic acid is preferable.

Examples of the monomer capable of imparting an acid group after polymerization include a monomer having a hydroxyl group, such as 2-hydroxyethyl (meth)acrylate; a monomer having an epoxy group such as glycidyl (meth) acrylate; and a monomer having an isocyanate group, such as 2-isocyanatoethyl(meth)acrylate. These monomers for introducing an acidic group may be used alone or in a combination of two or more thereof.

When the monomer capable of imparting an acidic group after polymerization is used, examples of the treatment for imparting an acidic group after polymerization include a treatment of partially modifying polar groups of the polymer side chain through polymer reaction.

Among these alkali-soluble binders, a polyhydroxystyrene resin, a polysiloxane resin, an acrylic resin, an acrylamide resin and an acryl/acrylamide copolymer resin are preferable in view of heat resistance, and an acrylic resin, an acrylamide resin and an acryl/acrylamide copolymer resin are preferable in view of controlling the developability.

Preferred examples of the acrylic resins include copolymers formed from a monomer selected from benzyl (meth) acrylate, (meth)acrylic acid, hydroxyethyl (meth)acrylate, (meth)acrylamide or the like, and commercial products such as KS RESIST-106 (trade name, manufactured by Osaka Organic Chemical Industry Ltd.) and CYCLOMER-P series (all trade names, manufactured by Daicel Chemical Industries, Ltd.)

The alkali-soluble binder is a polymer having a weight average molecular weight (polystyrene-converted value measured by GPC) of preferably from 1,000 to $2 \times 10^5$, more preferably from 2,000 to $1 \times 10^5$, and particularly preferably from 5,000 to $5 \times 10^4$, in view of developability, liquid viscosity or the like.

The acid value of the alkali-soluble binder is preferably in the range of from 50 mgKOH/g to 300 mgKOH/g, more preferably from 75 mgKOH/g to 200 mgKOH/g, and particularly preferably from 80 mgKOH/g to 160 mgKOH/g. When the acid value of the alkali-soluble binder is within the above-specified range, remaining of development residues during the formation of a pattern can be suppressed, and coating uniformity can be improved.

—Crosslinking Agent—

A crosslinking agent may be used as a supplemental agent in the colored curable composition of the first aspect of the invention, in order to further increase the hardness of the colored cured film formed from the colored curable composition.

The crosslinking agent is not particularly limited as long as it can cure a film by crosslinking reaction, and examples thereof include (a) an epoxy resin, (b) a melamine compound, a guanamine compound, a glycoluril compound or an urea compound substituted by at least one selected from a methylol group, an alkoxymethyl group or an acyloxymethyl group, and (c) a phenol compound, a naphthol compound or a hydroxyanthracene compound substituted by at least one selected from a methylol group, an alkoxymethyl group or an acyloxymethyl group. Among these, multifunctional epoxy resins are preferable.

Details of the specific examples and the like of the crosslinking agent can be found in the paragraphs [0134] to [0147] of JP-A No. 2004-295116.

—Polymerization Inhibitor—

In the colored curable composition of the first aspect of the invention, it is preferred to add a small amount of a polymerization inhibitor in order to prevent unnecessary thermal polymerization of the polymerizable compound during the production or storage.

Examples of the polymerization inhibitor useful in the first aspect of the invention include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitrosophenylhydroxyamine primary cerium salt.

The addition amount of the polymerization inhibitor is preferably in the range of about 0.01% by mass to about 5% by mass with respect to the total mass of the composition.

—Surfactant—

The colored curable composition of the first aspect of the invention may contain a surfactant in view of further improving the coatability. Examples of the surfactants that may be used in the prevent invention include various surfactants such as a fluorosurfactant, a nonionic surfactant, a cationic surfactant, an anionic surfactant, and a silicone surfactant.

In particular, by using a fluorosurfactant, liquid properties (in particular, fluidity) of the composition as a coating liquid can be further improved, thereby further improving the uniformity of the coating thickness and saving the amount of liquid to be used.

Specifically, when a colored curable composition containing a fluorosurfactant is used, the surface tension between a surface of the substrate to be coated and the coating liquid is decreased and the wettability to the surface to be coated is improved, thereby improving the coatability. As a result, a film having a uniform thickness with suppressed unevenness can be favorably formed even when a film having a thickness of as small as several micrometers is formed with a small liquid amount.

The fluorine content in the fluorosurfactant is preferably in the range of from 3% by mass to 40% by mass, more preferably from 5% by mass to 30% by mass, and particularly preferably from 7% by mass to 25% by mass. When the fluorine content is within the above-specified range, it is effective to achieve the uniformity in the coating film thickness and save the amount of liquid to be used, while the solubility in the composition is favorable.

Examples of the fluorosurfactant include MEGAFAC F171, F172, F173, F176, F177, F141, F142, F143, F144, R30, F437, F479, F482, F780 and F781 (all trade names, manufactured by DIC Corporation), FLUORAD FC430, FC431 and FC171 (all trade names, manufactured by Sumitomo 3M Limited), SURFLON S-382, SC-101, SC-103, SC-104, SC-105, SC1068, SC-381, SC-383, 5393 and KH-40 (all trade names, manufactured by Asahi Glass Co., Ltd.), and CW-1 (trade name, manufactured by Zeneca).

Specific examples of the cationic surfactant include a phthalocyanine derivative (commercial product, trade name: EFKA-745, manufactured by Morishita & Co., Ltd.), an organosiloxane polymer (trade name: KP341, manufactured by Shin-Etsu Chemical Co., Ltd.), (meth)acrylic acid (co)polymers POLYFLOW No. 75, No. 90 and No. 95 (all trade names, manufactured by Kyoeisha Chemical Co., Ltd.), and W001 (trade name, manufactured by Yusho Co., Ltd.).

Specific examples of the nonionic surfactant include polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate, and sorbitan fatty acid ester (such as PLURONIC L10, L31, L61, L62, 10R5, 17R2 and 25R2, and TETRONIC 304, 701, 704, 901, 904 and 150R1, all trade names, manufactured by BASF).

Specific examples of the anionic surfactant include W004, W005 and W017 (all trade names, manufactured by Yusho Co., Ltd.).

Examples of the silicone surfactant include "TORAY SILICONE DC3PA", "TORAY SILICONE SH7PA", "TORAY SILICONE DC11PA", "TORAY SILICONE SH21PA", "TORAY SILICONE SH28PA", "TORAY SILICONE SH29PA", "TORAY SILICONE SH30PA" and "TORAY SILICONE SH8400" (all trade names, manufactured by Toray Silicone Co., Ltd.), "TSF-4440", "TSF-4300", "TSF-4445", "TSF-444(4)(5)(6)(7)6", "TSF-44 60" and "TSF-4452" (all trade names, manufactured by Toshiba Silicone Co., Ltd.), "KP341" (trade name, manufactured by Silicone Co., Ltd.), and "BYK323" and "BYK330" (all trade names, manufactured by BYK Chemie).

These surfactants may be used in a combination of two or more kinds thereof.

—Organic Carboxylic Acid—

Further, in view of enhancing the alkali solubility of non-exposed portions and further improving the developability of the colored curable composition, an organic carboxylic acid, preferably a low-molecular-weight organic carboxylic acid having a molecular weight of 1,000 or less, is preferably added to the composition.

Specific examples of the organic carboxylic acid include aliphatic monocarboxylic acids such as formic acid, acetic acid, propionic acid, butyric acid, valeric acid, pivalic acid, caproic acid, diethyl acetate, enanthic acid and caprylic acid; aliphatic dicarboxylic acids such as oxalic acid, malonic acid, succinic acid, glutaric acid, adipic acid, pimelic acid, suberic acid, azelaic acid, sebacic acid, brassylic acid, methyl malonic acid, ethyl malonic acid, dimethyl malonic acid, methyl succinic acid, tetramethyl succinic acid and citraconic acid; aliphatic tricarboxylic acids such as tricarballylic acid, aconitic acid and camphoronic acid; aromatic monocarboxylic acids such as benzoic acid, toluic acid, cuminic acid, hemellitic acid and mesitylenic acid; aromatic polycarboxylic acids such as phthalic acid, isophthalic acid, terephthalic acid, trimellitic acid, trimesic acid, mellophanic acid and pyromellitic acid; and other carboxylic acids such as phenyl acetic acid, hydratropic acid, hydrocinnamic acid, mandelic acid, phenylsuccinic acid, atropic acid, cinnamic acid, methyl cinnamate, benzyl cinnamate, cinnamylidene acetic acid, coumaric acid and umbellic acid.

—Other Additives—

Various additives including fillers, polymer compounds other than those mentioned above, adhesion accelerating agents, antioxidants, ultraviolet absorbers, and aggregation inhibitors may be optionally incorporated into the colored curable composition. These additives include those described in the paragraphs [0155] to [0156] of JP-A No. 2004-295116.

Further, the colored curable composition of the first aspect of the invention may contain the sensitizer and light stabilizer described in the paragraph [0078] of JP-A No. 2004-295116 and the thermal polymerization inhibitor described in the paragraph [0081] of the same publication.

<Preparation Method of Colored Heat-Curable Composition>

The colored heat-curable composition of the first aspect of the invention is prepared by mixing the above-mentioned essential components, and optional components as necessary.

During the preparation of the colored curable composition, the components that constitute the colored curable composition may be mixed at one time, or may be mixed after dissolving or dispersing each component in a solvent, respectively. The order of addition during mixing or the operation conditions are not particularly limited. For example, the composition may be prepared by simultaneously dissolving or dispersing all components in a solvent, or alternatively, the composition may be prepared from previously prepared two or more solutions or dispersions each containing part of the components at the time of using (applying) the composition.

The thus prepared colored curable composition may be subjected to filteration prior to using the same, with a Millipore filter or the like having a pore diameter of preferably from about 0.01 μm to 3.0 μm, more preferably from about 0.05 μm to 0.5 μm.

Since the colored curable composition of the first aspect of the invention exhibits excellent storage stability and can form a colored cured film having excellent light fastness, the composition can be suitably used for forming color pixels of color filters used for liquid crystal display devices (LCDs) or solid-state image sensors (for example, CCD and CMOS image sensors). Further, the composition can be suitably used for preparing printing inks, inkjet inks, paints or the like. The composition is particularly suitably used for forming color pixels (color filters) for solid-state image sensors such as CCD and CMOS image sensors.

<Color Filter and Production Method Thereof>

In the following, a method for producing a color filter using the colored curable composition of the first aspect of the invention (method for producing the color filter of the first aspect of the invention) will be described.

The method for producing the color filter of the first aspect of the invention includes (A) a step of applying the colored curable composition of the first aspect of the invention onto a support to form a colored curable composition layer, and (B) a step of exposing the colored curable composition layer formed in the step (A) through a mask, and developing the exposed colored curable composition layer to form a colored pattern.

The method for producing the color filter of the first aspect of the invention preferably further includes (C) a step of irradiating the colored pattern formed in the step (B), with ultraviolet radiation, and (D) a step of heat-treating the colored pattern that has been irradiated with ultraviolet radiation in the step (C).

Hereinafter, the method for producing the color filter of the first aspect of the invention will be described more specifically.

—Step (A)—

In the method for producing the color filter of the first aspect of the invention, the colored curable composition of the first aspect of the invention is applied onto a support by a coating process such as spin coating, casting coating or roll coating, to form a colored curable composition layer, and optionally subjecting the colored curable composition layer to preliminary curing (pre-baking) for drying the same.

Examples of the support used for the production method of the color filter of the first aspect of the invention include soda glass, borosilicate glass (trade name: PYREX®) and quartz glass, which are used for LCDs or the like, and these glass supports on which a transparent electroconductive film has been attached, photoelectric conversion device substrates used for imaging devices, such as silicon substrates, and complementary metal oxide film semiconductor (CMOS) substrates. Black stripes that isolate the pixels from each other may be formed on the support. Further, a primer layer may be formed on these supports for the purpose of improving the adhesion to an upper layer, preventing diffusion of the materials, or smoothing the surface of the support.

When the colored curable composition is spin-coated on the support, in order to reduce the amount of the composition to be dropped on the support, a suitable organic solvent may be dropped on the support prior to dropping the composition and rotating the support so as to improve the compatibility of the composition with respect to the support.

The pre-baking may be performed by, for example, using a hot plate or an oven at 70° C. to 130° C. for from about 0.5 minutes to 15 minutes.

The thickness of the colored curable composition layer formed from the colored curable composition may be appropriately selected according to the purpose. In general, the thickness of the colored curable composition layer is preferably in the range of from 0.2 µm to 5.0 µm, more preferably from 0.3 µm to 2.5 µm, and most preferably from 0.3 µm to 1.5 µm. The thickness of the colored curable composition layer mentioned here refers to a film thickness after pre-baking.

—Step (B)—

In the production method of the color filter of the first aspect of the invention, subsequently, the colored curable composition layer that has been formed on the support is exposed to light through a mask.

The light or radiation use for the exposure is preferably g-line, h-line, i-line, KrF beam or ArF beam, and particularly preferably i-line. When i-line is used, the exposure amount is preferably from 100 mJ/cm$^2$ to 10,000 mJ/cm$^2$.

Examples of other usable exposure radiation source include an ultrahigh-pressure, high-pressure, medium-pressure or low-pressure mercury lamp, a chemical lamp, a carbon-arc lamp, a xenon lamp, a metal halide lamp, various visible and ultraviolet laser sources, a fluorescent lamp, a tungsten lamp, and sunlight.

(Exposure Step Using Laser Source)

In the exposure step performed with a laser light source, ultraviolet laser beam may be used as a light source. The term Laser is an acronym of Light Amplification by Stimulated Emission of Radiation. Lasers are produced from a phenomenon of induced emission that occurs in a substance having a population inversion, and examples of an oscillator, an amplifier or an exiton medium that produces monochromatic light having intensified coherency and directionality by means of amplification or oscillation of light waves includes crystals, glass, liquids, dyes and gases. From these media, known laser beams having an oscillation Wavelength in an ultraviolet region, such as solid laser, liquid laser, gas laser or semiconductor laser, are obtained. Among them, solid laser and gas laser are preferable in view of their output and oscillation wavelength.

The laser used for exposure with a laser light source is preferably ultraviolet laser having a wavelength of preferably from 300 nm to 380 nm, more preferably from 300 nm to 360 nm, since the wavelength of this range corresponds to the photosensitive wavelength of a resist (colored curable composition).

Specifically, Nd:YAG laser (third harmonic: 355 nm), which is relatively unexpensive solid laser with a high output, and excimer lasers (XeCl: 308 nm, XeF: 353 nm) are preferably used.

The exposure dose with respect to the target (colored curable composition) is preferably in the range of from 1 mJ/cm$^2$ to 100 mJ/cm$^2$, more preferably from 1 mJ/cm$^2$ to 50 mJ/cm$^2$. The exposure dose in this range is preferable in terms of the productivity of the formed pattern.

The exposure apparatus that can be used in the exposure step using a laser source is not particularly limited, and examples thereof include commercially available apparatuses such as CALLISTO (trade name, manufactured by V Technology Co., Ltd.), EGIS (trade name, manufactured by V Technology Co., Ltd.) and DF2200G (trade name, manufactured by Dainippon Screen Mfg. Co., Ltd.), and other apparatuses may also be preferably used.

Light-emitting diodes (LEDs) or laser diodes (LDs) may also be used as an active radiation source. Specifically, when an ultraviolet radiation source is desired, an ultraviolet LED or an ultraviolet LD may be used. Examples thereof include a violet LED having a main emission spectrum in a wavelength range between 365 nm and 420 nm, which is commercially available from Nichia Corporation. When a further shorter wavelength is desired, an LED that emits active radiation centered at a region between 300 nm and 370 nm disclosed in U.S. Pat. No. 6,084,250 may be used. Other types of ultraviolet LED are also available, which provide radiation in various ultraviolet ranges. The active radiation source particularly preferred in the invention is UV-LED, and even more preferably UV-LED having a peak wavelength in a range of from 340 nm to 370 nm.

Since ultraviolet lasers exhibit favorable parallelism, pattern exposure can be performed without a mask by using the same. However, it is preferred to use a mask during the pattern exposure from the viewpoint of further improving the linearity of the pattern.

The exposed colored curable composition layer may be heated with a hot plate or an oven at 70° C. to 180° C. for 0.5 minutes to 15 minutes, prior to the subsequent development treatment.

Further, the exposure may be performed while allowing a nitrogen gas to flow in a chamber, in order to suppress oxidation and discoloration of the colorant in the colored curable composition layer.

Subsequently, the exposed colored curable composition layer is developed using a developer. Thorough these processes, a colored pattern (resist pattern) is formed.

The developer may be a combination of various organic solvents or an alkaline aqueous solution, as long as it can dissolve uncured portions (unexposed portions) and does not dissolve cured portions (exposed portions) of the colored curable composition layer. When the developer is an alkaline aqueous solution, the alkali concentration is preferably adjusted such that the pH of the developer is from 11 to 13, more preferably from 11.5 to 12.5. In particular, an alkaline aqueous solution in which the concentration of tetraethylammonium hydroxide is adjusted to 0.001% by mass to 10% by mass, preferably 0.01% by mass to 5% by mass, may be suitably used as a developer.

The development time is preferably in the range of from 30 seconds to 300 seconds, more preferably from 30 seconds to 120 seconds. The development temperature is preferably from 20° C. to 40° C., more preferably 23° C.

The development may be performed by a puddle system, a shower system, a spray system or the like.

When the development is performed with an alkali aqueous solution, it is preferable to wash the colored curable composition layer with water after the development. The method of washing may be appropriately selected according to the purpose. For example, the washing may be performed by rotating the support such as a silicon wafer substrate at a revolution rate of from 10 rpm to 500 rpm and showering the same with pure water supplied from ejection nozzles positioned above the revolution center.

Thereafter, in the production method of the color filter of the first aspect of the invention, the colored pattern that has been developed may be optionally subjected to post-heating and/or post-exposure in order to accelerate curing of the colored pattern.

—Step (C)—

In particular, in the production method of the color filter of the first aspect of the invention, color transfer to the adjacent pixels or to the upper and lower layers from the colored curable composition can be effectively suppressed by performing post-exposure with ultraviolet radiation. Color transfer is a problem that occurs when a dye such as a specific complex is used as a colorant, but this problem can be alleviated by performing post-exposure with ultraviolet radiation.

(Post-Exposure by Ultraviolet Irradiation)

When performing post-exposure with ultraviolet irradiation, it is preferably performed at an exposure dose [mJ/cm$^2$] that is at least 10 times as large as the exposure dose used in the exposure prior to the development [mJ/cm$^2$].

By exposing the developed colored pattern to ultraviolet light (UV light) for a certain period of time between the development and the heat treatment at step (D) as mentioned below, occurrence of color transfer during the subsequent heating may be effectively suppressed, and light fastness may be improved.

As a light source for irradiating ultraviolet light, for example, an ultrahigh-pressure mercury lamp, a high-pressure mercury lamp, a low-pressure mercury lamp, a deep UV lamp or the like may be used. Among them, a light source that irradiates ultraviolet light including light at a wavelength of 275 nm or less, in which an irradiation illuminance [mW/cm$^2$] of the light at a wavelength of 275 nm or less is 5% or more with respect to the integral irradiation illuminance of the light of all wavelengths in ultraviolet light, is preferable. By adjusting the irradiation illuminance of the light at a wavelength of 275 nm or less in the ultraviolet light to be 5% or more, color transfer to the adjacent pixels or the upper and lower layers can be further suppressed, and light fastness can be further improved.

From these viewpoints, the post-exposure with ultraviolet irradiation is preferably performed by using a different type of light source from the light source used in the exposure in the step (B), i.e., bright line such as i-line. Specifically, the post-exposure is preferably performed by using a high-pressure mercury lamp, a low-pressure mercury lamp, or the like. Among them, for the same reasons as mentioned above, the irradiation illuminance [mW/cm$^2$] of light at a wavelength of 275 nm or less is preferably 7% or more with respect to the integral irradiation illuminance of the light of all wavelengths in the ultraviolet light. Further, the upper limit of the irradiation illuminance of the light at a wavelength of 275 nm or less is desirably 25% or less.

The "integral irradiation illuminance" refers to the sum (area) of illuminances of lights of wavelengths included in the exposure light, which is obtained by drawing a curve when the illuminance at each spectral wavelength (radiation energy passing through a unit area/unit time; [mW/m$^2$]) is the ordinate and the wavelength [nm] of the light is the abscissa.

It is preferable that ultraviolet light is irradiated at an irradiation dose [mJ/cm$^2$] of at least 10 times as large as the exposure dose used in the exposure of the step (B). When the irradiation dose in the step (C) is less than 10 times as large as the exposure dose used in the exposure of the step (B), color transfer between adjacent pixels or to the upper and lower layers may be not prevented, and light fastness may be deteriorated.

Among them, the irradiation dose of ultraviolet light is preferably from 12 times to 200 times, more preferably from 15 times to 100 times, as large as the exposure dose used in the exposure of the step (B).

In this case, the integral irradiation illuminance in the irradiated ultraviolet light is preferably 200 mW/cm$^2$ or more. When the integral irradiation illuminance is 200 mW/cm$^2$ or more, an effect of suppressing color transfer between adjacent pixels or to the upper and lower layers and an effect of improving light fastness may be more effectively achieved. Among them, the integral irradiation illuminance is preferably in the range of from 250 mW/cm$^2$ to 2,000 mW/cm$^2$, more preferably from 300 mW/cm$^2$ to 1,000 mW/cm$^2$.

—Step (D)—

The colored pattern that has been subjected to the post-exposure with ultraviolet irradiation as mentioned above is preferably subjected to a heat treatment. By heating (post-baking) the formed colored pattern, the colored pattern can be further cured.

The heat treatment may be performed by using, for example, a hot plate, various kinds of heaters, an oven or the like.

The temperature for the heat treatment is preferably in the range of 100° C. to 300° C., more preferably 150° C. to 250° C. The heating time is preferably in the range of 30 seconds to 30,000 seconds, more preferably 60 seconds to 1,000 seconds.

In the production method of the color filter of the first aspect of the invention, the post-exposure may be performed with g-line, h-line, i-line, KrF, ArF, electron beams or X-rays, instead of performing with ultraviolet radiations as mentioned in the step (C).

When the post-exposure is performed by using the light source as mentioned above, the irradiation time is typically in the range of from 10 seconds to 180 seconds, preferably from 20 seconds to 120 seconds, more preferably from 30 seconds to 60 seconds.

Alternatively, in the production method of the color filter of the first aspect of the invention, only the post-heating performed in the step (D) may be performed without performing the post-exposure with ultraviolet irradiation in the step (C).

Although either the post-exposure or the post-heating may be performed first, it is preferable to perform the post-exposure prior to the post-heating. This is because deformation of the shape of color pattern that occurs in the post-heating, such as thermal sagging (change of a rectangular pattern into a spherical shape) or hemming bottom (reflowing of the lower part of the pattern) of the colored pattern, can be suppressed by promoting the curing of the pattern by performing the post-exposure.

The thus obtained colored pattern constitutes pixels of the color filter.

A color filter having two or more colors of pixels can be obtained by repeating the processes (A) and (B), and optionally steps (C) and (D), for the number of times corresponding to the number of colors of the pixels.

The step (C) and/or the step (D) may be performed each time after the completion of formation, exposure and development of a colored curable composition layer of a single color, or may be performed after the completion of formation, exposure and development of colored curable composition layers of all colors.

The color filter obtained by the production method of the color filter of the first aspect of the invention (the color filter of the first aspect of the invention), which is produced from the colored curable composition of the first aspect of the invention, exhibits excellent light fastness.

Accordingly, the color filter of the first aspect of the invention may be used for liquid crystal display devices, solid-state image sensors including CCD image sensors and CMOS image sensors, and camera systems using them. Further, the color filter of the first aspect of the invention is suitably used for solid-state image sensors in which a colored pattern having an extremely small size is formed on a thin film and a favorable rectangular cross-sectional profile is required, in particular CCD and CMOS image sensors with a high resolution of more than 1,000,000 pixels.

The colored curable composition in accordance with the first aspect of the invention can be easily washed off with a known cleaning liquid, even when the colored curable composition is attached, for example, to nozzles of an ejection unit, pipings or the inside of a coating apparatus, or the like. In this case, in order to conduct washing off more efficiently, a solvent used in the colored curable composition according to the first aspect of the invention is preferably used as a cleaning liquid.

Further, cleaning liquids described in JP-A Nos. 7-128867, 7-146562, 8-278637, 2000-273370, 2006-85140, 2006-291191, 2007-2101, 2007-2102, 2007-281523 and the like are also suitably used as a cleaning liquid for washing off the colored curable composition according to the first aspect of the invention.

Among them, alkylene glycol monoalkyl ether carboxylate and alkylene glycol monoalkyl ether are preferable.

These solvents may be used alone or in a combination of two or more thereof. When two or more solvents are mixed, a mixture of a solvent having a hydroxyl group and a solvent having no hydroxyl group is preferably used. The mass ratio of a solvent with a hydroxyl group to a solvent without a hydroxyl group is in the range of from 1/99 to 99/1, preferably from 10/90 to 90/10, more preferably from 20/80 to 80/20. A mixed solvent of propylene glycol monomethyl ether acetate (PGMEA) and propylene glycol monomethyl ether (PGME) in which the mixing ratio as mentioned above is 60/40 is particularly preferable.

In order to enhance the permeability of the cleaning liquid into the colored curable composition, the cleaning liquid may contain a surfactant as previously mentioned.

<Solid-State Image Sensor>

The solid-state image sensor of the first aspect of the invention includes a color filter of the first aspect of the invention. Since a color filter of the first aspect of the invention exhibits high light fastness, a solid-state image sensor including the color filter may provide excellent color reproducibility.

The configuration of the solid-state image sensor is not particularly limited as long as it includes the color filter of the first aspect of the invention and acts as a solid-state image sensor.

One example of such a configuration includes, on a support, plural photodiodes that constitute a light receiving area for a CCD image sensor or CMOS image sensor (solid-state image sensor) and transfer electrodes made of polysilicon or the like formed on the support, the color filter of the first aspect of the invention formed thereon, and a microlens formed thereon.

Further, in view of preventing discoloration of the colorant, a camera system including the color filter of the first aspect of the invention desirably includes a camera lens and an IR cut film provides with a dichroic-coated cover glass, a microlens or the like, and materials thereof preferably have an optical property of absorbing part or all of UV light of 400 nm or less. Further, it is preferable that the camera system has a structure in which permeation of oxygen is decreased so as to suppress oxidative discoloration of the coloring material. For example, it is preferable that the camera system is partially or completely sealed with a nitrogen gas.

<Liquid Crystal Display Device>

The color filter of the first aspect of the invention exhibits excellent light fastness and has color pixels having a favorable color hue, and thus it is suitable as a color filter for a liquid crystal display device.

A liquid crystal display device having such a color filter can display a high quality image.

The definition of display devices and explanation of such display devices are described in, for example, "Electronic Display Device (Akio Sasaki, Kogyo Chosakai Publishing Co., Ltd., 1990", "Display Device (Sumiaki Ibuki, Sangyo Tosho Publishing Co., Ltd., 1989)". Liquid crystal display devices are described in, for example, "Next Generation Liquid Crystal Display Techniques (Tatsuo Uchida, Kogyo Chosakai Publishing Co., Ltd., 1994)". The liquid crystal display device to which the first aspect of the invention is applicable is not particularly limited, and the first aspect of the invention can be applied to various types of liquid crystal display devices described in, for example, "Next Generation Liquid Crystal Display Techniques".

The color filter of the first aspect of the invention is particularly effective when it is used in color TFT liquid crystal display devices. Color TFT liquid crystal display devices are described in, for example, "Color TFT Liquid Crystal Display (Kyoritsu Shuppan Co., Ltd., 1996)". Further, the first aspect of the invention is applicable to liquid crystal display devices with a wider view angle such as an in-plane switching (IPS) system or a multi-domain vertical alignment (MVA) system, as well as STN, TN, VA, OCS, FFS, R-OCB and the like.

The color filter of the first aspect of the invention may also be applied to a color-filter on array (COA) system, which exhibits high brightness and high definition. In COA liquid crystal display devices, the color filter layer needs to satisfy requirements for an interlayer dielectric film, such as a low dielectric constant and resistance to a removing liquid, in addition to satisfying ordinary requirements as mentioned above. It is presumed that by selecting the color or the thickness of the colored pixels, in addition to the type of UV laser exposure method, transmissivity of the color filter with respect to UV laser used as exposure light can be increased and, as a result, it is possible to increase the curability of colored pixels and produce the same without causing chipping, peeling or unevenness. Accordingly, in particular, it is possible to improve the resistance of a colored layer provided directly or indirectly on a TFT support, and such a color layer is useful for COA liquid crystal display devices. In order to satisfy a low dielectric constant, a resin coating may be provided on the color filter layer.

In the colored layer formed by a COA system, in order to electrically connect the ITO electrode disposed on the colored layer and the terminal of the driving substrate disposed below the colored layer, an electrically conductive path, such as a rectangular through hole having a side length of about 1 μm to 15 μm or a U-shaped depressed area, needs to be formed. The size (the side length) of the electrically conductive path is preferably 5 μm or less, and according to the first aspect of the invention, an electrically conductive path having a size of 5 μm or less may also be formed.

These image display systems are described, for example, on page 43 of "EL, PDP, LCD Display-Latest Trends of Technology and Markets (Research Study Division of Toray Research Center, Inc., 2001)".

The liquid crystal display device of the first aspect of the invention includes, in addition to the color filter of the first aspect of the invention, various kinds of members such as an electrode substrate, a polarization film, a phase difference film, a back light, a spacer, and a view angle compensation film. The color filter of the first aspect of the invention may be applied to liquid crystal display devices including these known members.

These members are described, for example, in "'94 Market of Liquid Crystal Display Related Materials And Chemicals (Kentaro Shima, CMC Publishing Co., Ltd., 1994)" and "2003 Current State And Perspective Of Liquid Crystal Related Market (Ryokichi Omote, Fuji Chimera Research Institute, Inc., 2003)".

Back lights are described, for example, in SID meeting Digest 1380 (2005) (A. Konno et al) and Monthly Display, 2005 December, pages 18-24 (Hiroyasu Shima) and pages 25-30 (Takaaki Yagi).

When the color filter of the first aspect of the invention is used in liquid crystal display devices, high contrast can be realized when combined with a known three-wavelength cold-cathode tube. Further, by using red, green and blue LED light sources (RGB-LED) as a back light, liquid crystal display devices having high brightness, high color purity, and favorable color reproducibility can be obtained.

<Second Aspect>

The second aspect of the present invention is a colored curable composition containing a phthalocyanine pigment, a dye multimer having a polymerizable group and a group derived from a dipyrromethene dye, a polymerization initiator, a polymerizable compound, and a solvent.

In has been proved that when a colored pattern is formed from a colored curable composition that includes a dye containing a dipyrromethene compound and a phthalocyanine pigment, a phenomenon in which the color of the colored pattern bleeds into the adjacent layers (also referred to as "color bleeding") may occur particularly when a heat treatment is performed to the colored pattern.

The second aspect of the invention has been made in view of the above circumstances, and aims to accomplish the following objects.

Specifically, an object of the second aspect of the invention is to provide a colored curable composition capable of forming a colored pattern that exhibits suppressed color bleeding.

Another object of the second aspect of the invention is to provide a color filter that exhibits suppressed color bleeding and a method for producing the color filter, and a solid-state. image sensor including the color filter.

According to the second aspect of the invention, a colored curable composition capable of forming a colored pattern that exhibits suppressed color bleeding can be provided.

Further, according to the second aspect of the invention, a color filter that exhibits suppressed color bleeding and a method for producing the color filter, and a solid-state image sensor including the color filter can be provided.

<Colored Curable Composition>

First, the colored curable composition of the second aspect of the invention will be described.

The colored curable composition of the second aspect of the invention includes a phthalocyanine pigment, a dye multimer having a polymerizable group and a group derived from a dipyrromethene dye, a polymerization initiator, a polymerizable compound, and a solvent.

When a colored pattern is formed from a colored curable composition including a dye containing a dipyrromethene compound and a phthalocyanine pigment, a phenomenon in which the color of the colored pattern bleeds into the adjacent layers or the laminated layers (color bleeding) may occur when the colored pattern is subjected to a heat treatment. This is believed to be because a dye containing a dipyrromethene compound can readily migrate into the adjacent layers or the laminated layers via a heat treatment.

In this regard, by using a colored curable composition according to the second aspect of the invention, occurrence of color bleeding during the formation of the colored pattern can be suppressed.

Although the reason why color bleeding is suppressed is not fully understood, it is believed to be because migration of the colorant to the adjacent layers or the laminated layers is suppressed as a result of using a dye multimer having a polymerizable group and a group derived from a dipyrromethene dye as a colorant containing a dipyrromethene compound. However, the present invention is not limited to this supposition.

<Phthalocyanine Pigment>

The phthalocyanine pigment used in the second aspect of the invention is not particularly limited as long as it is a pigment having a phthalocyanine backbone. The central metal included in the phthalocyanine pigment may be any metal capable of constituting a phthalocyanine backbone, and is not particularly limited. Among them, magnesium, titanium, iron, cobalt, nickel, copper, zinc and aluminum are preferably used as the central metal.

Specific examples of the phthalocyanine pigment used in the second aspect of the invention include C.I. Pigment Blue 15, C.I. Pigment Blue 15:1, C.I. Pigment Blue 15:2, C.I. Pigment Blue 15:3, C.I. Pigment Blue 15:4, C.I. Pigment Blue 15:5, C.I. Pigment Blue 15:6, C.I. Pigment Blue 16, C.I. Pigment Blue 17:1, C.I. Pigment Blue 75, C.I. Pigment Blue 79, C.I. Pigment Green 7, C.I. Pigment Green 36, C.I. Pigment Green 37, chloroaluminum phthalocyanine, hydroxyaluminum phthalocyanine, aluminum phthalocyanine oxide and zinc phthalocyanine. Among them, C.I. Pigment Blue 15, C.I. Pigment Blue 15:6, C.I. Pigment Blue 15:1 and C.I. Pigment Blue 15:2 are preferable, and C.I. Pigment Blue 15:6 is particularly preferable in view of light fastness and tinctorial strength.

The content of the phthalocyanine pigment in the colored curable composition used in the second aspect of the invention is preferably in the range of from 10% by mass to 60% by mass, more preferably from 20% by mass to 60% by mass, and most preferably from 35% by mass to 50% by mass, with respect to the total solid components of the colored curable composition.

<Dye Multimer Containing Polymerizable Group and Group Derived from Dipyrromethene Dye>

The colored curable composition of the second aspect of the invention includes at least one kind of dye multimer containing a polymerizable group and a group derived from a dipyrromethene dye (hereinafter, also referred to as a "polymerizable group-containing dye multimer"). The polymerizable group-containing dye multimer functions, for example, as a colorant in the colored curable composition of the second aspect of the invention.

The polymerizable group-containing dye multimer exhibits a favorable color hue and a high absorption coefficient since it is a dye multimer containing a group derived from a dipyrromethene dye, and the colored curable composition of the second aspect of the invention is capable of forming a cured film that exhibits excellent color purity even when it is formed into a thin film.

The polymerizable group-containing dye multimer may include a single type of dipyrromethene dye-derived group, or may include two or more types thereof.

Since the polymerizable group-containing dye multimer has a polymerizable group, the colored curable composition of the second aspect of the invention is capable of forming a cured film having excellent light fastness, heat resistance and solvent resistance, suppressed color bleeding, and favorable pattern formability, even when it is formed into a thin film.

The polymerizable group-containing dye multimer may include a single type of polymerizable group, or may include two or more types thereof.

Examples of the polymerizable group include an ethylenically unsaturated group (for example, a methacryl group, an acryl group or a styryl group), a cyclic ether group (for example, an epoxy group or an oxetanyl group), and the like. Among them, an ethylenically unsaturated group is preferable in view of heat resistance and solvent resistance after polymerization.

It is preferable that the polymerizable group-containing dye multimer contains a structural unit having a polymerizable group and a structural unit having a group derived from a dipyrromethene dye (hereinafter, also referred to as a "structural unit having a dye-derived group") as repeating units.

Further, the polymerizable group-containing dye multimer may contain other structural units, in addition to a "structural unit having a polymerizable group" and a "structural unit having a dye-derived group".

In the polymerizable group-containing dye multimer, in view of reducing the thickness of a color filter, the content of the structural unit having a dye-derived group is preferably, by mass ratio, in the range of from 60% by mass to 99% by mass, more preferably from 70% by mass to 97% by mass, and even more preferably from 80% by mass to 95% by mass.

Further, in view of heat resistance and solvent resistance, the content of the structural unit having a polymerizable group is preferably, by mass ratio, in the range of from 1% by mass to 40% by mass, more preferably from 3% by mass to 30% by mass, and even more preferably from 5% by mass to 20% by mass.

Although the weight average molecular weight of the polymerizable group-containing dye multimer (polystyrene-converted value measured by a GPC method) is not particularly limited, it is preferably in the range of from 3000 to 50000, more preferably from 5000 to 30000, and particularly preferably from 7000 to 20000, in view of more effectively suppressing color bleeding.

The structural unit having a dye-derived group may be introduced into the polymerizable group-containing dye multimer by performing, for example, radical polymerization of a dye compound in which a polymerizable group (for example, an acryloxy group, a methacryloxy group or a styryl group) is introduced into a dipyrromethene dye backbone. Alternatively, the structural unit having a dye-derived group may be introduced into the polymerizable group-containing dye multimer by allowing a dye compound, in which a group capable of polycondensation or polyaddition reaction is introduced into the dipyrromethene dye backbone, to react with a multifunctional crosslinking agent.

The structural unit having a polymerizable group may be introduced into the polymerizable group-containing dye multimer, for example, by the following method.

Specifically, the structural unit having a polymerizable group may be introduced by copolymerizing the dye compound and a copolymerization component that does not have a dye backbone (for example, methacrylic acid, acrylic acid or hydroxyethyl methacrylate) to obtain a multimer, and then adding a polymerizable compound having a group capable of reacting with the structural unit derived from the copolymerization component (for example, glycidyl methacrylate or methacryloxyethyl isocyanate).

Further, a polymerizable group-containing dye multimer may be obtained by introducing a polymerizable group, which is different from the polymerizable group responsible for multimerization of a dye compound, into the dipyrromethene dye backbone in the dye compound, and then polymerizing the dye compound.

Hereinafter, the dipyrromethene dye, the structural unit having a dye-derived group, and the structural unit having a polymerizable group will be described in more detail.

(1) Dipyrromethene Dye

Although the dipyrromethene dye is not particularly limited, the dipyrromethene dye represented by the following formula (C) is preferably used in view of light fastness and heat resistance.

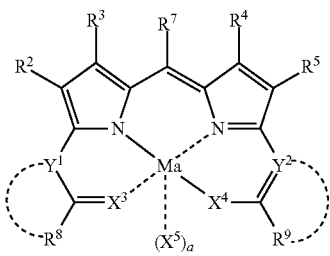

(C)

In the formula (C), each of $R^2$ to $R^5$ independently represents a hydrogen atom or a substituent, $R^7$ represents a hydrogen atom, a halogen atom, an alkyl group, an aryl group or a heterocyclic group, Ma represents a metal or a metal compound, each of $X^3$ and $X^4$ independently represents NR (wherein R represents a hydrogen atom, an alkyl group, an alkenyl group, an aryl group, a heterocyclic group, an acyl group, an alkylsulfonyl group or an arylsulfonyl group), an oxygen atom or a sulfur atom, $Y^1$ represents NRc (wherein Rc represents a hydrogen atom, an alkyl group, an alkenyl group, an aryl group, a heterocyclic group, an acyl group, an alkylsulfonyl group or an arylsulfonyl group) or a nitrogen atom, $Y^2$ represents a nitrogen atom or a carbon atom, each of $R^8$ and $R^9$ independently represents an alkyl group, an alkenyl group, an aryl group, a heterocyclic group, an alkoxy group, an aryloxy group, an alkylamino group, an arylamino group or a heterocyclic amino group, $R^8$ and $Y^1$ may be bonded to each other to form a 5-, 6- or 7-membered ring, $R^9$ and $Y^2$ may be bonded to each other to form a 5-, 6- or 7-membered ring, $X^5$ represents a group capable of being bonded to Ma, and a represents 0, 1 or 2. Further, the dipyrromethene dye represented by the formula (C) includes a tautomer thereof.

Substituents of the formula (C) will be described in more detail.

Each of $R^2$ to $R^5$ independently represents a hydrogen atom or a substituent. Examples of the substituent include a halogen atom (for example, fluorine, chlorine or bromine), an alkyl group (a linear, branched or cyclic alkyl group having preferably 1 to 48 carbon atoms, more preferably 1 to 24 carbon atoms, such as methyl, ethyl, propyl, isopropyl, butyl, t-butyl, pentyl, hexyl, heptyl, octyl, 2-ethylhexyl, dodecyl, hexadecyl, cyclopropyl, cyclopentyl, cyclohexyl, 1-norbornyl or 1-adamantyl), an alkenyl group (an alkenyl group having preferably 2 to 48 carbon atoms, more preferably 2 to 18 carbon atoms, such as vinyl, allyl or 3-buten-1-yl), an aryl group (an aryl group having preferably 6 to 48 carbon atoms, more preferably 6 to 24 carbon atoms, such as phenyl or naphthyl), a heterocyclic group (a heterocyclic group having preferably 1 to 32 carbon atoms, more preferably 1 to 18 carbon atoms, such as 2-thienyl, 4-pyridyl, 2-furyl, 2-pyrimidinyl, 1-pyridyl, 2-benzothiazolyl, 1-imidazolyl, 1-pyrazolyl or benzotriazol-1-yl), a silyl group (a silyl group having preferably 3 to 38 carbon atoms, more preferably 3 to 18 carbon atoms, such as trimethylsilyl, triethylsilyl, tributylsilyl, t-butyldimethylsilyl or t-hexyldimethylsilyl), a hydroxyl group, a cyano group, a nitro group, an alkoxy group (an alkoxy group having preferably 1 to 48 carbon atoms, more preferably 1 to 24 carbon atoms, such as methoxy, ethoxy, 1-butoxy, 2-butoxy, isopropoxy, t-butoxy, dodecyloxy or cycloalkyloxy, for example cyclopentyloxy or cyclohexyloxy), an aryloxy group (an aryloxy group having preferably 6 to 48 carbon atoms, more preferably 6 to 24 carbon atoms, such as phenoxy or 1-naphthoxy), a heterocyclic oxy group (a heterocyclic oxy group having preferably 1 to 32 carbon atoms, more preferably 1 to 18 carbon atoms, such as 1-phenyltetrazol-5-oxy or 2-tetrahydropyranyloxy), a silyloxy group (a silyloxy group having preferably 1 to 32 carbon atoms, more preferably 1 to 18 carbon atoms, such as trimethylsilyloxy, t-butyldimethylsilyloxy or diphenylmethylsilyloxy), an acyloxy group (an acyloxy group having preferably 2 to 48 carbon atoms, more preferably 2 to 24 carbon atoms, such as acetoxy, pivaloyloxy, benzoyloxy or dodecanoyloxy), an alkoxycarbonyloxy group (an alkoxycarbonyloxy group having preferably 2 to 48 carbon atoms, more preferably 2 to 24 carbon atoms, such as ethoxycarbonyloxy, t-butoxycarbonyloxy or cycloalkyloxycarbonyloxy, for example, cyclohexyloxycarbonyloxy), an aryloxycarbonyloxy group (an aryloxycarbonyloxy group having preferably 7 to 32 carbon atoms, more preferably 7 to 24 carbon atoms, such as phenoxycarbonyloxy), a carbamoyloxy group (a carbamoyloxy group having preferably 1 to 48 carbon atoms, more preferably 1 to 24 carbon atoms, such as N,N-dimethylcarbamoyloxy, N-butylcarbamoyloxy, N-phenylcarbamoyloxy or N-ethyl-N-phenylcarbamoyloxy), a sulfamoyloxy group (a sulfamoyloxy group having preferably 0 to 32 carbon atoms, more preferably 1 to 24 carbon atoms, such as N,N-diethylsulfamoyloxy or N-propylsulfamoyloxy), an alkylsulfonyloxy group (an alkylsulfonyloxy group having preferably 1 to 38 carbon atoms, more preferably 1 to 24 carbon atoms, such as methylsulfonyloxy, hexadecylsulfonyloxy or cyclohexylsulfonyloxy), an arylsulfonyloxy group (an arylsulfonyloxy group having preferably 6 to 32 carbon atoms, more preferably 6 to 24 carbon atoms, such as phenylsulfonyloxy), an acyl group (an acyl group having preferably 1 to 48 carbon atoms, more preferably 1 to 24 carbon atoms, such as formyl, acetyl, pivaloyl, benzoyl, tetradecanoyl or cyclohexanoyl), an alkoxycarbonyl group (an alkoxycarbonyl group having preferably 2 to 48 carbon atoms, more preferably 2 to 24 carbon atoms, such as methoxycarbonyl, ethoxycarbonyl, octadecyloxycarbonyl, cyclohexyloxycarbonyl or 2,6-di-tert-butyl-4-methylcyclohexyloxycarbonyl), an aryloxycarbonyl group (an aryloxycarbonyl group having preferably 7 to 32 carbon atoms, more preferably 7 to 24 carbon atoms, such as phenoxycarbonyl), a carbamoyl group (a carbamoyl group having preferably 1 to 48 carbon atoms, more preferably 1 to 24 carbon atoms, such as carbamoyl, N,N-diethylcarbamoyl, N-ethyl-N-octylcarbamoyl, N,N-dibutylcarbamoyl, N-propylcarbamoyl, N-phenylcarbamoyl, N-methyl-N-phenylcarbamoyl or N,N-dicyclohexylcarbamoyl), an amino group (an amino group having preferably 32 or less carbon atoms, more preferably 24 or less carbon atoms, such as amino, methylamino, N,N-dibutylamino, tetradecylamino, 2-ethylhexylamino or cyclohexylamino), an anilino group (an anilino group having preferably 6 to 32 carbon atoms, more preferably 6 to 24 carbon atoms, such as anilino or N-methylanilino), a heterocyclic amino group (a heterocyclic amino group having preferably 1 to 32 carbon atoms, more preferably 1 to 18 carbon atoms, such as 4-pyridylamino), a carbonamido group (a carbonamido group having preferably 2 to 48 carbon atoms, more preferably 2 to 24 carbon atoms, such as acetamido, benzamido, tetradecanamido, pivaloylamido or cyclohexanamido), a ureido group (a ureido group having preferably 1 to 32 carbon atoms, more preferably 1 to 24 carbon atoms, such as ureido, N,N-dimethylureido or N-phenylureido), an imide group (an imide group having preferably 36 or less carbon atoms, more preferably 24 or fewer carbon atoms, such as N-succinimide or N-phthalimide), an alkoxycarbonylamino group (an alkoxycarbonylamino group having preferably 2 to 48 carbon atoms, more preferably 2 to 24 carbon atoms, such as methoxycarbonylamino, ethoxycarbonylamino, t-butoxycarbonylamino, octadecyloxycarbonylamino or cyclohexyloxycarbonylamino), an aryloxycarbonylamino group (an aryloxycarbonylamino group having preferably 7 to 32 carbon atoms, more preferably 7 to 24 carbon atoms, such as phenoxycarbonylamino), a sulfonamido group (a sulfonamido group having preferably 1 to 48 carbon atoms, more preferably 1 to 24 carbon atoms, such as methanesulfonamido, butanesulfonamido, benzenesulfonamido, hexadecanesulfonamido or cyclohexanesulfonamido), a sulfamoylamino group (a sulfamoylamino group having preferably 1 to 48 carbon atoms, more preferably 1 to 24 carbon atoms, such as N,N-dipropylsulfamoylamino or N-ethyl-N-dodecylsulfamoylamino), an azo group (an azo group having preferably 1 to 32 carbon atoms, more preferably 1 to 24 carbon atoms, such as phenylazo or 3-pyrazolylazo), an alkylthio group (an alkylthio group having preferably 1 to 48 carbon atoms, more preferably 1 to 24 carbon atoms, such as methylthio, ethylthio, octylthio or cyclohexylthio), an arylthio group (an arylthio group having preferably 6 to 48 carbon atoms, more preferably 6 to 24 carbon atoms, such as phenylthio), a heterocyclic thio group (a heterocyclic thio group having preferably 1 to 32 carbon atoms, more preferably 1 to 18 carbon atoms, such as 2-benzothiazolylthio, 2-pyridylthio or 1-phenyltetrazolylthio), an alkylsulfinyl group (an alkylsulfinyl group having preferably 1 to 32 carbon atoms, more preferably 1 to 24 carbon atoms, such as dodecanesulfinyl), an arylsulfinyl group (an arylsulfinyl group having preferably 6 to 32 carbon atoms, more preferably 6 to 24 carbon atoms, such as phenylsulfinyl), an alkylsulfonyl group (an alkylsulfonyl group having preferably 1 to 48 carbon atoms, more preferably 1 to 24 carbon atoms, such as methylsulfonyl, ethylsulfonyl, propylsulfonyl, butylsulfonyl, isopropylsulfonyl, 2-ethylhexylsulfonyl, hexadecylsulfonyl, octylsulfonyl or cyclohexylsulfonyl), an arylsulfonyl group (an arylsulfonyl group having preferably 6 to 48 carbon atoms, more preferably 6 to 24 carbon atoms, such as phenylsulfonyl or 1-naphthylsulfonyl), a sulfamoyl group (a sulfamoyl group having preferably 32 or less carbon atoms, more preferably 24 or less carbon atoms, such as sulfamoyl, N,N-dipropylsulfamoyl, N-ethyl-N-dodecylsulfamoyl, N-ethyl-N-phenylsulfamoyl or N-cyclohexylsulfamoyl), a sulfo group, a phosphonyl group (a phosphonyl group having preferably 1 to 32 carbon atoms, more preferably 1 to 24 carbon atoms, such as phenoxyphosphonyl, octyloxyphosphonyl or phenylphosphonyl) and a phosphinoylamino group (a phosphinoylamino group having preferably 1 to 32 carbon atoms, more preferably 1 to 24 carbon atoms, such as diethoxyphosphinoylamino or dioctyloxyphosphinoylamino).

When the substituent represented by $R^2$ and $R^5$ is a substituent that may be further substituted, it may be further substituted, for example, by any of the above-mentioned substituents. When $R^2$ or $R^5$ is substituted by two or more substituents, these substituents may be the same or different from each other.

Among them, $R^2$ and $R^5$ preferably represent a cyano group, an alkoxycarbonyl group, a carbamoyl group, an acyl group or an alkylsulfonyl group, more preferably an alkoxycarbonyl group or a carbamoyl group. Among them, $R^3$ and $R^4$ preferably represent a substituted or unsubstituted alkyl group or a substituted or unsubstituted aryl group, more preferably a substituted or unsubstituted alkyl group having 1 to 10 carbon atoms, or a substituted or unsubstituted phenyl group.

$R^7$ preferably represents a hydrogen atom, a halogen atom, an alkyl group (an alkyl group preferably having 1 to 24 carbon atoms, more preferably having 1 to 12 carbon atoms, for example, methyl, ethyl, propyl, butyl, isopropyl, t-butyl, 2-ethylhexyl, dodecyl, cyclopropyl, cyclopentyl, cyclohexyl or adamantyl), an aryl group (an aryl group preferably having 6 to 24 carbon atoms, more preferably having 6 to 12 carbon atoms, for example, phenyl or naphthyl), or a heterocyclic group (a heterocyclic group preferably having 1 to 24 carbon atoms, more preferably having 1 to 12 carbon atoms, for example, 2-thienyl, 4-pyridyl, 2-furyl, 2-pyrimidinyl, 1-pyridyl, 2-benzothiazolyl, 1-imidazolyl, 1-pyrazolyl or benzotriazol-1-yl).

Among them, $R^7$ preferably represents a hydrogen atom, an alkyl group, an aryl group or a hetero ring, more preferably a hydrogen atom or an alkyl group, and even more preferably a hydrogen atom.

The alkyl group, aryl group or heterocyclic group of $R^7$ may be substituted, for example, by the substituents represented by $R^2$ to $R^5$ as previously mentioned, and when it is substituted by two or more substituents, these substituents may be the same or different from each other.

In the formula (C), Ma represents a metal atom or a metal compound. The metal atom or the metal compound may be any metal atom or metal compound as long as it can form a complex, and examples thereof include a divalent metal atom, a divalent metal oxide, a divalent metal hydroxide and a divalent metal chloride, such as Zn, Mg, Si, Sn, Rh, Pt, Pd, Mo, Mn, Pb, Cu, Ni, Co and Fe, as well as metal chlorides including $AlCl$, $InCl$, $FeCl$, $TiCl_2$, $SnCl_2$, $SiCl_2$ and $GeCl_2$, metal oxides including TiO and VO, and metal hydroxides including $Si(OH)_2$.

In the formula (C), each of $X^3$ and $X^4$ independently represents NR, an oxygen atom or a sulfur atom, wherein R represents a hydrogen atom, an alkyl group (a linear, branched or cyclic alkyl group having preferably 1 to 36 carbon atoms, more preferably 1 to 12 carbon atoms, such as methyl, ethyl, propyl, isopropyl, butyl, isobutyl, t-butyl, hexyl, 2-ethylhexyl, dodecyl, cyclopropyl, cyclopentyl, cyclohexyl or 1-adamantyl), an alkenyl group (an alkenyl group having preferably 2 to 24 carbon atoms, more preferably 2 to 12 carbon atoms, such as vinyl, allyl or 3-buten-1-yl), an aryl group (an aryl group having preferably 6 to 36 carbon atoms, more preferably 6 to 18 carbon atoms, such as phenyl or naphthyl), a heterocyclic group (a heterocyclic group having preferably 1 to 24 carbon atoms, more preferably 1 to 12 carbon atoms, such as 2-thienyl, 4-pyridyl, 2-furyl, 2-pyrimidinyl, 1-pyridyl, 2-benzothiazolyl, 1-imidazolyl, 1-pyrazolyl or benzotriazol-1-yl), an acyl group (an acyl group having preferably 1 to 24 carbon atoms, more preferably 2 to 18 carbon atoms, such as acetyl, pivaloyl, 2-ethylhexyl, benzoyl or cyclohexanoyl), an alkylsulfonyl group (an alkylsulfonyl group having preferably 1 to 24 carbon atoms, more preferably 1 to 18 carbon atoms, such as methylsulfonyl, ethylsulfonyl, isopropylsulfonyl or cyclohexylsulfonyl), or an arylsulfonyl group (an arylsulfonyl group having preferably 6 to 24 carbon atoms, more preferably 6 to 18 carbon atoms, such as phenylsulfonyl or naphthylsulfonyl).

The alkyl group, alkenyl group, aryl group, heterocyclic group, acyl group, alkylsulfonyl group or arylsulfonyl group represented by R may be substituted by, for example, any of the substituents represented by $R^2$ to $R^5$ as previously mentioned, and when it is substituted by two or more substituents, these substituents may be the same or different from each other.

In the formula (C), $Y^1$ represents NRc or a nitrogen atom, and Rc has the same definitions as that of R for $X^3$ and $X^4$, and preferable embodiments thereof are also the same.

In the formula (C), each of $R^8$ and $R^9$ independently represents an alkyl group (a linear, branched or cyclic alkyl group having preferably 1 to 36 carbon atoms, more preferably 1 to 12 carbon atoms, such as methyl, ethyl, propyl, isopropyl, butyl, isobutyl, t-butyl, hexyl, 2-ethylhexyl, dodecyl, cyclopropyl, cyclopentyl, cyclohexyl or 1-adamantyl), an alkenyl group (an alkenyl group having preferably 2 to 24 carbon atoms, more preferably 2 to 12 carbon atoms, such as vinyl, allyl or 3-buten-1-yl), an aryl group (an aryl group having preferably 6 to 36 carbon atoms, more preferably 6 to 18 carbon atoms, such as phenyl or naphthyl), a heterocyclic group (a heterocyclic group having preferably 1 to 24 carbon atoms, more preferably 1 to 12 carbon atoms, such as 2-thienyl, 4-pyridyl, 2-furyl, 2-pyrimidinyl, 1-pyridyl, 2-benzothiazolyl, 1-imidazolyl, 1-pyrazolyl or benzotriazol-1-yl), an alkoxy group (an alkoxy group having preferably 1 to 36 carbon atoms, more preferably 1 to 18 carbon atoms, such as methoxy, ethoxy, propyloxy, butoxy, hexyloxy, 2-ethylhexyloxy, dodecyloxy or cyclohexyloxy), an aryloxy group (an aryloxy group having preferably 6 to 24 carbon atoms, more preferably 6 to 18 carbon atoms, such as phenoxy or naphthyloxy), an alkylamino group (an alkylamino group having preferably 1 to 36 carbon atoms, more preferably 1 to 18 carbon atoms, such as methylamino, ethylamino, propylamino, butylamino, hexylamino, 2-ethylhexylamino, isopropylamino, t-butylamino, t-octylamino, cyclohexylamino, N,N-diethylamino, N,N-dipropylamino, N,N-dibutylamino or N-methyl-N-ethylamino), an arylamino group (an arylamino group having preferably 6 to 36 carbon atoms, more preferably 6 to 18 carbon atoms, such as phenylamino, naphthylamino, N,N-diphenylamino or N-ethyl-N-phenylamino), or a heterocyclic amino group (a heterocyclic amino group having preferably 1 to 24 carbon atoms, more preferably 1 to 12 carbon atoms, such as 2-aminopyrrole, 3-aminopyrazole, 2-aminopyridine or 3-aminopyridine).

Among them, $R^8$ and $R^9$ each preferably represent a substituted or unsubstituted alkyl group or a substituted or unsubstituted aryl group, more preferably a substituted or unsubstituted alkyl group having 1 to 15 carbon atoms or a substituted or unsubstituted phenyl group having 6 to 15 carbon atoms.

In the formula (C), when the alkyl group, alkenyl group, aryl group, heterocyclic group, alkoxy group, aryloxy group, alkylamino group, arylamino group or heterocyclic amino group represented by $R^8$ or $R^9$ is a group that can be further substituted, for example, it may be substituted by the substituents represented by $R^2$ to $R^5$ as previously mentioned, and when it is substituted by two or more substituents, these substituents may be the same or different from each other.

In the formula (C), $R^8$ and $Y^1$ may be bonded to each other to form, together with the carbon atom, a 5-membered ring (for example, cyclopentane, pyrrolidine, tetrahydrofuran, dioxolane, tetrahydrothiophene, pyrrole, furan, thiophene, indole, benzofuran or benzothiophene), a 6-membered ring (for example, cyclohexane, piperidine, piperazine, morpholine, tetrahydropyran, dioxane, pentamethylenesulfide, dithiane, benzene, piperidine, piperazine, pyridazine, quinoline or quinazoline) or a 7-membered ring (for example, cycloheptane or hexamethyleneimine).

In the formula (C), $R^9$ and $Y^2$ may be bonded to each other to form, together with the carbon atom, a 5-membered ring (for example, cyclopentane, pyrrolidine, tetrahydrofuran, dioxolane, tetrahydrothiophene, pyrrole, furan, thiophene, indole, benzofuran or benzothiophene), a 6-membered ring (for example, cyclohexane, piperidine, piperazine, morpholine, tetrahydropyran, dioxane, pentamethylenesulfide, dithiane, benzene, piperidine, piperazine, pyridazine, quinoline or quinazoline) or a 7-membered ring (for example, cycloheptane or hexamethyleneimine).

In the formula (C), when the 5-, 6- or 7-membered ring formed by $R^8$ and $Y^1$ or $R^9$ and $Y^2$ is a ring that can be substituted, it may be substituted by the substituents represented by $R^2$ to $R^5$ as previously mentioned, and when it is substituted by two or more substituents, these substituents may be the same or different from each other.

$X^5$ in the formula (C) may be any group as long as it is capable of being bonded to Ma, and specific examples thereof include water, alcohols (for example, methanol, ethanol and propanol) and the like, as well as the compounds described in "Metal Chelates" [1] Takeichi Sakaguchi and Kyohei Ueno (1995, Nankodo), "Metal Chelates" [2] (1996), "Metal Chelates" [3] (1997), and the like. Among them, water, carboxylic acid compounds, sulfonic acid compounds and alcohols are preferable, and water, carboxylic acid compounds and sulfonic acid compounds are more preferable, in view of production. a represents 0, 1 or 2.

In the compound represented by the formula (C), preferable embodiments of $R^2$ to $R^5$ are the same as that of $R^2$ to $R^5$ as previously described, preferable embodiments of $R^7$ are the same as that of $R^7$ as previously described, Ma represents Zn, Cu, Co or VO, each of $X^3$ and $X^4$ independently represents NR (wherein R represents a hydrogen atom or an alkyl group) or an oxygen atom, $Y^1$ represents NRc (wherein Rc represents a hydrogen atom or an alkyl group) or a nitrogen atom, $Y^2$ represents a nitrogen atom or a carbon atom, each of $R^8$ and $R^9$ independently represent an alkyl group, an aryl group, a heterocyclic group, an alkoxy group or an alkylamino group, $X^5$ represents a group that is bonded via an oxygen atom, and a represents 0 or 1. $R^8$ and $Y^1$ may be bonded to each other to form a 5-membered or a 6-membered ring, or $R^9$ and $Y^2$ may be bonded to each other to form a 5- or 6-membered ring.

In more preferable embodiments of the compound represented by the formula (C), each of $R^2$ and $R^5$ independently represents an alkoxycarbonyl group or a carbamoyl group, each of $R^3$ and $R^4$ independently represents a substituted or unsubstituted alkyl group or a substituted or unsubstituted phenyl group, $R^7$ represents a hydrogen atom or a methyl group, each of $R^8$ and $R^9$ independently represents a substituted or unsubstituted alkyl group or a substituted or unsubstituted phenyl group, $X^3$ and $X^4$ each represent an oxygen atom, $Y^1$ represents NRc (wherein Rc represents a hydrogen atom or an alkyl group) or a nitrogen atom, $Y^2$ represents a nitrogen atom, Ma represents Zn, and $X^5$ represents a carboxylic acid compound or a sulfonic acid compound.

In the formula (C), the position to which the polymerizable group responsible for multimerization (formation of a dye multimer) is to be introduced is not particularly limited, but is preferably any one or more of $R^2$ to $R^5$, $R^8$, $R^9$ and $X^5$, more preferably any one or more of $R^3$, $R^4$, $R^8$ and $R^9$, and even more preferably $R^8$ and/or $R^9$, in view of synthesis suitability.

The molar absorption coefficient of the dipyrromethene dye represented by the formula (C) is preferably as high as possible, in view of film thickness. The maximum absorption wavelength (λmax) is preferably in the range of from 520 nm to 580 nm, more preferably from 530 nm to 570 nm, in view of improving color purity. The maximum absorption wavelength and the molar absorption coefficient are measured by a spectrophotometer (UV-2400PC, trade name, manufactured by Shimadzu Corporation).

The melting point of the dipyrromethene dye represented by the formula (C) is preferably not too high, in view of solubility.

The method of synthesizing a dipyrromethene dye, the method of multimerizing a dye, and the method of introducing a polymerizable group into a dye may be selected from those described in JP-A No. 2007-147784, JP-A No. 2008-292970, and the like.

(2) Structural Unit Having Dye-Derived Group

The structural unit having a dye-derived group is preferably a structural unit having a group derived from the above-described preferable dyes. Specific examples of the structural unit having a dye-derived group are shown below, but the invention is not limited thereto. Hereinafter, the structural unit having a dye-derived group is also referred to as a "dye unit".

(1-1)

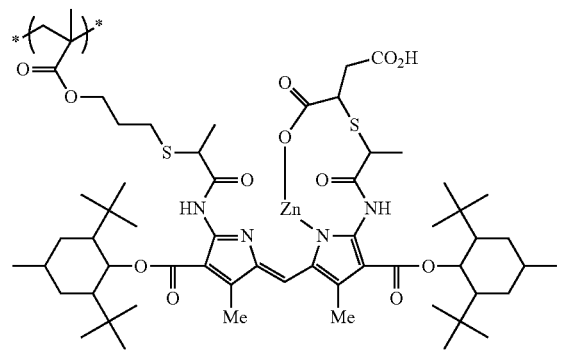

(1-2)

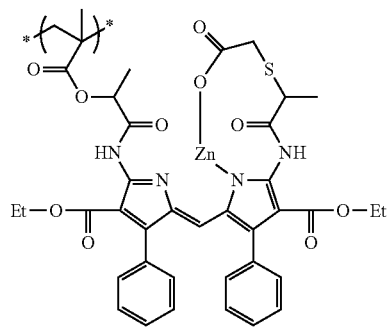

(1-3)

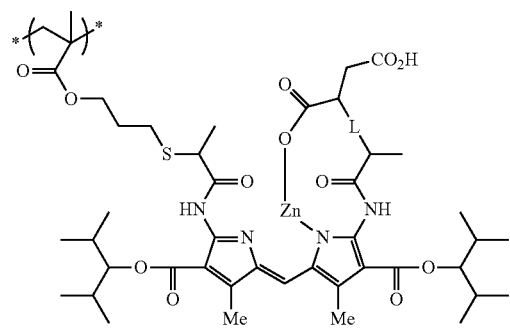

(1-4)

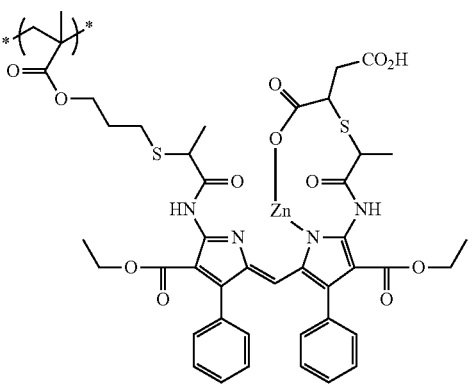

(1-5)

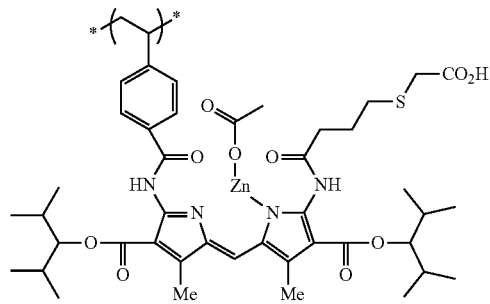

(1-6)

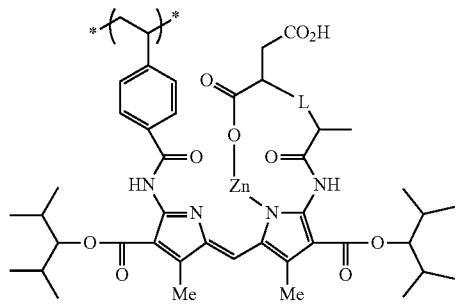

(1-7)
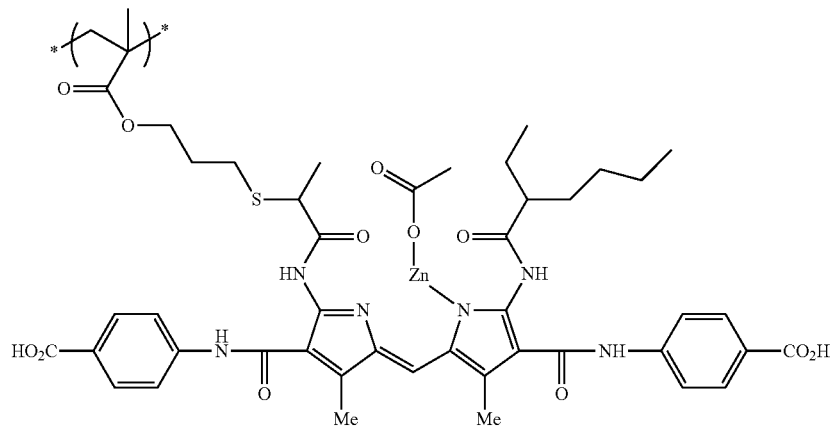
(1-8)
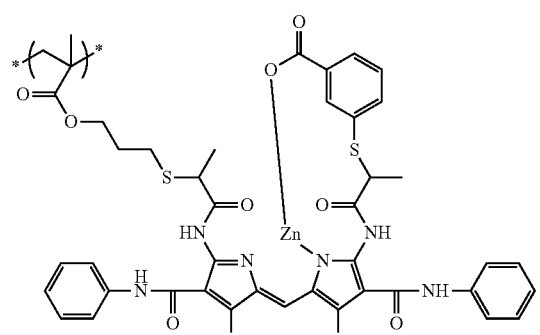
(2-1)
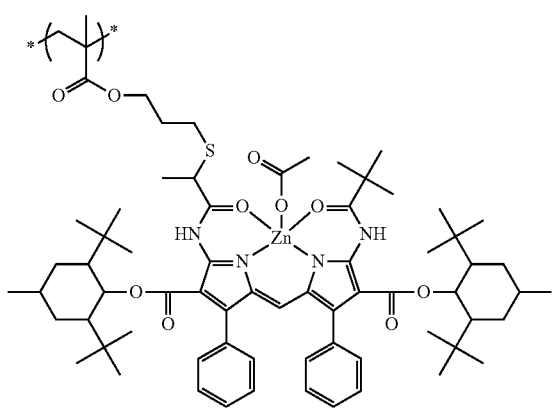
(2-2)
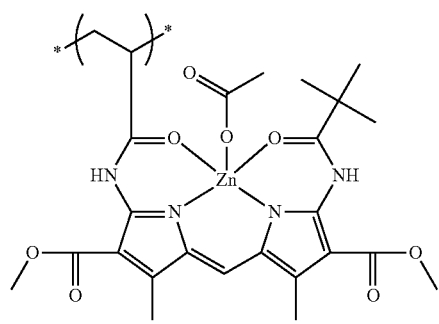

223
224
-continued
(2-3)
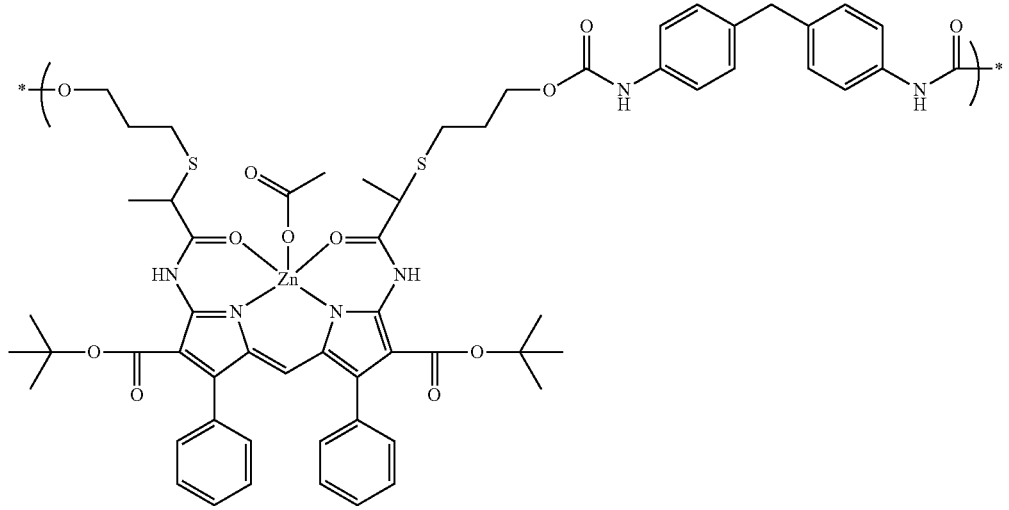
(2-4)
(2-5)
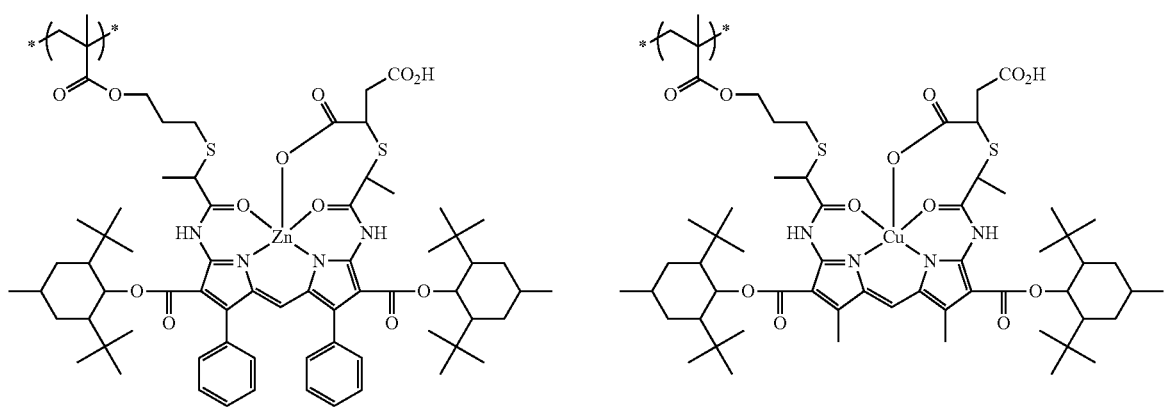
(2-6)
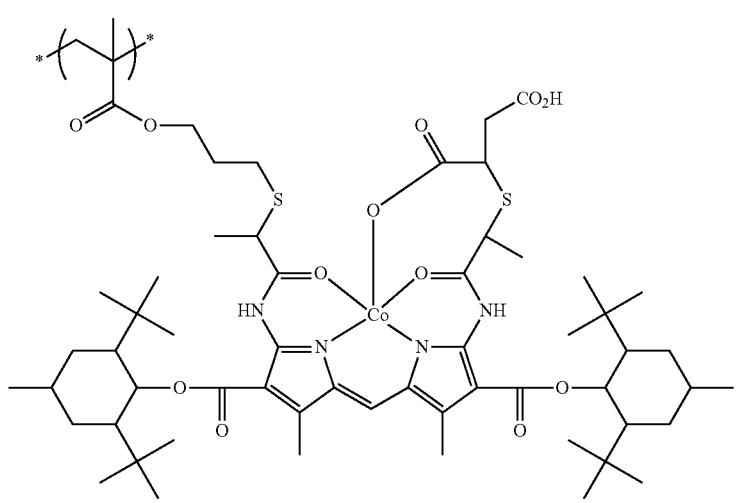

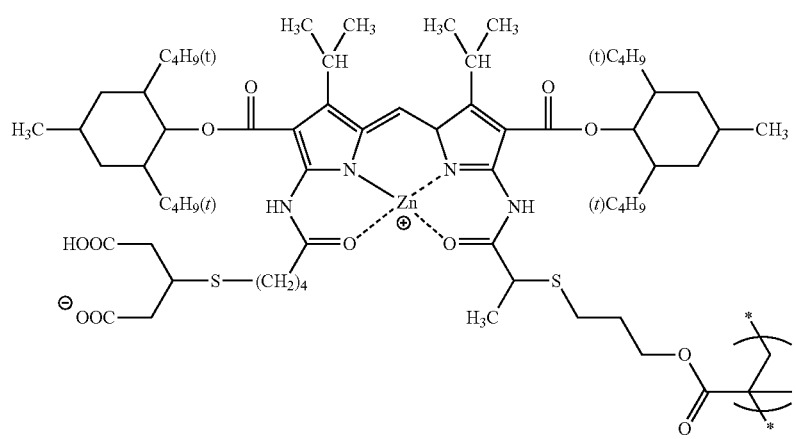

(3-1)

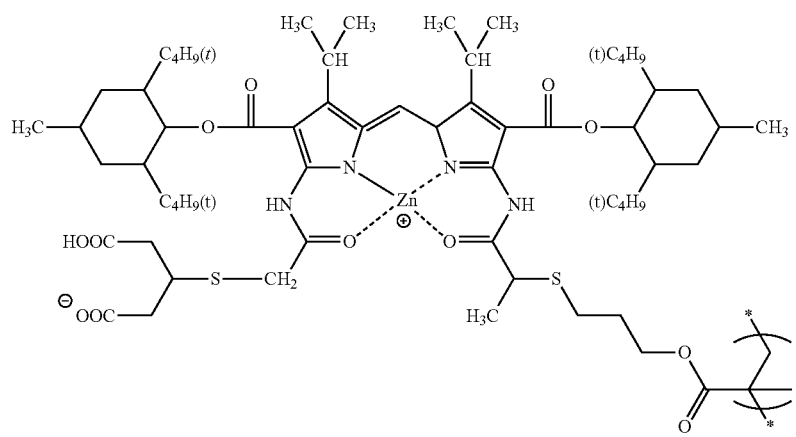

(3-2)

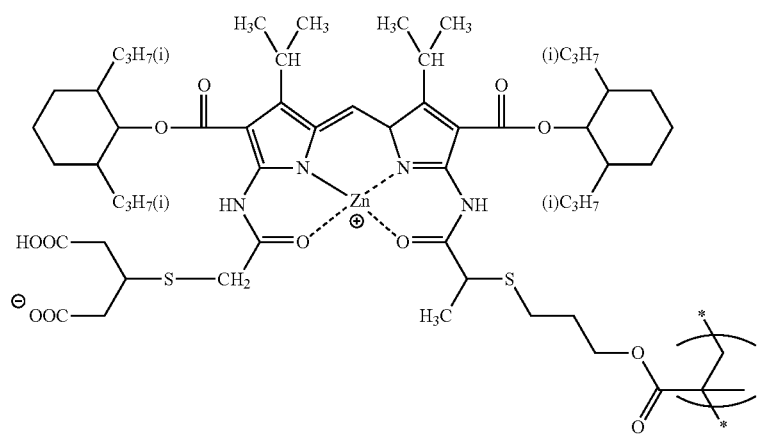

(3-3)

(3) Structural Unit Having Polymerizable Group

Examples of the structural unit having a polymerizable group, which is included in the polymerizable group-containing dye multimer, include a structural unit obtained by adding a polymerizable compound having a group that reacts with a structural unit (for example, glycidyl methacrylate or methacryloxyethyl isocyanate), the structural being derived from a copolymerization component (for example, methacrylic acid, acrylic acid, or hydroxyethyl methacrylate) that has been copolymerized with a known dye compound.

The polymerizable group in the structural unit having a polymerizable group (hereinafter, also referred to as a "polymerizable unit") is not particularly limited, and examples thereof include an ethylenically unsaturated group (for example, a methacryl group, an acryl group or a styryl group), and a cyclic ether group (for example, an epoxy group or an oxetanyl group). Among them, an ethylenically unsaturated group is preferable in view of heat resistance and solvent resistance.

Examples of the structural unit having a polymerizable group include the following specific examples. However, the invention is not limited thereto.

(G-1) 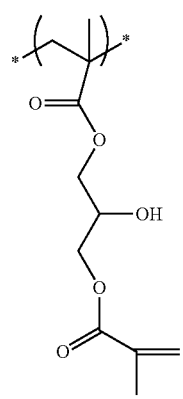
(G-2) 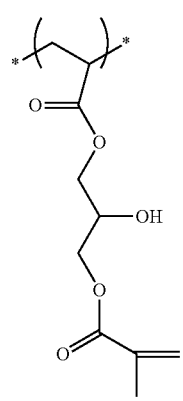
(G-3) 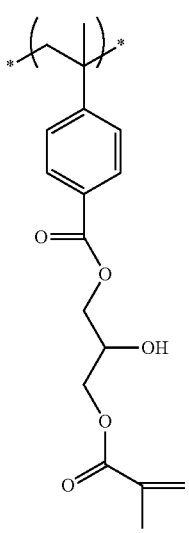
(G-4) 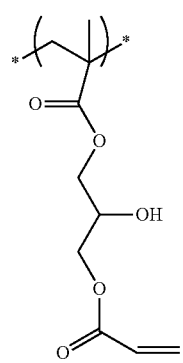
-continued
(G-5) 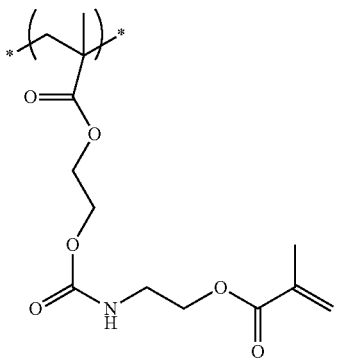
(G-6) 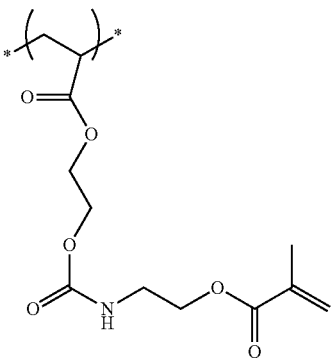
(G-7) 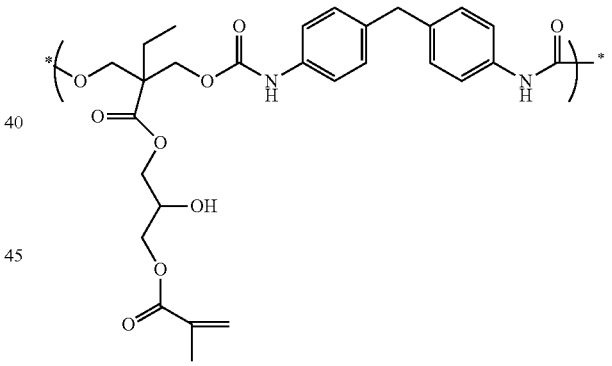
(G-8) 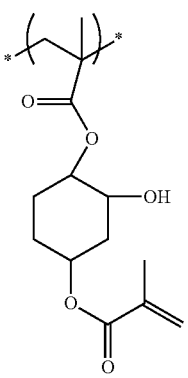

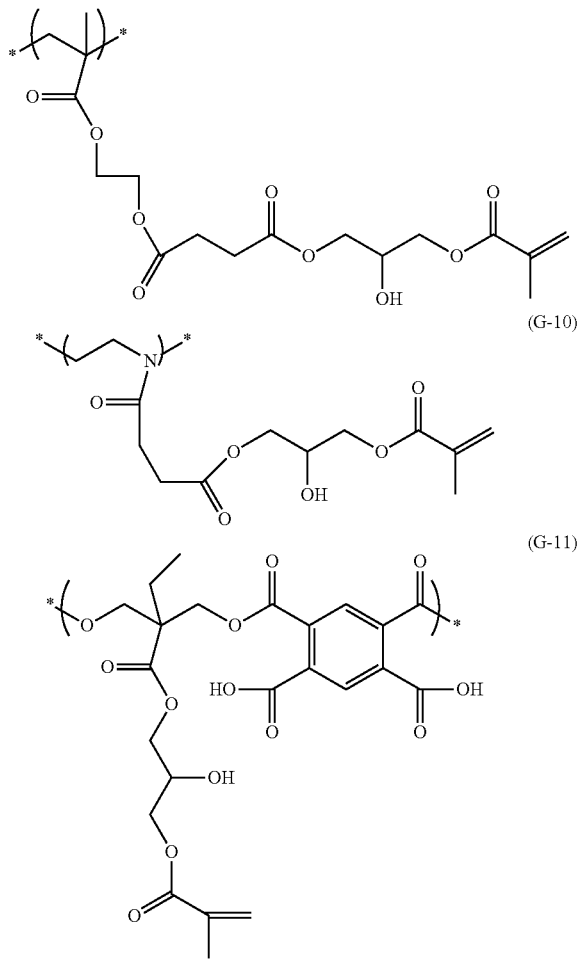

(4) Other Structural Units

The polymerizable group-containing dye multimer may include a further copolymerization component as a structural unit, as long as the effect of the invention is not impaired. When the polymerizable group-containing dye multimer is synthesized by radical polymerization, the copolymerization component may be any monomer as long as it is a monomer having at least one ethylene group, and specific examples thereof include the following monomers.

Examples of the copolymerizable monomer include acrylic acid, α-chloroacrylic acid, α-alkyl acrylic acid (for example, methacrylic acid or α-hydroxymethyl acrylic acid) and salts, esters or amides derived from acrylic acid (for example, sodium acrylate, tetramethylammonium methacrylate, sodium 2-acrylamido-2-methylpropane sulfonate, sodium 3-acryloyloxy propane sulfonate, acrylamide, methacrylamide, diacetone acrylamide, methyl acrylate, methyl methacrylate, ethyl methacrylate, n-butyl methacrylate, 2-ethylhexyl methacrylate, 2-hydroxyethyl methacrylate, 2-hydroxyethyl acrylate, 2-dimethylaminoethyl methacrylate, and benzyl methacrylate), vinyl esters (for example, vinyl acetate), acrylonitrile, aromatic vinyl compounds (for example, styrene, p-styrene carboxylic acid, and p-styrene sulfonic acid), vinylidene chloride, vinyl alkyl ether (for example, vinyl ethyl ether), maleic acid ester, itaconic acid, vinyl imidazole, vinyl pyridine, vinyl pyrrolidone, and vinyl carbazole.

When the polymerizable group-containing dye multimer is synthesized by polycondensation or polyaddition (for example, polyester, polyurea, polyamide or polyamide acid), the copolymerizable monomer may be any monomer as long as it is a monomer having at least two reactive groups, and examples thereof include alcohols (such as 1,6-hexanediol and 2,2-bishydroxymethyl propanoic acid), isocyanates (for example, 1,3-tolyl diisocyanate, 2,2-bishydroxymethyl propanoic acid), amines (for example, ethylenediamine and trimethylenediamine) and acid anhydrides.

In view of improving formation suitability of a color pattern, the copolymerizable monomer is preferably a monomer having an alkali-soluble group, such as methacrylic acid or acrylic acid.

The content of the alkali-soluble group in the polymerizable group-containing dye multimer is preferably in the range of from 1% by mass to 40% by mass, more preferably from 3% by mass to 20% by mass, yet more preferably from 5% by mass to 15% by mass, in view of forming a colored pattern from a colored curable composition including the polymerizable group-containing dye multimer.

Hereinafter, in the polymerizable group-containing dye multimer, a structural unit derived from a monomer having an alkali-soluble group is also referred to as an "alkali-soluble unit".

(5) Specific Examples of Polymerizable Group-Containing Dye Multimer

In the polymerizable group-containing dye multimer of the second aspect of the invention, the type of the dye unit, the polymerizable unit and the other structural unit (preferably an alkali-soluble unit), the combination thereof; and the content of each unit (mass %) are not particularly limited.

In one preferable embodiment of the combination of the structural units, the dye unit is a structural unit having a group derived from the above-described preferable dyes, more preferably a structural unit having a group derived from a dipyrromethene dye represented by the formula (C) or a structural unit having a group derived from an azo dye represented by the formula (E); the polymerizable unit is a structural unit having an ethylenically unsaturated group; and the alkali-soluble unit is a structural unit derived from methacrylic acid or acrylic acid.

Table 1 below shows specific examples of the polymerizable group-containing dye multimer of the second aspect of the invention. However, the invention is not limited thereto.

The number of each unit shown in Table 1 below corresponds to the number of the exemplary compound as preciously described.

TABLE 1

| Exemplary compound No. | Dye unit | Polymerizable unit | Alkali-soluble unit | Content ratio of each unit (mass %) | Weight average molecular weight |
|---|---|---|---|---|---|
| 101 | 1-1 | G-1 | Methacrylic acid | 85/10/5 | 6000 |
| 102 | 2-1 | G-1 | — | 90/10 | 13000 |
| 103 | 2-1 | G-1 | Methacrylic acid | 85/10/5 | 8000 |
| 104 | 2-1 | G-1 | Acrylic acid | 85/10/5 | 4000 |
| 105 | 2-3 | G-7 | — | 90/10 | 15000 |
| 106 | 2-4 | G-1 | — | 90/10 | 18000 |

The column "alkali-soluble unit" in Table 1 shows the monomer used in the copolymerization.

The content of the polymerizable group-containing dye multimer in the colored curable composition of the second aspect of the invention may vary depending on the molecular weight or the molar absorption coefficient thereof, but it is preferably in the range of from 5% by mass to 40% by mass, more preferably from 10% by mass to 30% by mass, and particularly preferably from 15% by mass to 25% by mass, with respect to the total solid components of the composition.

Further, the mass ratio of the phthalocyanine pigment to the polymerizable group-containing dye multimer (polymerizable group-containing dye multimer/phthalocyanine pigment) in the colored curable composition of the second aspect of the invention is preferably in the range of from 0.1 to 3.0, more preferably from 0.1 to 2.0, and particularly preferably from 0.5 to 1.0.

If the mass ratio (polymerizable group-containing dye multimer/phthalocyanine pigment) is greater than 0.1, it is possible to more effectively adjust the color hue properties.

If the mass ratio (polymerizable group-containing dye multimer/phthalocyanine pigment) is lower than 3.0, it is possible to more effectively improve the light fastness.

<Dioxazine Pigment>

The colored curable composition of the second aspect of the invention preferably further contains a dioxazine pigment. Specific examples, contents and preferable embodiments of the dioxazine pigment are the same as those according to the first aspect of the invention.

In the colored curable composition of the second aspect of the invention, the polymerizable group-containing dye multimer may be used in combination with a colorant having a different structure. The colorant having a different structure is not particularly limited and may be either a dye or a pigment, and known colorants that have been conventionally used in color filters may be used. For example, the colorants described in the first aspect may be used.

With respect to the colored curable composition of the second aspect of the invention, the polymerizable compound, the polymerization initiator and the solvent described in the first aspect may be used, and preferable examples and contents thereof are also the same.

The colored curable composition of the second aspect of the invention preferably contains a dispersant. For this purpose, those described in the first aspect may be used and preferable examples and contents are also the same.

The colored curable composition of the second aspect of the invention may contain other components in addition to the above-mentioned components, as long as the effect of the invention is not impaired. For this purpose, those described in the first aspect may be used, and preferable examples and contents thereof are also the same.

Explanations of the method of preparing a colored curable composition, the color filter and the method for producing the same, the solid-state image sensor, and the liquid crystal display device in accordance with the first aspect of the invention also apply to the second aspect of the invention.

EXAMPLES

Hereinafter, the present invention will be further described in detail with reference to the following Examples. However, the invention is not limited to these Examples. In the following, "part(s)" and "%" refer to "part(s) by mass" and "% by mass", respectively, unless otherwise specifically indicated.

First Aspect

Examples 1 to 14 and Comparative Examples 1 to 2

Preparation of Colored Curable Composition

The following components were mixed and dissolved to give a colored composition 1 (colored curable composition).
Cyclohexanone: 19.17 parts
Resin A (30% PGMEA solution of resin synthesized according to the following Synthesis Example (benzyl methacrylate/methacrylic acid copolymer)): 1.057 parts
Fluorosurfactant (trade name: CW-1, manufactured by Zeneca, 1% CyH (cyclohexanone) solution: 1.136 parts
Photopolymerization initiator (trade name: CGI-242, manufactured by BASF Japan): 0.327 parts
Polymerizable monomer (trade name: KAYARAD DPHA, manufactured by Nippon Kayaku Co., Ltd.): 0.8459 parts
Dye (Exemplary Compound Ia-5, the above-mentioned specific complex): 1.09 parts
Dispersion of C.I. Pigment Blue 15:6 (PB 15:6) and C.I. Pigment Violet 23 (PV 23) (solid content concentration: 13.2%, pigment concentration: 9.4%): 22.615 parts Synthesis Example of Resin The resin (benzyl methacrylate/methacrylic acid copolymer) was synthesized according to the following method.

70.0 g of benzyl methacrylate, 13.0 g of methacrylic acid, and 600 g of 2-methoxypropanol were placed in a three-necked flask equipped with a stirrer, a reflux condenser and a thermometer, and a catalytic amount of a polymerization initiator (V-65, trade name, manufactured by Wako Pure Chemical Industries, Ltd.) was added thereto at 65° C. under a nitrogen air flow, and the mixture was stirred for 10 hours. The resulting resin solution was added dropwise to 20 L of ion-exchanged water while vigorously stirring, thereby obtaining a white powder. The white powder was dried at 40° C. under vacuum for 24 hours to give 145 g of a resin (benzyl methacrylate/methacrylic acid copolymer). The resulting resin had a weight average molecular weight (Mw) of 28,000 and a number average molecular weight (Mn) of 11,000, as measured by GPC, respectively.

The colored composition 1 was prepared such that the mass ratio (dioxazine pigment/dye) (i.e., PV 23/Exemplary Compound Ia-5) was 0.70.

Next, colored compositions 2 to 14 and comparative colored compositions 1 and 2 were prepared in a similar manner to the preparation of colored composition 1, except that the type and the amount of the components were changed as shown in Table 2.

TABLE 2

| | Pigment dispersion | Dye (specific complex) | Mass ratio (dioxazine pigment/dye) | Photopolymerization initiator | Polymerizable monomer | Resin/additive | Solvent |
|---|---|---|---|---|---|---|---|
| Colored composition 2 | Dispersion of PB15:6 and PV23 (22.615) | Exemplary compound a-15 (0.85) | 0.797 | Initiator 1 (0.35) | Monomer 1 (0.85) | Resin A (1.06) | PGMEA (1130) |
| Colored composition 3 | Dispersion of PB15:6 and PV23 (22.615) | Exemplary compound a-37 (0.8) | 0.618 | Initiator 1 (0.41) | Monomer 2 (0.85) | — | PGMEA (1140) |

TABLE 2-continued

| | Pigment dispersion | Dye (specific complex) | Mass ratio (dioxazine pigment/dye) | Photopolymerization initiator | Polymerizable monomer | Resin/additive | Solvent |
|---|---|---|---|---|---|---|---|
| Colored composition 4 | Dispersion of PB15:6 and PV23 (22.615) | Exemplary compound a-39 (0.86) | 0.556 | Initiator 1 (0.5) | Monomer 2 (0.85) | — | PGMEA (1050) |
| Colored composition 5 | Dispersion of PB15:6 and PV23 (22.615) | Exemplary compound b-3 (0.88) | 0.525 | Initiator 2 (0.38) | Monomer 3 (0.85) | — | PGMEA/ Cyclohexane (700/350) |
| Colored composition 6 | Dispersion of PB15:6 and PV23 (22.615) | Exemplary compound b-37 (0.81) | 0.691 | Initiator 3 (0.41) | Monomer 1 (0.75) | — | PGMEA/ 2-heptanone (900/210) |
| Colored composition 7 | Dispersion of PB15:6 and PV23 (22.615) | Exemplary compound a-1/Exemplary compound a-15 (0.4/0.4) | 0.399 | Initiator 1/Initiator 3 (0.2/0.25) | Monomer 1 (0.78) | — | PGMEA (1300) |
| Colored composition 8 | Dispersion of PB15:6 and PV23 (22.615) | Exemplary compound a-1/Exemplary compound b-3 (0.6/0.2) | 0.478 | Initiator 1/Initiator 2 (0.3/0.11) | Monomer 1 (0.9) | — | PGMEA (1200) |
| Colored composition 9 | Dispersion of PB15:6 and PV23 (22.615) | Exemplary compound b-3/Exemplary compound b-37 (0.25/0.55) | 0.425 | Initiator 2/Initiator 3 (0.18/0.22) | Monomer 2 (0.9) | — | PGMEA (1150) |
| Colored composition 10 | Dispersion of PB15:6 and PV23 (22.615) | Exemplary compound a-1 (0.9) | 0.354 | Initiator 1 (0.4) | Monomer 2 (0.85) | — | PGMEA (1050) |
| Colored composition 11 | Dispersion of PB15:6 and PV23 (22.615) | Exemplary compound a-1 (0.95) | 0.671 | Initiator 1 (0.4) | Monomer 2 (0.85) | — | PGMEA (1100) |
| Colored composition 12 | Dispersion of PB15:6 and PV23 (22.615) | Exemplary compound IIa-II (0.85) | 0.797 | Initiator 1 (0.35) | Monomer 1 (0.85) | Resin A (1.06) | PGMEA (1130) |
| Colored composition 13 | Dispersion of PB15:6 and PV23 (22.615) | Exemplary compound 1-2 (0.85) | 0.797 | Initiator 1 (0.35) | Monomer 1 (0.85) | Resin A (1.06) | PGMEA (1130) |
| Colored composition 14 | Dispersion of PB15:6 and PV23 (22.615) | Exemplary compound Ia-3 (0.85) | 0.797 | Initiator 1 (0.35) | Monomer 1 (0.85) | Resin A (1.06) | PGMEA (1130) |
| Comparative 1 | Dispersion of PB15:6 (22.615) | Exemplary compound a-15 (0.85) | 0 | Initiator 1 (0.35) | Monomer 1 (0.85) | Resin A (1.06) | PGMEA (1130) |
| Comparative 2 | Dispersion of PB15:6 (22.615) | Exemplary compound a-37 (0.8) | 0 | Initiator 1 (0.41) | Monomer 2 (3.37) | — | PGMEA (1140) |

The numerical values in the parenthesis in Table 2 represent the content of the component (parts by mass).

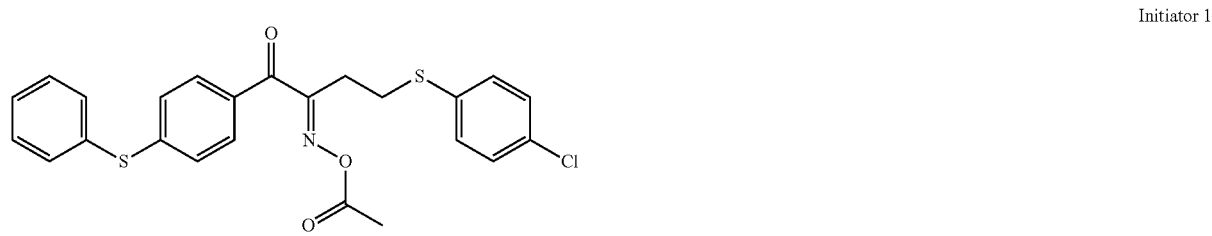

Initiator 1

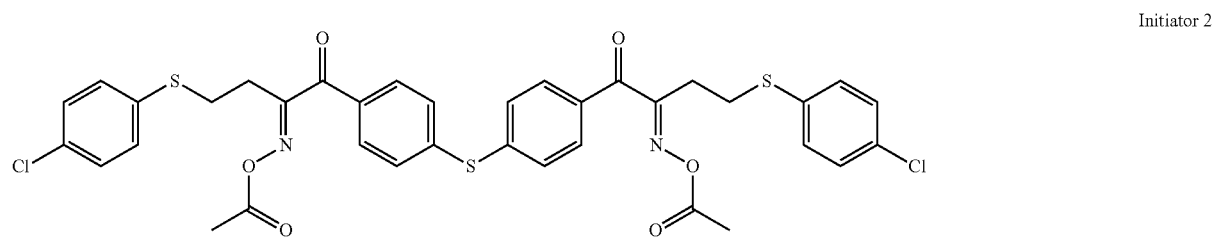

Initiator 2

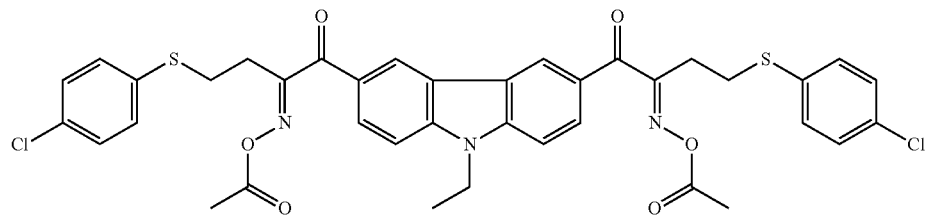

Initiator 3

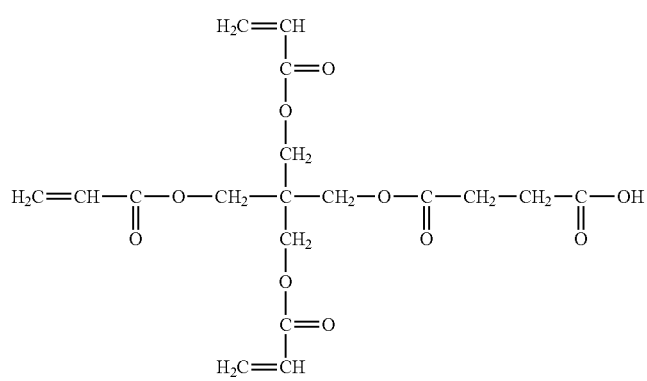

Monomer 1

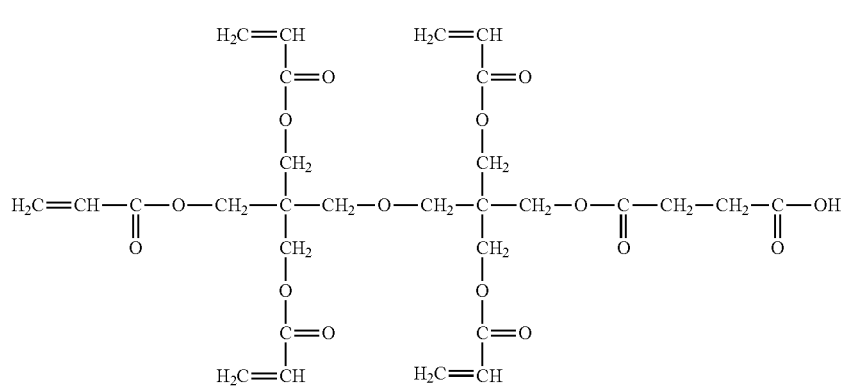

Monomer 2

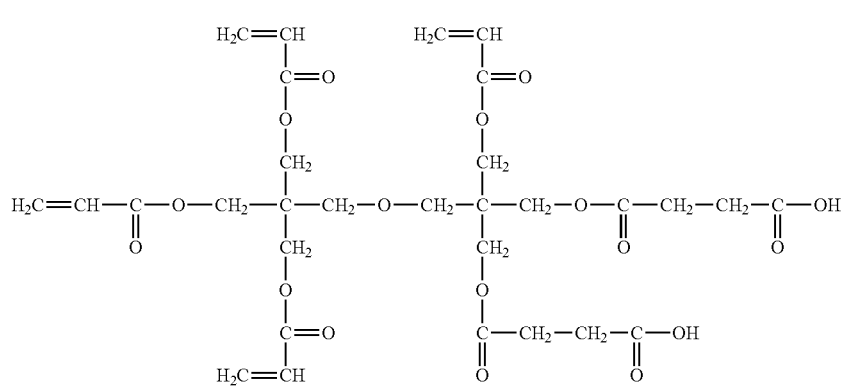

Monomer 3

—Preparation of Single-Color Color Filter and Evaluation of Light Fastness—

The colored curable compositions obtained in the above process (colored compositions 1 to 14) were applied onto a glass substrate using a spin coater so as to form a film having the thickness after drying of 0.6 μm, and pre-baked at 100° C. for 120 seconds to form a single-color color filter for evaluation of light fastness, respectively.

The resulting single-color color filter for evaluation of light fastness was exposed to light with a xenon lamp at 100,000 lux for 10 hours (i.e., 1,000,000 lux·h). The color difference (ΔE*ab value) of the single-color color filter before and after the exposure with the xenon lamp was measured and used as an index of light fastness. The smaller the ΔE*ab value is, the more favorable the light fastness is. The results are shown in Table 3.

TABLE 3

| | Colored curable composition | Light fastness (ΔE*ab) |
|---|---|---|
| Example 1 | Colored composition 1 | 2.6 |
| Example 2 | Colored composition 2 | 2.4 |
| Example 3 | Colored composition 3 | 3.1 |
| Example 4 | Colored composition 4 | 3.5 |
| Example 5 | Colored composition 5 | 3.8 |
| Example 6 | Colored composition 6 | 2.8 |
| Example 7 | Colored composition 7 | 4.1 |
| Example 8 | Colored composition 8 | 3.6 |
| Example 9 | Colored composition 9 | 3.9 |
| Example 10 | Colored composition 10 | 4.0 |
| Example 11 | Colored composition 11 | 2.9 |
| Example 12 | Colored composition 12 | 6.1 |
| Example 13 | Colored composition 13 | 5.8 |
| Example 14 | Colored composition 14 | 5.9 |
| Comparative Example 1 | Comparative colored composition 1 | 9.1 |
| Comparative Example 1 | Comparative colored composition 2 | 9.8 |

As shown in Table 3, color filters of Examples 1 to 14, which were produced using the colored compositions 1 to 14 each containing a phthalocyanine pigment, a dioxazine pigment, a dye, a polymerization initiator, a polymerizable compound, and a solvent, exhibited excellent light fastness.

On the other hand, color filters of Comparative Examples 1 and 2, which were produced using comparative colored composition 1 and comparative colored composition 2, in which a dioxazine pigment was not contained, exhibited poor light fastness.

Examples 2-1 to 2-14

—Formation of Blue Color Filter—

A 6-inch silicon wafer was subjected to a heat treatment in an oven at 200° C. for 30 minutes. A resist liquid, in which the components shown below were dissolved, was applied onto the silicon wafer to form a film having the dried film thickness of 1.0 μm, and the film was further dried in an oven at 220° C. for 1 hour to form a primer layer. A silicon wafer substrate having a primer layer was thus obtained.

Propylene glycol monomethyl ether acetate (PGMEA): 19.20 parts
Ethyl lactate: 36.67 parts
Binder: 41% EL solution of benzyl methacrylate/methacrylic acid/2-hydroxyethyl methacrylate copolymer: 30.51 parts
Dipentaerythritol hexaacrylate: 12.20 parts
Polymerization inhibitor (p-methoxyphenol): 0.0061 parts
Fluorosurfactant (trade name: CW-1, manufactured by Zeneca) 1% CyH (cyclohexanone) solution: 0.83 parts
Photopolymerization initiator (TAZ-107, trade name, manufactured by Midori Kagaku Co., Ltd.): 0.586 parts The above binder (benzyl methacrylate/methacrylic acid/2-hydroxyethyl methacrylate copolymer) was synthesized in accordance with the following process.

Specifically, 53.0 g (0.300 mol) of benzyl methacrylate, 11.7 g (0.090 mol) of 2-hydroxyethyl methacrylate, 7.92 g (0.110 mol) of methacrylic acid, and 50 g of propylene glycol monomethylether acetate were placed in a 300-ml four-necked flask and stirred at 80° C. under a nitrogen atmosphere. A solution prepared by dissolving 0.3118 g (1.91× $10^{-3}$ mol) of a thermal polymerization initiator (2,2'-azobisisobutylnitrile (AIBN) in 10 g of propylene glycol monomethylether acetate) was added thereto, and stirred for 6 hours. Subsequently, the supply of nitrogen was stopped, and a solution of 0.22 g (1.5× mol) of p-methoxyphenol dissolved in 15 g of propylene glycol monomethylether acetate was added thereto, and the temperature was elevated to 95° C. and stirred for 2 hours. A binder (benzyl methacrylate/methacrylic acid/2-hydroxyethyl methacrylate copolymer) was thus obtained. The resulting binder had an acid value of 30 mgKOH/g and a weight average molecular weight of 15,000.

The colored compositions used in Examples 1 to 14 were applied onto the primer layer of the resulting silicon wafer substrate, respectively, and a photocurable coating film (colored curable composition layer) having a dried film thickness of 0.6 μm was formed. A heat treatment (pre-baking) was then performed using a hot plate at 100° C. for 120 seconds. Next, the resulting coating film was exposed to light at a wavelength of 365 nm through an island pattern mask having the pattern size of 1.2 μm square, using an i-line stepper (FPA-3000i5+, trade name, manufactured by Canon Inc.) while changing the exposure dose by an amount of 100 mJ/cm² from 100 mJ/cm² to 2500 mJ/cm². Thereafter, the silicon wafer substrate with the coating film formed thereon was placed on a horizontal rotary table of a spin-shower developing machine (trade name: model DW-30, manufactured by Chemitronics Co., Ltd.) and subjected to puddle development at 23° C. for 60 seconds with a developer (CD-2000, trade name, manufactured by Fujifilm Electronic Materials Co., Ltd.), thereby forming a blue pattern on the silicon wafer substrate.

The silicon wafer substrate with a blue pattern formed thereon was fixed on the horizontal rotary table in a vacuum chuck mode, and rinsed with pure water shower supplied from ejection nozzles placed over the rotation center while rotating the silicon wafer substrate with a rotation apparatus at a revolution rate of 50 rpm. The resultant was spray-dried, thereby obtaining a color filter.

It was proved that each of the color filter had a blue pattern having a profile with a favorable rectangular cross-section, indicating that the color filter was suitable for solid-state image sensors.

The spectroscopic properties of the colored patterns were measured with a spectrophotometer (MCPD-3000, trade name, manufactured by Otsuka Electronics Co., Ltd.), and the results showed that each color filter exhibited favorable spectroscopic properties as a blue color filter for solid-state image sensors.

In the above section, examples of forming a blue pattern (color filter) on a silicon wafer substrate were illustrated by way of Example 2-1 to Example 2-14. A three-color color filter can be produced on a silicon wafer on which a device is formed, by forming a blue color filter using the colored compositions 1 to 14, a green color filter by a known method using a green color resist, and a red color filter by a known method using a red color resist, respectively, on a solid-state image sensor substrate (a silicon wafer substrate on which an imaging device such as CCD or CMOS has been formed). A solid-state image sensor having a three-color color filter produced by the above method exhibits excellent light fastness and favorable spectroscopic properties.

Examples 101 to 115 and Comparative Examples 101 to 113

—Preparation of Colored Curable Composition (Colored Composition I)—

The following components (combination I) were mixed and stirred to prepare a colored composition I.

<Composition of Colored Curable Composition I (Combination I)>

Dispersed composition I: 1002 parts
Dispersed composition II: 100 parts
Dye (exemplary compound of the specific complex shown in Table 4): 49 parts
Photopolymerizable compound I: 178 parts
Photopolymerization initiator I: 43 parts
Alkali-soluble resin I: 275 parts
Surfactant I: 0.3 parts
PGMEA: 1353 parts —Preparation of Colored Curable Compositions (Colored Compositions II to VII)—

Colored compositions II to VII were prepared in a similar manner as the preparation of colored composition I, except that combination I was changed to combination II to combination VII as shown in Table 4 below, respectively.

TABLE 4

| | Composition of colored compositions I to VII (combination) | | | | | | |
|---|---|---|---|---|---|---|---|
| | Combination I | Combination II | Combination III | Combination IV | Combination V | Combination VI | Combination VII |
| Dispersed composition I | 1002 | 977 | 912 | 977 | 671 | 1040 | 715 |
| Dispersed composition II | 100 | 196 | 455 | 196 | 135 | 0 | 0 |
| Dye | 49 | 40 | 14 | 40 | 27 | 57 | 39 |
| Photopolymerizable compound I | 178 | 178 | 178 | 161 | 185 | 178 | 185 |
| Photopolymerization initiator II | 43 | 43 | 43 | 77 | 89 | 43 | 89 |
| Alkali-soluble resin I | 275 | 263 | 229 | 218 | 345 | 286 | 361 |
| Surfactant I | 0.3 | 0.3 | 0.3 | 0.3 | 0.3 | 0.3 | 0.3 |
| PGMEA | 1353 | 1304 | 1169 | 1331 | 1548 | 1397 | 1611 |

(parts by mass)

Details of the components shown in Table 4 are as follows.
Dispersed composition I: PB 15:6 dispersed composition (solid content: 20%, PB 15:6 concentration: 12%)
Dispersed composition II: PB 15:6/PV 23 dispersed composition (solid content: 20%, PB 15:6 concentration: 8.57%, PV 23 concentration: 3.43%)
Photopolymerizable compound I: Dipentaerythritol penta/hexaacrylate
Alkali-soluble resin I: 40% PGMEA solution of benzyl methacrylate/methacrylic acid copolymer (molar ratio: 70/30, Mw: 10,000)
Surfactant I: MEGAFAC F-781 F (trade name, manufactured by DIC Corporation)
PGMEA: Propylene glycol monomethyl ether acetate —Evaluation Step II—

The colored curable compositions obtained in the above process (colored compositions I to VII) were evaluated in accordance with the following process (Evaluation step I).

Each of the colored curable compositions was applied onto a glass substrate having a size of 100 mm×100 mm (trade name: 1737, manufactured by Corning Inc.) with a spin coater to form a film having the thickness of 2.3 μm, and the resultant was pre-baked (dried in an oven at 100° C. for 80 seconds).

Thereafter, the entire surface of the coating film was exposed to light at 100 mJ/cm$^2$ (illuminance: 20 mW/cm$^2$).

The coating film, which had been exposed to light and developed, was subjected to a heat treatment (post-baking) in an oven at 220° C. for 0.5 hours, thereby obtaining a colored filter substrate (color filter).

The colored filter substrate was exposed to light with a xenon lamp at 120,000 lux for 60 hours (i.e., 7,200,000 lux·h). The color difference (ΔE*ab value) of the single-color color filter before and after the exposure with the xenon lamp was measured and used as an index of light fastness. The smaller the ΔE*ab value is, the more favorable the light fastness is.

Based on the ΔE*ab value, the light fastness was evaluated according to the following evaluation criteria. The evaluation results are shown in Table 5 below.

—Evaluation Criteria for Light Fastness—
A: ΔE*ab is less than 3
B: ΔE*ab is from 3 to less than 6
C: ΔE*ab is 6 or greater —Evaluation Step II—

The colored curable compositions obtained in the above process (colored compositions I to VII) were subjected to the following evaluation (Evaluation step II).

The colored curable composition was applied onto a glass substrate having a size of 100 mm×100 mm (trade name: 1737, manufactured by Corning Inc.) using a spin coater to form a film having a thickness of 2.3 μm, and the film was pre-baked (dried in an oven at 100° C. for 80 seconds).

Thereafter, the entire surface of the colored curable composition layer formed on the substrate was subjected to pulse irradiation at about 1 mJ/cm$^2$ using a laser exposure apparatus (EGIS, trade name, manufactured by V Technology Co., Ltd., third harmonic of YAG laser, wavelength: 355 nm, pulse width: 6 nsec) and the pulse irradiation was performed sixty times (exposure).

The coating film, which had been exposed as above and developed, was subjected to a heat treatment (post-baking) in an oven at 220° C. for 0.5 hours, thereby producing a colored filter substrate (color filter).

The colored filter substrate was irradiated with a xenon lamp at 120,000 lux for 60 hours (corresponding to 7,200,000 lux·h). The color difference (ΔE*ab value) of the single-color color filter before and after the irradiation with a xenon lamp was measured and used as an index of light fastness. The smaller the ΔE*ab value is, the more favorable the light fastness is.

Based on the measured ΔE*ab value, light fastness was evaluated in accordance with the same evaluation criteria as that used in the evaluation step I. The evaluation results are shown in Table 5 below.

—Evaluation Step III—

The colored curable compositions obtained in the above process (colored compositions I to VII) were subjected to the following evaluation (Evaluation step III).

The colored curable composition was applied onto a glass substrate having a size of 100 mm×100 mm (trade name: 1737, manufactured by Corning Inc.) using a spin coater to form a film having a thickness of 3.5 μm, and the film was pre-baked (dried in an oven at 100° C. for 80 seconds).

Thereafter, the entire surface of the colored curable composition layer formed on the substrate was subjected to pulse irradiation at about 1 mJ/cm$^2$ using a laser exposure apparatus (EGIS, trade name, manufactured by V Technology Co., Ltd., third harmonic of YAG laser, wavelength: 355 nm, pulse width: 6 nsec) and the pulse irradiation was performed sixty times (exposure).

The coating film, which had been exposed as above and developed, was subjected to a heat treatment (post-baking) in an oven at 220° C. for 0.5 hours, thereby producing a colored filter substrate (color filter).

The colored filter substrate was exposed to light with a xenon lamp at 120,000 lux for 60 hours (i.e., 7,200,000 lux·h). The color difference (ΔE*ab value) of the single-color color filter before and after the irradiation with a xenon lamp was measured and used as an index of light fastness. The smaller the ΔE*ab value is, the more favorable the light fastness is.

Based on the measured ΔE*ab value, light fastness was evaluated in accordance with the same evaluation criteria as that used in the evaluation step I. The evaluation results are shown in Table 5 below.

As shown in Table 5, color filters of Examples 101 to 115 prepared from colored compositions I, II, III, IV and V, containing a phthalocyanine pigment, a dioxazine pigment, a dye, a polymerization initiator, a polymerizable compound and a solvent, exhibited excellent light fastness.

On the other hand, color filters of Comparative Examples 101 to 113, prepared from colored compositions VI and VII, not containing a dioxazine pigment, exhibited poor light fastness.

Second Aspect

<Synthesis of Exemplary Compound 101 (Dye Multimer)>

A dye unit 1-1 (3.45 g), polymerizable unit G-1 (1.55 g), methacrylic acid (0.5 g) and n-dodecanethiol (420 mg) were dissolved in 28.3 ml of propylene glycol monomethyl ether acetate (PGMEA), and the mixture was stirred at 85° C. under nitrogen, and 478 mg of dimethyl 2,2'-azobis(2-methylpropionate) were added thereto. Then, 478 mg of dimethyl 2,2'-azobis(2-methylpropionate) were further added twice with an interval of two hours, and the temperature was elevated to 90° C. and stirred for another 2 hours. After the completion of the reaction, the reaction liquid was added dropwise to 400 ml of acetonitrile. The resulting crystal was filtered to give an exemplary compound 101 (4.11 g).

The above synthesis example relates to the preparation of exemplary compound 101. However, it is also possible to synthesize other types of polymerizable group-containing dye multimer in accordance with a similar method from a chemical viewpoint.

TABLE 5

|  | Colored compdsition No. (Combination No.) | Dye (Exemplary compound No.) | Evaluation step | Lightfastness ΔE*ab |
| --- | --- | --- | --- | --- |
| Example 101 | I | III-48 | I | B |
| Example 102 | II | III-48 | I | A |
| Example 103 | III | III-48 | I | A |
| Example 104 | II | III-47 | I | A |
| Example 105 | II | III-51 | I | A |
| Example 106 | II | III-58 | I | B |
| Example 107 | II | III-61 | I | B |
| Example 108 | II | III-64 | I | B |
| Example 109 | II | III-64-2 | I | A |
| Example 110 | IV | III-48 | II | A |
| Example 111 | V | III-48 | III | A |
| Example 112 | IV | III-47 | II | A |
| Example 113 | V | III-47 | III | A |
| Example 114 | IV | III-64 | II | B |
| Example 115 | V | III-64 | III | B |
| Comparative Example 101 | VI | III-48 | I | C |
| Comparative Example 102 | VI | III-47 | I | C |
| Comparative Example 103 | VI | III-51 | I | C |
| Comparative Example 104 | VI | III-58 | I | C |
| Comparative Example 105 | VI | III-61 | I | C |
| Comparative Example 106 | VI | III-64 | I | C |
| Comparative Example 107 | VI | III-64-2 | I | C |
| Comparative Example 108 | VI | III-48 | II | C |
| Comparative Example 109 | VII | III-48 | III | C |
| Comparative Example 110 | VI | III-47 | II | C |
| Comparative Example 111 | VII | III-47 | III | C |
| Comparative Example 112 | VI | III-64 | II | C |
| Comparative Example 113 | VII | III-64 | III | C |

Examples 201 to 208 and Comparative Examples 201 and 202

<Preparation of Colored Curable Composition>
The following components were mixed and dissolved to give a colored composition 1 (colored curable composition).
Pigment Blue 15:6 dispersion (solid content concentration: 15%, pigment concentration: 11.54%): 55.47 parts
Dye (Exemplary compound 101 of the above-mentioned dye multimer): 3.20 parts
Polymerizable monomer (trade name: KAYARAD DPHA, manufactured by Nippon Kayaku Co., Ltd.): 3.34 parts
Polymerization initiator (trade name: CGI-242, manufactured by BASF Japan, oxime polymerization initiator): 0.96 parts
Resin (30% PGMEA solution of benzyl methacrylate/methacrylic acid copolymer (Resin A), molar ratio=70:30, weight average molecular weight: 30,000): 0.53 parts
Fluorosurfactant (CW-1, trade name, manufactured by Zeneca, 1% CyH solution): 0.1 parts
Propylene glycol monomethyl ether acetate (PGMEA): 34.79 parts Next, colored compositions 2 to 10 (colored curable compositions) were prepared in a similar manner to the preparation of the colored composition 1, except that the type and the amount of the components were changed to those as shown in Table 6 below.

The numerical values in the parenthesis of the components in Table 6 represent the proportion (% by mass) of each component in the colored composition.

In Table 6, "PGME" represents propylene glycol monomethyl ether, "PB 15:6" represents Pigment Blue 15:6, and "PV 23" represents Pigment Violet 23.

The "PB 15:6 dispersion" used in the colored compositions 2 to 5 and 7 to 10 is the same as "PB 15:6 dispersion" used in the colored composition 1.

The "dispersion of PB 15:6 and PV 23" used in the colored composition 6 has a mass ratio (PV23/PB15:6) of 8.0/1.0.

The structures of Initiator 1 to Initiator 3, Monomer 1 to Monomer 3, Comparative Dye A and Comparative Dye B in the column "photopolymerization initiator" of Table 6 are shown below.

TABLE 6

| | Pigment dispersion | Dye | Polymerization initiator | Polymerizable compound | Resin/additive | Surfactant | Solvent |
|---|---|---|---|---|---|---|---|
| Colored composition 2 | Dispersion of PB15:6 (55.47) | Exemplary compound 101 (3.20) | Initiator 1 (0.96) | Monomer 1 (3.34) | Resin A (1.06) | CW-1 (0.1) | PGMEA (34.5) |
| Colored composition 3 | Dispersion of PB15:6 (53.8) | Exemplary compound 102 (3.31) | Initiator 1 (0.96) | Monomer 2 (3.37) | — | CW-1 (0.1) | PGMEA/cyclohexanone (20/15.1) |
| Colored composition 4 | Dispersion of PB15:6 (54.1) | Exemplary compound 103 (3.15) | Initiator 1 (0.89) | Monomer 2 (3.51) | — | CW-1 (0.1) | PGMEA/2-heptanone (20/15.1) |
| Colored composition 5 | Dispersion of PB15:6 (55.3) | Exemplary compound 101/Exemplary compound 103 (1.7/1.7) | Initiator 2 (0.91) | Monomer 3 (3.6) | — | CW-1 (0.1) | PGMEA/PGME (20/15.1) |
| Colored composition 6 | Dispersion of PB15:6 and PV 23 (54.3) | Exemplary compound 104 (3.25) | Initiator 3 (0.93) | Monomer 1 (3.26) | — | CW-1 (0.1) | PGMEA/2-heptanone (20/15.1) |
| Colored composition 7 | Dispersion of PB15:6 (51.5) | Exemplary compound 105 (3.18) | Initiator 1/Initiator 3 (0.5/0.5) | Monomer 1 (3.5) | — | CW-1 (0.1) | PGMEA (38.3) |
| Colored composition 8 | Dispersion of PB15:6 (52.3) | Exemplary compound 106 (3.21) | Initiator 1/Initiator 2 (0.6/0.4) | Monomer 1 (3.42) | — | — | PGMEA (39.6) |
| Colored composition 9 | Dispersion of PB15:6 (55.47) | Comparative dye A (3.20) | Initiator 1 (0.96) | Monomer 1 (3.34) | Resin A (1.06) | CW-1 (0.1) | PGMEA (34.5) |
| Colored composition 10 | Dispersion of PB15:6 (53.8) | Comparative dye B (3.31) | Initiator 1 (0.96) | Monomer 2 (3.37) | — | CW-1 (0.1) | PGMEA/cyclohexanone (20/15.1) |

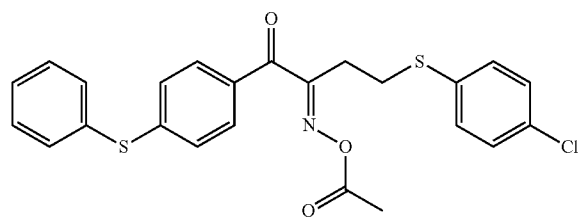
Initiator 1
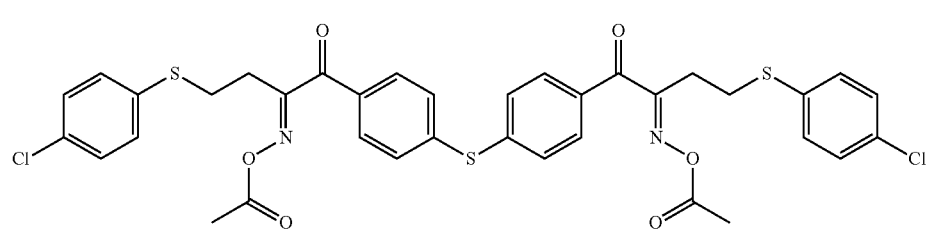
Initiator 2
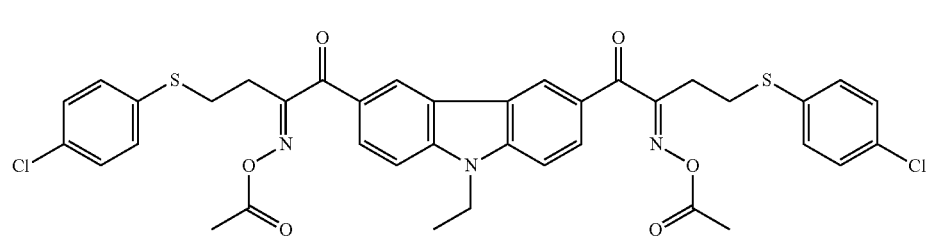
initiator 3
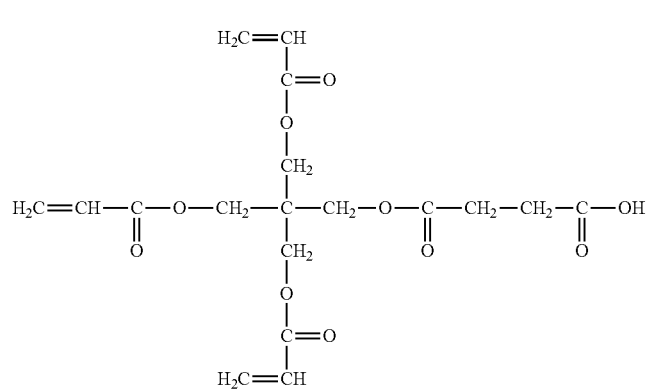
Monomer 1
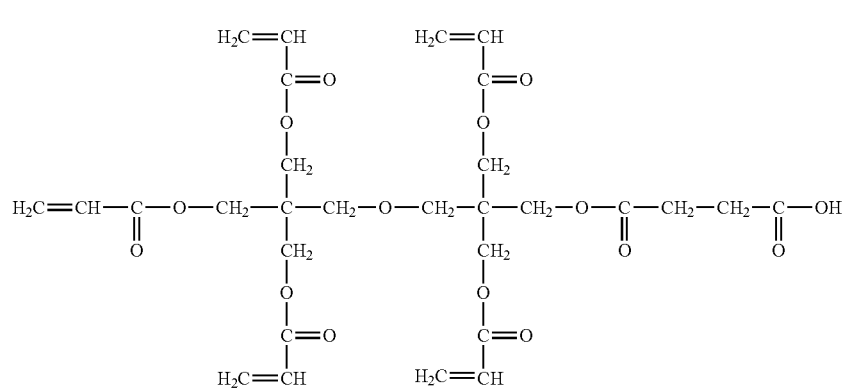
Monomer 2

Monomer 3

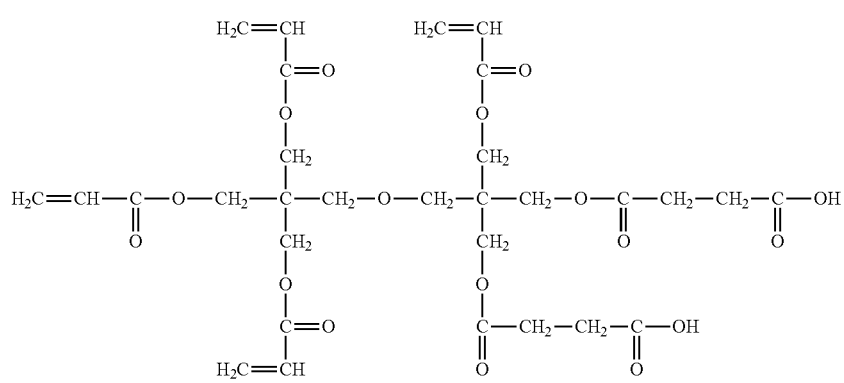

Comparative Dye A

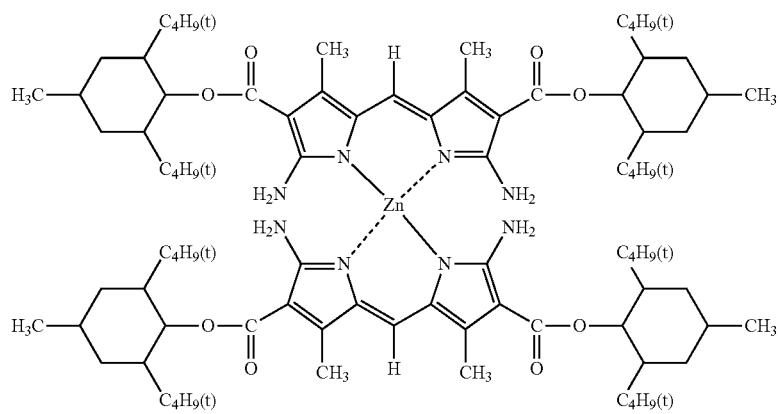

Comparative Dye B

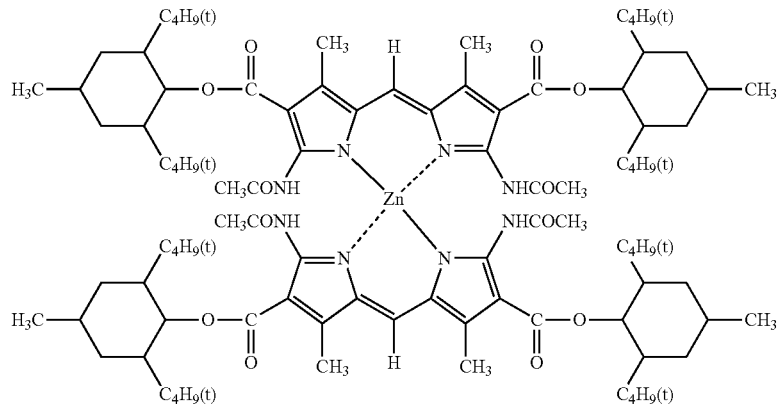

<Preparation of Single-Color Color Filter and Evaluation of Color Bleeding>

(1) Preparation of Silicon Wafer with Primer Layer

A 6-inch silicon wafer was subjected to a heat treatment in an oven at 200° C. for 30 minutes. Then, a primer layer forming solution (CT-4000, trade name, manufactured by Fujifilm Electronic Materials Co., Ltd.) was applied onto the silicon wafer to form a layer having a dried thickness of 1 μm, and further dried on a hot plate at 200° C. for 5 minutes to form a primer layer, whereby a silicon wafer with a primer layer was obtained.

(2) Application, Exposure and Development of Colored Curable Composition

The colored curable composition (colored compositions 1 to 10) was applied onto the primer layer formed on the silicon wafer obtained in the above step (1), thereby forming a photocurable coating film. A heat treatment (pre-baking) was performed using a hot plate at 100° C. for 120 seconds so as to make the dried thickness of the coating film be 0.6 μm. Next, the resulting coating film was exposed to light at a wavelength of 365 nm through a Bayer pattern mask having a pattern size of 10.0 μm square, using an i-line stepper (FPA-3000i5+, trade name, manufactured by Canon Inc.) while changing the exposure amount by 100 mJ/cm$^2$ from 100 mJ/cm$^2$ to 2500 mJ/cm$^2$.

Thereafter, the silicon wafer with the exposed coating film was placed on a horizontal rotary table of a spin-shower developing machine (trade name: MODEL DW-30, manufactured by Chemitronics Co., Ltd.) and subjected to puddle development at 23° C. for 60 seconds with a developer (CD-2000, trade name, manufactured by Fujifilm Electronic Materials Co., Ltd.) Then, the silicon wafer was rinsed with pure water shower supplied from ejection nozzles placed over the rotation center of the rotary table while rotating the silicon wafer at a revolution rate of 50 rpm, and then spray-dried to give a colored pattern.

(3) Post-Cure Treatment of Colored Pattern

The resulting colored pattern was exposed to light with a UV irradiation apparatus (trade name: UMA-802-HC552FFAL, manufactured by Ushio Inc.) at an irradiation dose of 350 mW/cm$^2$ for 30 seconds at 35° C. After the exposure, the silicon wafer was heated at 200° C. for 300 seconds to cure the colored pattern.

The silicon wafer with a colored pattern (monochromatic blue color filter) was thus prepared.

(4) Preparation of Transparent Film Composition Solution

The following components were mixed and dissolved to prepare a transparent film composition solution (CT-1).

Propylene glycol monomethyl ether acetate (PGMEA): 63.0 parts

Ethyl ethoxy propionate (EEP): 27.0 parts

Resin (benzyl methacrylate/methacrylic acid, molar ratio=70:30): 4.88 parts

KAYARAD DPHA (trade name, manufactured by Nippon Kayaku Co., Ltd., polymerizable compound): 4.88 parts Polymerization inhibitor (p-methoxyphenol): 0.0001 parts Fluorosurfactant (trade name: F-475, manufactured by DIC Corporation): 0.01 parts Photopolymerization initiator (2(O-benzoyloxime)-1-[4-(phenylthio)phenyl]-1,2-octadiene, manufactured by BASF Japan): 0.23 parts (5) Application of Transparent Film Composition The transparent film composition CT-1 prepared in the above step (4) was applied to the colored pattern formed on the silicon wafer obtained in the above step (3). Then, a heat treatment (pre-baking) was performed using a hot plate at 100° C. for 120 seconds.

(6) Post-Cure Treatment of Transparent Film Composition

The wafer on which the transparent film composition had been applied was exposed to light using a UV irradiation apparatus (UMA-802-HC552FFAL, trade name, manufactured by Ushio Inc.) at an irradiation dose of 350 mW/cm$^2$ for 30 seconds at 35° C. Thereafter, the silicon wafer with the exposed coating film was subjected to a heat treatment for 300 seconds at 200° C.

A transparent film was thus formed on the colored pattern formed on the silicon wafer.

(7) Evaluation

The resulting colored pattern having the size of 10.0 μm square (Bayer pattern), which was protected with a transparent film, was examined with an optical microscope (×500) from directly above the pattern, and whether or not the dye was bleeding from a pattern edge into the transparent film was evaluated in accordance with the following evaluation criteria.

The evaluation results are shown in Table 7 below.

—Evaluation Criteria—

A: color bleeding was not observed, or a region in which color bleeding occurred was less than 1.0 μm from the pattern edge.

B: color bleeding was observed in a region ranging from 1.0 μm to 5.0 μm from the pattern edge.

C: color bleeding was observed in a region exceeding 5.0 μm from the pattern edge.

TABLE 7

|  | Colored curable composition | Color bleeding evaluation |
| --- | --- | --- |
| Example 201 | Colored composition 1 | A |
| Example 202 | Colored composition 2 | A |
| Example 203 | Colored composition 3 | A |
| Example 204 | Colored composition 4 | A |
| Example 205 | Colored composition 5 | A |
| Example 206 | Colored composition 6 | A |
| Example 207 | Colored composition 7 | A |
| Example 208 | Colored composition 8 | A |
| Comparative Example 201 | Colored composition 9 | C |
| Comparative Example 202 | Colored composition 10 | C |

As shown in Table 7, Examples 201 to 208, in which a colored pattern was formed from colored compositions 1 to 8, containing a phthalocyanine pigment and a dye multimer having a polymerizable group and a dipyrromethene dye-derived group, exhibited suppressed color bleeding. On the other hand, in Comparative Examples 201 and 202, in which a colored pattern was formed from colored compositions 9 and 10, containing a dye other than the dye multimer according to the invention, color bleeding reached a significant level.

Although a colored pattern having the size of 10 μm square was used in the above Examples, color bleeding is also suppressed when a fine colored pattern (for example, having the size of 1.0 μm square) was used, similarly to the Examples.

In Examples 201 to 208, a blue colored pattern (color filter) was formed on a silicon wafer substrate from colored compositions 1 to 8. However, it is also possible to obtain a three-color color filter by forming a blue color filter using any of colored compositions 201 to 208, a green color filter by a known method using a green color resist, and a red color filter by a known method using a red color resist, respectively, on a solid-state image sensor substrate (a silicon wafer substrate on which an image sensor such as CCD or CMOS is formed). A solid-state image sensor including the three-color color filter exhibits suppressed color bleeding in a blue color filter, and exhibits excellent color reproducibility.

All publications, patent applications, and technical standards mentioned in this specification are herein incorporated by reference to the same extent as if each individual publication, patent application, or technical standard was specifically and individually indicated to be incorporated by reference.

What is claimed is:

1. A colored curable composition comprising a phthalocyanine pigment, a dye multimer having a polymerizable group and a group derived from a dipyrromethene dye, a polymerization initiator, a polymerizable compound and a solvent.

2. The colored curable composition according to claim 1, wherein the dye multimer comprises, as repeating units, a structural unit that includes the polymerizable group and a structural unit that includes the group derived from a dipyrromethene dye.

3. The colored curable composition according to claim 1, wherein the polymerizable group is an ethylenically unsaturated group.

4. The colored curable composition according to claim 1, wherein the dipyrromethene dye comprises a dipyrromethene dye represented by following formula (C):

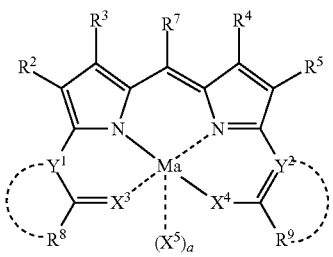

(C)

wherein, in formula (C), each of $R^2$ to $R^5$ independently represents a hydrogen atom or a substituent; $R^7$ represents a hydrogen atom, a halogen atom, an alkyl group, an aryl group or a heterocyclic group; Ma represents a metal or a metal compound; each of $X^3$ and $X^4$ independently represents NR (R representing a hydrogen atom, an alkyl group, an alkenyl group, an aryl group, a heterocyclic group, an acyl group, an alkylsulfonyl group or an arylsulfonyl group), an oxygen atom or a sulfur atom; $Y^1$ represents NRc (Rc representing a hydrogen atom, an alkyl group, an alkenyl group, an aryl group, a heterocyclic group, an acyl group, an alkylsulfonyl group or an arylsulfonyl group) or a nitrogen atom; $Y^2$ represents a nitrogen atom or a carbon atom; each of $R^8$ and $R^9$ independently represents an alkyl group, an alkenyl group, an aryl group, a heterocyclic group, an alkoxy group, an aryloxy group, an alkylamino group, an arylamino group or a heterocyclic amino group); $R^8$ and $Y^1$ may be bonded to each other to form a five, six or seven-membered ring; $R^9$ and $Y^2$ may be bonded to each other to form a five, six or seven-membered ring; $X^5$ represents a group capable of being bonded to Ma; and a represents 0, 1 or 2.

5. The colored curable composition according to claim 1, further comprising a dioxazine pigment.

6. The colored curable composition according to claim 5, wherein the dioxazine pigment comprises C.I. Pigment Violet 23.

7. The colored curable composition according to claim 1, wherein the polymerization initiator comprises an oxime photopolymerization initiator.

8. A color filter produced by using the colored curable composition according to claim 1.

9. A solid-state image sensor comprising the color filter according to claim 8.

10. A method of producing a color filter, the method comprising;
    (A) applying the colored curable composition according to claim 1 to a support to form a colored curable composition layer; and
    (B) forming a colored pattern by exposing the colored curable composition layer to light via a mask and developing the exposed colored curable composition layer.

* * * * *